US012479918B2

(12) United States Patent
Twitty et al.

(10) Patent No.: US 12,479,918 B2
(45) Date of Patent: Nov. 25, 2025

(54) PLASMID CONSTRUCTS FOR TREATING CANCER AND METHODS OF USE

(71) Applicant: Grand Decade Developments Limited, Hong Kong (HK)

(72) Inventors: Christopher Twitty, San Diego, CA (US); Anandaroop Mukhopadhyay, San Diego, CA (US); David A. Canton, San Diego, CA (US); Mia Han, San Diego, CA (US); Erica Browning, San Diego, CA (US)

(73) Assignee: Grand Decade Developments Limited, Hong Kong (HK)

( * ) Notice: Subject to any disclaimer, the term of this patent is extended or adjusted under 35 U.S.C. 154(b) by 1184 days.

(21) Appl. No.: 17/296,327

(22) PCT Filed: Nov. 27, 2019

(86) PCT No.: PCT/US2019/063590

§ 371 (c)(1),
(2) Date: May 24, 2021

(87) PCT Pub. No.: WO2020/112987

PCT Pub. Date: Jun. 4, 2020

(65) Prior Publication Data

US 2022/0041724 A1 Feb. 10, 2022

Related U.S. Application Data

(60) Provisional application No. 62/826,439, filed on Mar. 29, 2019, provisional application No. 62/771,928, filed on Nov. 27, 2018.

(51) Int. Cl.

| | |
|---|---|
| ***A61P 35/00*** | (2006.01) |
| ***A61N 1/00*** | (2006.01) |
| ***C07K 14/52*** | (2006.01) |
| ***C07K 14/54*** | (2006.01) |
| ***C07K 14/71*** | (2006.01) |
| ***C07K 16/28*** | (2006.01) |

(52) U.S. Cl.

CPC ............ *C07K 16/2818* (2013.01); *A61N 1/00* (2013.01); *A61P 35/00* (2018.01); *C07K 14/522* (2013.01); *C07K 14/5434* (2013.01); *C07K 14/71* (2013.01); *C07K 16/2809* (2013.01)

(58) Field of Classification Search

None

See application file for complete search history.

(56) References Cited

U.S. PATENT DOCUMENTS

| | | | |
|---|---|---|---|
| 5,439,440 | A | 8/1995 | Hofmann |
| 6,009,347 | A | 12/1999 | Hofmann |
| 6,055,453 | A | 4/2000 | Hoffmann et al. |
| 7,245,963 | B2 | 7/2007 | Draghia-Akli et al. |
| 9,020,605 | B2 | 4/2015 | McClusky et al. |
| 9,037,230 | B2 | 5/2015 | Goldfarb et al. |
| 2005/0052630 | A1 | 3/2005 | Smith et al. |
| 2006/0177896 | A1 | 8/2006 | Mach et al. |
| 2008/0233122 | A1 | 9/2008 | Hanson et al. |
| 2010/0183554 | A1 | 7/2010 | Mach et al. |
| 2011/0296546 | A1 | 12/2011 | Korman et al. |
| 2012/0148597 | A1 | 6/2012 | Hanson et al. |
| 2013/0136749 | A1 | 5/2013 | Korman et al. |
| 2014/0099325 | A1 | 4/2014 | Hanson et al. |
| 2014/0104409 | A1 | 4/2014 | Bishop et al. |
| 2014/0193399 | A1 | 7/2014 | Mach et al. |
| 2018/0117152 | A1 | 5/2018 | Lee et al. |
| 2019/0030437 | A1 | 1/2019 | Subbiah et al. |
| 2019/0048096 | A1 | 2/2019 | Hermann et al. |
| 2019/0117964 | A1 | 4/2019 | Bahrami et al. |
| 2020/0246612 | A1 | 8/2020 | Rodriguez et al. |
| 2023/0277624 | A1 * | 9/2023 | Twitty ................ C07K 16/2866 424/85.2 |

FOREIGN PATENT DOCUMENTS

| | | | | |
|---|---|---|---|---|
| JP | 2013-527753 | A | 7/2013 | |
| WO | WO 2010/042189 | A2 | 4/2010 | |
| WO | WO 2013/176772 | A1 | 11/2013 | |
| WO | WO 2017/106795 | A1 | 6/2017 | |
| WO | WO-2017134100 | A1 * | 8/2017 | ............. A61K 35/14 |
| WO | WO 2018/038945 | A1 | 3/2018 | |
| WO | WO 2018/229696 | A1 | 12/2018 | |
| WO | WO 2019/213421 | A1 | 11/2019 | |

OTHER PUBLICATIONS

Witkowski et al, Biochemistry 38:11643-11650, 1999. (Year: 1999).*
Seffernick et al, Bacteriol. 183(8): 2405-2410, 2001. (Year: 2001).*
Compte et al., "Functional comparison of single-chain and two-chain anti-CD3-based bispecific antibodies in gene immunotherapy applications," OncoImmunology, 3(e28810):1-8 abstract: and p. 1 (May 2014).
Ding et al., "CXCL9: evidence and contradictions for its role in tumor progression," Cancer Medicine, 5(11):3246-3259 abstract and p. 3250 (2016).
Liu et al., "MGD011, a CD19×CD3 Dual-Affinity Retargeting Bi-specific Molecule Incorporating Extended Circulating Half-life for the Treatment of B-Cell Malignancies," Clinical Cancer Research, 23(6):1506-1518, Mar. 15, 2017).
Speck et al., Targeted BiTE Expression by an Oncolytic Vector Augments Therapeutic Efficacy Against Solid Tumors, Clinical Cancer Research, 24(9):OF1-OF10, abstract: and pp. OF1, OF3, OF4 (May 2018).

(Continued)

*Primary Examiner* — Gary B Nickol
*Assistant Examiner* — Cheom-Gil Cheong
(74) *Attorney, Agent, or Firm* — Wolf, Greenfield & Sacks, P.C.

(57) ABSTRACT

Described are expression cassettes encoding CD3-half-BiTE, CXCL9 and CTLA-4 scFv. The described expression cassettes can be used to treat cancer in a subject. Methods of delivering the expression cassettes to a tumor by direct intratumoral injection and electroporation are also described.

14 Claims, 32 Drawing Sheets

Specification includes a Sequence Listing.

(56) References Cited

OTHER PUBLICATIONS

Tamura et al., "Intratumoral Delivery of Interleukin 12 Expression Plasmids with In Vivo Electroporation Is Effective for Colon and Renal Cancer," Human Gene Therapy, 12:1256-1276, (Jul. 1, 2001).
WIPO Application No. PCT/US2019/063590, PCT International Preliminary Report on Patentability mailed May 25, 2021.
WIPO Application No. PCT/US2019/063590, PCT International Search Report and Written Opinion of the International Searching Authority mailed Mar. 20, 2020.
Examination Report for AU Application No. 2019386131 dated Jan. 30, 2023, 4 pgs.
Extended European Search Report for EP App No. 19889338.0 dated Nov. 28, 2022, 12 pgs.
Callahan et al., "Anti-CTLA-4 Antibody Therapy: Immune Monitoring During Clinical Development of a Novel Immunotherapy," Seminars in Oncology, 37(5):473-484, (Oct. 1, 2010).
Han et al., "Abstract 3195: Intratumoral electroporation of plasmid IL-12 an CXCL9 with membrane-bound anti-CD3 elicits robust anti-tumor immunity," Cancer Research, 79:3195, (Jul. 1, 2019).
Hosseinzadeh et al., "Production and Evaluation of Specific Single-Chain Antibodies against CTLA-4 for Cancer-Targeted Therapy," Reports of Biochemistry and Molecular Biology, 6(1):10-14, (Oct. 1, 2017).
Lee et al., "Amplification of the CXCR3/CXCL9 axis via intratumoral electroporation of plasmid CXCL9 synergizes with plasmid IL-12 therapy to elicit robust anti-tumor immunity," Molecular Therapy—Oncolytics, 25:174-188, (Jun. 1, 2022).
Mukhopadhyay et al., "Characterization of abscopal effects of intratumoral electroporation- mediated IL-12 gene therapy," Gene Therapy, 26:1-15, (2019).
CA Application No. 3,120,564, Office Action mailed Aug. 3, 2022.
EP Application No. 19889338.0, partial supplementary EP Search Report mailed Aug. 25, 2022.

* cited by examiner

A.

Mouse OT1 cells

Human PBMCs

A.
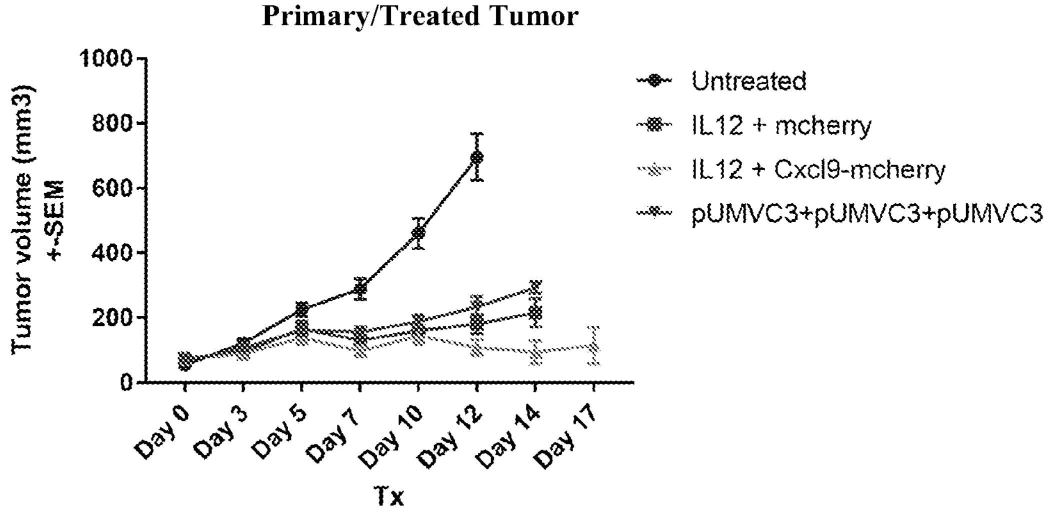
B.
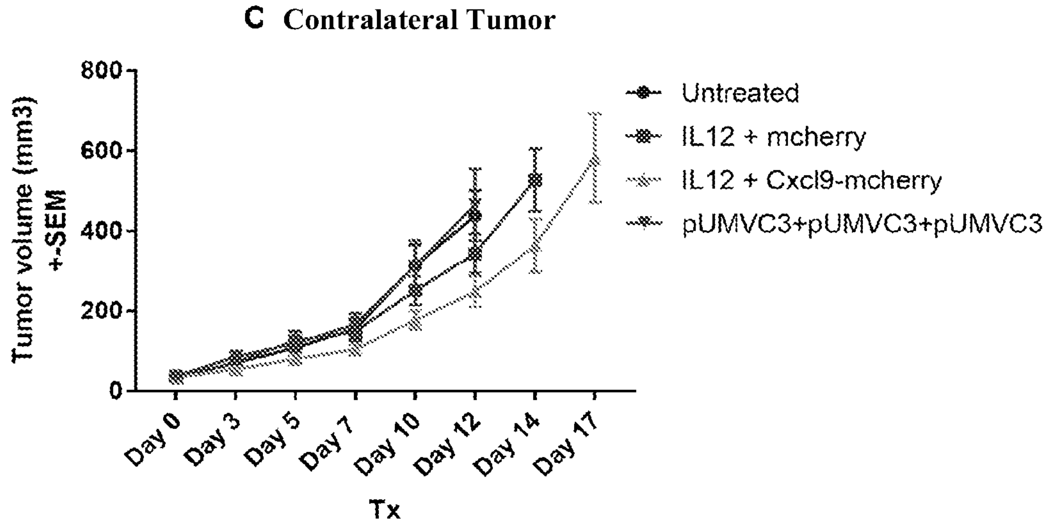
FIG. 7

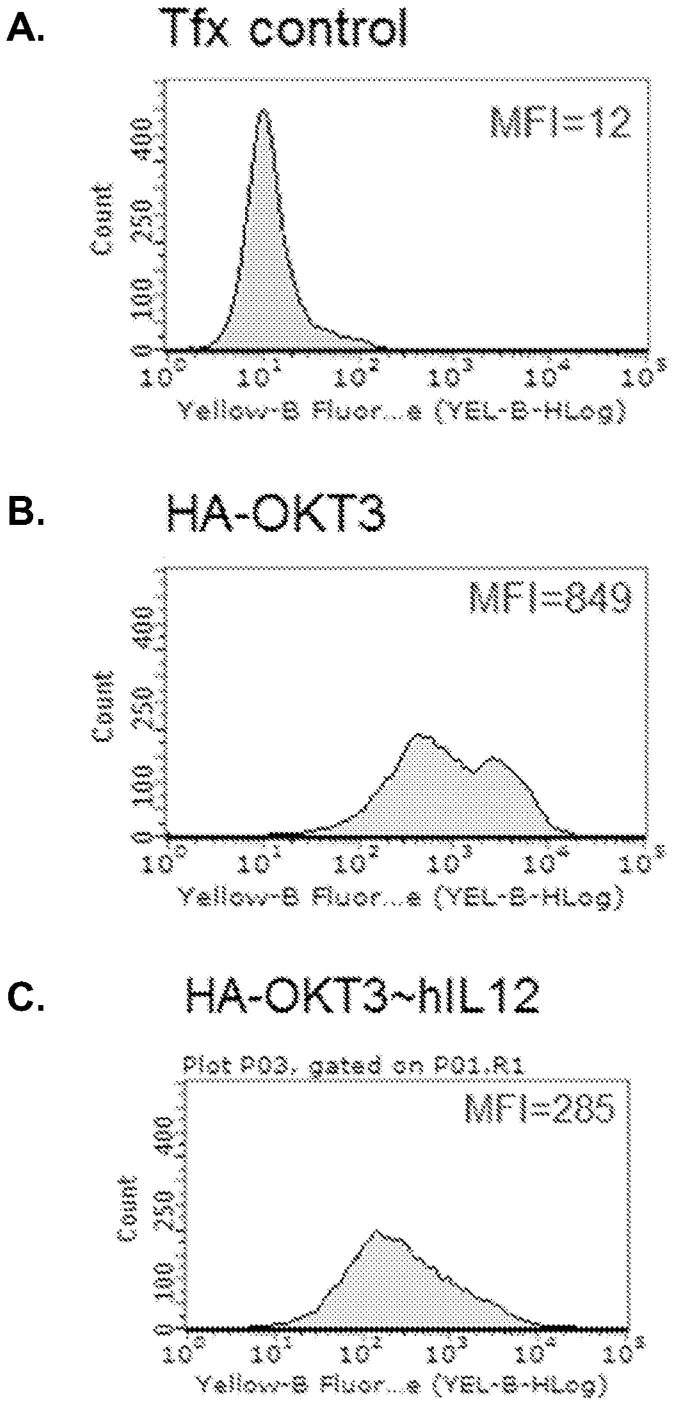
FIG. 14A-C

D.
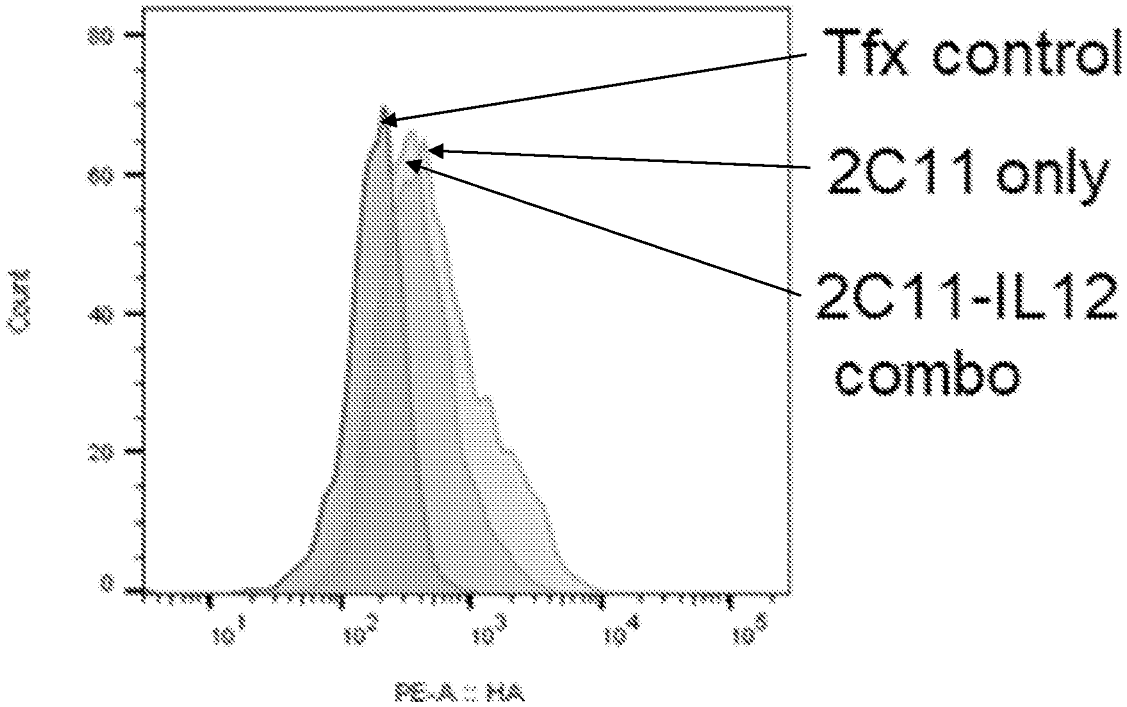
E.
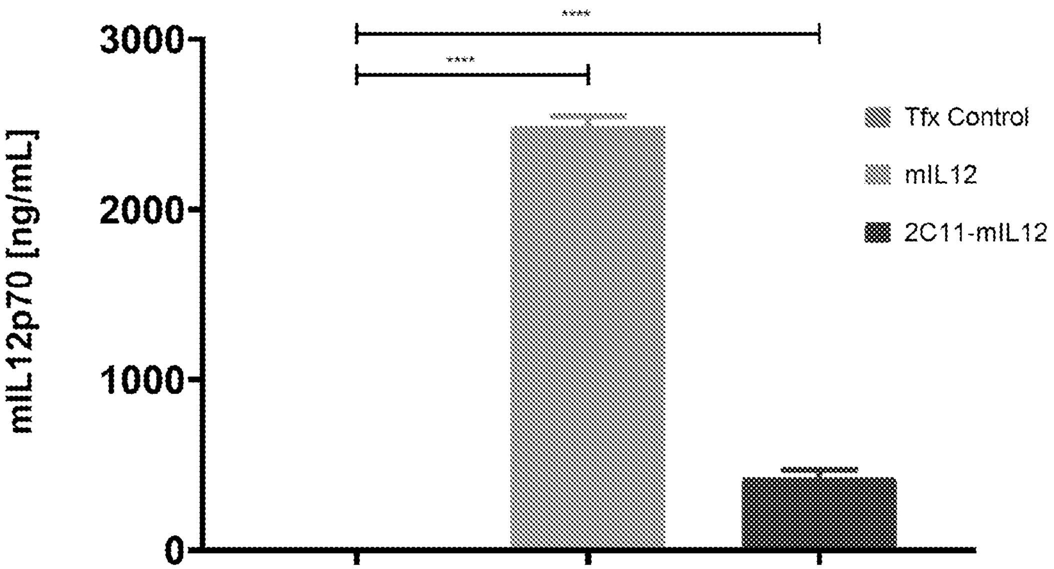
FIG. 14D-E

A.
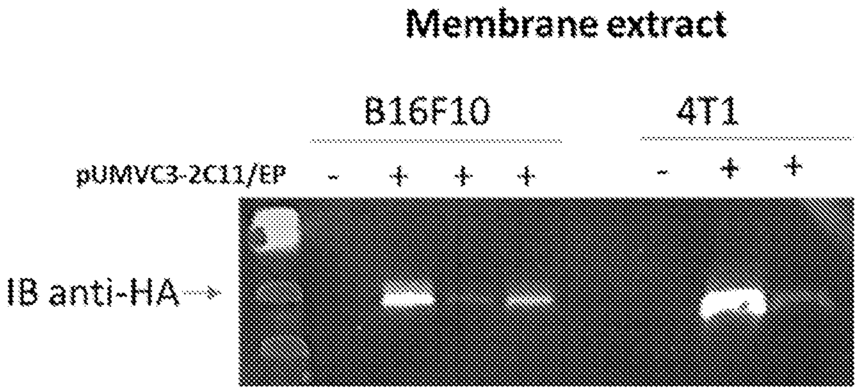
B.
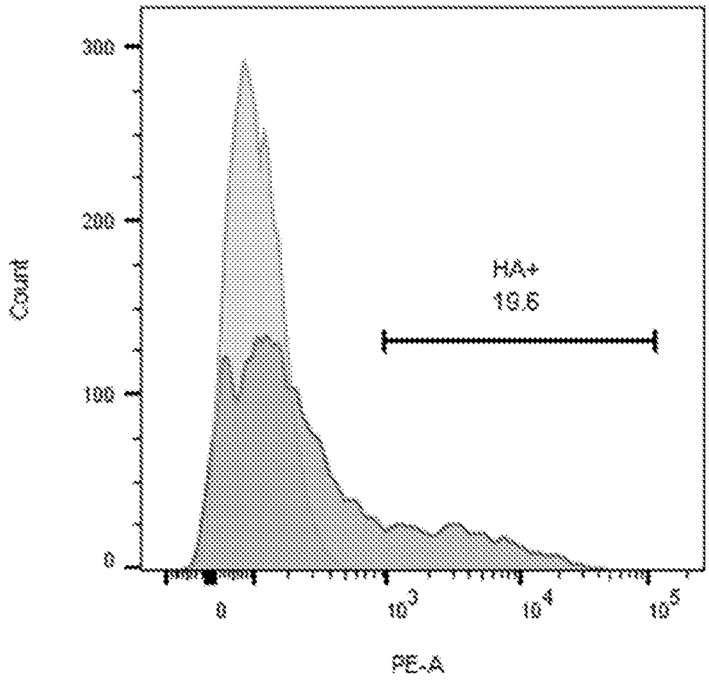
FIG. 16A-B

A.
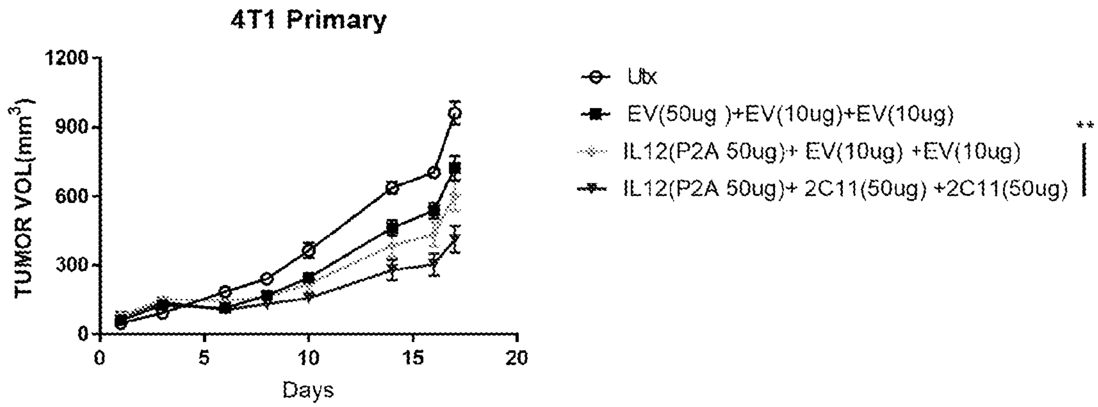
EP on day 1, 3, 6
B.
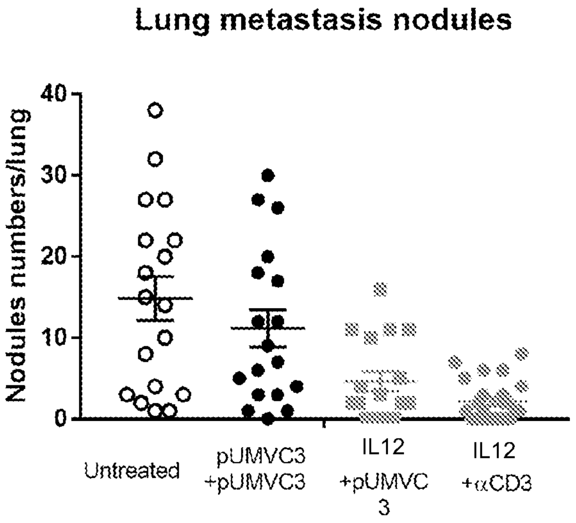
FIG. 26A-B

C.

A. hIL-12 expression
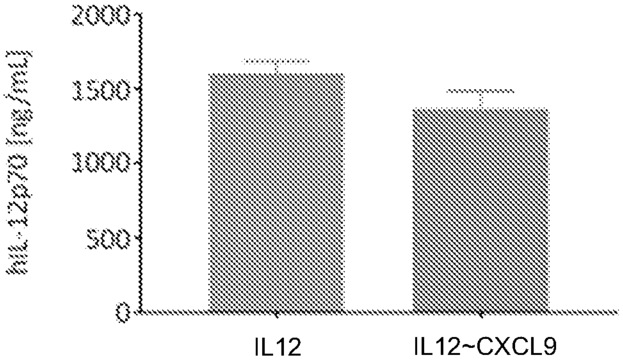
B. hCXCL9 expression
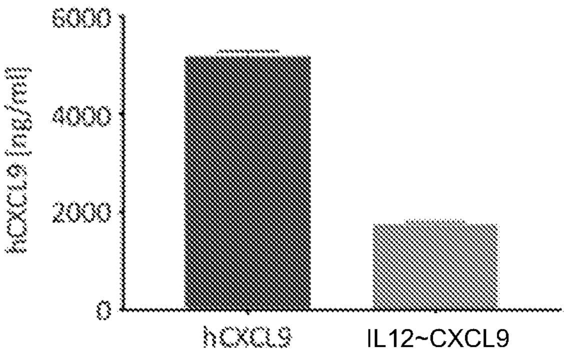
FIG. 27

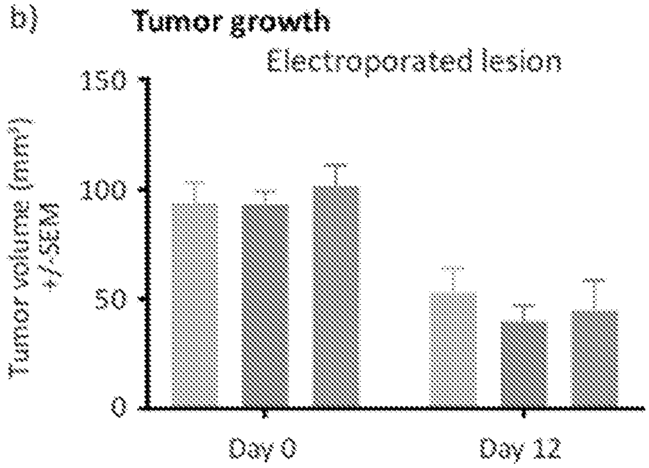
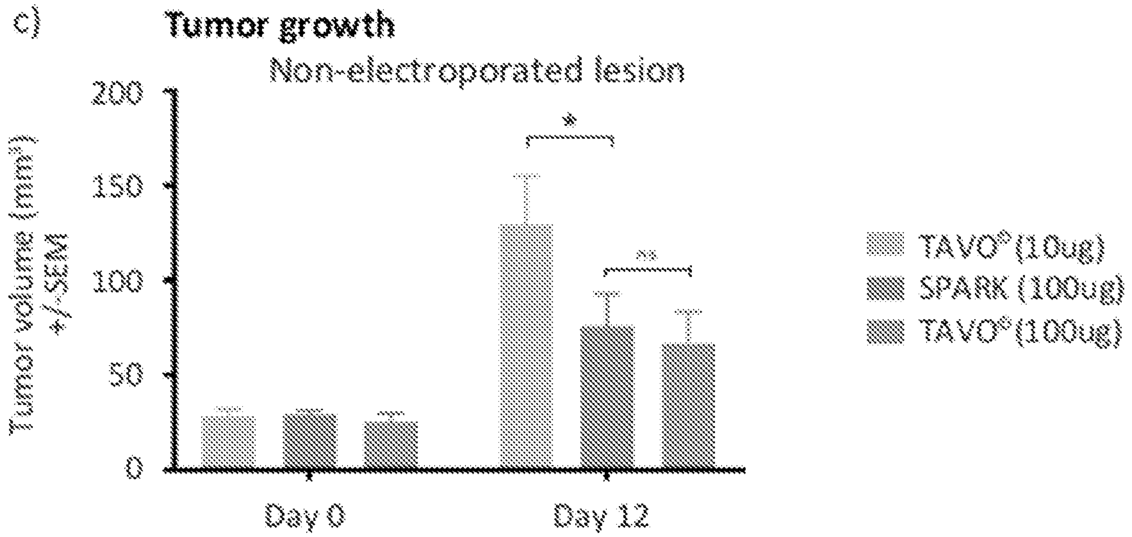
FIG. 29B-C

PLASMID CONSTRUCTS FOR TREATING CANCER AND METHODS OF USE

CROSS-REFERENCE TO RELATED APPLICATIONS

This application is a US National Stage entry of International Application No. PCT/US2019/063590, filed Nov. 27, 2019, which claims priority to U.S. Provisional Application Ser. No. 62/771,928, filed Nov. 27, 2018, and U.S. Provisional Application Ser. No. 62/826,439, filed Mar. 29, 2019 each of which is incorporated herein by reference in its entirety for all purposes.

SEQUENCE LISTING

The Sequence Listing written in file G105670002US00-SUBSEQ-ZJG.txt is 147.907 bytes in size, was created Feb. 14, 2025, and is hereby incorporated by reference.

BACKGROUND

Cancer immunoediting is responsible for eliminating tumors and sculpting the immunogenic phenotypes of tumors that eventually form in immunocompetent hosts following tumor escape from immune destruction. Immune system-tumor interactions are postulated to occur in three continuous phases: elimination, equilibrium, and escape. Elimination entails the destruction of tumor cells by T lymphocytes In equilibrium, a population of immune-resistant tumor cells appears. During escape, the tumor has developed strategies to evade immune detection or destruction. Escape may occur through loss or ineffective presentation of tumor antigens, secretion of inhibitory cytokines, or downregulation of major histocompatibility complex molecules.

Cancer immunotherapy aims to elicit successful T-cell response that leads to cancer regression. Various efforts have been made to activate effector T-cell responses, such as though presentation of tumor antigen by antigen presenting cells (APCs), prime T cells to successfully target and infiltrate tumors, and enhancing infiltrating T cells to bind to the MHCI-peptide complex to activate the cytotoxic T-cell response.

Studies have shown a survival benefit associated with the presence of tumor infiltrating lymphocytes (TILs). There is evidence that immunostimulatory cytokines, such as IL-12, can increase the immune cell infiltrate in solid tumors. However, systemic administration of IL-12 has a narrow therapeutic index and is often accompanied by unacceptable levels of adverse events. The limitations of systemic administration of IL-12 can be overcome by therapies that result in local expression of IL-12, such as intratumoral electroporation of plasmid encoding IL-12.

While IL-12 can increase the number of TILs, there remains a need to increase the presence and number of tumor-specific T cells in a tumor. CD3 (cluster of differentiation 3) T cell co-receptor helps to activate both the cytotoxic T cell (CD8+ naive T cells) and also T helper cells (CD44 naive T cells). Because of its role in activating T cell response, anti-CD3 antibodies have been explored for use as immunosuppressant therapies. Bispecific antibodies, including Bi-specific T-cell engagers (BiTEs), targeting CD3 and a cancer antigen (tumor marker) have been developed to target T cells to cancer cells.

SUMMARY

Described are expression cassettes encoding CXCL9, CXCL9 plus IL-12, anti-CTLA-4 scFv, anti-CTLA-4 scFv plus IL-12, CD3 half-BiTE and CD3 half-BiTE plus IL-12. The describe expression cassettes are useful in the treatment of cancer. Methods of using the described expression cassettes to treat tumors, including cancers and metastatic cancers, are also described. The described expression cassettes, when delivered to a tumor, such as by electroporation, result in local tumor expression of the encoded proteins, leading to T cell recruitment and anti-tumor activity. In some embodiments, the methods also result in abscopal effects, i.e., regression of one or more untreated tumors. In some embodiments, regression includes debulking of a solid tumor.

Expression cassettes encoding CXCL9 are described. In some embodiments, an expression cassette encoding CXCL9 further encodes IL-12 The described CXCL9 expression cassettes can be delivered intratumorally, peritumorally, into a lymph node, intradermally, and/or intramuscularly. In some embodiments, the CXCL9 and IL12 coding sequences are expressed on a multicistronic expression cassette from a single promoter and separated by an IRES or 2A translation modification element. In some embodiments, the 2A element is a P2A element. IL-12 is a heterodimeric cytokine having both IL-12A (p35) and IL-12B (p40) subunits. The encoded IL-12 can comprise a fusion construct encoding an IL-12 p35-IL-12 p40 fusion protein (IL12 p70). In some embodiments, the IL-12 p35 and p40 coding sequences are expressed from a multicistronic expression cassette from a single promoter and separated by an IRES or 2A element. In some embodiments, the 2A element is a P2A element. In some embodiments, multicistronic expression cassettes are described, comprising CXCL9, IL12 p35, and IL-12 p40 coding regions separated by IRES or 2A elements. In some embodiments, the 2A element is a P2A element.

Expression cassettes encoding anti-CTLA-4 scFv's are described. An anti-CTLA-4 scFv comprises an anti-CTLA-4 single-chain variable fragment. The described anti-CTLA-4 scFv expression cassettes can be delivered intratumorally, peritumorally, into a lymph node, intradermally, and/or intramuscularly. The lymph node can be a draining lymph node. An anti-CTLA-4 scFv expression cassette can also be delivered in a peritumoral region between the tumor and the draining lymph node. For each of intratumoral, peritumoral, lymph node, intradermal, and/or intramuscular delivery of an anti-CTLA-4 scFv expression cassette, the delivery can be facilitated by electroporation. Direct expression of an anti-CTLA-4 scFv expression cassette can result in fewer side effects and/or toxicity when compared to systemic administration of anti-CTLA-4 antibodies. The described anti-CTLA-4 scFv expression cassettes facilitate delivery of local yet efficacious dose of anti-CTLA-4.

CD3 half-BiTEs and expression cassettes encoding CD3 half-BiTEs are described. CD3 half-BiTEs comprise anti-CD3 single-chain variable fragment (scFv) fused to a transmembrane domain (TM). In some embodiments, an expression cassette encoding a CD3 half-BiTE further encodes a signal peptide. The encoded signal peptide can be operably linked to the 5' end of the anti-CD3 single-chain variable fragment coding sequence. In some embodiments, an expression cassette encoding a CD3 half-BiTE further encodes IL-12. The described CD3 half-BiTE expression cassettes can be delivered intratumorally, peritumorally, into a lymph node, intradermally, and/or intramuscularly. In some embodiments, the CD3 half-BiTE and IL12 coding sequences are expressed on a multicistronic expression cassette from a single promoter and separated by an IRES or 2A translation modification element. In some embodiments, the 2A element is a P2A element. IL-12 is heterodimeric cytokine having both IL-12A (p35) and IL-12B (p40) subunits. The encoded IL-12 can contain a fusion construct encoding an IL-12 p35-IL-12 p40 fusion protein (IL12 p70). In some embodiments, the IL-12 p35 and p40 coding sequences are expressed from a multicistronic expression cassette from a single promoter and separated by an IRES or 2A translation modification element. In some embodiments, the 2A element is a P2A element. In some embodiments, multicistronic expression cassettes are described, comprising a CD3 half-BiTE, IL12 p35, and IL-12 p40 coding regions separated by IRES or 2A translation modification elements. In some embodiments, the 2A element is a P2A element.

Described are methods of treating a cancer comprising administering to a subject, by intratumoral electroporation (IT-EP), a composition comprising a therapeutically effective amount one or more of the described expression cassettes. The composition is injected into a tumor, tumor microenvironment, and/or tumor margin tissue and electroporation therapy is applied to the tumor, tumor microenvironment, and/or tumor margin tissue. The electroporation therapy may be applied by any suitable electroporation system known in the art. In some embodiments, the electroporation is at a field strength of about 60 V/cm to about 1500 V/cm, and a duration of about 10 microseconds to about 20 milliseconds. In some embodiments, the electroporation incorporates. Electrochemical Impedance Spectroscopy (EIS). The subject can be a mammal. The mammal can be, but is not limited to, a human, canine, feline, or equine.

In some embodiments, the methods further comprise administering to the subject a therapeutically effect amount of an immunostimulatory cytokine. The immunostimulatory cytokine can be an expression cassette encoding the immunostimulatory cytokine delivered by IT-EP. The immunostimulatory cytokine can be, but is not limited to, IL-12. The immunostimulatory cytokine can be delivered prior to, subsequent to, or concurrent with one or more of the described CXCL9, CTLA-4 scFv and CD3 half-BiTE expression cassettes.

In some embodiments, the methods further comprise administration of one or more additional therapies. The one or more additional therapies can be, but are not limited to, immune checkpoint therapy. Immune checkpoint therapy can be, but is not limited to, administration of one or more immune checkpoint inhibitors. "Immune checkpoint" molecules refer to a group of immune cell surface receptor/ligands which induce T cell dysfunction or apoptosis. These immune inhibitory targets attenuate excessive immune reactions and ensure self-tolerance. Tumor cells harness the suppressive effects of these checkpoint molecules. Immune checkpoint target molecules include, but are not limited to, Cytotoxic T Lymphocyte Antigen-4 (CTLA-4), Programmed Death 1 (PD-1), Programmed Death Ligand 1 (PD-L1), Lymphocyte Activation Gene-3 (LAG-3), T cell Immunoglobulin Mucin-3 (TIM3), Killer Cell Immunoglobulin-like Receptor (MR), B- and T-Lymphocyte Attenuator (BTLA), Adenosine A2a Receptor (A2aR), and Herpes Virus Entry Mediator (HVEM). "immune checkpoint inhibitors" include molecules that prevent immune suppression by blocking the effects of immune checkpoint molecules. Checkpoint inhibitors include, but are not limited to, antibodies and antibody fragments, nanobodies, diabodies, soluble binding partners of checkpoint molecules, small molecule therapeutics, and peptide antagonists. An immune checkpoint inhibitor can be, but is not limited to, a PD-1 and/or PD-L1 antagonist. A PD-1 and/or PD-L1 antagonist can be, but is not limited to, an anti-PD-1 or anti-PD-L1 antibody. Anti-PD-1/PD-L1 antibodies include, but are not limited to, nivolumab, pembrolizumab, pidilizumab, and atezolizumab.

Described are methods of treating a tumor in a subject comprising: administering at least one treatment cycle to the subject, the cycle comprising: administering to the tumor, by IT-EP, a composition comprising a therapeutically effective amount of one or more of the described CXCL9, CXCL9 plus IL-12 (i.e., IL12-CXCL9), anti-CTLA-4 scFv, anti-CTLA-4 scFv plus IL-12. CD3 half-BiTE, or CD3 half-BiTE plus IL-12 (i.e., CD3 half-BiTE-IL12) expression cassettes. In some embodiments, the cycle is a three week cycle. In some embodiments, the cycle is a four, five, or six week cycle. The composition can be administered by IT-EP on 1, 2, 3, 4, 5, or 6 days of a cycle. In some embodiments, the composition is administered by 1IT-EP on day 1 of each cycle. In some embodiments, the composition administered by IT-EP on days 1 and 5-2 of each cycle. In some embodiments, the composition is administered by IT-EP on days 1 and 8±2 of each cycle. In some embodiments, the composition is administered by IT-EP on days 1, 5±2, and 8±2 of each cycle. The cycles can be repeated as often as is necessary to treat the subject. In some embodiments, a cycle further comprises administration of an additional therapeutic. The additional therapeutic can be, but is not limited to, an immune checkpoint therapy. In some embodiments, the immune checkpoint therapy is administered to the subject on day 1, 2, or 3 of the cycle.

In some embodiments, a subject is treated with one of more cycles of IT-EP therapy with one or more of the described expression cassettes. Any of the above cycles can be repeated in subsequent cycles. The subsequent cycles can be consecutive cycles or alternating cycles. Alternating cycles can have one or more intervening cycles of no therapy of alternative therapy (e.g., immune checkpoint therapy). For example, any of the described expression cassettes can be administered on days 1, 5±2, and 8±2 of alternating cycles (e.g., cycles 1, 3, 5, etc. as needed) and an alternative therapy can be administered. e.g., on day 1, 2, or 3, of consecutive cycles (e.g., cycles 1, 2, 3, 4, 5, etc. as needed).

In some embodiments, a subject is administered alternating cycles of IT-EP of any of the described CXCL9, CTLA-4 scFv, and/or CD3 half-BiTE expression cassettes, with or without immune checkpoint inhibitor therapy, and immune checkpoint inhibitor therapy. In other words, a subject can be administered, by IT-EP, a composition comprising a therapeutically effective amount of one or more of the described CXCL9. CXCL9 plus IL-12, anti-CTLA-4 scFv, anti-CTLA-4 scFv plus IL-12, CD3 half-BiTE, or CD3 half-BiTE plus IL-12 expression cassettes and optionally administered immune checkpoint inhibitor therapy on odd numbered cycles (cycles 1, 3, etc.) and administered immune checkpoint inhibitor therapy on even numbered cycles (cycles 2, 4, etc.). Alternatively, a patient can be administered immune checkpoint inhibitor therapy on odd numbered cycles (cycles 1, 3, etc.) and administered, by IT-EP, a composition comprising a therapeutically effective amount of one or more of the described CXCL9, CXCL9 plus IL-12, anti-CTLA-4 scFv, anti-CTLA-4 scFv plus IL-12, CD3 half-BiTE, or CD3 half-BiTE plus IL-12 expression cassettes and optionally administered immune checkpoint inhibitor therapy on even numbered cycles (cycles 2, 4, etc.).

The expression cassettes and methods can be used to treat a subject having advanced, metastatic, treatment refractory tumor. A treatment refractory tumor can be, but is not limited to, an immune checkpoint inhibitor refractory tumor, a hormone refractory tumor, a radiation refractory tumor, and a chemotherapy refractory tumor. In some embodiments, the subject has failed to respond to at least one course of immune checkpoint inhibitor therapy. In some embodiments, the subject is progressing on or has progressed on one or more anti-cancer therapies, such as, but not limited to, checkpoint inhibitor therapy.

The expression cassettes and methods can be used to treat subjects having tumors predicted to be refractory to or not respond to one or more anti-cancer therapies. In some embodiments, the subject has low tumor infiltrating lymphocytes, low partially cytotoxic lymphocytes, or exhausted T cells. In some embodiments, the subject has advanced on one or more prior cancer therapies.

BRIEF DESCRIPTION OF THE DRAWINGS

FIG. 7. Graphs illustrating (A) decreased tumor volume, and (B) decreased contralateral (untreated) tumor volume, in tumor bearing mice treated with IT-EP therapy with mIL12-2A plus mCXCL9 compared to IL-12 therapy alone on control plasmid.

FIG. 14A-C. Flow cytometry showing the surface expression of anti-CD3 scFv in HEK 293 cells transfected with HA-OKT3 scFv and HA-OKT3 scFv-hIL12 expression vectors.

FIG. 14D-E. (D) Flow cytometry showing the surface expression of anti-CD3 scFv in B16-F10 cells transfected with HA-2C11 scFv and HA-2C11 scFv~mIL12 expression vectors. (E) Graph illustrating IL12p70 expression in B16-F10 cells following transfection with mIL12-2A, HA-2C11 scFv~mIL12 expression vector.

FIG. 16A-B. (A) Western blot showing expression of CD3 scFv in B16F10 melanoma or 4T1 breast cancer cells in vivo following intratumoral electroporation of HA-2C11 scFv. (B) Flow analysis of surface expression of CD3 scFv on 4T1 breast cancer cells in vivo following intratumoral electroporation of HA-2C11 scFv.

FIG. 27. Graphs illustrating (A) hIL12p70 protein secretion, and (B) hCXCL9 protein secretion in HEK293 cells following transfection with hIL12-2A, hCXCL9, and hIL12~hCXCL9 expression vectors. Protein detected by ELISA, n=5.

FIG. 29B-C Graph illustrating primary (B) and secondary (C) tumor growth in mice bearing B16.F10 tumors after treatment with 10 μg or 100 μg of IL12-2A (TAVO) on days 1, 5, and 8, or 100 μg of IL12~CXCL9 or CD3 half-BiTE~IL12 (SPARK) on each of days 1, 5, and 8. (From left to right for each of days 0 and 12: 10 μg IL12-2A, SPARK, 100 μg of IL12-2A).

DETAILED DESCRIPTION

I. Definitions

Figure 1A:
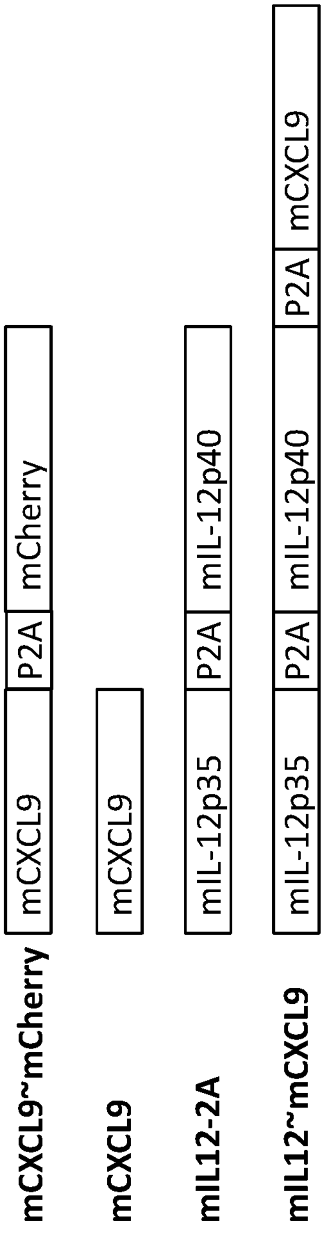
FIG. 1A. Illustrations of the expression constructs for mCXCL9-mCherry (mCXCL9-PTA-mCherry), mCXCL9, mIL-2-2A (mIL-12 p35-P2A-mIL-12 p40), mIL12~mCXCL9 (mIL-12 p35-P2A-mIL-12 p40-P2A-mCXCL9).

A "nucleic acid" includes both RNA and DNA. RNA and DNA include, but are not limited to, cDNA, genomic DNA, plasmid DNA, condensed nucleic acid, nucleic acid formulated with cationic lipids, nucleic acid formulated with peptides or cationic polymers, RNA and mRNA. Nucleic acid also includes modified RNA or DNA.

An "expression cassette" refers to an RNA or DNA coding sequence or segment of RNA or DNA that codes for an expression product (e.g., peptide(s) (i.e., polypeptide(s) or protein(s)) or RNA). An expression cassette can be present in a plasmid. An expression cassette is capable of expressing one or more polypeptides in a cell, such a mammalian cell. The expression cassette may comprise one or more sequences necessary for expression of the encoded expression product. The expression cassette may comprise one or more of an enhancer, a promoter, a terminator, and a polyA signal operably linked to the DNA coding sequence.

The term "plasmid" refers to a nucleic acid that includes at least one sequence encoding a polypeptide (such as any of the described expression cassettes) that is capable of being expressed in a mammalian cell. A plasmid can be a closed circular DNA molecule. A variety of sequences can be incorporated into a plasmid to alter expression of the coding sequence are to facilitate replication of the plasmid in a cell. Sequences can be used that influence transcription, stability of a messenger RNA (mRNA), RNA processing, or efficiency of translation. Such sequences include, but are not limited to, 5' untranslated region (5' UTR), promoter, introns, and 3' untranslated region (3' UTR). Plasmids can be manufactured in large scale quantities and/or in high yield. Plasmids can further be manufacture using cGMP manufacturing. Plasmids can be transformed into bacteria, such as *E. coli*. The DNA plasmids are can be formulated to be safe and effective for injection into a mammalian subject.

"Protein," "peptide," or "polypeptide" includes a contiguous string of two or more amino acids. A "protein sequence," "peptide sequence," "polypeptide sequence," or "amino acid sequence" refers to a series of two or more amino acids in a protein, peptide or polypeptide.

The terms "express" and "expression" mean allowing or causing the information in a gene, RNA or DNA sequence to become manifest; for example, producing a protein by activating the cellular functions involved in transcription and translation of a corresponding gene. A DNA sequence is expressed in or by a cell to form an expression product such as an RNA (e.g., mRNA) or a protein. The expression product itself may also be said to be expressed by the cell.

"Operably linked" refers to the juxtaposition of two or more components (e.g., a promoter and another sequence element) such that both components function normally and allow the possibility that at least one of the components can mediate a function that is exerted upon at least one of the other components. For example, a promoter operably linked to a coding sequence will direct RNA polymerase mediated transcription of the coding sequence into RNA, including mRNA, which may then be spliced (if it contains introns) and, optionally, translated into a protein encoded by the coding sequence. A coding sequence can be "operably linked" to one or more transcriptional or translational control sequences. A terminator/polyA signal operably linked to a gene terminates transcription of the gene into RNA and directs addition of a polyA signal onto the RNA.

A "promoter" is a DNA regulatory region capable of binding an RNA polymerase in a cell (e.g., directly or through other promoter-bound proteins or substances) and initiating transcription of a coding sequence. A promoter may comprise one or more additional regions or elements that influence transcription initiation rate, including, but not limited to, enhancers. A promoter can be, but is not limited to, a constitutively active promoter, a conditional promoter, an inducible promoter, or a cell-type specific promoter. Examples of promoters can be found, for example, in WO 2013/176772. The promoter can be, but is not limited to, CMV promoter, IgK promoter, mPGK, SV40 promoter, β-actin promoter, α-actin promoter, SRα promoter, herpes thymidine kinase promoter, herpes simplex virus (ISV) promoter, mouse mammary tumor virus long terminal repeat (LTR) promoter, adenovirus major late promoter (Ad MLP), rous sarcoma virus (RSV) promoter, and EF1α promoter. The CMV promoter can be, but is not limited to, CMV immediate early promoter, human CMV promoter, mouse CNV promoter, and simian CMV promoter.

A "translation modification element" enables translation of two or more genes from a single transcript. Translation modification elements include Internal Ribosome Entry Sites (RES), which allow for initiation of translation from an internal region of an mRNA, and 2A peptides, derived from picornavirus, which cause the ribosome to skip the synthesis of a peptide bond at the C-terminus of the element. Incorporation of a translation modulating element results in co-expression of two or more polypeptide from a single polycistronic mRNA. 2A modulators include, but are not limited to, P2A, T2A, E2A or F2A. 2A modulators contain a PG/P cleavage site.

A "homologous" sequence (e.g., nucleic acid sequence or amino acid sequence) refers to a sequence that is either identical or substantially similar to a known reference sequence, such that it is, for example, at least 75%, at least 80%, at least 85%, at least 90%, at least 95%, at least 96%, at least 97%, at least 980%, at least 99%, or 100% identical to the known reference sequence. Sequence identity can be determined by aligning sequences using algorithms, such as BESTFIT, FASTA, and TFASTA in the Wisconsin Genetics Software Package Release 7.0, Genetics Computer Group, 575 Science Dr., Madison, Wis.), using default gap parameters, or by inspection, and the best alignment (i.e., resulting in the highest percentage of sequence similarity over a comparison window). Percentage of sequence identity is calculated by comparing two optimally aligned sequences over a window of comparison, determining the number of positions at which the identical residues occurs in both sequences to yield the number of matched positions, dividing the number of matched positions by the total number of matched and mismatched positions not counting gaps in the window of comparison (i.e., the window size), and multiplying the result by 100 to yield the percentage of sequence identity. Unless otherwise indicated the window of comparison between two sequences is defined by the entire length of the shorter of the two sequences "immunostimulatory cytokine" includes cytokines that mediate or enhance the immune response to a foreign antigen, including viral, bacterial, or tumor antigens. Immunostimulatory cytokines can include, but are not limited to: TNFα, IL-1, IL-10, IL-12, IL-12 p35, IL-12 p40, IL-15, IL-15Rα, IL-23, IL-27, IFNα, IFNβ, IFNγ, IL-2, IL-4, IL-5, IL-7. IL-9, IL-21, and TGFβ.

The term "cancer" includes a myriad of diseases generally characterized by inappropriate cellular proliferation, abnormal or excessive cellular proliferation. Examples of cancer include, but are not limited to, breast cancer, triple negative breast cancer, colon cancer, prostate cancer, pancreatic cancer, melanoma, lung cancer, ovarian cancer, kidney cancer, brain cancer, or sarcomas.

A "treatment-refractory cancer" is a cancer that does not respond, or has not responded, to at least one prior medical treatment. In some embodiments, a treatment-refractory, with respect to a treatment, indicates an inadequate response to a treatment or the lack of a partial or complete response to the treatment. For example, patients may be considered refractory to a treatment, (e.g., checkpoint inhibitor therapy such as a PD-1 or PD-L1 inhibitor therapy) if they do not show at least a partial response after receiving at least 2 doses of the treatment.

The "tumor microenvironment" refers to the environment around a tumor and includes the non-malignant vascular and stromal tissue that aid in growth and/or survival of a tumor, such as by providing the tumor with oxygen, growth factors, and nutrients, or inhibiting immune response to the tumor. A tumor microenvironment includes the cellular environment in which the tumor exists, including surrounding blood vessels, immune cells, fibroblasts, bone marrow-derived inflammatory cells, lymphocytes, signaling molecules and the extracellular matrix.

The "tumor margin" or "margin tissue" is the visually normal tissue immediately near or surrounding a tumor. Typically, the margin tissue is the visually normal tissue within 0.1-2 cm of the tissue. Tumor margin tissue is often removed when a tumor is surgically resected.

The term "treatment" includes, but is not limited to, a medicament or therapy for inhibition or reduction of proliferation of cancer cells, destruction of cancer cells, prevention of proliferation of cancer cells, prevention of initiation of malignant cells, arrest or reversal of the progression of transformed premalignant cells to malignant disease, or amelioration of the disease.

The term "electroporation" refers to the use of an electroporative pulse to facilitate entry of biomolecules such as a plasmid, nucleic acid, or drug, into a cell.

A "draining lymph node" is a lymph node that filters lymph from a particular region or organ. In context of tumors and tumor treatment, a draining lymph node lies immediately downstream of the tumor.

An "epitope tag" is a short amino acid sequence (or nucleic acid sequence encoding the short amino acid sequence) to which a high affinity antibody binds. Exemplary epitope tags include, but are not limited to, V5-tag, Myc-tag, HA-tag, Spot-tag, T7-tag and NE-tag. Epitope tags can be used to facilitate immunodetection.

II. CXCL9

C-X-C Motif Chemokine ligand 9 (CXCL9) is a small cytokine belonging to the CXC chemokine family. CXCL9 is also known as Monokine Induced by Gamma interferon (MIG). CXCL9 is a T-cell chemoattractant, and facilitates chemotactic recruitment of tumor infiltrating lymphocytes (TIL). The mouse and human CXCL9 amino acid sequences are represented by SEQ ID NO: 35 and SEQ ID NO: 58, respectively. In some embodiments, a CXCL9 comprises: (a) the amino acid sequence of SEQ ID NO: 35 or 58 or a functional equivalent thereof; or (b) an amino acid sequence having at least 90%, at least 95%, at least 96%, at least 97%, at least 98%, or at least 99% identify to the amino acid sequence of SEQ ID NO: 35 or 58.

III. Anti-CTLA-4 scFv

An anti-CTLA-4 scFv comprises an anti-CTLA-4 single-chain variable fragment (scFv) having affinity for an extracellular domain of CTLA-4 and/or inhibiting CTLA-4 signaling. An scFv comprises a fusion protein of the variable regions of the heavy (VH) and light chains (VL) of immunoglobulins, connected with a short linker peptide. Exemplary mouse anti-CTLA-4 heavy chain variable region amino acid sequences are represented by SEQ ID NO: 39 and 43. Exemplary mouse anti-CTLA-4 light chain variable region amino acid sequences are represented by SEQ ID NO: 37 and 41.

An anti-CTLA4 scFv can be identified from phage display. An anti-CTLA-4 scFv can also be generated by subcloning the VH and VL from a known anti-CTLA-4 antibody, such as from a hybridoma. Known anti-CTLA-4 antibodies have been described, for instance in 20190048096, 20130136749, 20120148597, 20140099325, 20150104409, 20110296546, and 20080233122, among others. Known anti-CTLA-4 antibodies include, but are not limited to, ipilimumab and tremelimumab. In some embodiments, the VH and or VL domains of an anti-CTLA-4 scFv can be humanized. A humanized antibody (or antibody fragment or domain) is an antibody from a non-human species whose protein sequences have been modified to increase their similarity to antibody variants produced naturally in humans. In some embodiments, humanized antibodies can be made by inserting the relevant complementarity-determining regions (CDRs, also termed hypervariable regions (HVRs)) of an anti-CTLA-4 antibody into human VH and VL domain scaffolds.

An anti-CTLA-4 scFv can be formed by linking the C-terminus of the VH chain with the N-terminus of the VL. Alternatively, the C-terminus of the VL can be linked to the N-terminus of the VH. The peptide linker can be about 10 to about 25 amino acids. In some embodiments, the scFv peptide linker is rich in glycine. An scFv peptide linker can be, but is not limited to, $(G_4S)_x$ where x is an integer from 2 to 5 (inclusive) (SEQ ID NO: 91). In some embodiments, the scFv peptide linked comprises Gly-Gly-Gly-Gly-Gly-Ser-Gly-Gly-Gly-Gly-Ser-Gly-Gly-Gly-Gly-Ser (SEQ ID NO: 92 (i.e., also termed $[(Gly)_4Ser]_3$ (SEQ ID NO:15), $(G_4S)_3$ (SEQ ID NO: 15) or $G_4S$ (×3) (SEQ ID NO: 15)). In some embodiments, the scFv peptide linker consists of $G_4S$ (×3) (SEQ ID NO: 15). In some embodiments, the encoded anti-CTLA-4 scFv polypeptide includes a signal peptide such as an IgK signal peptide. Exemplary anti-CTLA-4 scFv amino acid sequences are represented by SEQ ID NO: 70 and 72. In some embodiments, an anti-CTLA-4 scFv comprises: (a) the amino acid sequence of SEQ ID NO: 70 or 72 or a functional equivalent thereof, or (b) an amino acid sequence having at least 90%, at least 95%, at least 96%, at least 97%, at least 98%, or at least 99% identify to the amino acid sequence of SEQ ID NO: 70 or 72.

IV. CD3 Half-BiTE

A CD3 half-BiTE comprises an anti-CD3 single-chain variable fragment (scFv) fused to a transmembrane domain (TM). An scFv comprises a fusion protein of the variable regions of the heavy (VH) and light chains (VL) of immunoglobulins, connected with a short linker peptide. Exemplary anti-CD3 heavy chain variable region amino acid sequences are represented by SEQ ID NO: 8 and 47. Exemplary mouse anti-CD3 light chain variable region amino acid sequences are represented by SEQ ID NO: 11 and 50.

An anti-CD3 scFv can be identified from phage display. An anti-CD3 scFv can also be generated by subcloning the VH and VL from a known anti-CD3 antibody, such as from a hybridoma. Known anti-CD3 antibodies have been described, for instance in US20180117152, US20140193399, US20100183554, and US20060177896. Known anti-CD3 antibodies also include, but are not limited to, OKT3 (Muromonab-CD3), 145-2C11, 17A2, SP7, and UCHT1. In some embodiments, the VH and or VL domains of an anti-CD3 scFv can be humanized. A humanized antibody (or antibody fragment or domain) is an antibody from a non-human species whose protein sequences have been modified to increase their similarity to antibody variants produced naturally in humans. In some embodiments, humanized antibodies can be made by inserting the relevant complementarity-determining regions (CDRs, also termed hypervariable regions (HVRs)) of an anti-CD3 antibody into human VH and VL domain scaffolds.

An anti-CD3 scFv can be formed by linking the C-terminus of the VH chain with the N-terminus of the VL. Alternatively, the C-terminus of the VL can be linked to the N-terminus of the VH. The peptide linker can be about 10 to about 25 amino acids. In some embodiments, the scFv peptide linker is rich in glycine. An scFv peptide linker can be, but is not limited to, $(G_4S)_x$ where x is an integer from 2 to 5 (inclusive) (SEQ ID NO 91). In some embodiments, the scFv peptide linker comprises Gly-Gly-Gly-Gly-Gly-Ser-Gly-Gly-Gly-Gly-Ser-Gly-Gly-Gly-Gly-Ser (SEQ ID NO: 92) (i.e., also termed $[(Gly)_4Ser]_3$ (SEQ ID NO: 15), $(G_4S)_3$ (SEQ ID NO: 15) or $G_4S$ (×3) (SEQ ID NO: 15)). In some embodiments, the scFv peptide linker consists of $G_4S$ (×3) (SEQ ID NO:15).

A transmembrane domain (TM) comprises a polypeptide capable of being inserted into a biological lipid bilayer (membrane) and anchoring the CD3 half-BiTE to the membrane. TMs are known in the art and typically consist predominantly of nonpolar amino acids. The transmembrane domain can be, but is not limited to, a PDGFRβ transmembrane domain or a PDGFRα transmembrane domain (PDGFR is Platelet-derived growth factor receptor). In some embodiments, a spacer is included between the anti-CD3 scFv and the transmembrane domain. In some embodiments, the TM domain comprises an amino acid sequence selected from the group comprising: VGQDTQEVIVVPHSLPFKVVVISAILALVVLTIISLIILIMLWQKKPR (SEQ ID NO: 25), AVGQDTQEVIVVPHSLPFKVVVISAILALVVLTIISLIILIMLWQKKPR (SEQ ID NO: 27), PDGFRβ: VVISAILALVVLTVISLIHLI (SEQ ID NO: 83). PDGFRβ: VVISAILALVVLTIISLIILI (SEQ ID NO: 84), PDGFRα: AAVLVLLVIVIISLIVLVVIW (SEQ ID NO: 85), and PDGFRα: AAVLVLLVIVIVSLIVLVVIW (SEQ ID NO: 86). In some embodiments, the TM domain is encoded by a nucleic acid sequence selected from the group comprising:

(SEQ ID NO: 24)
gtgggccaggacacgcaggaggtcatcgtggtgccaca
ctccttgccctttaaggtggtggtgatctcagccatcc
tggccctggtggtgctcaccatcatctcccttatcatc
ctcatcatgctttggcagaagaagccacgt, (SEQ ID NO: 26)
gctgtgggccaggacacgcaggaggtcatcgtggtgcc
acactccttgccctttaaggtggtggtgatctcagcca
tcctggccctggtggtgctcaccatcatctcccttatc
atcctcatcatgctttggcagaagaagccacgt, PDGFRβ:
(SEQ ID NO: 87)
tggtgatctcagccatcctggccctggtggtgctcac
catcatctcccttatcatcctcatc, PDGFRβ:
(SEQ ID NO: 88)
gtggtgatctcagccatcctggccctggtggtgctc
accatcatctcccttatcatcctcatc, PDGFRα:
(SEQ ID NO: 89)
gctgcagtcctggtgctgttggtgattgtgatcatc
tcacttattgtcctggttgtcatttggaa.

In some embodiments, the encoded anti-CD3 half-BiTE polypeptide includes a signal peptide such as an Igκ signal peptide.

Exemplary CD3 half-BiTE amino acid sequences are represented by SEQ ID NO: 60, 62, 74, and 76 In some embodiments, a CD3 half-BiTE comprises: (a) the amino acid sequence of SEQ ID NO: 60, 62, 74, or 76 or a functional equivalent thereof, or (b) an amino acid sequence having at least 90%, at least 95%, at least 96%, at least 97%, at least 98%, or at least 99%, identify to the amino acid sequence of SEQ ID NO: 60, 62, 74, or 76.

V. Expression Cassettes

Any of the described polypeptides, CXCL9, CD3 half-BiTE, anti-CTLA4 scFv, and IL-12, may be encoded on a nucleic acid. The nucleic acid can be, but is not limited an expression cassette. The expression cassette can be on a plasmid. The term "plasmid" includes any nucleic acid vector including a bacterial vector, a viral vector, an episomal plasmid, an integrative plasmid, or a phage vector. As used herein, delivery of an expression cassette includes delivery of a plasmid or nucleic acid vector (as termed "expression vector" or "vector") containing the expression cassette.

An encoded polypeptide may be linked, in an expression cassette, to a sequence encoding a second polypeptide. In some embodiments, an expression cassette encodes a fusion protein. The term "fusion protein" refers to a protein comprising two or more polypeptides linked together by peptide bonds or other chemical bonds. In some embodiments, a fusion protein is recombinantly expressed as a single-chain polypeptide containing the two polypeptides. The two or more polypeptides can be linked directly or via a linker comprising one or more amino acids.

An expression cassette or plasmid may contain a multicistronic expression cassette Multicistronic expression cassettes express two or more separate proteins from the same mRNA and contain one or more translation modification elements.

In some embodiments, the described expression cassettes encode two or three polypeptides expressed from a single promoter, with one or more translation modification elements to allow the two or three polypeptides to be expressed from a single mRNA. In some embodiments, the expression cassettes comprise:

P-A-T-B, a)

P-B-T-A, b)

P-B-T-B' c)

P-A-T-B-T-B' or c)

P-B-T-B'-T-A d)

wherein P is a promoter, A encodes CXCL9 or a CD3 half-BiTE, B and B' encode cytokines or cytokine subunits, and T is a translation modification element.

A promoter can be, but is not limited to, a constitutively active promoter, a conditional promoter, an inducible promoter, or a cell-type specific promoter. Examples of promoters can be found, for example, in WO 2013/176772. The promoter can be, but is not limited to, a CMV promoter, a Igκ promoter, a mPGK, a SV40 promoter, a β-actin promoter, an α-actin promoter, a SRα promoter, a herpes thymidine kinase promoter, a herpes simplex virus (HSV) promoter, a mouse mammary tumor virus long terminal repeat (LTR) promoter, an adenovirus major late promoter (Ad MLP), a rous sarcoma virus (RSV) promoter, and an EF1α promoter. A CMV promoter can be, but is not limited to, a CMV immediate early promoter, a human CMV promoter, a mouse CNV promoter, and a simian CMV promoter.

In some embodiments, T is an internal ribosome entry site (IRES) element or a ribosomal skipping modulator. A ribosome skipping modulator can be, but is not limited to, a 2A element (also termed 2A peptide or 2A self-cleaving peptide). The 2A element can be, but is not limited to, a P2A (SEQ ID NO: 29), T2A, E2A or F2A element.

The CXCL9 can be, but is not limited to, mouse CXCL9 and human CXCL9, or a functional equivalent thereof.

The CD3 half-BiTE can be, but is not limited to: anti-CD3 scFv-transmembrane domain (TM), epitope tag (ET)-anti-CD3 scFv-E-TM, ET-anti-CD3 scFv-TM, anti-CD3, scFv-ET-TM. HA-anti-CD3 scFv-Myc-TM, HA-anti-CD3 scFv-TM, anti-CD3, scFv-Myc-TM, anti-CD3 scFv-TM, or anti-CD3 scFv-TM. The anti-CD3 scFv can be an anti-mouse CD3 scFv or an anti-human CD3 scFv. Each of these can include a signal peptide. The signal peptide can be, but is not limited to, an Igκ signal peptide. The TM can be, but is not limited to, a PDGFR TM. The anti-CD3 scFv can be, but is not limited to, 2C11 or OKT3.

In some embodiments, the cytokine is an immunostimulatory cytokine. In some embodiments, the immunostimulatory cytokine is an interleukin. Cytokines include, but are not limited to, IL-1, IL-2, IL-10, IL-12, IL-15, IL-23, IL-27, IL-35, IFN-α, IFN-β, IFN-γ, and TGF-β. In some embodiments. B and/or B' encode an IL-12, IL-12 p35-IL-12 p40 fusion, IL-12 p70, IL-12 p35, or IL-12 p40 polypeptide. The IL-12, IL-12 p35-IL-12 p40 fusion, IL-12 p70, IL-12 p35, or IL-12 p40 polypeptide may be, but are not limited to, a mouse or human IL-2, IL-12 p35-IL-12 p40 fusion, IL-12 p70, IL-12 p35, or IL-12 p40 polypeptide. In some embodiments, B encodes IL-12 p35 and B' encodes IL-12 p40.

In some embodiments P is a CMV promoter, A encodes CXCL9, T is a P2A element. B encodes IL-12 p35 and B' encodes IL-12 p40.

In some embodiments P is a CMV promoter, A encodes a human CXCL9, T is a P2A element, B encodes IL-12 p35 and B' encodes IL-12 p40.

In some embodiments P is a CMV promoter, A encodes a mouse CXCL9, T is a P2A element. B encodes IL-12 p35 and B' encodes IL-12 p40.

In some embodiments P is a CMV promoter. A encodes an Igκ-HA-anti-CD3 scFv-PDGFR TM CD3 half-BiTE, T is a P2A element, B encodes IL-12 p35 and B' encodes IL-12 p40.

In some embodiments P is a CMV promoter, A encodes an Igκ-anti-CD3 scFv-PDGFR TM CD3 half-BiTE, T is a P2A element, B encodes IL-12 p35 and B' encodes IL-12 p40.

In some embodiments P is a CMV promoter, A encodes an Igκ-HA-2C11-PDGFR TM CD3 halt-BiTE, T is a P2A element, B encodes IL-12 p35 and B' encodes IL-12 p40.

In some embodiments P is a CMV promoter, A encodes an Igκ-2C11-PDGFR TM CD3 half-BiTE. T is a P2A element, B encodes IL-12 p35 and B' encodes IL-12 p40.

In some embodiments P is a CMV promoter, A encodes an Igκ-HA-OCT3-PDGFR TM CD3 half-BiTE, T is a P2A element, B encodes IL-12 p35 and B' encodes IL-12 p40.

In some embodiments P is a CMV promoter, A encodes an Igκ-OKT3-PDGFR TM CD3 half-BiTE, T is a P2A element, B encodes IL-12 p35 and B' encodes IL-12 p40.

In some embodiments, B encodes IL-12 p35, T is a P2A element, and B' encodes IL-12 p40. In some embodiments, B encodes IL-12 p35, T is an IRES element, and B' encodes IL-12 p40. The promoter can be, but is not limited to, a CMV promoter.

In some embodiments, we describe expression cassettes encoding a polypeptide comprising the amino acid sequence of SEQ ID NO: 60, 62, 74, or 76 or a polypeptide having at least 70% identity to the amino acid sequence of SEQ ID NO: 60, 62, 74, or 76. In some embodiments, an expression cassette encodes a polypeptide comprising an amino acid sequence having greater than 70%, 72%, 75%, 78%, 80%, 82%, 83%, 85%, 87%, 88%, 90%, 92%, 93%, 95%, 96%, 97%, 98%, or 99% identity to the amino acid sequence of SEQ ID NO 60, 62, 74, or 76, wherein the encoded polypeptide retains the functional activity of an CD3 half-BiTE polypeptide.

In some embodiments, we describe expression cassettes encoding a polypeptide comprising the amino acid sequence of SEQ ID NO: 64, 66, 78, or 70, or a polypeptide having at least 70% identity to the amino acid sequence of SEQ ID NO: 64, 66, 78, or 70. In some embodiments, an expression cassette encodes a polypeptide comprising an amino acid sequence having greater than 70%, 72%, 75%, 78%, 80%, 82%, 83%, 85%, 87%, 88%, 90%, 92%, 93%, 95%, 96%, 97%, 98%, or 99% identity to the amino acid sequence of SEQ ID NO: 64, 66, 78, or 70, wherein encoded the polypeptides retain the functional activity of an CD3 half-BiTE polypeptide and an IL-12 polypeptide.

In some embodiments, we describe expression cassettes encoding a polypeptide comprising the amino acid sequence of SEQ ID NO: 35 or 58, or a polypeptide having at least 70% identity to the amino acid sequence of SEQ ID NO: 35 or 58. In some embodiments, an expression cassette encodes a polypeptide comprising an amino acid sequence having greater than 70%, 72%, 75%, 78%, 80%, 82%, 83%, 85%, 87%, 88%, 90%, 92%, 93%, 95%, 96%, 97%, 98%, or 99% identity to the amino acid sequence of SEQ ID NO: 35 or 58, wherein the encoded polypeptide retains the functional activity of a CXCL9 polypeptide.

In some embodiments, we describe expression cassettes encoding a polypeptide comprising the amino acid sequence of SEQ ID NO: 68 or 82, or a polypeptide having at least 70% identity to the amino acid sequence of SEQ ID NO: 68 or 82. In some embodiments, an expression cassette encodes a polypeptide comprising an amino acid sequence having greater than 70%, 72%, 75%, 78%, 80%, 82%, 83%, 85%, 87%, 88%, 90%, 92%, 93%, 95%, 96%, 97%, 98%, or 99% identity to the amino acid sequence of SEQ ID NO: 68 or 82, wherein encoded the polypeptides retain the functional activity of a CXCL9 polypeptide and an IL-12 polypeptide.

In some embodiments, we describe expression cassettes encoding a polypeptide comprising the amino acid sequence of SEQ ID NO: 70 or 72 or a polypeptide having at least 70% identity to the amino acid sequence of SEQ ID NO: 70 or 72. In some embodiments, an expression cassette encodes a polypeptide comprising an amino acid sequence having greater than 70%, 72%, 75%, 78%, 80%, 82%, 83%, 85%, 87%, 88%, 90%, 92%, 93%, 95%, 96%, 97%, 98%, or 99% identity to the amino acid sequence of SEQ ID NO: 70 or 72, wherein the encoded polypeptide retains the functional activity of an anti-CTLA-4 scFv polypeptide.

In some embodiments, we describe expression cassettes comprising the nucleotide sequence of SEQ ID NO: 59, 61, 73, or 75, or a nucleotide sequence having at least 70% identity to the nucleotide sequence of SEQ ID NO: 59, 61, 73, or 75 In some embodiments, an expression cassette comprises a sequence having greater than 70%, 72%, 75%, 78%, 80%, 82%, 83%, 85%, 87%, 88%, 90%, 92%, 93%, 95%, 96%, 97%, 98%, or 99% identity to the nucleotide sequence of SEQ ID NO: 59, 61, 73, or 75 and encodes a polypeptide having the functional activity of an CD3 half-BiTE polypeptide. In some embodiments, the nucleotide sequence of SEQ ID NO: 59, 61, 73, or 75 or the nucleotide sequence having at least 709% identity to the nucleotide sequence of SEQ ID NO: 59, 61, 73, or 75 is operably linked to a CMV promoter.

In some embodiments, we describe expression cassettes comprising the nucleotide sequence of SEQ ID NO: 63, 65, 77, or 79, or a nucleotide sequence having at least 70% identity to the nucleotide sequence of SEQ ID NO: 63, 65, 77, or 79. In some embodiments, an expression cassette comprises a sequence having greater than 70%, 72%, 75%, 78%, 80%, 82%, 83%, 85%, 87%, 88%, 90%, 92%, 93%, 95%, 96%, 97%, 98%, or 99% identity to the nucleotide sequence of SEQ ID NO: 63, 65, 77, or 79, and encode polypeptides having the functional activity of an CD3 half-BiTE polypeptide and an IL-12 polypeptide. In some embodiments, the nucleotide sequence of SEQ ID NO: 63, 65, 77, or 79 or the nucleotide sequence having at least 70% identity to the nucleotide sequence of SEQ ID NO: 63, 65, 77, or 79 is operably linked to a CMV promoter.

In some embodiments, we describe expression cassettes comprising the nucleotide sequence of SEQ ID NO: 34 or 57, or a nucleotide sequence having at least 70% identity to the nucleotide sequence of SEQ ID NO: 34 or 57. In some embodiments, an expression cassette comprises a sequence having greater than 70%, 72%, 75%, 78%, 80%, 82%, 83%, 85%, 87%, 88%, 90%, 92%, 93%, 95%, 96%, 97%, 98%, or 99% identity to the nucleotide sequence of SEQ ID NO: 34 or 57, and encodes a polypeptide having the functional activity of a CXCL9 polypeptide. In some embodiments, the nucleotide sequence of SEQ ID NO: 34 or 57 or the nucleotide sequence having at least 70% identity to the nucleotide sequence of SEQ ID NO: 34 or 57 is operably linked to a CMV promoter.

In some embodiments, we describe expression cassettes comprising the nucleotide sequence of SEQ ID NO: 67 or 81 or a nucleotide sequence having at least 70% identity to the nucleotide sequence of SEQ ID NO: 67 or 81. In some embodiments, an expression cassette comprises a sequence having greater than 70%, 72%, 75% 78%, 80% 82%, 83%, 85%, 87%, 88%, 90%, 92%, 93%, 95%, 96%, 97%, 98%, or 99% identity to the nucleotide sequence of SEQ ID NO: 67 or 81, and encodes polypeptides having the functional activity of a CXCL9 polypeptide and an IL-12 polypeptide in some embodiments, the nucleotide sequence of SEQ ID NO: 67 or 81 or the nucleotide sequence having at least 70% identity to the nucleotide sequence of SEQ ID NO: 67 or 81 is operably linked to a CMV promoter.

In some embodiments, we describe expression cassettes comprising the nucleotide sequence of SEQ ID NO: 69 or 71, or a nucleotide sequence having at least 70% identity to the nucleotide sequence of SEQ ID NO: 69 or 71. In some embodiments, an expression cassette comprises a sequence having greater than 70%, 72%, 75%, 78%, 80%, 82%, 83% 85%, 87%, 88%, 90%, 92%, 93%, 95%, 96%, 97%, 98%, or 99% identity to the nucleotide sequence of SEQ ID NO: 69 or 71, and encodes a polypeptide having the functional activity of an anti-CTLA-4 scFv polypeptide. In some embodiments, the nucleotide sequence of SEQ ID NO: 69 or 71 or the nucleotide sequence having at least 70% identity to the nucleotide sequence of SEQ ID NO: 69 or 71 is operably linked to a CMV promoter.

VI. Methods of Treatment

Described are methods for treatment of a tumor in a subject comprising, administering a composition comprising an effective dose of one or more of the described CXCL9, CD3 half-BiTE, and or CTLA-4 scFv expression cassettes to the tumor, tumor microenvironment, and/or a tumor margin tissue and administering electroporation therapy to the tumor, tumor microenvironment, and/or a tumor margin tissue (IT-EP therapy). The CXCL9 or CD3 half-BiTE expression cassette may further encode IL-12.

The treated tumor can be a cutaneous tumor, a subcutaneous tumor, or a visceral tumor. The tumor can be cancerous or non-cancerous. The tumor can be, but is not limited to, a solid tumor, a surface lesion, a non-surface lesion, a lesion within 15 cm of body surface, or a visceral lesion. In some embodiments, the described methods and expression vectors can be used to treat primary tumors as well as distant (i.e., untreated) tumors and metastases. In some embodiments, the described methods provide for reducing the size of or inhibiting the grow of a tumor, inhibiting the growth of cancer cells, inhibiting or reducing metastasis, reducing or inhibiting the development of metastatic cancer, and/or reducing recurrence of cancer in a subject suffering from cancer. The tumor is not limited to a specific type of tumor or cancer.

In some embodiments, the methods further comprise administering an effective dose of an immunostimulatory cytokine. The immunostimulatory cytokine can be administered by IT-EP of an expression cassette encoding the cytokine. In some embodiments, the cytokine is encoded on the expression cassette encoding the CXCL9 or CD3 half-BiTE. In some embodiments, the cytokine is encoded on a second expression vector and delivered to the cancerous tumor by IT-EP. In some embodiments, the cytokine is IL-12. In some embodiments, the expression cassette comprises B-T-B', wherein B encodes IL-12 p35, T is a P2A element, and B' encodes IL-12 p40. The cytokine may be administered prior to, concurrent with, or subsequent to IT-EP CXCL9 therapy or IT-EP CD3 half-BiTE therapy.

IT-EP CXCL9 therapy or treatment comprises injecting a tumor, tumor microenvironment, and/or tumor margin tissue with an effective does of a described expression cassette encoding CXCL9 and administering electroporation therapy to the tumor.

IT-EP IL2-CXCL9 therapy or treatment comprises injecting a tumor, tumor microenvironment, and/or tumor margin tissue with an effective does of a described expression cassette encoding CXCL9 and IL-12 and administering electroporation therapy to the tumor.

IT-EP CD3 half-BiTE therapy or treatment comprises injecting a tumor, tumor microenvironment, and/or tumor margin tissue with an effective does of a described expression cassette encoding a CD3 half-BiTE and administering electroporation therapy to the tumor.

IT-EP CD3 half-BiTE-IL-12 or treatment therapy comprises injecting a tumor, tumor microenvironment, and/or tumor margin tissue with an effective does of a described expression cassette encoding CD3 half-BiTE and IL-12 and administering electroporation therapy to the tumor.

IT-EP anti-CTLA-4 scFv therapy or treatment comprises injecting a tumor, tumor microenvironment, and/or tumor margin tissue with an effective does of a described expression cassette encoding anti-CTLA-4 scFv and administering electroporation therapy to the tumor.

Figure 1B:
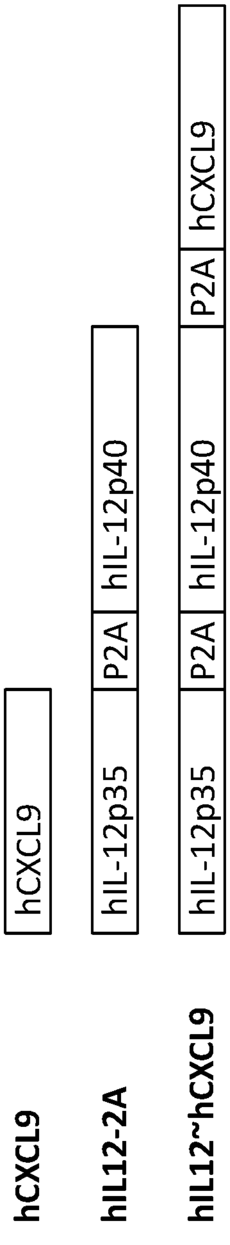
FIG. 1B. Illustrations of expression constructs for hCXCL9, hIL12-2A (hIL-12 p35-P2A-hIL-12 p40), hIL12~hCXCL9 (hIL-12 p35-P2A-hIL-12 p40-P2A-hCXCL9).

IT-EP IL12 therapy or treatment comprises injecting a tumor, tumor microenvironment, and/or tumor margin tissue with an effective does of an expression cassette encoding IL-12 and administering electroporation therapy to the tumor In some embodiments the expression cassette encoding IL-12 comprises IL12-2A (mIL12-2A and hIL12-2A; FIG. 1).

In some embodiments, the described expression cassettes, plasmids containing the described expression cassettes, and methods can be used to treat one or more tumors, tumor cells, or tumor lesions. The tumor cells can be, but are not limited to cancer cells. The term "cancer" includes a myriad of diseases generally characterized by inappropriate cellular proliferation, abnormal or excessive cellular proliferation. The cancer can be, but is not limited to, solid cancer, sarcoma, carcinoma, and lymphoma. The cancer can also be, but is not limited to, pancreas, skin, brain, liver, gall bladder, stomach, lymph node, breast, lung, head and neck, larynx, pharynx, lip, throat, heart, kidney, muscle, colon, prostate, thymus, testis, uterine, ovary, cutaneous, and subcutaneous cancers. Skin cancer can be, but is not limited to, melanoma and basal cell carcinoma. Breast cancer can be, but is not limited to, ER positive breast cancer, ER negative breast cancer, and triple negative breast cancer. In some embodiments, the described methods can be used to treat cell proliferative disorders. The term "cell proliferative disorder" denotes malignant as well as non-malignant cell populations which often appear to differ from the surrounding tissue both morphologically and genotypically. In some embodiments, the described methods can be used to treat a human. In some embodiments, the described methods can be used to treat non-human animals or mammals. A non-human mammal can be, but is not limited to, mouse, rat, rabbit, dog, cat, pig, cow, sheep and horse.

The described expression cassettes and methods are contemplated for use in subjects afflicted with cancer or other non-cancerous (benign) growths. Tumors treated with the methods of the present embodiment may be any of noninvasive, invasive, superficial, papillary, flat, metastatic, localized, unicentric, multicentric, low grade, and high grade tumors. These growths may manifest themselves as any of a lesion, polyp, neoplasm (e.g. papillary urothelial neoplasm), papilloma, malignancy, tumor (e.g. Klatskin tumor, hilar tumor, noninvasive papillary urothelial tumor, germ cell tumor, Ewing's tumor, Askin's tumor, primitive neuroectodermal tumor, Leydig cell tumor, Wilms' tumor, Sertoli cell tumor), sarcoma, carcinoma (e.g. squamous cell carcinoma, cloacogenic carcinoma, adenocarcinoma, adenosquamous carcinoma, cholangiocarcinoma, hepatocellular carcinoma, invasive papillary urothelial carcinoma, flat urothelial carcinoma), lump, or any other type of cancerous or non-cancerous growth. The expression cassettes and methods can be used to treat advanced, metastatic, or treatment refractory cancer.

The expression cassettes and methods described herein are contemplated for use in, e.g., adrenal cortical cancer, anal cancer, bile duct cancer (e.g. periphilar cancer, distal bile duct cancer, intrahepatic bile duct cancer) bladder cancer, benign and cancerous bone cancer (e.g. osteoma, osteoid osteoma, osteoblastoma, osteochrondroma, hemangioma, chondromyxoid fibroma, osteosarcoma, chondrosarcoma, fibrosarcoma, malignant fibrous histiocytoma, giant cell tumor of the bone, chordoma, lymphoma, multiple myeloma), brain and central nervous system cancer (e.g. meningioma, astrocytoma, oligodendrogliomas, ependymoma, gliomas, medulloblastoma, ganglioglioma, Schwannoma, germinoma, craniopharyngioma), breast cancer (e.g. ductal carcinoma in situ, infiltrating ductal carcinoma, infiltrating lobular carcinoma, lobular carcinoma in situ, gynecomastia), Castleman disease (e.g. giant lymph node hyperplasia, angiofollicular lymph node hyperplasia), cervical cancer, colorectal cancer, endometrial cancer (e.g. endometrial adenocarcinoma, adenoacanthoma, papillary serous adenocarcinoma, clear cell) esophagus cancer, gallbladder cancer (mucinous adenocarcinoma, small cell carcinoma), gastrointestinal carcinoid tumors (e.g. choriocarcinoma, chorioadenoma *destruens*), Hodgkin's disease, non-Hodgkin's lymphoma, Kaposi's sarcoma, kidney cancer (e.g. renal cell cancer), laryngeal and hypopharyngeal cancer, liver cancer (e.g. hemangioma, hepatic adenoma, focal nodular hyperplasia, hepatocellular carcinoma), lung cancer (e.g. small cell lung cancer, non-small cell lung cancer), mesothelioma, plasmacytoma, nasal cavity and paranasal sinus cancer (e.g. esthesioneuroblastoma, midline granuloma), nasopharyngeal cancer, neuroblastoma, oral cavity and oropharyngeal cancer, ovarian cancer, pancreatic cancer, penile cancer, pituitary cancer, prostate cancer, retinoblastoma, rhabdomyosarcoma (e.g. embryonal rhabdomyosarcoma, alveolar rhabdomyosarcoma, pleomorphic rhabdomyosarcoma), salivary gland cancer, skin cancer, both melanoma and non-melanoma skin cancer), stomach cancer, testicular cancer (e.g. seminoma, nonseminoma germ cell cancer), thymus cancer, thyroid cancer (e.g. follicular carcinoma, anaplastic carcinoma, poorly differentiated carcinoma, medullary thyroid carcinoma, thyroid lymphoma), vaginal cancer, vulvar cancer, and uterine cancer (e.g. uterine leiomyosarcoma).

In some embodiments, the subject has low tumor infiltrating lymphocytes (TILs) and/or impaired tumoral IFNγ signaling.

The described methods can be used to cause one or more of the following: inflame a tumor, induce T cell infiltration to the tumor or tumor microenvironment (increase the number of tumor infiltrating lymphocytes (TILs)), enhance systemic T cell response, induce activation of tumor-specific T cells, increase antigen-specific T cell response, increase proliferation of antigen-specific T cells, increase polyclonal T cells response, enhance an immune response against treated and/or untreated tumors, decrease T cell exhaustion, increase lymphocyte and monocyte cell surface markers in one or more treated or untreated tumors, increase intratumoral levels of INFγ regulated genes in one or more treated or untreated tumors, increase proliferating effector memory T cells in the subject's blood, increase short-lived effector cells in the subject's blood, increase expression of genes present in activated natural killer cells in a cancerous tumor, increase expression of genes that function in antigen presentation in a cancerous tumor, increase expression of genes that function in T cell survival and T cell mediated cytotoxicity in a cancerous tumor, induce regression of treated and/or untreated tumors, induce debulking of a treated and/or untreated tumor, and improve response to a second therapy, such as, but not limited to, immune checkpoint inhibitor therapy. In some embodiments, enhancement of immune reaction to the tumor leads to increased survival of the subject.

In some embodiments, the described methods comprise treating a subject having a cancerous tumor comprising: injecting the cancerous tumor with an effective dose of a plasmid encoding CXCL9, and administering electroporation therapy to the tumor. In some embodiments, the described methods comprise treating a subject having a cancerous tumor comprising: injecting the cancerous tumor with an effective dose of a plasmid encoding CD3 half-BiTE, and administering electroporation therapy to the tumor. In some embodiments, the described methods comprise treating a subject having a cancerous tumor comprising: injecting the cancerous tumor with an effective dose of a plasmid encoding an anti-CTLA-4 scFv, and administering electroporation therapy to the tumor. In some embodiments, the plasmid is administered substantially contemporaneously with the electroporation treatment. The term "substantially contemporaneously" means that the molecule and the electroporation treatment are administered reasonably close together with respect to time, i.e., before the effect of the electrical pulses on the cells diminishes.

In some embodiments, the described methods result in increased NK cells and T cell populations in a tumor or tumor microenvironment. IT-EP of CXCL9, IL12-CXCL9, CD3 half-BiTE-IL12, and/or CD3 half-BiTE increases homing of tumor-specific T cells to tumors, increases activation and/or proliferation of tumor-specific T cells, and/or increases recruitment of CD8+ T cells, NK cells, and NKT cells to the tumor microenvironment. Activation of T cells can lead to increased tumor cell killing by the activated T cells.

In some embodiments, administration of IL-12 therapy by IT-EP enhances T cell infiltration of the tumor. Subsequent expression of CD3 half-BiTE in the tumor can activate the T cells to enhance the population of antigen specific T cells.

In some embodiments, IT-EP CXCL9 therapy enhances an IL-12 effect resulting in increased effective trafficking of tumor specific lymphocytes.

In some embodiments, IT-EP CXCL9 therapy inhibits angiogenesis in a tumor or tumor microenvironment in some embodiments, combining IT-EP CXCL9 with IL-12 therapy increases trafficking of tumor-specific lymphocytes to tumors.

In some embodiments, intratumoral electroporation of an expression cassette encoding a CXCL9 can be administered with other therapeutic entities. In some embodiments, IT-EP CXCL9 therapy is combined IL-12 therapy. IL-12 therapy may occur before, concurrent with, and/or after IT-EP CXCL9 therapy IL-12 therapy can occur before and concurrent with IT-EP CXCL9 therapy. IL-12 therapy can occur before and after IT-EP CXCL9 therapy. IL-12 therapy can occur concurrent with and after IT-EP CXCL9 therapy. IL-12 therapy may occur before, concurrent with, and after IT-EP CXCL9 therapy. IT-EP CXCL9 therapy may occur before, concurrent with, and/or after IL-12 therapy. IT-EP CXCL9 therapy may occur before and concurrent with IL-12 therapy. IT-EP CXCL9 therapy may occur before and after IL-12 therapy. IT-EP CXCL9 therapy may occur concurrent with and after IL-12 therapy. IT-EP CXCL9 therapy may occur before, concurrent with, and after IL-12 therapy. In some embodiments, the IL-12 therapy is administered by IT-EP of an expression cassette encoding IL-12. The CXCL9 and IL-12 can be expressed from a single expression cassette or plasmid or from multiple expression cassettes or plasmids. In some embodiments, for concurrent therapy, IT-EP CXCL9-IL12 therapy. CXCL9 and IL-12 are expressed from a single expression cassette or plasmid.

In some embodiments, intratumoral electroporation of an expression cassette encoding a CD3 half-BiTE can be administered with other therapeutic entities. In some embodiments, IT-EP CD3 half-BiTE therapy is combined IL-12 therapy. IL-12 therapy may occur before, concurrent with, and/or after IT-EP CD3 half-BiTE therapy. IL-12 therapy can occur before and concurrent with IT-EP CD3 half-BiTE therapy IL-12 therapy can occur before and after IT-EP CD3 half-BiTE therapy. IL-12 therapy can occur concurrent with and after IT-EP CD3 half-BiTE therapy. IL-12 therapy may occur before, concurrent with, and after IT-EP CD3 half-BiTE therapy. IT-EP CD3 half-BiTE therapy may occur before, concurrent with, and/or after IL-12 therapy IT-EP CD3 half-BiTE therapy may occur before and concurrent with IL-12 therapy. IT-EP CD3 half-BiTE therapy may occur before and after IL-12 therapy IT-EP CD3 half-BiTE therapy may occur concurrent with and after IL-12 therapy. IT-EP CD3 half-BiTE therapy may occur before, concurrent with, and after IL-12 therapy. In some embodiments, IL-12 therapy is administered by IT-EP of an expression cassette encoding IL-12. The CD half-BiTE and IL-12 can be expressed from a single expression cassette or plasmid or from multiple expression cassettes or plasmids. In some embodiments, for concurrent therapy, 1IT-EP CD3 half-BiTE-IL12 therapy, CD3 half-BiTE and IL-12 are expressed from a single expression cassette or plasmid In some embodiments, IT-EP CXCL9 therapy is combined with IT-EP CD3 half-BiTE therapy. In some embodiments, IT-EP CXCL9 and/or IT-EP CD3 half-BiTE therapy is combined with IL-12 therapy. IT-EP CD3 half-BiTE therapy may occur before, concurrent with, and/or after IT-EP CXCL9 therapy. IT-EP CD3 half-BiTE therapy can occur before and concurrent with IT-EP CXCL9 therapy. IT-EP CD3 half-BiTE therapy can occur before and after IT-EP CXCL9 therapy. IT-EP CD3 half-BiTE therapy can occur concurrent with and after IT-EP CXCL9 therapy. IT-EP CD3 half-BiTE therapy may occur before, concurrent with, and after IT-EP CXCL9 therapy. IT-EP CXCL9 therapy may occur before, concurrent with, and/or after IT-EP CD3 half-BiTE therapy. IT-EP CXCL9 therapy may occur before and concurrent with IT-EP CD3 half-BiTE therapy. IT-EP CXCL9 therapy may occur before and after IT-EP CD3 half-BiTE therapy. IT-EP CXCL9 therapy may occur concurrent with and after IT-EP CD3 half-BiTE therapy. IT-EP CXCL9 therapy may occur before, concurrent with, and after IT-EP CD3 half-BiTE therapy. Either CXCL3 or CD half-BiTE therapy can be combined with IL-12 therapy, such as by IT-EP of an expression cassette or plasmid encoding both CXCL9 and IL-12 or CD3-half-BiTe and IL-12, respectively (i.e., IT-EP IL-12~CXCL9 and IT-EP CD3 half-BiTE~IL12 therapies).

In some embodiments, IT-EP CD3 half-BiTE therapy or IT-EP CD3 half-BiTE-IL-12 therapy can be co-administered with one or more of IT-EP IL12 therapy, IT-EP CXCL9 therapy, and IT-EP IL12~CXCL9 therapy.

In some embodiments, a described expression cassette is combined with one or more pharmaceutically acceptable excipients. Pharmaceutically acceptable excipients (excipients) are substances other than an active pharmaceutical ingredient (API, therapeutic product) that are intentionally included with the API (molecule). Excipients do not exert or are not intended to exert a therapeutic effect at the intended dosage. Excipients may act to a) aid in processing of the API during manufacture, b) protect, support or enhance stability, bioavailability or subject acceptability of the API, c) assist in product identification, and/or d) enhance any other attribute of the overall safety, effectiveness, of delivery of the API during storage or use. A pharmaceutically acceptable excipient may or may not be an inert substance. Excipients include, but are not limited to: absorption enhancers, anti-adherents, anti-foaming agents, anti-oxidants, binders, buffering agents, carriers, coating agents, colors, delivery enhancers, delivery polymers, dextran, dextrose, diluents, disintegrants, emulsifiers, extenders, fillers, flavors, glidants, humectants, lubricants, oils, polymers, preservatives, saline, salts, solvents, sugars, suspending agents, sustained release matrices, sweeteners, thickening agents, tonicity agents, vehicles, water-repelling agents, and wetting agents.

VII. Treatment Regimens/Cycles

The described IT-EP therapies can be administered at various intervals, depending upon such factors, for example, as the nature of the tumor, the condition of the subject, the size and chemical characteristics of the molecule and half-life of the molecule.

In some embodiments, methods for treating a tumor are described comprising, administering IT-EP IL12 therapy, followed by IT-EP CXCL9 and/or IT-EP IL12-CXCL9 therapy. IT-EP CXCL or IT-EP IL12-CXCL9 therapy can increase recruitment of tumor-specific T cells to the tumor or tumor microenvironment and/or increase activation of T cells. In some embodiments, IT-EP IL12 therapy is given to a tumor on day 0 (±1 day) and IT-EP CXCL9 therapy is given to the tumor on day 4 (±2 days) and day 7 (±2 days). In some embodiments, 1IT-EP IL12 therapy is given to a tumor on day 0 and IT-EP IL12-CXCL9 therapy is given to the tumor on day 4 (±2 days) and day 7 (±2 days).

In some embodiments, methods for treating a tumor are described comprising, administering IT-EP IL12 therapy, followed by IT-EP CD3 half-BiTE and/or CD3 half-BiTE~IL12 therapy. In some embodiments, IT-EP IL12 therapy is given to a tumor on day 0 (±1 day) and IT-EP CD3 half-BiTE therapy is given to the tumor on day 4 (±2 days) and day 7 (±2 days). In some embodiments, IT-EP IL12 therapy is given to a tumor on day 0 and IT-EP CD3 half-BiTE~IL12 therapy is given to the tumor on day 4 (±2 days) and day 7 (±2 days).

In some embodiments, methods for treating a tumor are described comprising, IT-EP IL12 therapy, following by IT-EP CXCL or IT-EP IL12-CXCL9 therapy, and/or IT-EP CD3 half-BiTE or IT-EP CD3 half-BiTE~IL-12 therapy.

In some embodiments, IT-EP IL12 therapy is administered first to increase tumor infiltrating lymphocytes. The tumor is subsequently treated with IT-EP CXCL9 or IL12~CXCL9 therapy and/or IT-EP CD3 half-BiTE or IT-EP CD3 half-BiTE~IL-12 therapy.

A treatment cycle can comprise 1-6 IT-EP treatments. In some embodiments, a treatment cycle comprises 1, 2, or 3 IT-EP treatments. A cycle can be from about 1 week to about 6 weeks, or from about 2 weeks to about 5 weeks. In some embodiments, a cycle is about 3 weeks.

In some embodiments, a cycle comprises 1-3 IT-EP treatments. The treatments can occur on days 1 (±2 days), 5 (±2 days) and/or day 8 (±2 days) (i.e., days 0 (±2 days), 4 (±2 days) and/or day 7 (±2 days)). Each treatment can comprise one or more of IT-EP IL2, IT-EP CXCL9, IT-EP IL12-CXCL9, IT-EP CD3 half-BiTE, IT-EP CD3 half-BiTE~IL12, and IT-EP anti-CTLA4 scFv.

In some embodiments, methods for treating a tumor are described comprising: administering IT-EP IL12 therapy on day 1 of a cycle and administering IT-EP CXCL9 or IT-EP IL12~CXCL9 on days 5 (±2 days) and day 8 (±2 days) of the cycle. In some embodiments, methods for treating a tumor are described comprising: administering IT-EP IL12 therapy on day 1 of a cycle and administering IT-EP CD3 half-BiTE, IT-EP CD3 half-BiTE~IL12 on days 5 (±2 days) and day 8 (±2 days) of the cycle. In some embodiments, methods for treating a tumor are described comprising: administering IT-EP IL12 therapy on day 1 of a cycle and administering one or more of IT-EP CXCL9, IT-EP IL12-CXCL9, IT-EP CD3 half-BiTE, and IT-EP CD3 half-BiTE~IL12 on days 5 (±2 days) and day 8 (±2 days) of the cycle.

In some embodiments, methods for treating a tumor are described comprising: a) administering IT-EP IL12 therapy in a first cycle, b) administering IT-EP CXCL9 or IT-EP IL12-CXCL9 therapy in a second cycle, and c) administering IT-EP CD3 half-BiTE or IT-EP CD3 half-BiTE~IL-12 therapy in a third cycle. Each cycle can comprise 1-3 administrations of the corresponding IT-EP therapy.

Described are dosing regimens encompassing administering IT-EP IL12 therapy in combination IT-EP CXCL9 therapy and/or IT-EP CD3 half-BiTE therapy. Also described are dosing regimens encompassing administering IT-EP CXCL9 or IL12~CXCL9 therapy with IT-EP CD3 half-BiTE or IT-EP CD3 half-BiTE~IL12 therapy. The therapies may be administered concurrently, sequentially, or separately. In some embodiments, IT-EP IL12 therapy is administered in a first cycle and IT-EP CXCL9 therapy or IT-EP IL12~CXCL9 therapy is administered in a second cycle. In some embodiments, IT-EP IL12 therapy is administered in a first cycle and IT-EP CD3 half-BiTE therapy or 1IT-EP CD3 half-BiTE-IL12 therapy is administered in a second cycle. In some embodiments. IT-EP IL12 therapy is administered in a first cycle, IT-EP (CXCL9 therapy or IT-EP CXCL9-IL12 therapy is administered in a second cycle, and IT-EP CD3 half-BiTE therapy or IT-EP CD3 half-BiTE-IL12 therapy is administered in a third cycle. The IT-EP therapy may be delivered on day 1 of each cycle. One or more of the cycles may be repeated as necessary. Within a cycle, the IT-EP therapy may be administered on a least one, two, or three days of the cycle. For example, a given expression cassette may be administered on day 1, day 5 (±2 days) and/or day 8 (±2 days).

In some embodiments, a CXCL9 or IL12~CXCL9 plus IL-12 expression cassette is administered on days 1, 5-12, and 812 of a cycle. In some embodiments, a CTLA-4 scFv or anti-CTLA-4 scFv plus IL-12 expression cassette is administered on days 1, 5±2, and 8±2 of a cycle. In some embodiments, a CD3 half-BiTE or CD3 half-BiTE plus IL-12 expression cassette is administered on days 1, 5±2, and 8±2 of a cycle.

In some embodiments, a CXCL9 or CXCL9 plus IL-12 expression cassette (e.g., IL12~CXCL9) is administered on days 1 and 5±2, and a CD3 half-BiTE or CD3 half-BiTE plus IL-12 expression cassette (e.g., CD3 half-BiTE~IL12) is administered on day 8±2 of a cycle. In some embodiments, a CXCL9 or CXCL9 plus IL-12 expression cassette is administered on day 1, and a CD3 half-BiTE or CD3 half-BiTE plus IL-12 expression cassette is administered on days 5±2 and 8±2 of a cycle. In some embodiments, a CXCL9 or CXCL9 plus IL-12 expression cassette is administered on days 1 and 8±2, and a CD3 half-BiTE or CD3 half-BiTE plus IL-12 expression cassette is administered on day 5±2 of a cycle.

In some embodiments, a CD3 half-BiTE or CD3 half-BiTE plus IL-12 expression cassette is administered on days 1 and 5±2, and a CXCL9 or CXCL9 plus IL-12 expression cassette is administered on day 8±2 of a cycle. In some embodiments, a CD3 half-BiTE or CD3 half-BiTE plus IL-12 expression cassette is administered on days 1, and a CXCL9 or CXCL9 plus IL-12 expression cassette is administered on days 5±2 and 8±2 of a cycle. In some embodiments, a CD3 half-BiTE or CD3 half-BiTE plus IL-12 expression cassette is administered on days 1 and 8±2, and a CXCL9 or CXCL9 plus IL-12 expression cassette is administered on day 5±2 of a cycle.

In some embodiments, an IL-12-2A expression cassette is administered on day 1 and, and a CXCL9 or IL12-CXCL9 expression cassette is administered on days 5±2 and 8±2 of a cycle. In some embodiments, an IL-12-2A expression cassette is administered on days 1 and 5±2, and a CXCL9 or IL12~CXCL9 expression cassette is administered on day 8±2 of a cycle.

In some embodiments, an IL-12-2A expression cassette is administered on day 1 and, and a CD3 half-BiTE or CD3 half-BiTE~IL-12 expression cassette is administered on days 5±2 and 8±2 of a cycle. In some embodiments, an IL-12-2A expression cassette is administered on days 1 and 5±2, and a CD3 half-BiTE or CD3 half-BiTE~IL-12 expression cassette is administered on day 8±2 of a cycle.

In some embodiments, an IL12-2A expression cassette is administered on day 1, a CD3 half-BiTE or CD3 half-BiTE~IL-12 expression cassette is administered on day 5±2, and a CXCL9 or IL12-CXCL9 expression cassette is administered on day 8±2 of a cycle. In some embodiments, an IL-12-2A expression cassette is administered on day 1, a CXCL9 or IL12~CXCL9 expression cassette is administered on day 5±2, and a CD3 half-BiTE or CD3 half-BiTE~IL-12 expression cassette is administered on day 8±2 of a cycle.

In some embodiments, a subject is administered either IT-EP IL-12~CXCL9 therapy or IT-EP CD3 half-BiTE~IL12 therapy on days 0, 4 (±2 days), and 7 (±2 days) provided the subject receives at least one IT-EP treatment with IL-12~CXCL9 and one IT-EP treatment with CD3 half-BiTE~IL12.

In some embodiments, a treatment can be administered every cycle or every other cycle. A cycle may be repeated such that 2 or more cycles are administered to a subject. Repeated cycles may be administered consecutively, alternated with one or more different cycles of treatment, or run concurrently with one or more difference cycles of treatment. Any of the above described treatments can be combined with other cancer therapies. For example, an IT-EP cycle can be combined with checkpoint inhibitor therapy.

VIII. Combination Therapy

In some embodiments, a therapeutic method includes a combination therapy. A combination therapy comprises a combination of therapeutic molecules or treatments. Therapeutic treatments include, but are not limited to, electric pulse (i.e., electroporation), radiation, antibody therapy, checkpoint inhibitor therapy, and chemotherapy. In some embodiments, administration of a combination therapy is achieved by electroporation alone. In some embodiments, administration of a combination therapy is achieved by a combination of electroporation and systemic delivery. In some embodiments, administration of a combination therapy is achieved by a combination of electroporation and radiation. In some embodiments, administration of a combination therapy is achieved by a combination of electroporation and oral medication. Therapeutic electroporation can be combined with, or administered with, one or more additional therapeutic treatments. The one or more additional therapeutics can be delivered by systemic delivery, intratumoral injection, intratumoral injection with electroporation, and/or radiation. The one or more additional therapeutics can be administered prior to, concurrent with, or subsequent to the CXCL9 and/or CD3 half-BiTE electroporation therapy.

In some embodiments, methods of treating cancer as described comprising: administering IT-EP therapy on day 1, days 1 and 5 (±2 days), days 1 and 8 (±2 days), or days 1, 5 (±2 days), and 8 (±2 days) and administering an additional therapeutic treatment on day 1 of a 3-6 week cycle. In some embodiments, methods of treating cancer as described comprising: administering IT-EP therapy on day 1, days 1 and 5 (±2 days), days 1 and 8 (±2 days), or days 1, 5 (±2 days), and 8 (±2 days) of every other cycle (i.e., every 6 weeks) and administering an additional therapeutic treatment on day 1 of each 3 week cycle (i.e., every 3 weeks). In some embodiments, the additional therapeutic treatment comprises a checkpoint inhibitor.

IX. Electroporation (EP) Therapy

Electroporation therapy comprises administering at least one electroporative pulse to a cell, tissue, or tumor. Electroporation therapy can be performed using any known electroporation device suitable for use in a mammalian subject. The described expression cassettes can be administered to a subject before, during, or after administration of the electric pulse. The expression cassette can be administered at or near the tumor in a subject. The described expression cassettes can be injected into a tumor using a hypodermic needle.

In some embodiments, electroporation therapy comprises the administration of one or more voltage pulses. The nature of the electric field to be generated is determined by the nature of the tissue, the size of the selected tissue and its location. The voltage pulse that can be delivered to the tumor may be about 100 V/cm to about 1500V/cm. In some embodiments, the voltage pulse is about 700 V/cm to 1500 V/cm. In some embodiments, the voltage pulse may be about 600 V/cm, 650 V/cm, 700 V/cm, 750 V/cm, 800 V/cm, 850 V/cm, 900 V/cm, 950 V/cm, 1000 V/cm, 1050 V/cm, 1100 V/cm, 1150 V/cm, 1200 V/cm, 1250 V/cm, 1300 V/cm, 1350 V/cm, 1400 V/cm, 1450 V/cm, or 1500 V/cm. In some embodiments, the voltage pulse is about 10 V/cm to 700 V/cm. In some embodiments, the electric is about 100 V/cm, 150 V/cm, 200 V/cm, 250 V/cm, 300 V/cm, 350 V/cm, or 400 V/cm, 450 V/cm, 500 V/cm, 550 V/cm, 600 V/cm 650 V/cm or 700 V/cm.

The pulse duration of the electroporative pulse of the may be from 10 μsec to 1 second. In some embodiments, the pulse duration is from about 10 sec to about 100 milliseconds (ms). In some embodiments, the pulse duration is 100 μsec, 1 ms, 10 ms, or 100 ms. The interval between pulses sets can be any desired time, such as one second. The waveform, electric field strength and pulse duration may also depend upon the type of cells and the type of molecules that are to enter the cells via electroporation.

The waveform of the electrical signal provided by the pulse generator can be an exponentially decaying pulse, a square pulse, a unipolar oscillating pulse train, a bipolar oscillating pulse train, or a combination of any of these forms. Square wave electroporation systems deliver controlled electric pulses that rise quickly to a set voltage, stay at that level for a set length of time (pulse length), and then quickly drop to zero.

1 to 100 pulses may be administered. In some embodiments, 1, 2, 3, 4, 5, 6, 7, 8, 9, or 10 pulses are administered. In some embodiments, 6 pulses are administered. In some embodiments, 6×0.1 msec pulses are administered. In some embodiments, 6 pulses are administered. In some embodiments. 6×0.1 msec pulses are administered at 1300-1500 V/cm. In some embodiments 8 pulses are administered. In some embodiments 8×10 msec pulses are administered. In some embodiments 8×10 msec pulses are administered at 300-500 V/cm.

The electroporation device can comprise a single needle electrode, a pair of needle electrode, or a plurality or array of needle electrodes. In some embodiments, the electroporation device an comprise a hypodermic needle or equivalent. In some embodiments, the electroporation device can comprise an electro-kinetic device ("EKD device") able to produce a series of programmable constant-current pulse patterns between electrodes in an array based on user control and input of the pulse parameters.

Electroporation devices suitable for use with the described compounds, compositions, and methods include, but are not limited to, those described in U.S. Pat. Nos. 7,245,963, 5,439,440, 6,055,453, 6,009,347, 9,020,605, and 9,037,230, and U.S. Patent Publication Nos. 2005/0052630, 2019/0117964, and patent applications PCT/US2019/030437 and U.S. patent application Ser. No. 16/269,022.

LIST OF EMBODIMENTS

1. An expression cassette comprising: a first nucleotide sequence encoding a CD3 half-BiTE, wherein the CD3 half-BiTE comprises an anti-CD3 scFv and a transmembrane domain wherein the transmembrane domain is linked to the C-terminal end of the anti-CD3 scFv.
2. The expression cassette of embodiment 1, wherein the first nucleotide sequence is operatively linked to a promoter.
3. The expression cassette of embodiment 2, wherein the promoter is selected from the group consisting of: CMV promoter, mPGK, SV40 promoter, β-actin promoter, SRα promoter, herpes thymidine kinase promoter, herpes simplex virus (HSV) promoter, mouse mammary tumor virus long terminal repeat (LTR) promoter, adenovirus major late promoter (Ad MLP), rous sarcoma virus (RSV) promoter, and EF1α promoter.
4. The expression cassette any one of embodiments 1-3, wherein the anti-CD3 scFv comprises CDR regions of the VH and VL domains of OKT3 (Muromonab-CD3), 145-2C11, 17A2, SP7, or UCHT1 antibodies 5. The expression cassette of embodiment 4, wherein the anti-CD3 scFv comprises the VF and VL domains of OKT3 (Muromonab-CD3), 145-2C11, 17A2, SP7, or UCHT1 or a humanized version thereof.
6. The expression cassette of any one of embodiments 1-5, wherein the transmembrane domain is selected from the group consisting of: PDGFRα transmembrane domain, and PDGFRβ transmembrane domain.
7. The expression cassette of any one of embodiments 1-6, wherein the first nucleotide sequence encodes a polypeptide comprising the amino acid sequence of SEQ ID NO: 60, 62, 74, or 76 or a polypeptide having at least 70%, 72%, 75%, 78%, 80%, 82%, 83%, 85%, 87%, 88%, 90%, 92%, 93%, 95%, 96%, 97%, 98%, or 99% amino acid sequence identify to SEQ ID NO: 60, 62, 74, or 76.
8. The expression cassette any one of embodiments 1-7, wherein the first nucleotide sequence comprises the nucleotide sequence of SEQ ID NO: 59, 61, 73, or 75 or a nucleotide sequence having at least 70%, 72%, 75%, 78%, 80%, 82%, 83%, 85%, 87%, 88%, 90%, 92%, 93%, 95%, 96%, 97%, 98%, or 99% sequence identify to SEQ ID NO: 59, 61, 73, or 75.
9. The expression cassette of any one of embodiments 2-8, further comprising a second nucleotide sequence encoding IL-12.
10. The expression cassette of embodiment 9, wherein the second nucleotide sequence encoding IL-12 comprises a first coding sequence encoding IL-12 p35 and a second coding sequence encoding IL-12 p40.
11. The expression cassette of embodiment 10, wherein the expression cassette comprises the formula represented by:

P-A-T-B-T-B' wherein P is the promoter, A encodes the CD3 half-BiTE, T is a translation modification element, B encodes IL-12 p35, and B' encodes IL-12 p40.
12. The expression cassette of embodiment 11, wherein T encodes a 2A peptide selected from the group consisting of: a P2A peptide, a T2A peptide, a E2A peptide, and a F2A peptide.
13. The expression cassette of embodiment 12, wherein A encodes a polypeptide comprising the amino acid sequence of SEQ ID NO: 60, 62, 74, or 76 or a polypeptide having at least 70%, 72%, 75%, 78%, 80%, 82%, 83%, 85%, 87%, 88%, 90%, 92%, 93%, 95%, 96%, 97%, 98%, or 99% amino acid sequence identify to SEQ ID NO: 60, 62, 74, or 76, B encodes a polypeptide comprising the amino acid sequence of SEQ ID NO: 31 or 53, or a polypeptide having at least 70%, 72%, 75%, 78%, 80%, 82%, 83%, 85%, 87%, 88%, 90%, 92%, 93%, 95%, 96%, 97%, 98%, or 99% amino acid sequence identity to SEQ ID NO: 31 or 53; and B' encodes a polypeptide comprising the amino acid sequence of SEQ ID NO: 33 or 56 or a polypeptide having at least 70%, 72%, 75%, 78%, 80%, 82%, 83%, 85%, 87%, 88%, 90%, 92%, 93%, 95%, 96%, 97%, 98%, or 99% amino acid sequence identity to SEQ ID NO: 33 or 56.
14. The expression cassette of embodiment 12, wherein the A comprises the nucleotide sequence of SEQ ID NO: 59, 61, 73, or 75 or a nucleotide sequence having at least 70%, 72%, 75%, 78%, 80%, 82%, 83%, 85%, 87%, 88%, 90%, 92%, 93%, 95%, 96%, 97%, 98%, or 99% to the nucleotide sequence of SEQ ID NO: 59, 61, 73, or 75; B comprises the nucleotide sequence of SEQ ID NO: 30, 51, or 52 or a nucleotide sequence having at least 70%, 72%, 75%, 78%, 80%, 82%, 83%, 85%, 87%, 88%, 90%, 92%, 93%, 95%, 96%, 97%, 98%, or 99% identity to the nucleotide sequence of SEQ ID NO: 30, 51, or 52; and B' comprises the nucleotide sequence of SEQ ID NO: 32, 54, or 55 or a nucleotide sequence having at least 70%, 72%, 75%, 78%, 80%, 82%, 83%, 85%, 87%, 88%, 90%, 92%, 93%, 95%, 96%, 97%, 98%, or 99% identity to the nucleotide sequence of SEQ ID NO: 32, 54, or 55.
15 The expression cassette of any one of embodiments 1-14, wherein the first nucleotide sequence encodes a polypeptide comprising the amino acid sequence of SEQ ID NO: 64, 66, 78, or 80 or a polypeptide having at least 70%, 72%, 75%, 78%, 80%, 82%, 83%, 85%, 87%, 88%, 90%, 92%, 93%, 95%, 96%, 97%, 98%, or 99% amino acid sequence identify to SEQ ID NO: 64, 66, 78, or 80.
16. The expression cassette of any one of embodiments 1-15 wherein the expression cassette comprises the sequence of SEQ ID NO: 63, 65, 77, or 79 or a nucleotide sequence having at least 70%, 72%, 75%, 78%, 80%, 82%, 83%, 85%, 87%, 88%, 90%, 92%, 93%, 95%, 96%, 97%, 98%, or 99% to the nucleotide sequence of SEQ ID NO: 63, 65, 77, or 79.
17. The expression cassette of any one of embodiments 1-14, wherein the expression cassette further encodes a tag sequence linked to either the N-terminal or C-terminal end of the anti-CD3 scFv.
18. The expression cassette of embodiment 17, wherein the tag sequence comprises at least one tag sequence selected from the group consisting of an HA tag and a Myc tag.
19. A plasmid for expressing a CD3 half-BiTE comprising the expression cassette of any one of embodiments 1-18.
20. A CD3 half-BiTE comprising: anti-CD3 single-chain variable fragment (scFv) fused to a transmembrane domain.
21. The expression cassette of any one of embodiments 1-18 or the plasmid of embodiment 19, for use in treating cancer.
22. An expression cassette comprising the formula represented by:

P-B-T-B'-T-A wherein P is a promoter, A encodes a CXCL9, T is a translation modification element, B encodes IL-12 p35, and B' encodes IL-12 p40.
23. The expression cassette of embodiment 22, wherein T comprises a 2A peptide selected from the group consisting of: a P2A peptide, a T2A peptide, a E2A peptide, and a F2A peptide.
24. The expression cassette of embodiment 22 or 23, wherein A encodes a polypeptide comprising the amino acid sequence of SEQ ID NO: 35 or 58 or a polypeptide having at least 70%, 72%, 75%, 78%, 80%, 82%, 83%, 85%, 87%, 88%, 90%, 92%, 93%, 95%, 96%, 97%, 98%, or 99% amino acid sequence identify to SEQ ID NO: 35 or 57; B encodes a polypeptide comprising the amino acid sequence of SEQ ID NO: 31 or 53 or a polypeptide having at least 70%, 72%, 75%, 78%, 80%, 82%, 83%, 85%, 87%, 88%, 90%, 92%, 93%, 95%, 96%, 97%, 98%, or 99% amino acid sequence identity to SEQ ID NO: 31 or 53; and B' encodes a polypeptide comprising the amino acid sequence of SEQ ID NO: 33 or 56 or a polypeptide having at least 70%, 72%, 75%, 78%, 80%, 82%, 83%, 85%, 87%, 88%, 90%, 92%, 93%, 95%, 96%, 97%, 98%, or 99% amino acid sequence identity to SEQ ID NO: 33 or 56.

25. The expression cassette of any one of embodiments 22-24, wherein A comprises the nucleotide sequence of SEQ ID NO: 34 or 57 or a nucleotide sequence having at least 70%, 72%, 75%, 78%, 80%, 82%, 83%, 85%, 87%, 88%, 90%, 92%, 93%, 95%, 96%, 97%, 98%, or 99% to the nucleotide sequence of SEQ ID NO: 34 or 57; B comprises the nucleotide sequence of SEQ ID NO: 30, 51, or 52 or a nucleotide sequence having at least 70%, 72%, 75%, 78%, 80%, 82%, 83%, 85%, 87%, 88%, 90%, 92%, 93%, 95%, 96%, 97%, 98%, or 99% identity to the nucleotide sequence of SEQ ID NO: 30, 51, or 52; and B' comprises the nucleotide sequence of SEQ ID NO: 32, 54, or 55 or a nucleotide sequence having at least 70%, 72%, 75%, 78%, 80%, 82%, 83%, 85%, 87%, 88%, 90%, 92%, 93%, 95%, 96%, 97%, 98%, or 99% identity to the nucleotide sequence of SEQ ID NO: 32, 54, or 55.

26. The expression cassette of any one of embodiments 22-25, wherein the expression cassette encodes a polypeptide comprising the amino acid sequence of SEQ ID NO: 68 or 82 or a polypeptide having at least 70%, 72%, 75%, 78%, 80%, 82%, 83%, 85%, 87%, 88%, 90%, 92%, 93%, 95%, 96%, 97%, 98%, or 99% amino acid sequence identify to SEQ ID NO: 68 or 82.

27. The expression cassette of any one of embodiments 22-26, wherein the expression cassette comprises the nucleotide sequence of SEQ ID NO: 67 or 81 or a nucleotide sequence having at least 70%, 72%, 75%, 78%, 80%, 82%, 83%, 85%, 87%, 88%, 90%, 92%, 93%, 95%, 96%, 97%, 98%, or 99% to the nucleotide sequence of SEQ ID NO: 67 or 81.

28. A plasmid for expressing CXCL9 and IL-12, comprising the expression cassette of any one of embodiments 22-27.

29. The expression cassette of any one of embodiments 22-27 or the plasmid of embodiment 28, for use in treating cancer.

30. An expression cassette encoding a CD3 half-BiTE and an expression cassette encoding CXCL9 for use in treating cancer, wherein the expression cassettes are formulated for intratumoral electroporation therapy.

31. A method of treating a subject having a tumor comprising injecting the tumor with an effective dose of at least one plasmid according to embodiment 19 or 28 and administering electroporation therapy to the tumor.

32. The method of embodiment 31, wherein the electroporation therapy comprises administration of at least one voltage pulse over a duration of about 100 microseconds to about 1 millisecond.

33. The method of embodiment 32, wherein the electroporation therapy comprises administration of 1-6 voltage pulses.

34. The method of embodiment 32 or 33, wherein the 1-10 voltage pulses have a field strength of about 200 V/cm to about 1500 V/cm.

35. The method of any one of embodiments 31-34, wherein the at least one plasmid is injected into the tumor and the electroporation therapy is administered on day 1, day 5±2 days, and day 8±2 days.

36. The method of any one of embodiments 31-34, wherein (a) the plasmid according to embodiment 19 is injected into the tumor and the electroporation therapy is administered on day 1 and day 5±2 days, and the plasmid according to embodiment 28 is injected into the tumor and the electroporation therapy is administered on day 8±2 days;

(b) the plasmid according to embodiment 19 is injected into the tumor and the electroporation therapy is administered on day 1 and day 8±2 days, and the plasmid according to embodiment 28 is injected into the tumor and the electroporation therapy is administered on day 5±2 days;

(c) the plasmid according to embodiment 19 is injected into the tumor and the electroporation therapy is administered on day 5±2 days and day 8±2 days, and the plasmid according to embodiment 28 is injected into the tumor and the electroporation therapy is administered on day 1;

(d) the plasmid according to embodiment 28 is injected into the tumor and the electroporation therapy is administered on day 1 and day 5±2 days, and the plasmid according to embodiment 19 is injected into the tumor and the electroporation therapy is administered on day 8±2 days;

(e) the plasmid according to embodiment 28 is injected into the tumor and the electroporation therapy is administered on day 1 and day 8±2 days, and the plasmid according to embodiment 19 is injected into the tumor and the electroporation therapy is administered on day 5±2 days; and (f) the plasmid according to embodiment 28 is injected into the tumor and the electroporation therapy is administered on days 5±2 days and 8±2 days, and the plasmid according to embodiment 19 is injected into the tumor and the electroporation therapy is administered on day 1.

37. The method of any one of embodiments 31-36, further comprising administering to the subject at least one additional therapeutic.

38. The method of any one of embodiments 31-37, wherein the method results in one or more or: increased tumor infiltrating lymphocytes, increased activation and/or proliferation of tumor-specific T cells, regression of the treated tumor, and regression of one or more untreated tumors.

39. The method of claim 37, wherein the at least one additional therapy comprises administering IT-EP anti-CLTA-4 scFv therapy.

40. A method for treating of treating a subject having a tumor comprising injecting the tumor with an effective dose of at least one plasmid encoding an anti-CTLA-4 scFv and administering electroporation therapy to the tumor 41. The method of claim 40, wherein the method further comprises one or more of: IT-EP IL12 therapy. IT-EP CXCL9 therapy, IT-EP IL12~CXCL9 therapy, IT-EP CD3 half-BiTE therapy, and IT-EP CD3 half-BiTE~IL12 therapy.

TABLE 1

| Sequences (nucleotides or amino acids in parenthesis may or may not be present) |
|---|
| Igκ signal peptide nucleic acid sequence (SEQ ID NO: 1)<br>atggagacagacacactcctgctatgggtactgctgct ctgggttccaggttccactggtgac |

TABLE 1-continued

| Sequences (nucleotides or amino acids in parenthesis may or may not be present) |
|---|
| Igκ signal peptide amino acid sequence (SEQ ID NO: 2) METDTLLLWVLLLWVPGSTGD |
| HA tag nucleic acid sequence (SEQ ID NO: 3) tatccatatgatgttccagattatgct |
| HA tag amino acid sequence (SEQ ID NO: 4) YPYDVPDYA |
| Myc tag nucleic acid sequence (SEQ ID NO: 5) gaacaaaaactcatctcagaagaggatctg |
| Myc tag amino acid sequence (SEQ ID NO: 6) EQKLISEEDL |
| 2C11 Variable heavy chain nucleic acid sequence (SEQ ID NO: 7) gaggtgcagctggtggagtctgggggaggcttggtgcagcctggaaagtccctgaaactctcctgtgaggcctctggattcaccttcagcggctatggcatgcactgggtccgccaggctccagggagggggctggagtcggtcgcatacattactagtagtagtattaatatcaaatatgctgacgctgtgaaaggccggttcaccgtctccagagacaatgccaagaacttactgtttctacaaatgaacattctcaagtctgaggacacagccatgtactactgtgcaagattcgactgggacaaaaattactggggccaaggaaccatggtcaccgtctcctcaggtggcggt |
| 2C11 Variable heavy chain amino acid sequence (SEQ ID NO: 8) EVQLVESGGGLVQPGKSLKLSCEASGETFSGYGMHWVRQAPGRGLESVAYITSSSINIKYADAVKGRFTVSRDNAKNLLFLQMNILKSEDTAMYYCAREDWDKNYWGQGTMVIVSSGGG |
| 2C11 Variable light chain nucleic acid sequence (SEQ ID NO: 9) atgacccagtctccatcatcactgcctgcctccctggggagacagagtcactatcaattgtcaggccagtcaggacattagcaattatttaaactggtaccagcagaaaccagggaaagctcctaagctcctgatctattatacaaataaattggcagatggagtcccatcaaggttcagtggcagtggttctgggagagattcttctttcactatcagcagcctggaatccgaagatattggatcttattactgtcaacagtattataactatccgtggacgttcggacctggcaccaagctggaaatcaaa |
| 2C11 Variable light chain nucleic acid sequence (SEQ ID NO: 10) atgacccagtctccatcatcactgcctgcctccctggggagacagagtcactatcaattgtcaggccagtcaggacattagcaattatttaaactggtatcagcagaaaccagggaaagctcctaagctcctgatctattatacaaataaattggcagatggagtcccatcaaggttcagtggcagtggttctgggagagattcttctttcactatcagcagcctggaatccgaagatattggatcttattactgtcaacagtattataactatccgtggacgttcggacctggcaccaagctggaaatcaaa |
| 2C11 Variable light chain amino acid sequence (SEQ ID NO: 11) MTQSPSSLPASLGDRVTINCQASQDISNYLNWYQQKPGKAPKLLIYYTNKLADGVPSRFSGSGSGRDSSFTISSLESEDIGSYYCQQYYNYPWTFGPGTKLEIK |
| Linker nucleic acid sequence (SEQ ID NO: 12) agtggctctggagggggctctggcggtggatctgggggtggaagt |

TABLE 1-continued

| Sequences (nucleotides or amino acids in parenthesis may or may not be present) |
|---|
| Linker amino acid sequence (SEQ ID NO: 13) SGSGGGSGGGSGGGS |
| Linker nucleic acid sequence (SEQ ID NO: 14) ggtggcggtggctccggcggtggtgggtcgggtggcggcggatct |
| Linker amino acid sequence (SEQ ID NO: 15) GGGGSGGGGSGGGGS |
| Linker nucleic acid sequence (SEQ ID NO: 16) ggctccggcggtggtgggtcgggtggcggcggatct |
| Linker amino acid sequence (SEQ ID NO: 17) GSGGGGSGGGG |
| Linker nucleic acid sequence (SEQ ID NO: 18) ggcagtgggagtgggagtgggagtggg |
| Linker amino acid sequence (SEQ ID NO: 19) GSGSGSGSG |
| Linker nucleic acid sequence (SEQ ID NO: 20) ggcagtgggagtggg |
| Linker amino acid sequence (SEQ ID NO: 21) GSGSG |
| Linker nucleic acid sequence (SEQ ID NO: 22) tctagtggatccggt |
| Linker amino acid sequence (SEQ ID NO: 23) SSGSG |
| PDGFR TM segment nucleic acid sequence (SEQ ID NO: 24) gtgggccaggacacgcaggaggtcatcgtggtgccacactccttgccctttaaggtggtggtgatctcagccatcctggccctggtggtgctcaccatcatctcccttatcatcctcatcatgctttggcagaagaagccacgt |
| PDGFR TM segment amino acid sequence (SEQ ID NO: 25) VGQDTQEVIVVPHSLPFKVVVISAILALVVLTIISLIILIMLWQKKPR |
| PDGFR TM segment nucleic acid sequence (SEQ ID NO: 26) gctgtgggccaggacacgcaggaggtcatcgtggtgccacactccttgccctttaaggtggtggtgatctcagccatcctggccctggtggtgctcaccatcatctcccttatcatcctcatcatgctttggcagaagaagccacgt |
| PDGFR TM segment amino acid sequence (SEQ ID NO: 27) AVGQDTQEVIVVPHSLPFKVVVISAILALVVLTIISLIILIMLWQKKPR |
| P2A nucleic acid sequence (SEQ ID NO: 28) ggatctggggccaccaacttttcattgctcaagcaggcgggcgatgtggaggaaaaccctggcccc |

TABLE 1-continued

Sequences (nucleotides or amino acids in parenthesis may or may not be present)

P2A amino acid sequence
(SEQ ID NO: 29)
GSGATNFSLLKQAGDVEENPGP mIL12-p35 nucleic acid sequence
(SEQ ID NO: 30)
(ggtacc or atg)
gtcagcgttccaacagcctcaccctcggcatccagcag
ctcctctcagtgccggtccagcatgtgtcaatcacgct
acctcctctttttggccacccttgccctcctaaaccac
ctcagtttggccagggtcattccagtctctggacctgc
caggtgtcttagccagtcccgaaacctgctgaagacca
cagatgacatggtgaagacggccagagaaaaactgaaa
cattattcctgcactgctgaagacatcgatcatgaaga
catcacacgggaccaaaccagcacattgaagacctgtt
taccactggaactacacaagaacgagagttgcctggct
actagagagacttcttccacaacaagagggagctgcct
gcccccacagaagacgtctttgatgatgaccctgtgcc
ttggtagcatctatgaggacttgaagatgtaccagaca
gagttccaggccatcaacgcagcacttcagaatcacaa
ccatcagcagatcattctTgacaagggcatgctggtgg
ccatcgatgagctgatgcagtctctgaatcataatggc
gagactctgcgccagaaacctcctgtgggagaagcaga
cccttacagagtgaaaatgaagctctgcatcctgcttc
acgccttcagcacccgcgtcgtgaccatcaacagggtg
atgggctatctgagctccgcc mIL12-35 amino acid sequence
(SEQ ID NO: 31)
(M)VSVPTASPSASSSSSQCRSSMCQSRYLLFLATLAL
LNHLSLARVIPVSGPARCLSQSRNLLKTIDDMVKTARE
KLKHYSCIAEDIDHEDITRDQTSTLKTCLPLELHKNES
CLATRETSSITRGSCLPPQKTSLMMTLCLGSIYEDLKM
YQTEFQAINAALQNHNHQQIILDKGMLVAIDELMQSLN
HNGETLRQKPPVGEADPYRVKMKLCILLHAFSTRVVTI
NRVMGYLSSAAAA mIL12-p40 nucleic acid sequence
(SEQ ID NO: 32)
tgtcctcagaagctaaccatctcctggtttgccatcgt
tttgctggtgtctccactcatggccatgtgggagctgg
agaaagacgtttatgttgtagaggtggactggactccc
gatgcccctggagaaacagtgaacctcacctgtgacac
gcctgaagaagatgacatcacctggacctcagaccaga
gacatggagtcataggctctggaaagaccctgaccatc
actgtcaaagagtttctTgatgctggccagtacacctg
ccacaaaggaggcgagactctgagccactcacatctgc
tgctccacaagaaggaaaatggaatttggtccactgaa
attttaaaGaatttcaaGaacaagactttcctgaagtg
tgaagcaccaaattactccggacggttcacgtgctcat
ggctggtgcaaagaaacatggacttgaagttcaacatc
aagagcagtagcagttcccctgactctcgggcagtgac
atgtggaatggcgtctctgtctgcagagaaggtcacac
tggaccaaagggactatgagaagtattcagtgtcctgc
caggaggatgtcacctgcccaactgccgaggagaccct
gcccattgaactggcgttggaagcacggcagcagaata
aatatgagaactacagcaccagcttcttcatcagggac
atcatcaaaccagacccgcccaagaacttgcagatgaa
gcctttgaagaactcacaggtggaggtcagctgggagt
accctgactcctggagcactccccattcctacttctcc
ctcaagttctttgttcgaatccagcgcaagaaagaaaa
gatgaaggagacagaggaggggtgtaaccagaaaggtg
cgttcctcgtagagaagacatctaccgaagtccaatgc
aaaggcgggaatgtctgcgtgcaagctcaggatcgcta
ttacaattcctcatgcagcaagtgggcatgtgttccct
gcagggtccgatcc(tag or tcg)

mIL12-p40 amino acid sequence
(SEQ ID NO: 33)
CPQKLTISWFAIVLLVSPLMAMWELEKDVYVVEVDWIP
DAPGETVNLICDTPEEDDITWISDQRHGVIGSGKILTI
TVKEFLDAGQYTCHKGGETLSHSHLLLHKKENGIWSTE
ILKNFKNKTFLKCEAPNYSGRFICSWLVQRNMDLKFNI
KSSSSSPDSRAVICGMASLSAEKVILDQRDYEKYSVSC
QEDVICPTAEETLPIELALEARQQNKYENYSTSFFIRD
IIKPDPPKNLQMKPLKNSQVEVSWEYPDSWSTPHSYFS
LKFFVRIQRKKEKMKETEEGCNQKGAFLVEKTSTEVQC
KGGNVCVQAQDRYYNSSCSKWACVPCRVRS(S)

mCXCL9 nucleic acid sequence
(SEQ ID NO: 34)
(atg)aagtccgctgttcttttcctcttgggcatcatc
ttcctggagcagtgtggagttcgaggaaccctagtgat
aaggaatgcacgatgctcctgcatcagcaccagccgag
gcacgatccactacaaatccctcaaagacctcaaacag
tttgccccaagccccaattgcaacaaaactgaaatcat
tgctacactgaagaacggagatcaaacctgcctagatc
cggactcggcaaatgtgaagaagctgatgaaagaatgg
gaaaagaagatcagccaaaagaaaaagcaaaagagggg
gaaaaaacatcaaaagaacatgaaaaacagaaaaccca
aaacaccccaaagtcgtcgtcgttcaaggaagactaca
(taa)

mCXCL9 amino acid sequence
(SEQ ID NO: 35)
(M)KSAVLFLLGIIFLEQCGVRGILVIRNARCSCISTS
RGTIHYKSLKDLKQFAPSPNCNKTEIIATLKNGDQTCL
DPDSANVKKLMKEWEKKISQKKKQKRGKKHQKNMKNRK
PKTPQSRRRSRKTT Mouse anti-CTLA-4 9D9 variable light chain nucleic acid sequence
(SEQ ID NO: 36)
gacattgtgatgacacagaccacactcagtctccccgt
ttcccttggtgatcaagcctccatatcctgtaggtcta
gtcaatctatcgtccactccaacggcaatacctatctg
gaatggtatcttcaaaagcccggacaatcaccaaagct
tcttatctataaggtgagcaatagatttagcggggtcc
ctgaccgattctctggaagtggctctggcacagacttt
accttgaaaatctccagagttgaggctgaggaccttgg
tgtatactactgcttccaaggctctcatgttccctaca
ctttcggaggcggaacaaaactggagataaaacgagcc
gacgcagcccccactgtg Mouse anti-CTLA-4 9D9 variable light chain amino acid sequence
(SEQ ID NO: 37)
DIVMTQTTLSLPVSLGDQASISCRSSQSIVHSNGNTYL
EWYLQKPGQSPKLLIYKVSNRFSGVPDRFSGSGSGTDF
TLKISRVEAEDLGVYYCFQGSHVPYTFGGGTKLEIKRA
DAAPTV Mouse anti-CTLA-4 9D9 variable heavy chain nucleic acid sequence
(SEQ ID NO: 38)
gaggcaaagcttcaggaatctggtccagtgttggtgaa
accaggtgcatccgtgaaaatgtcctgcaaagcaagcg
gttacacttttactgactattatatgaactgggtaaag
caatcccacggcaaatccctggaatggattggtgtcat
caacccttacaacggtgatacaagttacaaccaaaagt
tcaaaggtaaggctacattgaccgtagataagagtagc
agtactgcatacatggaacttaactctcttacatccga
ggactccgctgtttactattgtgcacgctactacggga
gctggttcgcttactggggtcaaggcaccctgataaca
gtgtccacagccaaaaccacacctccctccgtctatcc
tctcgctcca Mouse anti-CTLA-4 9D9 variable heavy chain amino acid sequence
(SEQ ID NO: 39)
EAKLQESGPVLVKPGASVKMSCKASGYTFTDYYMNWVK
QSHGKSLEWIGVINPYNGDTSYNQKFKGKATLTVDKSS
STAYMELNSLTSEDSAVYYCARYYGSWFAYWGQGTLIT
VSTAKTTPPSVYPLAP Mouse anti-CTLA-4 9H10 variable light chain nucleic acid sequence
(SEQ ID NO: 40)
gacattgtgatgacacagagtccttcatcccttgcagt
cagtgtcggcgaaaaagtaacaatttcatgcaagtcta
gtcaatctctgttgtacggctcctctcattacctcgca
tggtatcaacaaaaagtgggtcaatctcccaaattgtt
gatatactgggcttcaactagacacactggaatccctg TABLE 1-continued Sequences (nucleotides or amino acids in parenthesis may or may not be present)

acaggttcattggtagcggatcagggactgactttaca
ctgtccctcagcagcgtacaagcagaagacatggccga
ctatttctgccaacaatactttagtacaccatggacct
ttggggctgggaccagagttgagataaaa Mouse anti-CTLA-4 9H10 variable light chain amino acid sequence
(SEQ ID NO: 41)
DIVMTQSPSSLAVSVGEKVTISCKSSQSLLYGSSHYLA
WYQQKVGQSPKLLIYWASTRHTGIPDRFIGSGSGTDFT
LSLSSVQAEDMADYFCQQYFSTPWTFGAGTRVEIK Mouse anti-CTLA-4 9H10 variable heavy chain nucleic acid sequence
(SEQ ID NO: 42)
caagtgcagctgcttcaatccgaatcagaactcgtgaa
gccaggcgcttcagtgaaattgtcttgtaagacttcag
gatacactttcactgattactatatacactgggttaag
cagaagcctggtcagggtcttgaatggattggcctcat
caatcccaataacgatggcacaaactacaaccagaaat
ttcaaggaaaagccacacttaccgcagacaaatccagt
tctaccgcatacatggaacttaatagtctcacttttga
tgactcagtaatatatttctgtgccagggccagtagcc
gacttagaatggctaggactacctctgactactatgcc
atggactattggggacagggcattcaagtgaccgtgag
ctct Mouse anti-CTLA-4 9H10 variable heavy chain amino acid sequence
(SEQ ID NO: 43)
QVQLLQSESELVKPGASVKLSCKTSGYTFTDYYIHWVK
QKPGQGLEWIGLINPNNDGTNYNQKFQGKATLTADKSS
STAYMELNSLTFDDSVIYFCARASSRLRMARTTSDYYA
MDYWGQGIQVTVSS mIgG1 Fc domain nucleic acid sequence
(SEQ ID NO: 44)
ggttgtaagccttgcatatgtacagtcccagaagtatc
atctgtcttcatcttccccccaaagcccaaggatgtgc
tcaccattactctgactcctaaggtcacgtgtgttgtg
gtagacatcagcaaggatgatcccgaggtccagttcag
ctggtttgtagatgatgtggaggtgcacacagctcaga
cgcaaccccgggaggagcagttcaacagcactttccgc
tcagtcagtgaacttcccatcatgcaccaggactggct
caatggcaaggagttcaaatgcagggtcaacagtgcag
ctttccctgcccccatcgagaaaaccatctccaaaacc
aaaggcagaccgaaggctccacaggtgtacaccattcc
acctcccaaggagcagatggccaaggataaagtcagtc
tgacctgcatgataacagacttcttccctgaagacatt
actgtggagtggcagtggaatgggcagccagcggagaa
ctacaagaacactcagcccatcatggacacagatggct
cttacttcgtctacagcaagctcaatgtgcagaagagc
aactgggaggcaggaaatactttcacctgctctgtgtt
acatgagggcctgcacaaccaccatactgagaagagcc
tctcccactctcctggtaaatga mIgG1 Fc domain amino acid sequence
(SEQ ID NO: 45)
GCKPCICTVPEVSSVFIFPPKPKDVLTITLTPKVTCVV
VDISKDDPEVQFSWFVDDVEVHTAQTQPREEQENSTFR
SVSELPIMHQDWLNGKEFKCRVNSAAFPAPIEKTISKT
KGRPKAPQVYTIPPPKEQMAKDKVSLTCMITDFFPEDI
TVEWQWNGQPAENYKNTQPIMDTDGSYFVYSKLNVQKS
NWEAGNTFTCSVLHEGLHNHHTEKSLSHSPGK OKT3 Variable heavy chain nucleic acid sequence (SEQ ID NO: 46)
caggtgcagctgcagcaatctggggctgaactggcaag
acctggggcctcagtgaagatgtcctgcaaggcttctg
gctacacctttactaggtacacgatgcactgggtaaaa
cagaggcctggacagggtctggaatggattggatacat
taatcctagccgtggttatactaattacaatcagaagt
tcaaggacaaggccacattgactacagacaaatcctcc
agcacagcctacatgcaactgagcagcctgacatctga
ggactctgcagtctattactgtgcaagatattatgatg
atcattactgccttgactactggggccaaggcaccaca
ctcaccgtctcctca OKT3 Variable heavy chain amino acid sequence (SEQ ID NO: 47)
QVQLQQSGAELARPGASVKMSCKASGYTFTRYTMHWVK
QRPGQGLEWIGYINPSRGYTNYNQKFKDKATLTTDKSS
STAYMQLSSLTSEDSAVYYCARYYDDHYCLDYWGQGTT
LTVSS OKT3 Variable light chain nucleic acid sequence (SEQ ID NO: 48)
Cagattgtgctcacccagtctccagcaatcatgtctgc
atctccaggggagaaggttaccatgacctgcagtgcca
gctcaagtgtaagttacatgaactggtaccagcagaag
tcaggcacctcccccaaaagatggatttatgacacatc
caaactggcttctggagtccctgctcacttcaggggca
gtgggtctgggacctcttactctctcacaatcagcggc
atggaggctgaagatgctgccacttattactgccagca
gtggagtagtaacccattcacgttcggctcggggacca
agctggagatcaatcgt OKT3 Variable light chain nucleic acid sequence (SEQ ID NO: 49)
cagattgtgctcacccagtctccagcaatcatgtctgc
atctccaggggagaaggttaccatgacctgcagtgcca
gctcaagtgtaagttacatgaactggtatcagcagaag
tcaggcacctcccccaaaagatggatttatgacacatc
caaactggcttctggagtccctgctcacttcaggggca
gtgggtctgggacctcttactctctcacaatcagcggc
atggaggctgaagatgctgccacttattactgccagca
gtggagtagtaacccattcacgttcggctcggggacca
agctggagatcaatcgt OKT3 Variable light chain amino acid sequence (SEQ ID NO: 50)
QIVLTQSPAIMSASPGEKVTMTCSASSSVSYMNWYQQK
SGTSPKRWIYDTSKLASGVPAHFRGSGSGTSYSLTISG
MEAEDAATYYCQQWSSNPFTFGSGTKLEINR hIL12-p35 nucleic acid sequence
(SEQ ID NO: 51)
tggcccccctgggtcagcctcccagccaccgccctcacc
tgccgcggccacaggtctgcatccagcggctcgccctg
tgtccctgcagtgccggctcagcatgtgtccagcgcgc
agcctcctccttgtggctaccctggtcctcctggacca
cctcagtttggccagaaacctccccgtggccactccag
acccaggaatgttcccatgccttcaccactcccaaaac
ctgctgagggccgtcagcaacatgctccagaaggccag
acaaactctagaattttacccttgcacttctgaagaga
ttgatcatgaagatatcacaaaagataaaaccagcaca
gtggaggcctgtttaccattggaattaaccaagaatga
gagttgcctaaattccagagagacctctttcataacta
atgggagttgcctggcctccagaaagacctcttttatg
atggccctgtgccttagtagtatttatgaagacttgaa
gatgtaccaggtggagttcaagaccatgaatgcaaagc
ttctgatggatcctaagaggcagatctttctagatcaa
aacatgctggcagttattgatgagctgatgcaggccct
gaatttcaacagtgagactgtgccacaaaaatcctccc
ttgaagaaccggatttttataaaactaaaatcaagctc
tgcatacttcttcatgctttcagaattcgggcagtgac
tattgatagagtgatgagctatctgaatgcttcc hIL12-p35 nucleic acid sequence
(SEQ ID NO: 52)
(atg)tggcccccctgggtcagcctcccagccaccgccc
tcacctgccgcggccacaggtctgcatccagcggctcg
ccctgtgtccctgcagtgccggctcagcatgtgtccag
cgcgcagcctcctccttgtggctaccctggtcctcctg
gaccacctcagtttggccagaaacctccccgtggccac
tccagacccaggaatgttcccatgccttcaccactccc
aaaacctgctgagggccgtcagcaacatgctccagaag
gccagacaaactctcgaattttacccttgcacttctga
agagattgatcatgaagatatcacaaaagataaaacca
gcacagtggaggcctgtttaccattggaattaaccaag
aatgagagttgcctaaattccagagagacctctttcat
aactaatgggagttgcctggcctccagaaagacctctt
ttatgatggccctgtgccttagtagtatttatgaagac
ttgaagatgtaccaggtggagttcaagaccatgaatgc TABLE 1-continued

| Sequences (nucleotides or amino acids in parenthesis may or may not be present) |
|---|
| aaagcttctgatggaccctaagaggcaaatcttcctag<br>atcaaaacatgctggcagttattgatgagctgatgcag<br>gccctgaatttcaacagtgagactgtgccacaaaaatc<br>ctcccttgaagaaccggatttctacaagactaaaatca<br>agctctgcatacttcttcatgctttcagaatccgggca<br>gtgactattgatagagtgatgagctatctgaatgcttc<br>c |
| hIL12-p35 amino acid sequence<br>(SEQ ID NO: 53)<br>(M)WPPGSASQPPPSPAAATGLHPAARPVSLQCRLSMC<br>PARSLLLVATLVLLDHLSLARNLPVATPDPGMFPCLHH<br>SQNLLRAVSNMLQKARQTLEFYPCTSEEIDHEDITKDK<br>TSTVEACLPLELTKNESCLNSRETSFITNGSCLASRKT<br>SFMMALCLSSIYEDLKMYQVEFKTMNAKLLMDPKRQIF<br>LDQNMLAVIDELMQALNFNSETVPQKSSLEEPDFYKTK<br>IKLCILLHAFRIRAVTIDRVMSYLNAS |
| hIL12-p40 nucleic acid sequence<br>(SEQ ID NO: 54)<br>Tgtcaccagcagttggtcatctcttggttttccctggt<br>tttctggcatctcccctcgtggccatatgggaactga<br>agaaagatgtttatgtcgtagaattggattggtatccg<br>gatgcccctggagaaatggtggtcctcacctgtgacac<br>ccctgaagaagatggtatcacctggaccttggaccaga<br>gcagtgaggtcttaggctctggcaaaaccctgaccatc<br>caagtcaaagagtttggagatgctggccagtacacctg<br>tcacaaaggaggcgaggttctaagccattcgctcctgc<br>tgcttcacaaaaaggaagatggaatttggtccactgat<br>attttaaaggaccagaaagaacccaaaaataagacctt<br>tctaagatgcgaggccaagaattattctggacgtttca<br>cctgctggtggctgacgacaatcagtactgatttgaca<br>ttcagtgtcaaaagcagcagaggctcttctgaccccca<br>aggggtgacgtgcggagctgctacactctctgcagaga<br>gagtcagaggggacaacaaggagtatgagtactcagtg<br>gagtgccaggaggacagtgcctgcccagctgctgagga<br>gagtctgcccattgaggtcatggtggatgccgttcaca<br>agctcaagtatgaaaactacaccagcagcttcttcatc<br>agggacatcatcaaacctgacccacccaagaacttgca<br>gctgaagccattaaagaattctcggcaggtggaggtca<br>gctgggagtaccctgacacctggagtactccacattcc<br>tacttctccctgacattctgcgttcaggtccagggcaa<br>gagcaagagagaaaagaaagatagagtcttcacggaca<br>agacctcagccacggtcatctgccgcaaaaatgccagc<br>attagcgtgcgggcccaggaccgctactatagctcatc<br>ttggagcgaatgggcatctgtgccctgcagt<br>(tag) |
| hIL12-p40 nucleic acid sequence<br>(SEQ ID NO: 55)<br>tgtcaccagcagttggtcatctcttggttttccctggt<br>tttctggcatctcccctcgtggccatatgggaactga<br>agaaagatgtttatgtcgtagaattggattggtatccg<br>gatgcccctggagaaatggtggtcctcacctgtgacac<br>ccctgaagaagatggtatcacctggaccttggaccaga<br>gcagtgaggtcttaggctctggcaaaaccctgaccatc<br>caagtcaaagagtttggagatgctggccagtacacctg<br>tcacaaaggaggcgaggttctaagccattcgctcctgc<br>tgcttcacaaaaaggaagatggaatttggtccactgat<br>attttaaaggaccagaaagaacccaaaaataagacctt<br>tctaagatgcgaggccaagaattattctggacgtttca<br>cctgctggtggctgacgacaatcagtactgatttgaca<br>ttcagtgtcaaaagcagcagaggctcttctgaccccca<br>aggggtgacgtgcggagctgctacactctctgcagaga<br>gagtcagaggggacaacaaggagtatgagtactcagtg<br>gagtgccaggaggacagtgcctgcccagctgctgagga<br>gagtctgcccattgaggtcatggtggatgccgttcaca<br>agctcaagtatgaaaactacaccagcagcttcttcatc<br>agggacatcatcaaacctgacccacccaagaacttgca<br>gctgaagccattaaagaactctcggcaggtggaggtca<br>gctgggagtaccctgacacctggagtactccacattcc<br>tacttctccctgacattctgcgttcaggtccagggcaa<br>gagcaagagagaaaagaaagatagagtcttcacggaca<br>agacctcagccacggtcatctgccgcaaaaatgccagc<br>attagcgtgcgggcccaggaccgctactatagctcatc<br>ttggagcgaatgggcatctgtgccctgcagttcg |

TABLE 1-continued

| Sequences (nucleotides or amino acids in parenthesis may or may not be present) |
|---|
| hIL-12p40 amino acid sequence<br>(SEQ ID NO: 56)<br>CHQQLVISWFSLVFLASPLVAIWELKKDVYVVELDWYP<br>DAPGEMVVLTCDTPEEDGITWTLDQSSEVLGSGKTLTI<br>QVKEFGDAGQYTCHKGGEVLSHSLLLLHKKEDGIWSTD<br>ILKDQKEPKNKTFLRCEAKNYSGRFTCWWLITISTDLI<br>FSVKSSRGSSDPQGVICGAATLSAERVRGDNKEYEYSV<br>ECQEDSACPAAEESLPIEVMVDAVHKLKYENYTSSFFI<br>RDIIKPDPPKNLQLKPLKNSRQVEVSWEYPDTWSTPHS<br>YFSLTFCVQVQGKSKREKKDRVFTDKTSATVICRKNAS<br>ISVRAQDRYYSSSWSEWASVPCS |
| Human CXCL9<br>(hCXCL9) nucleic acid sequence<br>(SEQ ID NO: 57)<br>(atg)aagaaaagtggtgttcttttcctcttgggcatc<br>atcttgctggttctgattggagtgcaaggaaccccagt<br>agtgagaaagggtcgctgttcctgcatcagcaccaacc<br>aagggactatccacctacaatccttgaaagaccttaaa<br>caatttgccccaagcccttcctgcgagaaaattgaaat<br>cattgctacactgaagaatggagttcaaacatgtctaa<br>acccagattcagcagatgtgaaggaactgattaaaaag<br>tgggagaaacaggtcagccaaaagaaaaagcaaaagaa<br>tgggaaaaaacatcaaaaaaagaaagttctgaaagttc<br>gaaaatctcaacgttctcgtcaaaagaagactacataa |
| Human CXCL9<br>(hCXCL9) amino acid sequence<br>(SEQ ID NO: 58)<br>(M)KKSGVLELLGIILLVLIGVQGTPVVRKGRCSCIST<br>NQGTIHLQSLKDLKQEAPSPSCEKIEIIATLKNGVQTC<br>LNPDSADVKELIKKWEKQVSQKKKQKNGKKHQKKKVLK<br>VRKSQRSRQKKTT |
| Igκ-HA-2C11VHC-Linker-C211VLC-Myc-<br>PDGFR nucleic acid sequence<br>(SEQ ID NO: 59)<br>Atggagacagacacactcctgctatgggtactgctgct<br>ctgggttccaggttccactggtgactatccatatgatg<br>ttccagattatgctggggcccagccggccagatctgag<br>gtgcagctggtggagtctgggggaggcttggtgcagcc<br>tggaaagtccctgaaactctcctgtgaggcctctggat<br>tcaccttcagcggctatggcatgcactgggtccgccag<br>gctccagggagggggctggagtcggtcgcatacattac<br>tagtagtagtattaatatcaaatatgctgacgctgtga<br>aaggccggttcaccgtctccagagacaatgccaagaac<br>ttactgtttctacaaatgaacattctcaagtctgagga<br>cacagccatgtactactgtgcaagattcgactgggaca<br>aaaattactggggccaaggaaccatggtcaccgtctcc<br>tcaggtggcggtggctccggcggtggtgggtcgggtgg<br>cggcggatctgacatccagatgacccagtctccatcat<br>cactgcctgcctccctgggagacagagtcactatcaat<br>tgtcaggccagtcaggacattagcaattatttaaactg<br>gtaccagcagaaaccagggaaagctcctaagctcctga<br>tctattatacaaataaattggcagatggagtcccatca<br>aggttcagtggcagtggttctgggagagattcttcttt<br>cactatcagcagcctggaatccgaagatattggatctt<br>attactgtcaacagtattataactatccgtggacgttc<br>ggacctggcaccaagctggaaatcaaagtcgacgaaca<br>aaaactcatctcagaagaggatctgtacactgtgggcc<br>aggacacgcaggaggtcatcgtggtgccacactccttg<br>ccctttaaggtggtggtgatctcagccatcctggccct<br>ggtggtgctcaccatcatctcccttatcatcctcatca<br>tgctttggcagaagaagccacgt<br>(tag |
| Igκ-HA-2C11VHC-Linker-C211VLC-Myc-PDGFR<br>amino acid sequence<br>(SEQ ID NO: 60)<br>METDTLLLWVLLLWVPGSTGDYPYDVPDYAGAQPARSE<br>VQLVESGGGLVQPGKSLKLSCEASGFTFSGYGMHWVRQ<br>APGRGLESVAYITSSSINIKYADAVKGRFTVSRDNAKN<br>LLFLQMNILKSEDTAMYYCARFDWDKNYWGQGTMVTVS<br>SGGGGSGGGGSGGGGSDIQMTQSPSSLPASLGDRVTIN<br>CQASQDISNYLNWYQQKPGKAPKLLIYYTNKLADGVPS<br>RFSGSGSGRDSSETISSLESEDIGSYYCQQYYNYPWTE |

TABLE 1-continued

Sequences (nucleotides or amino acids in parenthesis may or may not be present)

GPGTKLEIKVDEQKLISEEDLYTVGQDTQEVIVVPHSL
PFKVVVISAILALVVLTIISLIILIMLWQKKPR

IgK-HA-2C11VHC-Linker-2C11VLC-Linker-PDGFR nucleic acid sequence
(SEQ ID NO: 61)
Atggagacagacacactcctgctatgggtactgctgct
ctgggttccaggttccactggtgactatccatatgatg
ttccagattatgctggggcccagccggccagatctgag
gtgcagctggtggagtctgggggaggcttggtgcagcc
tggaaagtccctgaaactctcctgtgaggcctctggat
tcaccttcagcggctatggcatgcactgggtccgccag
gctccagggagggggctggagtcggtcgcatacattac
tagtagtagtattaatatcaaatatgctgacgctgtga
aaggccggttcaccgtctccagagacaatgccaagaac
ttactgtttctacaaatgaacattctcaagtctgagga
cacagccatgtactactgtgcaagattcgactgggaca
aaaattactggggccaaggaaccatggtcaccgtctcc
tcaggtggcggtggctccggcggtggtgggtcgggtgg
cggcggatctgacatccagatgacccagtctccatcat
cactgcctgcctccctgggagacagagtcactatcaat
tgtcaggccagtcaggacattagcaattatttaaactg
gtatcagcagaaaccagggaaagctcctaagctcctga
tctattatacaaataaattggcagatggagtcccatca
aggttcagtggcagtggttctgggagagattcttcttt
cactatcagcagcctggaatccgaagatattggatctt
attactgtcaacagtattataactatccgtggacgttc
ggacctggcaccaagctggaaatcaaaggcagtgggag
tgggagtgggagtgggaatgctgtgggccaggacacgc
aggaggtcatcgtggtgccacactccttgccctttaag
gtggtggtgatctcagccatcctggccctggtggtgct
caccatcatctcccttatcatcctcatcatgctttggc
agaagaagccacgt
(TAG)

IgK-HA-2C11VHC-Linker-2C11VLC-Linker-PDGFR amino acid sequence
(SEQ ID NO: 62)
METDTLLLWVLLLWVPGSTGDYPYDVPDYAGAQPARSE
VQLVESGGGLVQPGKSLKLSCEASGFTFSGYGMHWVRQ
APGRGLESVAYITSSSINIKYADAVKGRFTVSRDNAKN
LLFLQMNILKSEDTAMYYCARFDWDKNYWGQGTMVTVS
SGGGGSGGGGSGGGGSDIQMTQSPSSLPASLGDRVTIN
CQASQDISNYLNWYQQKPGKAPKLLIYYTNKLADGVPS
RFSGSGSGRDSSETISSLESEDIGSYYCQQYYNYPWTE
GPGTKLEIKGSGSGSGSGNAVGQDTQEVIVVPHSLPFK
VVVISAILALVVLTIISLIILIMLWQKKPR Igκ-HA-2C11VHC-Linker-2C11VLC-Linker-PDGFR-P2A-mIL12-p35-P2A-mIL12-p40 nucleic acid sequence
(SEQ ID NO: 63)
Atggagacagacacactcctgctatgggtactgctgct
ctgggttccaggttccactggtgactatccatatgatg
ttccagattatgctggggcccagccggccagatctgag
gtgcagctggtggagtctgggggaggcttggtgcagcc
tggaaagtccctgaaactctcctgtgaggcctctggat
tcaccttcagcggctatggcatgcactgggtccgccag
gctccagggagggggctggagtcggtcgcatacattac
tagtagtagtattaatatcaaatatgctgacgctgtga
aaggccggttcaccgtctccagagacaatgccaagaac
ttactgtttctacaaatgaacattctcaagtctgagga
cacagccatgtactactgtgcaagattcgactgggaca
aaaattactggggccaaggaaccatggtcaccgtctcc
tcaggtggcggtggctccggcggtggtgggtcgggtgg
cggcggatctgacatccagatgacccagtctccatcat
cactgcctgcctccctgggagacagagtcactatcaat
tgtcaggccagtcaggacattagcaattatttaaactg
gtatcagcagaaaccagggaaagctcctaagctcctga
tctattatacaaataaattggcagatggagtcccatca
aggttcagtggcagtggttctgggagagattcttcttt
cactatcagcagcctggaatccgaagatattggatctt
attactgtcaacagtattataactatccgtggacgttc
ggacctggcaccaagctggaaatcaaaggcagtgggag
tgggaatgctgtgggccaggacacgcaggaggtcatcg
tggtgccacactccttgccctttaaggtggtggtgatc
tcagccatcctggccctggtggtgctcaccatcatctc
ccttatcatcctcatcatgctttggcagaagaagccac
gtggatctggggccaccaacttttcattgctcaagcag
gcgggcgatgtggaggaaaaccctggccccggtaccgt
cagcgttccaacagcctcaccctcggcatccagcagct
cctctcagtgccggtccagcatgtgtcaatcacgctac
ctcctctttttggccacccttgccctcctaaaccacct
cagtttggccagggtcattccagtctctggacctgcca
ggtgtcttagccagtcccgaaacctgctgaagaccaca
gatgacatggtgaagacggccagagaaaaactgaaaca
ttattcctgcactgctgaagacatcgatcatgaagaca
tcacacgggaccaaaccagcacattgaagacctgttta
ccactggaactacacaagaacgagagttgcctggctac
tagagagacttcttccacaacaagagggagctgcctgc
ccccacagaagacgtctttgatgatgaccctgtgcctt
ggtagcatctatgaggacttgaagatgtaccagacaga
gttccaggccatcaacgcagcacttcagaatcacaacc
atcagcagatcattcttgacaagggcatgctggtggcc
atcgatgagctgatgcagtctctgaatcataatggcga
gactctgcgccagaaacctcctgtgggagaagcagacc
cttacagagtgaaaatgaagctctgcatcctgcttcac
gccttcagcacccgcgtcgtgaccatcaacagggtgat
gggctatctgagctccgccgcggccgcaggatctgggg
ccaccaacttttcattgctcaagcaggcgggcgatgtg
gaggaaaaccctggccccggatcctgtcctcagaagct
aaccatctcctggtttgccatcgttttgctggtgtctc
cactcatggccatgtgggagctggagaaagacgtttat
gttgtagaggtggactggactcccgatgcccctggaga
aacagtgaacctcacctgtgacacgcctgaagaagatg
acatcacctggacctcagaccagagacatggagtcata
ggctctggaaagaccctgaccatcactgtcaaagagtt
tcttgatgctggccagtacacctgccacaaaggaggcg
agactctgagccactcacatctgctgctccacaagaag
gaaaatggaatttggtccactgaaattttaaagaattt
caagaacaagactttcctgaagtgtgaagcaccaaatt
actccggacggttcacgtgctcatggctggtgcaaaga
aacatggacttgaagttcaacatcaagagcagtagcag
ttcccctgactctcgggcagtgacatgtggaatggcgt
ctctgtctgcagagaaggtcacactggaccaaagggac
tatgagaagtattcagtgtcctgccaggaggatgtcac
ctgcccaactgccgaggagaccctgcccattgaactgg
cgttggaagcacggcagcagaataaatatgagaactac
agcaccagcttcttcatcagggacatcatcaaaccaga
cccgcccaagaacttgcagatgaagcctttgaagaact
cacaggtggaggtcagctgggagtaccctgactcctgg
agcactccccattcctacttctccctcaagttctttgt
tcgaatccagcgcaagaaagaaaagatgaaggagacag
aggaggggtgtaaccagaaaggtgcgttcctcgtagag
aagacatctaccgaagtccaatgcaaaggcgggaatgt
ctgcgtgcaagctcaggatcgctattacaattcctcat
gcagcaagtgggcatgtgttccctgcagggtccgatcc
tag Igκ-HA-2C11VHC-Linker-2C11VLC-Linker-PDGFR-P2A-mIL12-p35-P2A-mIL12-p40 amino acid sequence
(SEQ ID NO: 64)
METDTLLLWVLLLWVPGSTGDYPYDVPDYAGAQPARSE
VQLVESGGGLVQPGKSLKLSCEASGFTFSGYGMHWVRQ
APGRGLESVAYITSSSINIKYADAVKGRFTVSRDNAKN
LLFLQMNILKSEDTAMYYCAREDWDKNYWGQGTMVTVS
SGGGGSGGGGSGGGGSDIQMTQSPSSLPASLGDRVTIN
CQASQDISNYLNWYQQKPGKAPKLLIYYTNKLADGVPS
RFSGSGSGRDSSETISSLESEDIGSYYCQQYYNYPWTE
GPGTKLEIKGSGSGNAVGQDTQEVIVVPHSLPFKVVVI
SAILALVVLTIISLIILIMLWQKKPRGSGATNFSLLKQ
AGDVEENPGPGTVSVPTASPSASSSSSQCRSSMCQSRY
LLFLATLALLNHLSLARVIPVSGPARCLSQSRNLLKTT
DDMVKTAREKLKHYSCTAEDIDHEDITRDQTSTLKTCL
PLELHKNESCLATRETSSTTRGSCLPPQKTSLMMTLCL
GSIYEDLKMYQTEFQAINAALQNHNHQQIILDKGMLVA
IDELMQSLNHNGETLRQKPPVGEADPYRVKMKLCILLH
AFSTRVVTINRVMGYLSSAAAAGSGATNESLLKQAGDV
EENPGPGSCPQKLTISWFAIVLLVSPLMAMWELEKDVY
VVEVDWTPDAPGETVNLTCDTPEEDDITWTSDQRHGVI
GSGKTLTITVKEFLDAGQYTCHKGGETLSHSHLLLHKK
ENGIWSTEILKNEKNKTFLKCEAPNYSGRETCSWLVQR
NMDLKENIKSSSSSPDSRAVTCGMASLSAEKVTLDQRD TABLE 1-continued Sequences (nucleotides or amino acids in parenthesis may or may not be present)

YEKYSVSCQEDVTCPTAEETLPIELALEARQQNKYENY
STSFFIRDIIKPDPPKNLQMKPLKNSQVEVSWEYPDSW
STPHSYFSLKFFVRIQRKKEKMKETEEGCNQKGAFLVE
KTSTEVQCKGGNVCVQAQDRYYNSSCSKWACVPCRVRS

Igκ-2C11VHC-Linker-2C11VLC-Linker-PDGFR-P2A-mIL12-p35-P2A-mIL12-p40 nucleic acid sequence
(SEQ ID NO: 65)
atggagacagacacactcctgctatgggtactgctgct
ctgggttccaggttccactggtgacggggcccagccgg
ccagatctgaggtgcagctggtggagtctgggggaggc
ttggtgcagcctggaaagtccctgaaactctcctgtga
ggcctctggattcaccttcagcggctatggcatgcact
gggtccgccaggctccagggaggggctggagtcggtc
gcatacattactagtagtagtattaatatcaaatatgc
tgacgctgtgaaaggccggttcaccgtctccagagaca
atgccaagaacttactgtttctacaaatgaacattctc
aagtctgaggacacagccatgtactactgtgcaagatt
cgactgggacaaaaattactggggccaaggaaccatgg
tcaccgtctcctcaggtggcggtggctccggcggtggt
gggtcgggtggcggcggatctgacatccagatgaccca
gtctccatcatcactgcctgcctccctgggagacagag
tcactatcaattgtcaggccagtcaggacattagcaat
tatttaaactggtatcagcagaaaccagggaaagctcc
taagctcctgatctattatacaaataaattggcagatg
gagtcccatcaaggttcagtggcagtggttctgggaga
gattcttctttcactatcagcagcctggaatccgaaga
tattggatcttattactgtcaacagtattataactatc
cgtggacgttcggacctggcaccaagctggaaatcaaa
ggcagtgggagtgggaatgctgtgggccaggacacgca
ggaggtcatcgtggtgccacactccttgccctttaagg
tggtggtgatctcagccatcctggccctggtggtgctc
accatcatctcccttatcatcctcatcatgctttggca
gaagaagccacgtggatctggggccaccaacttttcat
tgctcaagcaggcgggcgatgtggaggaaaaccctggc
cccggtaccgtcagcgttccaacagcctcaccctcggc
atccagcagctcctctcagtgccggtccagcatgtgtc
aatcacgctacctcctctttttggccacccttgccctc
ctaaaccacctcagtttggccagggtcattccagtctc
tggacctgccaggtgtcttagccagtcccgaaacctgc
tgaagaccacagatgacatggtgaagacggccagagaa
aaactgaaacattattcctgcactgctgaagacatcga
tcatgaagacatcacacgggaccaaaccagcacattga
agacctgtttaccactggaactacacaagaacgagagt
tgcctggctactagagagacttcttccacaacaagagg
gagctgcctgcccccacagaagacgtctttgatgatga
ccctgtgccttggtagcatctatgaggacttgaagatg
taccagacagagttccaggccatcaacgcagcacttca
gaatcacaaccatcagcagatcattcttgacaagggca
tgctggtggccatcgatgagctgatgcagtctctgaat
cataatggcgagactctgcgccagaaacctcctgtggg
agaagcagacccttacagagtgaaaatgaagctctgca
tcctgcttcacgccttcagcacccgcgtcgtgaccatc
aacagggtgatgggctatctgagctccgccgcggccgc
aggatctggggccaccaacttttcattgctcaagcagg
cgggcgatgtggaggaaaaccctggccccggatcctgt
cctcagaagctaaccatctcctggtttgccatcgtttt
gctggtgtctccactcatggccatgtgggagctggaga
aagacgtttatgttgtagaggtggactggactcccgat
gcccctggagaaacagtgaacctcacctgtgacacgcc
tgaagaagatgacatcacctggacctcagaccagagac
atggagtcataggctctggaaagaccctgaccatcact
gtcaaagagtttcttgatgctggccagtacacctgcca
caaaggaggcgagactctgagccactcacatctgctgc
tccacaagaaggaaaatggaatttggtccactgaaatt
ttaaagaatttcaagaacaagactttcctgaagtgtga
agcaccaaattactccggacggttcacgtgctcatggc
tggtgcaaagaaacatggacttgaagttcaacatcaag
agcagtagcagttcccctgactctcgggcagtgacatg
tggaatggcgtctctgtctgcagagaaggtcacactgg
accaaagggactatgagaagtattcagtgtcctgccag
gaggatgtcacctgcccaactgccgaggagaccctgcc
cattgaactggcgttggaagcacggcagcagaataaat
atgagaactacagcaccagcttcttcatcagggacatc
atcaaaccagacccgcccaagaacttgcagatgaagcc
tttgaagaactcacaggtggaggtcagctgggagtacc
ctgactcctggagcactccccattcctacttctccctc
aagttctttgttcgaatccagcgcaagaaagaaaagat
gaaggagacagaggaggggtgtaaccagaaaggtgcgt
tcctcgtagagaagacatctaccgaagtccaatgcaaa
ggcgggaatgtctgcgtgcaagctcaggatcgctatta
caattcctcatgcagcaagtgggcatgtgttccctgca
gggtccgatcctag Igκ-2C11VHC-Linker-2C11VLC-Linker-PDGFR-P2A-mIL12-p35-P2A-mIL12-p40 amino acid sequence
(SEQ ID NO: 66)
METDTLLLWVLLLWVPGSTGDGAQPARSEVQLVESGGG
LVQPGKSLKLSCEASGFTFSGYGMHWVRQAPGRGLESV
AYITSSSINIKYADAVKGRFTVSRDNAKNLLFLQMNIL
KSEDTAMYYCAREDWDKNYWGQGTMVTVSSGGGGSGGG
GSGGGGSDIQMTQSPSSLPASLGDRVTINCQASQDISN
YLNWYQQKPGKAPKLLIYYTNKLADGVPSRFSGSGSGR
DSSETISSLESEDIGSYYCQQYYNYPWTEGPGTKLEIK
GSGSGNAVGQDTQEVIVVPHSLPFKVVVISAILALVVL
TIISLIILIMLWQKKPRGSGATNFSLLKQAGDVEENPG
PGTVSVPTASPSASSSSSQCRSSMCQSRYLLFLATLAL
LNHLSLARVIPVSGPARCLSQSRNLLKTTDDMVKTARE
KLKHYSCTAEDIDHEDITRDQTSTLKTCLPLELHKNES
CLATRETSSTTRGSCLPPQKTSLMMTLCLGSIYEDLKM
YQTEFQAINAALQNHNHQQIILDKGMLVAIDELMQSLN
HNGETLRQKPPVGEADPYRVKMKLCILLHAFSTRVVTI
NRVMGYLSSAAAAGSGATNFSLLKQAGDVEENPGPGSC
PQKLTISWFAIVLLVSPLMAMWELEKDVYVVEVDWTPD
APGETVNLTCDTPEEDDITWTSDQRHGVIGSGKTLTIT
VKEFLDAGQYTCHKGGETLSHSHLLLHKKENGIWSTEI
LKNEKNKTFLKCEAPNYSGRETCSWLVQRNMDLKENIK
SSSSSPDSRAVTCGMASLSAEKVTLDQRDYEKYSVSCQ
EDVTCPTAEETLPIELALEARQQNKYENYSTSFFIRDI
IKPDPPKNLQMKPLKNSQVEVSWEYPDSWSTPHSYFSL
KFFVRIQRKKEKMKETEEGCNQKGAFLVEKTSTEVQCK
GGNVCVQAQDRYYNSSCSKWACVPCRVRS mIL12-p35-P2A-mIL12-p40-P2A-mCXCL9 nucleic acid sequence
(SEQ ID NO: 67)
atggtcagcgttccaacagcctcaccctcggcatccag
cagctcctctcagtgccggtccagcatgtgtcaatcac
gctacctcctctttttggccacccttgccctcctaaac
cacctcagtttggccagggtcattccagtctctggacc
tgccaggtgtcttagccagtcccgaaacctgctgaaga
ccacagatgacatggtgaagacggccagagaaaaactg
aaacattattcctgcactgctgaagacatcgatcatga
agacatcacacgggaccaaaccagcacattgaagacct
gtttaccactggaactacacaagaacgagagttgcctg
gctactagagagacttcttccacaacaagagggagctg
cctgcccccacagaagacgtctttgatgatgaccctgt
gccttggtagcatctatgaggacttgaagatgtaccag
acagagttccaggccatcaacgcagcacttcagaatca
caaccatcagcagatcattctTgacaagggcatgctgg
tggccatcgatgagctgatgcagtctctgaatcataat
ggcgagactctgcgccagaaacctcctgtgggagaagc
agacccttacagagtgaaaatgaagctctgcatcctgc
ttcacgccttcagcacccgcgtcgtgaccatcaacagg
gtgatgggctatctgagctccgccGCGGCCGCAggatc
tggggccaccaacttttcattgctcaagcaggcgggcg
atgtggaggaaaaccctggccccGGATCCtgtcctcag
aagctaaccatctcctggtttgccatcgttttgctggt
gtctccactcatggccatgtgggagctggagaaagacg
tttatgttgtagaggtggactggactcccgatgcccct
ggagaaacagtgaacctcacctgtgacacgcctgaaga
agatgacatcacctggacctcagaccagagacatggag
tcataggctctggaaagaccctgaccatcactgtcaaa
gagtttcttgatgctggccagtacacctgccacaaagg
aggcgagactctgagccactcacatctgctgctccaca
agaaggaaaatggaatttggtccactgaaattttaaaG
aatttcaaGaacaagactttcctgaagtgtgaagcacc
aaattactccggacggttcacgtgctcatggctggtgc
aaagaaacatggacttgaagttcaacatcaagagcagt
agcagttcccctgactctcgggcagtgacatgtggaat
ggcgtctctgtctgcagagaaggtcacactggaccaaa
gggactatgagaagtattcagtgtcctgccaggaggat TABLE 1-continued Sequences (nucleotides or amino acids in parenthesis may or may not be present)

gtcacctgcccaactgccgaggagaccctgcccattga
actggcgttggaagcacggcagcagaataaatatgaga
actacagcaccagcttcttcatcagggacatcatcaaa
ccagacccgcccaagaacttgcagatgaagcctttgaa
gaactcacaggtggaggtcagctgggagtaccctgact
cctggagcactccccattcctacttctccctcaagttc
tttgttcgaatccagcgcaagaaagaaaagatgaagga
gacagaggaggggtgtaaccagaaaggtgcgttcctcg
tagagaagacatctaccgaagtccaatgcaaaggcggg
aatgtctgcgtgcaagctcaggatcgctattacaattc
ctcatgcagcaagtgggcatgtgttccctgcagggtcc
gatcctCgTCTAGAggatctggggccaccaacttttca
ttgctcaagcaggcgggcgatgtggaggaaaaccctgg
ccccaagtccgctgttcttttcctcttgggcatcatct
tcctggagcagtgtggagttcgaggaaccctagtgata
aggaatgcacgatgctcctgcatcagcaccagccgagg
cacgatccactacaaatccctcaaagacctcaaacagt
ttgccccaagccccaattgcaacaaaactgaaatcatt
gctacactgaagaacggagatcaaacctgcctagatcc
ggactcggcaaatgtgaagaagctgatgaaagaatggg
aaaagaagatcagccaaaagaaaaagcaaaagaggggg
aaaaaacatcaaaagaacatgaaaaacagaaaacccaa
aacaccccaaagtcgtcgtcgttcaaggaagactacat
aa mIL12-p35-P2A-mIL12-p40-P2A-mCXCL9 amino acid sequence
(SEQ ID NO: 68)

MVSVPTASPSASSSSSQCRSSMCQSRYLLFLATLALLN
HLSLARVIPVSGPARCLSQSRNLLKTTDDMVKTAREKL
KHYSCTAEDIDHEDITRDQTSTLKTCLPLELHKNESCL
ATRETSSTTRGSCLPPQKTSLMMTLCLGSIYEDLKMYQ
TEFQAINAALQNHNHQQIILDKGMLVAIDELMQSLNHN
GETLRQKPPVGEADPYRVKMKLCILLHAFSTRVVTINR
VMGYLSSAAAAGSGATNFSLLKQAGDVEENPGPGSCPQ
KLTISWFAIVLLVSPLMAMWELEKDVYVVEVDWTPDAP
GETVNLTCDTPEEDDITWTSDQRHGVIGSGKTLTITVK
EFLDAGQYTCHKGGETLSHSHLLLHKKENGIWSTEILK
NEKNKTFLKCEAPNYSGRETCSWLVQRNMDLKENIKSS
SSSPDSRAVTCGMASLSAEKVTLDQRDYEKYSVSCQED
VTCPTAEETLPIELALEARQQNKYENYSTSFFIRDIIK
PDPPKNLQMKPLKNSQVEVSWEYPDSWSTPHSYFSLKF
FVRIQRKKEKMKETEEGCNQKGAFLVEKTSTEVQCKGG
NVCVQAQDRYYNSSCSKWACVPCRVRSSSRGSGATNFS
LLKQAGDVEENPGPKSAVLFLLGIIFLEQCGVRGTLVI
RNARCSCISTSRGTIHYKSLKDLKQEAPSPNCNKTEIT
ATLKNGDQTCLDPDSANVKKLMKEWEKKISQKKKQKRG
KKHQKNMKNRKPKTPQSRRRSRKTT

Igκ-HA-9D9 VLC-Linker-9D9 VHC-Linker-mIgG1 Fc domain (anti-CTLA-4 scFv) nucleic acid sequence
(SEQ ID NO: 69)

atggagacagacacactcctgctatgggtactgctgct
ctgggttccaggttccactggtgactatccatatgatg
ttccagattatgctggggcccagccggccagatctgac
attgtgatgacacagaccacactcagtctccccgtttc
ccttggtgatcaagcctccatatcctgtaggtctagtc
aatctatcgtccactccaacggcaatacctatctggaa
tggtatcttcaaaagcccggacaatcaccaaagcttct
tatctataaggtgagcaatagatttagcggggtccctg
accgattctctggaagtggctctggcacagactttacc
ttgaaaatctccagagttgaggctgaggaccttggtgt
atactactgcttccaaggctctcatgttccctacactt
tcggaggcggaacaaaactggagataaaacgagccgac
gcagcccccactgtgagtggctctggagggggctctgg
cggtggatctgggggtggaagtgaggcaaagcttcagg
aatctggtccagtgttggtgaaaccaggtgcatccgtg
aaaatgtcctgcaaagcaagcggttacacttttactga
ctattatatgaactgggtaaagcaatcccacggcaaat
ccctggaatggattggtgtcatcaacccttacaacggt
gatacaagttacaaccaaaagttcaaaggtaaggctac
attgaccgtagataagagtagcagtactgcatacatgg
aacttaactctcttacatccgaggactccgctgtttac
tattgtgcacgctactacgggagctggttcgcttactg
gggtcaaggcaccctgataacagtgtccacagccaaaa
ccacacctccctccgtctatcctctcgctccagtcgac
tctagtggatccggtggttgtaagccttgcatatgtac
agtcccagaagtatcatctgtcttcatcttccccccaa
agcccaaggatgtgctcaccattactctgactcctaag
gtcacgtgtgttgtggtagacatcagcaaggatgatcc
cgaggtccagttcagctggtttgtagatgatgtggagg
tgcacacagctcagacgcaaccccgggaggagcagttc
aacagcactttccgctcagtcagtgaacttcccatcat
gcaccaggactggctcaatggcaaggagttcaaatgca
gggtcaacagtgcagctttccctgcccccatcgagaaa
accatctccaaaaccaaaggcagaccgaaggctccaca
ggtgtacaccattccacctcccaaggagcagatggcca
aggataaagtcagtctgacctgcatgataacagacttc
ttccctgaagacattactgtggagtggcagtggaatgg
gcagccagcggagaactacaagaacactcagcccatca
tggacacagatggctcttacttcgtctacagcaagctc
aatgtgcagaagagcaactgggaggcaggaaatacttt
cacctgctctgtgttacatgagggcctgcacaaccacc
atactgagaagagcctctcccactctcctggtaaatga Igκ-HA-9D9 VLC-Linker-9D9 VHC-Linker-mIgG1 Fc domain (anti-CTLA-4 scFv) amino acid sequence
(SEQ ID NO: 70)

METDTLLLWVLLLWVPGSTGDYPYDVPDYAGAQPARSD
IVMTQTTLSLPVSLGDQASISCRSSQSIVHSNGNTYLE
WYLQKPGQSPKLLIYKVSNRFSGVPDRFSGSGSGTDFT
LKISRVEAEDLGVYYCFQGSHVPYTFGGGTKLEIKRAD
AAPTVSGSGGGSGGGSGGGSEAKLQESGPVLVKPGASV
KMSCKASGYTFTDYYMNWVKQSHGKSLEWIGVINPYNG
DTSYNQKFKGKATLTVDKSSSTAYMELNSLTSEDSAVY
YCARYYGSWFAYWGQGTLITVSTAKTTPPSVYPLAPVD
SSGSGGCKPCICTVPEVSSVFIFPPKPKDVLTITLTPK
VTCVVVDISKDDPEVQFSWFVDDVEVHTAQTQPREEQF
NSTERSVSELPIMHQDWLNGKEEKCRVNSAAFPAPIEK
TISKTKGRPKAPQVYTIPPPKEQMAKDKVSLTCMITDF
FPEDITVEWQWNGQPAENYKNTQPIMDTDGSYFVYSKL
NVQKSNWEAGNTFTCSVLHEGLHNHHTEKSLSHSPGK

Igκ-HA-9H10 VLC-Linker-9H10 VHC-Linker-mIgG1 Fc domain (anti-CTLA-4 scFv) nucleic acid sequence
(SEQ ID NO: 71)

atggagacagacacactcctgctatgggtactgctgct
ctgggttccaggttccactggtgactatccatatgatg
ttccagattatgctggggcccagccggccagatctgac
attgtgatgacacagagtccttcatcccttgcagtcag
tgtcggcgaaaaagtaacaatttcatgcaagtctagtc
aatctctgttgtacggctcctctcattacctcgcatgg
tatcaacaaaaagtgggtcaatctcccaaattgttgat
atactgggcttcaactagacacactggaatccctgaca
ggttcattggtagcggatcagggactgactttacactg
tccctcagcagcgtacaagcagaagacatggccgacta
tttctgccaacaatactttagtacaccatggaccttttg
gggctgggaccagagttgagataaaaagtggctctgga
gggggctctggcggtggatctgggggtggaagtcaagt
gcagctgcttcaatccgaatcagaactcgtgaagccag
gcgcttcagtgaaattgtcttgtaagacttcaggatac
actttcactgattactatatacactgggttaagcagaa
gcctggtcagggtcttgaatggattggcctcatcaatc
ccaataacgatggcacaaactacaaccagaaatttcaa
ggaaaagccacacttaccgcagacaaatccagttctac
cgcatacatggaacttaatagtctcacttttgatgact
cagtaatatatttctgtgccagggccagtagccgactt
agaatggctaggactacctctgactactatgccatgga
ctattggggacagggcattcaagtgaccgtgagctctg
tcgactctagtggatccggtggttgtaagccttgcata
tgtacagtcccagaagtatcatctgtcttcatcttccc
cccaaagcccaaggatgtgctcaccattactctgactc
ctaaggtcacgtgtgttgtggtagacatcagcaaggat
gatcccgaggtccagttcagctggtttgtagatgatgt
ggaggtgcacacagctcagacgcaaccccgggaggagc
agttcaacagcactttccgctcagtcagtgaacttccc
atcatgcaccaggactggctcaatggcaaggagttcaa
atgcagggtcaacagtgcagctttccctgcccccatcg TABLE 1-continued Sequences (nucleotides or amino acids in parenthesis may or may not be present)

agaaaaccatctccaaaaccaaaggcagaccgaaggct
ccacaggtgtacaccattccacctcccaaggagcagat
ggccaaggataaagtcagtctgacctgcatgataacag
acttcttccctgaagacattactgtggagtggcagtgg
aatgggcagccagcggagaactacaagaacactcagcc
catcatggacacagatggctcttacttcgtctacagca
agctcaatgtgcagaagagcaactgggaggcaggaaat
actttcacctgctctgtgttacatgagggcctgcacaa
ccaccatactgagaagagcctctcccactctcctggta
aatga Igκ-HA-9H10 VLC-Linker-9H10 VHC-Linker-mIgG1 Fc domain (anti-CTLA-4 scFv) amino acid sequence (SEQ ID NO: 72)

METDTLLLWVLLLWVPGSTGDYPYDVPDYAGAQPARSD
IVMTQSPSSLAVSVGEKVTISCKSSQSLLYGSSHYLAW
YQQKVGQSPKLLIYWASTRHTGIPDRFIGSGSGTDFTL
SLSSVQAEDMADYFCQQYFSTPWTEGAGTRVEIKSGSG
GGSGGGSGGGSQVQLLQSESELVKPGASVKLSCKTSGY
TFTDYYTHWVKQKPGQGLEWIGLINPNNDGTNYNQKFQ
GKATLTADKSSSTAYMELNSLTFDDSVIYFCARASSRL
RMARTTSDYYAMDYWGQGIQVTVSSVDSSGSGGCKPCI
CTVPEVSSVFIFPPKPKDVLTITLTPKVTCVVVDISKD
DPEVQFSWFVDDVEVHTAQTQPREEQFNSTFRSVSELP
IMHQDWLNGKEFKCRVNSAAFPAPIEKTISKTKGRPKA
PQVYTIPPPKEQMAKDKVSLTCMITDFFPEDITVEWQW
NGQPAENYKNTQPIMDTDGSYFVYSKLNVQKSNWEAGN
TFTCSVLHEGLHNHHTEKSLSHSPGK

Igκ-HA-OKT3 VHC-Linker-OKT3 VLC-Myc-PDGFR nucleic acid sequence (SEQ ID NO: 73)

atggagacagacacactcctgctatgggtactgctgct
ctgggttccaggttccactggtgactatccatatgatg
ttccagattatgctggggcccagccggccagatctcag
gtgcagctgCAGCAAtctggggctgaactggcaagacc
tggggcctcagtgaagatgtcctgcaaggcttctggct
acacctttactaggtacacgatgcactgggtaaaacag
aggcctggacagggtctggaatggattggatacattaa
tcctagccgtggttatactaattacaatcagaagttca
aggacaaggccacattgactacagacaaatcctccagc
acagcctacatgcaactgagcagcctgacatctgagga
ctctgcagtctattactgtgcaAgatattatgatgatc
attactgccttgactactggggccaaggcaccACACTC
accgtctcctcaggtggcggtggctccggcggtggtgg
gtcgggtggcggcggatctCAGattgtgCTCacccagt
ctccagcaatcatgtctgcatctccaggggagaaggtt
accatgacctgcagtgccagctcaagtgtaagttacat
gaactggtaccagcagaagtcaggcacctcccccaaaa
gatggatttatgacacatccaaactggcttctggagtc
cctgctcacttcaggggcagtgggtctgggacctctta
ctctctcacaatcagcggcatggaggctgaagatgctg
ccacttattactgccagcagtggagtagtaacccattc
acgttcggctcggggaccaagctggagatcaaTcgtgt
cgacgaacaaaaactcatctcagaagaggatctgaatg
ctgtgggccaggacacgcaggaggtcatcgtggtgcca
cactccttgccctttaaggtggtggtgatctcagccat
cctggccctggtggtgctcaccatcatctcccttatca
tcctcatcatgctttggcagaagaagccacgt(tag)

Igκ-HA-OKT3 VHC-Linker-OKT3 VLC-Myc-PDGFR amino acid sequence (SEQ ID NO: 74)

METDTLLLWVLLLWVPGSTGDYPYDVPDYAGAQPARSQ
VQLQQSGAELARPGASVKMSCKASGYTFTRYTMHWVKQ
RPGQGLEWIGYINPSRGYTNYNQKFKDKATLTTDKSSS
TAYMQLSSLTSEDSAVYYCARYYDDHYCLDYWGQGTTL
TVSSGGGGSGGGGSGGGGSQIVLTQSPAIMSASPGEKV
TMTCSASSSVSYMNWYQQKSGTSPKRWIYDTSKLASGV
PAHERGSGSGTSYSLTISGMEAEDAATYYCQQWSSNPF
TEGSGTKLEINRVDEQKLISEEDLNAVGQDTQEVIVVP
HSLPFKVVVISAILALVVLTIISLIILIMLWQKKPR

Igκ-HA-OKT3 VHC-Linker-OKT3 VLC-Linker-PDGFR nucleic acid sequence

TABLE 1-continued

Sequences (nucleotides or amino acids in parenthesis may or may not be present)

(SEQ ID NO: 75)

atggagacagacacactcctgctatgggtactgctgct
ctgggttccaggttccactggtgactatccatatgatg
ttccagattatgctggggcccagccggccagatctcag
gtgcagctgCAGCAAtctggggctgaactggcaagacc
tggggcctcagtgaagatgtcctgcaaggcttctggct
acacctttactaggtacacgatgcactgggtaaaacag
aggcctggacagggtctggaatggattggatacattaa
tcctagccgtggttatactaattacaatcagaagttca
aggacaaggccacattgactacagacaaatcctccagc
acagcctacatgcaactgagcagcctgacatctgagga
ctctgcagtctattactgtgcaAgatattatgatgatc
attactgccttgactactggggccaaggcaccACACTC
accgtctcctcaggtggcggtggctccggcggtggtgg
gtcgggtggcggcggatctCAGattgtgCTCacccagt
ctccagcaatcatgtctgcatctccaggggagaaggtt
accatgacctgcagtgccagctcaagtgtaagttacat
gaactggtaTcagcagaagtcaggcacctcccccaaaa
gatggatttatgacacatccaaactggcttctggagtc
cctgctcacttcaggggcagtgggtctgggacctctta
ctctctcacaatcagcggcatggaggctgaagatgctg
ccacttattactgccagcagtggagtagtaacccattc
acgttcggctcggggaccaagctggagatcaaTcgtGG
CAGTGGgAGTGGgAGTGGgAGTGGgaatgctgtgggcc
aggacacgcaggaggtcatcgtggtgccacactccttg
ccctttaaggtggtggtgatctcagccatcctggccct
ggtggtgctcaccatcatctcccttatcatcctcatca
tgctttggcagaagaagccacgt(tag)

Igκ-HA-OKT3 VHC-Linker-OKT3 VLC-Linker-PDGFR amino acid sequence (SEQ ID NO: 76)

METDTLLLWVLLLWVPGSTGDYPYDVPDYAGAQPARSQ
VQLQQSGAELARPGASVKMSCKASGYTFTRYTMHWVKQ
RPGQGLEWIGYINPSRGYTNYNQKFKDKATLTTDKSSS
TAYMQLSSLTSEDSAVYYCARYYDDHYCLDYWGQGTTL
TVSSGGGGSGGGGSGGGGSQIVLTQSPAIMSASPGEKV
TMTCSASSSVSYMNWYQQKSGTSPKRWIYDTSKLASGV
PAHERGSGSGTSYSLTISGMEAEDAATYYCQQWSSNPF
TEGSGTKLEINRGSGSGSGSGNAVGQDTQEVIVVPHSL
PFKVVVISAILALVVLTIISLIILIMLWQKKPR

Igκ-HA-OKT3 VHC-Linker-OKT3 VLC-Linker-PDGFR-P2A-hIL12-p35-P2A-hIL12-p40 nucleic acid sequence (SEQ ID NO: 77)

atggagacagacacactcctgctatgggtactgctgct
ctgggttccaggttccactggtgactatccatatgatg
ttccagattatgctggggcccagccggccagatctcag
gtgcagctgCAGCAAtctggggctgaactggcaagacc
tggggcctcagtgaagatgtcctgcaaggcttctggct
acacctttactaggtacacgatgcactgggtaaaacag
aggcctggacagggtctggaatggattggatacattaa
tcctagccgtggttatactaattacaatcagaagttca
aggacaaggccacattgactacagacaaatcctccagc
acagcctacatgcaactgagcagcctgacatctgagga
ctctgcagtctattactgtgcaAgatattatgatgatc
attactgccttgactactggggccaaggcaccACACTC
accgtctcctcaggtggcggtggctccggcggtggtgg
gtcgggtggcggcggatctCAGattgtgCTCacccagt
ctccagcaatcatgtctgcatctccaggggagaaggtt
accatgacctgcagtgccagctcaagtgtaagttacat
gaactggtaTcagcagaagtcaggcacctcccccaaaa
gatggatttatgacacatccaaactggcttctggagtc
cctgctcacttcaggggcagtgggtctgggacctctta
ctctctcacaatcagcggcatggaggctgaagatgctg
ccacttattactgccagcagtggagtagtaacccattc
acgttcggctcggggaccaagctggagatcaaTcgtGG
CAGTGGgAGTGGgaatgctgtgggccaggacacgcagg
aggtcatcgtggtgccacactccttgccctttaaggtg
gtggtgatctcagccatcctggccctggtggtgctcac
catcatctcccttatcatcctcatcatgctttggcaga
agaagccacgtggatctggggccaccaacttttcattg
ctcaagcaggcgggcgatgtggaggaaaaccctggccc
cGGTACCtggccccctgggtcagcctcccagccaccgc
cctcacctgccgcggccacaggtctgcatccagcggct
cgccctgtgtccctgcagtgccggctcagcatgtgtcc TABLE 1-continued Sequences (nucleotides or amino acids in parenthesis may or may not be present)

agcgcgcagcctcctccttgtggctaccctggtcctcc
tggaccacctcagtttggccagaaacctccccgtggcc
actccagacccaggaatgttcccatgccttcaccactc
ccaaaacctgctgagggccgtcagcaacatgctccaga
aggccagacaaactctagaattttacccttgcacttct
gaagagattgatcatgaagatatcacaaaagataaaac
cagcacagtggaggcctgtttaccattggaattaacca
agaatgagagttgcctaaattccagagagacctctttc
ataactaatgggagttgcctggcctccagaaagacctc
ttttatgatggccctgtgccttagtagtatttatgaag
acttgaagatgtaccaggtggagttcaagaccatgaat
gcaaagcttctgatggatcctaagaggcagatctttct
agatcaaaacatgctggcagttattgatgagctgatgc
aggccctgaatttcaacagtgagactgtgccacaaaaa
tcctcccttgaagaaccggattttttataaaactaaaat
caagctctgcatacttcttcatgctttcagaattcggg
cagtgactattgatagagtgatgagctatctgaatgct
tccggatctggggccaccaacttttcattgctcaagca
ggcgggcgatgtggaggaaaaccctggcccctgtcacc
agcagttggtcatctcttggttttccctggtttttctg
gcatctcccctcgtggccatatgggaactgaagaaaga
tgtttatgtcgtagaattggattggtatccggatgccc
ctggagaaatggtggtcctcacctgtgacacccctgaa
gaagatggtatcacctggaccttggaccagagcagtga
ggtcttaggctctggcaaaaccctgaccatccaagtca
aagagtttggagatgctggccagtacacctgtcacaaa
ggaggcgaggttctaagccattcgctcctgctgcttca
caaaaaggaagatggaatttggtccactgatattttaa
aggaccagaaagaacccaaaaataagacctttctaaga
tgcgaggccaagaattattctggacgtttcacctgctg
gtggctgacgacaatcagtactgatttgacattcagtg
tcaaaagcagcagaggctcttctgacccccaaggggtg
acgtgcggagctgctacactctctgcagagagagtcag
aggggacaacaaggagtatgagtactcagtggagtgcc
aggaggacagtgcctgcccagctgctgaggagagtctg
cccattgaggtcatggtggatgccgttcacaagctcaa
gtatgaaaactacaccagcagcttcttcatcagggaca
tcatcaaacctgacccacccaagaacttgcagctgaag
ccattaaagaattctcggcaggtggaggtcagctggga
gtaccctgacacctggagtactccacattcctacttct
ccctgacattctgcgttcaggtccagggcaagagcaag
agagaaaagaaagatagagtcttcacggacaagacctc
agccacggtcatctgccgcaaaaatgccagcattagcg
tgcgggcccaggaccgctactatagctcatcttggagc
gaatgggcatctgtgccctgcagttag Igκ-HA-OKT3 VHC-Linker-OKT3
VLC-Linker-PDGFR-P2A-hIL12-p35-
P2A-hIL12-p40 amino acid sequence
(SEQ ID NO: 78)
METDTLLLWVLLLWVPGSTGDYPYDVPDYAGAQPARSQ
VQLQQSGAELARPGASVKMSCKASGYTFTRYTMHWVKQ
RPGQGLEWIGYINPSRGYTNYNQKFKDKATLTTDKSSS
TAYMQLSSLTSEDSAVYYCARYYDDHYCLDYWGQGTTL
TVSSGGGGSGGGGSGGGGSQIVLTQSPAIMSASPGEKV
TMTCSASSSVSYMNWYQQKSGTSPKRWIYDTSKLASGV
PAHERGSGSGTSYSLTISGMEAEDAATYYCQQWSSNPF
TEGSGTKLEINRGSGSGNAVGQDTQEVIVVPHSLPFKV
VVISAILALVVLTIISLIILIMLWQKKPRGSGATNFSL
LKQAGDVEENPGPGTWPPGSASQPPPSPAAATGLHPAA
RPVSLQCRLSMCPARSLLLVATLVLLDHLSLARNLPVA
TPDPGMFPCLHHSQNLLRAVSNMLQKARQTLEFYPCTS
EEIDHEDITKDKTSTVEACLPLELTKNESCLNSRETSF
ITNGSCLASRKTSFMMALCLSSIYEDLKMYQVEFKTMN
AKLLMDPKRQIFLDQNMLAVIDELMQALNENSETVPQK
SSLEEPDFYKTKIKLCILLHAFRIRAVTIDRVMSYLNA
SGSGATNESLLKQAGDVEENPGPCHQQLVISWFSLVFL
ASPLVAIWELKKDVYVVELDWYPDAPGEMVVLTCDTPE
EDGITWTLDQSSEVLGSGKTLTIQVKEFGDAGQYTCHK
GGEVLSHSLLLLHKKEDGIWSTDILKDQKEPKNKTFLR
CEAKNYSGRFTCWWLTTISTDLTESVKSSRGSSDPQGV
TCGAATLSAERVRGDNKEYEYSVECQEDSACPAAEESL
PIEVMVDAVHKLKYENYTSSFFIRDIIKPDPPKNLQLK
PLKNSRQVEVSWEYPDTWSTPHSYFSLTFCVQVQGKSK
REKKDRVFTDKTSATVICRKNASISVRAQDRYYSSSWS
EWASVPCS TABLE 1-continued Sequences (nucleotides or amino acids in parenthesis may or may not be present)

Igκ-OKT3 VHC-Linker-OKT3 VLC-Linker-
PDGFR-P2A-hIL12-p35-P2A-hIL12-p40
nucleic acid sequence
(SEQ ID NO: 79)
atggagacagacacactcctgctatgggtactgctgct
ctgggttccaggttccactggtgacggggcccagccgg
ccagatctcaggtgcagctgCAGCAAtctggggctgaa
ctggcaagacctggggcctcagtgaagatgtcctgcaa
ggcttctggctacacctttactaggtacacgatgcact
gggtaaaacagaggcctggacagggtctggaatggatt
ggatacattaatcctagccgtggttatactaattacaa
tcagaagttcaaggacaaggccacattgactacagaca
aatcctccagcacagcctacatgcaactgagcagcctg
acatctgaggactctgcagtctattactgtgcaAgata
ttatgatgatcattactgccttgactactggggccaag
gcaccACACTCaccgtotcctcaggtggcggtggctcc
ggcggtggtgggtogggtggcggcggatctCAGattgt
gCTCacccagtctccagcaatcatgtctgcatctccag
gggagaaggttaccatgacctgcagtgccagctcaagt
gtaagttacatgaactggtaTcagcagaagtcaggcac
ctcccccaaaagatggatttatgacacatccaaactgg
cttctggagtccctgctcacttcaggggcagtgggtct
gggacctcttactctctcacaatcagcggcatggaggc
tgaagatgctgccacttattactgccagcagtggagta
gtaacccattcacgttcggctcggggaccaagctggag
atcaaTcgtGGCAGTGGgAGTGGgaatgctgtgggcca
ggacacgcaggaggtcatcgtggtgccacactccttgc
cctttaaggtggtggtgatctcagccatcctggccctg
gtggtgctcaccatcatctcccttatcatcctcatcat
gctttggcagaagaagccacgtggatctggggccacca
acttttcattgctcaagcaggcgggcgatgtggaggaa
aaccctggccccGGTACCtggccccctgggtcagcctc
ccagccaccgccctcacctgccgcggccacaggtctgc
atccagcggctcgccctgtgtccctgcagtgccggctc
agcatgtgtccagcgcgcagcctcctccttgtggctac
cctggtcctcctggaccacctcagtttggccagaaacc
tccccgtggccactccagacccaggaatgttcccatgc
cttcaccactcccaaaacctgctgagggccgtcagcaa
catgctccagaaggccagacaaactctagaattttacc
cttgcacttctgaagagattgatcatgaagatatcaca
aaagataaaaccagcacagtggaggcctgtttaccatt
ggaattaaccaagaatgagagttgcctaaattccagag
agacctctttcataactaatgggagttgcctggcctcc
agaaagacctcttttatgatggccctgtgccttagtag
tatttatgaagacttgaagatgtaccaggtggagttca
agaccatgaatgcaaagcttctgatggatcctaagagg
cagatctttctagatcaaaacatgctggcagttattga
tgagctgatgcaggccctgaatttcaacagtgagactg
tgccacaaaaatcctcccttgaagaaccggattttttat
aaaactaaaatcaagctctgcatacttcttcatgcttt
cagaattcgggcagtgactattgatagagtgatgagct
atctgaatgcttccggatctggggccaccaacttttca
ttgctcaagcaggcgggcgatgtggaggaaaaccctgg
cccctgtcaccagcagttggtcatctcttggttttccc
tggtttttctggcatctcccctcgtggccatatgggaa
ctgaagaaagatgtttatgtcgtagaattggattggta
tccggatgcccctggagaaatggtggtcctcacctgtg
acacccctgaagaagatggtatcacctggaccttggac
cagagcagtgaggtcttaggctctggcaaaaccctgac
catccaagtcaaagagtttggagatgctggccagtaca
cctgtcacaaaggaggcgaggttctaagccattcgctc
ctgctgcttcacaaaaaggaagatggaatttggtccac
tgatattttaaaggaccagaaagaacccaaaaataaga
cctttctaagatgcgaggccaagaattattctggacgt
ttcacctgctggtggctgacgacaatcagtactgattt
gacattcagtgtcaaaagcagcagaggctcttctgacc
cccaaggggtgacgtgcggagctgctacactctctgca
gagagagtcagaggggacaacaaggagtatgagtactc
agtggagtgccaggaggacagtgcctgcccagctgctg
aggagagtctgcccattgaggtcatggtggatgccgtt
cacaagctcaagtatgaaaactacaccagcagcttctt
catcagggacatcatcaaacctgacccacccaagaact
tgcagctgaagccattaaagaattctcggcaggtggag
gtcagctgggagtaccctgacacctggagtactccaca
ttcctacttctccctgacattctgcgttcaggtccagg
gcaagagcaagagagaaaagaaagatagagtcttcacg
gacaagacctcagccacggtcatctgccgcaaaaatgc TABLE 1-continued

| Sequences (nucleotides or amino acids in parenthesis may or may not be present) |
|---|
| cagcattagcgtgcgggcccaggaccgctactatagct<br>catcttggagcgaatgggcatctgtgccctgcagttag |
| Igκ-OKT3 VHC-Linker-OKT3 VLC-Linker-PDGFR-P2A-hIL12-p35-P2A-hIL12-p40 amino acid sequence (SEQ ID NO: 80)<br>METDTLLLWVLLLWVPGSTGDGAQPARSQVQLQQSGAE<br>LARPGASVKMSCKASGYTFTRYTMHWVKQRPGQGLEWI<br>GYINPSRGYTNYNQKFKDKATLTTDKSSSTAYMQLSSL<br>TSEDSAVYYCARYYDDHYCLDYWGQGTTLTVSSGGGGS<br>GGGGSGGGGSQIVLTQSPAIMSASPGEKVTMTCSASSS<br>VSYMNWYQQKSGTSPKRWIYDTSKLASGVPAHFRGSGS<br>GTSYSLTISGMEAEDAATYYCQQWSSNPFTFGSGTKLE<br>INRGSGSGNAVGQDTQEVIVVPHSLPFKVVVISAILAL<br>VVLTIISLIILIMLWQKKPRGSGATNFSLLKQAGDVEE<br>NPGPGTWPPGSASQPPPSPAAATGLHPAARPVSLQCRL<br>SMCPARSLLLVATLVLLDHLSLARNLPVATPDPGMFPC<br>LHHSQNLLRAVSNMLQKARQTLEFYPCTSEEIDHEDIT<br>KDKTSTVEACLPLELTKNESCLNSRETSFITNGSCLAS<br>RKTSFMMALCLSSIYEDLKMYQVEFKTMNAKLLMDPKR<br>QIFLDQNMLAVIDELMQALNFNSETVPQKSSLEEPDFY<br>KTKIKLCILLHAFRIRAVTIDRVMSYLNASGSGATNES<br>LLKQAGDVEENPGPCHQQLVISWFSLVFLASPLVAIWE<br>LKKDVYVVELDWYPDAPGEMVVLTCDTPEEDGITWTLD<br>QSSEVLGSGKTLTIQVKEFGDAGQYTCHKGGEVLSHSL<br>LLLHKKEDGIWSTDILKDQKEPKNKTFLRCEAKNYSGR<br>FTCWWLTTISTDLTFSVKSSRGSSDPQGVTCGAATLSA<br>ERVRGDNKEYEYSVECQEDSACPAAEESLPIEVMVDAV<br>HKLKYENYTSSFFIRDIIKPDPPKNLQLKPLKNSRQVE<br>VSWEYPDTWSTPHSYFSLTFCVQVQGKSKREKKDRVFT<br>DKTSATVICRKNASISVRAQDRYYSSSWSEWASVPCS |
| hIL12-p35-P2A-hIL12-p40-P2A-hCXCL9 nucleic acid sequence (SEQ ID NO: 81)<br>atgtggccccctgggtcagcctcccagccaccgccctc<br>acctgccgcggccacaggtctgcatccagcggctcgcc<br>ctgtgtccctgcagtgccggctcagcatgtgtccagcg<br>cgcagcctcctccttgtggctaccctggtcctcctgga<br>ccacctcagtttggccagaaacctccccgtggccactc<br>cagacccaggaatgttcccatgccttcaccactcccaa<br>aacctgctgagggccgtcagcaacatgctccagaaggc<br>cagacaaactctcgaattttacccttgcacttctgaag<br>agattgatcatgaagatatcacaaaagataaaaccagc<br>acagtggaggcctgtttaccattggaattaaccaagaa<br>tgagagttgcctaaattccagagagacctctttcataa<br>ctaatgggagttgcctggcctccagaaagacctctttt<br>atgatggccctgtgccttagtagtatttatgaagactt<br>gaagatgtaccaggtggagttcaagaccatgaatgcaa<br>agcttctgatggaccctaagaggcaaatcttcctagat<br>caaaacatgctggcagttattgatgagctgatgcaggc<br>cctgaatttcaacagtgagactgtgccacaaaaatcct<br>cccttgaagaaccggatttctacaagactaaaatcaag<br>ctctgcatacttcttcatgctttcagaatCcgggcagt<br>gactattgatagagtgatgagctatctgaatgcttccG<br>CGGCCGCAggatctggggccaccaacttttcattgctc<br>aagcaggcgggcgatgtggaggaaaaccctggccccGG<br>ATCCtgtcaccagcagttggtcatctcttggttttccc<br>tggtttttctggcatctcccctcgtggccatatgggaa<br>ctgaagaaagatgtttatgtcgtagaattggattggta<br>tccggatgcccctggagaaatggtggtcctcacctgtg<br>acacccctgaagaagatggtatcacctggaccttggac<br>cagagcagtgaggtcttaggctctggcaaaaccctgac<br>catccaagtcaaagagtttggagatgctggccagtaca<br>cctgtcacaaaggaggcgaggttctaagccattcgctc<br>ctgctgcttcacaaaaaggaagatggaatttggtccac<br>tgatattttaaaggaccagaaagaacccaaaaataaga<br>cctttctaagatgcgaggccaagaattattctggacgt<br>ttcacctgctggtggctgacgacaatcagtactgattt<br>gacattcagtgtcaaaagcagcagaggctcttctgacc<br>cccaaggggtgacgtgcggagctgctacactctctgca<br>gagagagtcagaggggacaacaaggagtatgagtactc<br>agtggagtgccaggaggacagtgcctgcccagctgctg<br>aggagagtctgcccattgaggtcatggtggatgccgtt<br>cacaagctcaagtatgaaaactacaccagcagcttctt<br>catcagggacatcatcaaacctgacccacccaagaact |

TABLE 1-continued

| Sequences (nucleotides or amino acids in parenthesis may or may not be present) |
|---|
| tgcagctgaagccattaaagaaCtctcggcaggtggag<br>gtcagctgggagtaccctgacacctggagtactccaca<br>ttcctacttctccctgacattctgcgttcaggtccagg<br>gcaagagcaagagagaaaagaaagatagagtcttcacg<br>gacaagacctcagccacggtcatctgccgcaaaaatgc<br>cagcattagcgtgcgggcccaggaccgctactatagct<br>catcttggagcgaatgggcatctgtgccctgcagttCg<br>ICTAGAggatctggggccaccaacttttcattgctcaa<br>gcaggcgggcgatgtggaggaaaaccctggccccaaga<br>aaagtggtgttcttttcctcttgggcatcatcttgctg<br>gttctgattggagtgcaaggaaccccagtagtgagaaa<br>gggtcgctgttcctgcatcagcaccaaccaagggacta<br>tccacctacaatccttgaaagaccttaaacaatttgcc<br>ccaagcccttcctgcgagaaaattgaaatcattgctac<br>actgaagaatggagttcaaacatgtctaaacccagatt<br>cagcagatgtgaaggaactgattaaaaagtgggagaaa<br>caggtcagccaaaagaaaaagcaaaagaatgggaaaaa<br>acatcaaaaaaagaaagttctgaaagttcgaaaatctc<br>aacgttctcgtcaaaagaagactacataa |
| hIL12-p35-P2A-hIL12-p40-P2A-hCXCL9 amino acid sequence (SEQ ID NO: 82)<br>MWPPGSASQPPPSPAAATGLHPAARPVSLQCRLSMCPA<br>RSLLLVATLVLLDHLSLARNLPVATPDPGMFPCLHHSQ<br>NLLRAVSNMLQKARQTLEFYPCTSEEIDHEDITKDKTS<br>TVEACLPLELTKNESCLNSRETSFITNGSCLASRKTSF<br>MMALCLSSIYEDLKMYQVEFKTMNAKLLMDPKRQIFLD<br>QNMLAVIDELMQALNFNSETVPQKSSLEEPDFYKTKIK<br>LCILLHAFRIRAVTIDRVMSYLNASAAAGSGATNESLL<br>KQAGDVEENPGPGSCHQQLVISWFSLVFLASPLVAIWE<br>LKKDVYVVELDWYPDAPGEMVVLICDTPEEDGITWILD<br>QSSEVLGSGKILTIQVKEFGDAGQYTCHKGGEVLSHSL<br>LLLHKKEDGIWSTDILKDQKEPKNKTFLRCEAKNYSGR<br>FTCWWLITISTDLIFSVKSSRGSSDPQGVICGAATLSA<br>ERVRGDNKEYEYSVECQEDSACPAAEESLPIEVMVDAV<br>HKLKYENYTSSFFIRDIIKPDPPKNLQLKPLKNSRQVE<br>VSWEYPDTWSTPHSYFSLTFCVQVQGKSKREKKDRVFT<br>DKTSATVICRKNASISVRAQDRYYSSSWSEWASVPCSS<br>SRGSGATNESLLKQAGDVEENPGPKKSGVLELLGIILL<br>VLIGVQGTPVVRKGRCSCISTNQGTIHLQSLKDLKQEA<br>PSPSCEKIEIIATLKNGVQTCLNPDSADVKELIKKWEK<br>QVSQKKKQKNGKKHQKKKVLKVRKSQRSRQKKTT |
| PDGFRβ transmembrane domain (SEQ ID NO: 83)<br>VVISAILALVVLTVISLIILI |
| PDGFRβ transmembrane domain (SEQ ID NO: 84)<br>VVISAILALVVLTIISLIILI |
| PDGFRα transmembrane domain (SEQ ID NO: 85)<br>AAVLVLLVIVI I SLIVLVVIW |
| PDGFRα transmembrane domain (SEQ ID NO: 86)<br>AAVLVLLVIVIVSLIVLVVIW |
| PDGFRβ transmembrane domain (SEQ ID NO: 87)<br>tggtgatctcagccatcctggccctggtggtgctcacc<br>atcatctcccttatcatcctcatc |
| PDGFRβ transmembrane domain (SEQ ID NO: 88)<br>gtggtgatctcagccatcctggccctggtggtgctcac<br>catcatctcccttatcatcctcatc |
| PDGFRα transmembrane domain (SEQ ID NO: 89)<br>gctgcagtcctggtgctgttggtgattgtgatcatctc<br>acttattgtcctggttgtcatttggaa |

Although the invention has been described in detail for purposes of clarity of understanding, certain modifications may be practiced within the scope of the appended claims. All publications, accession numbers, web sites, patent documents and the like cited in this application are hereby incorporated by reference in their entirety for all purposes to the same extent as if each were so individually denoted. To the extent different information is associated with a citation at different times, the information present as of the effective filing date of this application is meant. Unless otherwise apparent from the context any element, embodiment, step, feature or aspect of the invention can be performed in combination with any other.

EXAMPLES

CXCL9

Example 1. CXCL9 plasmid construction. Mouse CXCL9 (mCXCL9) or human CXCL9 (hCXCL9) nucleic acid sequence was cloned into an expression vector using standard molecular biology techniques to. Alternatively, mCXCL9 or hCXCL9 was cloned downstream of mouse (mIL12-2A) or human (hIL12-2A) IL12 p35-P2A-IL12 p40 to yield mIL12-mCXCL9 and hIL12~hCXCL9 (FIG. 1A-B. IL12 p35-P2A-IL12 p40 constructs were made essentially as described in WO2017/106795 or WO2018/229696.

Figure 2:
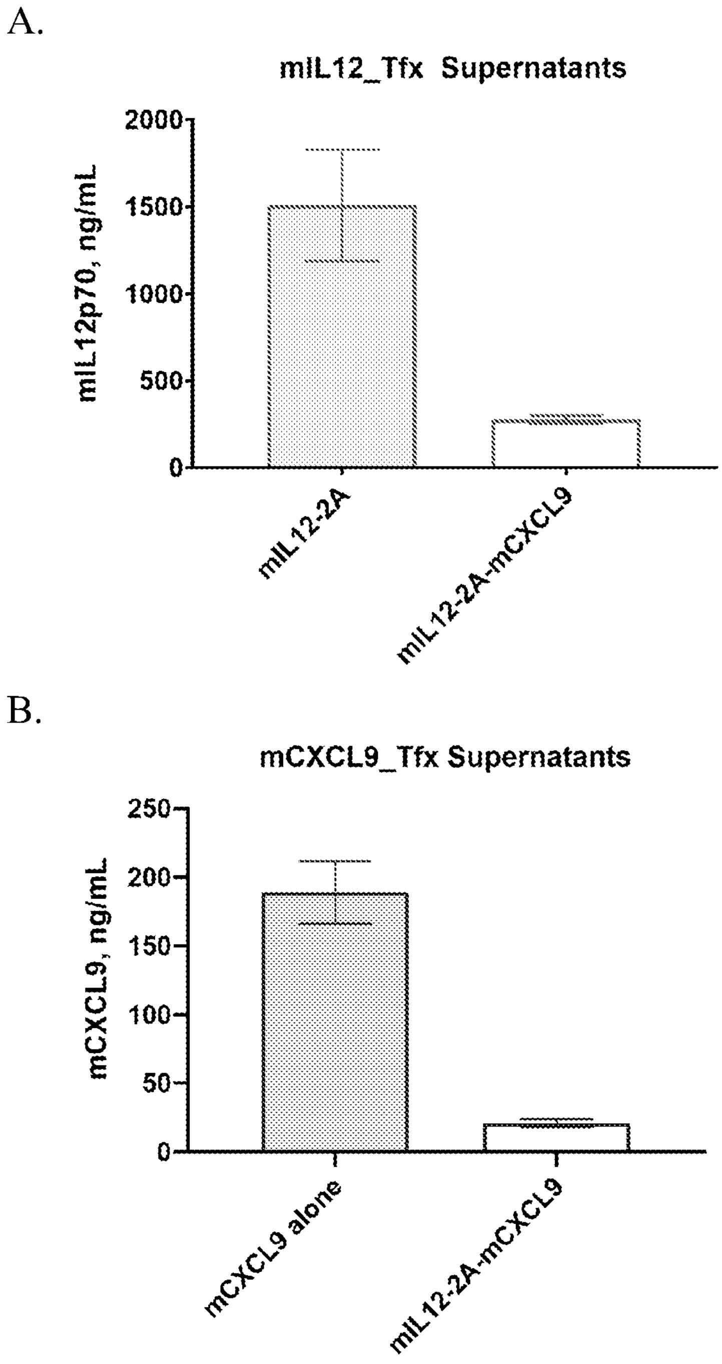
FIG. 2. Graphs illustrating (A) mIL12p74 protein expression, and (B) mCXCL9 protein expression in HEK293 cells following transfection with mIL12-2A, mCXCL9, and mIL12~mCXCL9 expression vectors.

The resulting plasmids contained IL-12 p35, IL-12 p40 and CXCL9, all expressed from the same promoter, with intervening exon skipping (P2A) motifs to allow all three proteins to be expressed from a single polycistronic message. Similar methods were sued to make mCXCL9~mCherry Example 2. Protein expression. The mIL12-2A, mCXCL9, and mIL12~mCXCL9 expression vectors were transfected into HEK293 cells in vitro. 96 h after transfection, supernatants were collected and IL12 and CXCL9 protein expression were assayed by ELISA. The results, shown in FIG. 2 show that, while expression was decreased in the cells transfected with the mIL12~mCXCL9 expression vector, detectable levels of both IL12 and CXCL9 were produced. FIG. 27 shows high levels of secreted hIL12 and hCXCL9 in cells transfected with hIL-12-hCXCL9 expression vector.

Figure 3:
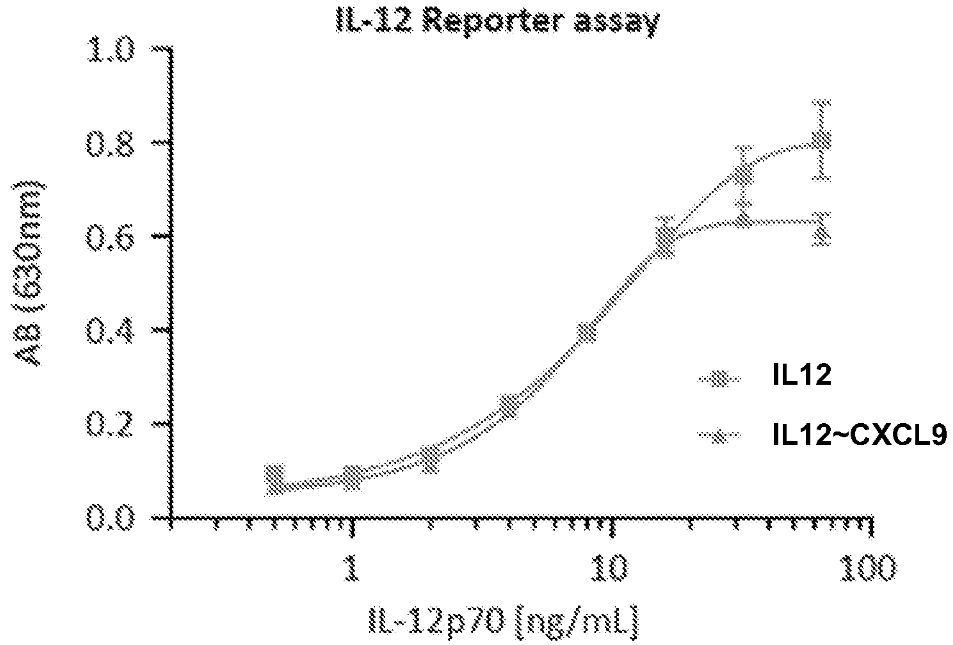
FIG. 3. Graph illustrating dose-response to mIL-12p70 from transiently transfected HEK293 cells with mouse IL-12 or mouse IL-12-CXC constructs. Both constructs encode biologically active IL-12.
Figure 10:
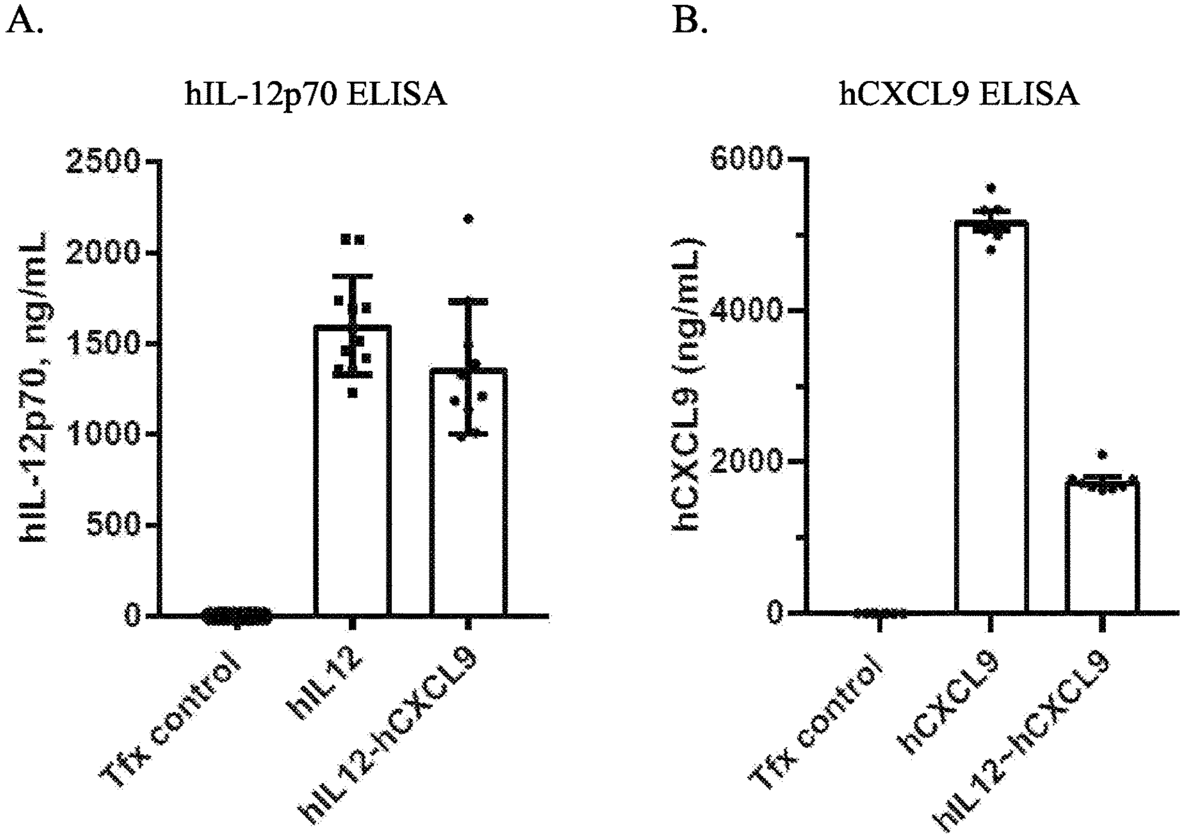
FIG. 10. Graphs illustrating (A) hIL-12 protein expression in HEK293 cells transfected with hIL12-2A and hIL12~hCXCL9 expression vectors and (B) hCXCL9 protein expression in HEK293 cells transfected with hCXCL9 and hIL12~hCXCL9 expression vectors.

Similarly, hIL12-2A, hCXCL9, and hIL12~hCXCL9 expression vectors were transfected into HEK293 cells in vitro. 96 h after transfection, supernatants were collected and IL12 and CXCL9 protein expression were assayed by ELISA hIL12 was expressed nearly equally from both the hIL12-2A (1.59 μg/mL) and hIL12~hCXCL9 (1.37 μg/mL) expression vectors (FIG. 10A). Decreased, but still substantial levels of hCXCL9 was expressed in cells transfected with the hIL12~hCXCL9 expression vector (1.75 μg/mL) compared to cells transfected with the hCXCL9 expression vector (5.19 μg/mL) (FIG. 10B).

mIL12 protein produced from the mIL2~mCXCL9 expression vector was further tested for activity. mIL12 produced from cells transfected with the mIL12-2A or mIL12~mCXCL9 expression vectors was incubated with HEK-Blue IL-12 cells. HEK-Blue IL-12 cells are used to detect bioactive human and mouse IL-12. HEK-Blue IL-12 cells are used to validate the functionality of recombinant native or engineered human or mouse IL-12. Functional IL-12 binds to IL-12 receptor in HEK-Blue IL-12 cells and activates a STAT-4 pathway and a STAT4-inducible SEAP reporter gene. SEAP expression is then assayed. The response ratio was calculated by dividing the OD at 630 nm for treated cells by the OD at 630 nm for untreated cells. The results, shown in FIG. 3, demonstrate that IL-12, produced from either the mIL12-2A or the mIL12~mCXCL9 expression vectors is functional.

Figure 11:
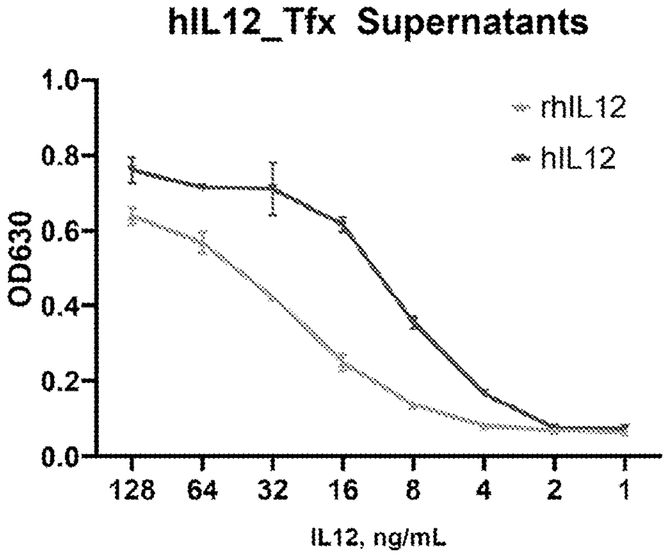
FIG. 11. Graph illustrating activation of STAT4 pathway in HEK-Blue IL-12 cells using recombinant human IL-12 (rhIL12, positive control), or hIL12 produced from cells expressing an hIL12-2A expression vectors.

Similarly, hIL12 protein produced from the hIL12~hCXCL9 expression vector was also tested for activity. hIL12 produced from cells transfected with the hIL12~hCXCL9 expression vector was incubated with HEK-Blue IL-12 cells. The results, shown in FIG. 11, demonstrate that IL-12, produced from the hIL12-2A expression vector, is functional.

Figure 4A:
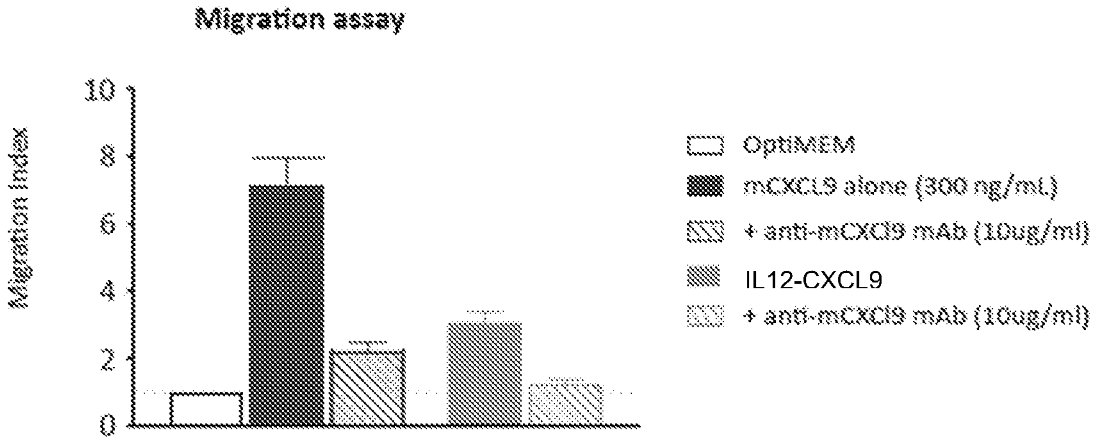
FIG. 4A. Graph illustrating transfection-derived mouse CXCL9 induced chemotaxis of SIINFEKL-pulsed (24 hr@μg/mL, 72 hr recovery) OT-1 splenocytes through polycarbonate membranes with 5.0-micron pores (Costar 3421). Migration index is defined as the number of observed chemotactic cells after 2.5 hours at 37° C., normalized to the number of cells that passively migrated through the membrane in the OptiMEM negative control. Abrogation of chemotaxis was observed with the pre-incubation of anti-mCXCL9 neutralizing monoclonal antibody (BioXCell BE0309).
Figure 4B:
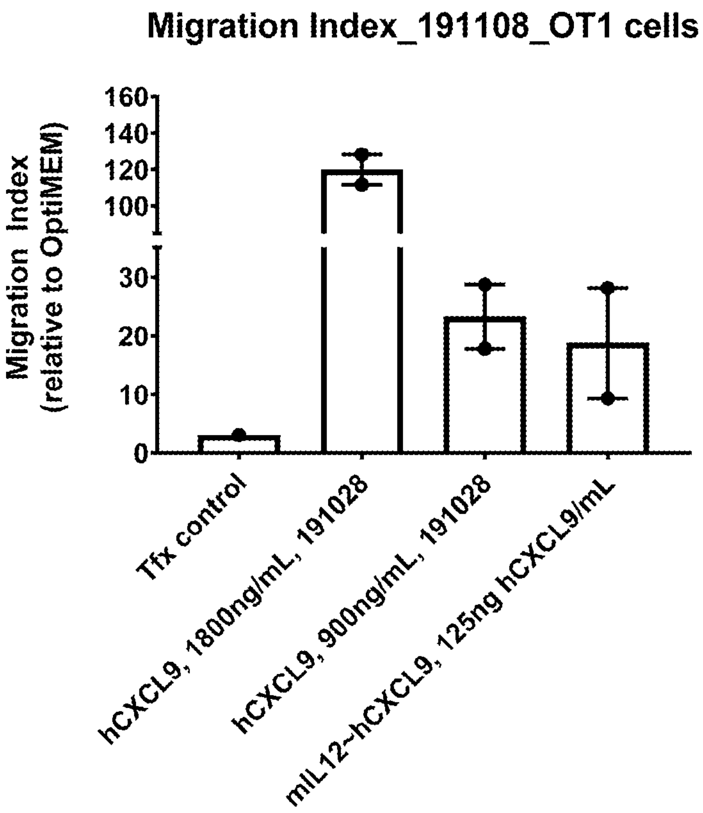
FIG. 4B. Graph illustrating transfection-derived (HEK293) human CXCL9-induced chemotaxis of SIINFEKL-pulsed (24 hr@1 μg/mL, 72 hr recovery) OT-I splenocytes through polycarbonate membranes with 5.0-micron pores (Costar 3421). Migration index is defined as the number of observed chemotactic cells after 2 hours at 37° C., normalized to the number of cells that passively migrated through the membrane towards the OptiMEM negative control.
Figure 4C:
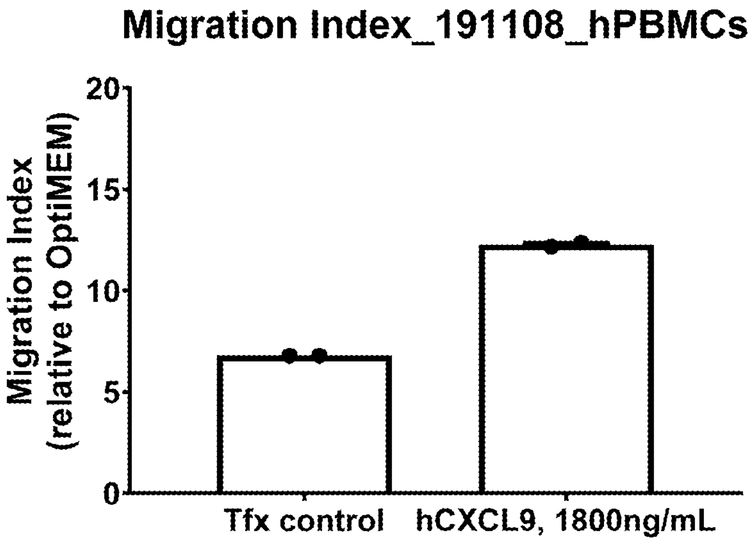
FIG. 4C. Graph illustrating transfection-derived (HEK293) human CXCL9-induced chemotaxis of human peripheral mononuclear cells (thawed from cryopreservation, rested for 24 hr in X-VIVO15 medium) through polycarbonate membranes with 5.0-micron pores (Costar 3421). Migration index is defined as the number of observed chemotactic cells after 2 hours at 37° C., normalized to the number of cells that passively migrated through the membrane towards the OptiMEM negative control.

Example 3. CXCL9-induced migration of T cells in vitro. Mammalian (HEK293) cells were transfected with CXCL9 expression vectors (CXCL9 or IL12~CXCL9), OT-I mouse splenocytes were pulsed with 1 μg/mL SIINFEKL peptide for 24 h, then allowed to recover for 72 h. The CXCL9 transfected cells were then assayed for the induction of chemotaxis of the SIINFEKL-pulsed OT-1 splenocytes through polycarbonate membranes with 5.0-micron pores. Migration index was defined as the number of observed chemotactic cells, normalized to the number of cells that passively migrated through the membrane in the OptiMEM negative control. Results are shown in FIGS. 4A, 4B, and 4C. mCXCL9, produced from mCXCL9 and mIL12~mCXCL9 expression vectors caused about 7-fold and about 3-fold increases in chemotactic cells, respectively. The increase in chemotaxis was inhibited by the addition of CXCL9 neutralizing antibodies, indicating the effect was dependent on mCXCL9.

Figure 5:
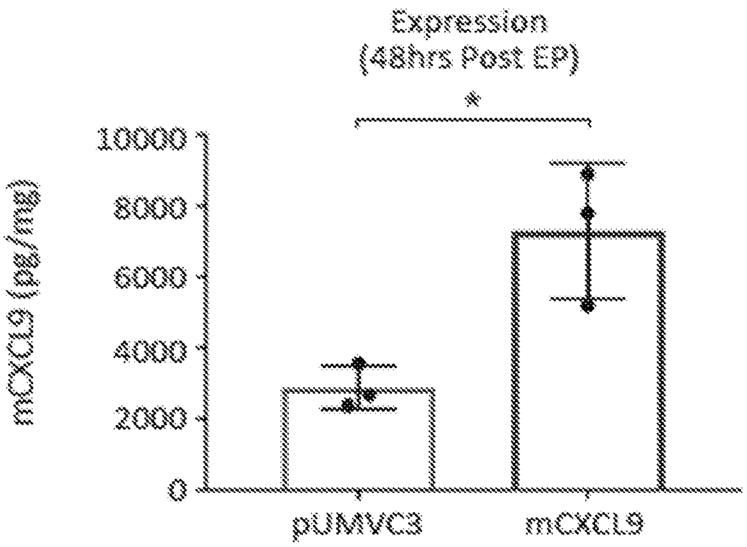
FIG. 5. Graph illustrating intratumoral expression of mCXCL9 using ELISA for mCXCL9 (DuoSet ELISA DY392) 48 hrs post-electroporation in tumor lysates from mice bearing CT26 tumors (n=3; * P<0.05; T test with Welch correction).

Example 4. In vivo expression of mCXCL9. CT-26 (colon carcinoma) tumors were implanted in mice. Tumors were subsequently treated with IT-EP pUMCV3 control vector or IT-EP mCXCL9 expression vector. 48 h after IT-EP, tumors were homogenized and assay for CXCL9 expression by ELISA (DuoSet ELISA DY392; n=3; * $P<0.05$; T test with Welch correction). The results in FIG. 5 show that the IT-EP treated tumors expressed CXCL9.

Example 5. Tumor regression in mice treated with mIL12-2A and mCXCL9. Mice were implanted with tumor cells. Anesthetized mice were subcutaneously injected with cells into the right and/or left flank. Tumor growth was monitored by digital caliper measurements until average tumor volume reached ~100 $mm^3$.

Tumors were treated on day 0 with IT-EP control vector or IT-EP IL12-2 A expression vector and on days 4 and 7 with IT-EP control vector or IT-EP CXCL9 (optionally with mcherry reported protein). Tumor volumes and survival were monitored. Mice were euthanized when the total tumor burden of the primary and contralateral reached 2000 $mm^3$.

Figure 6:
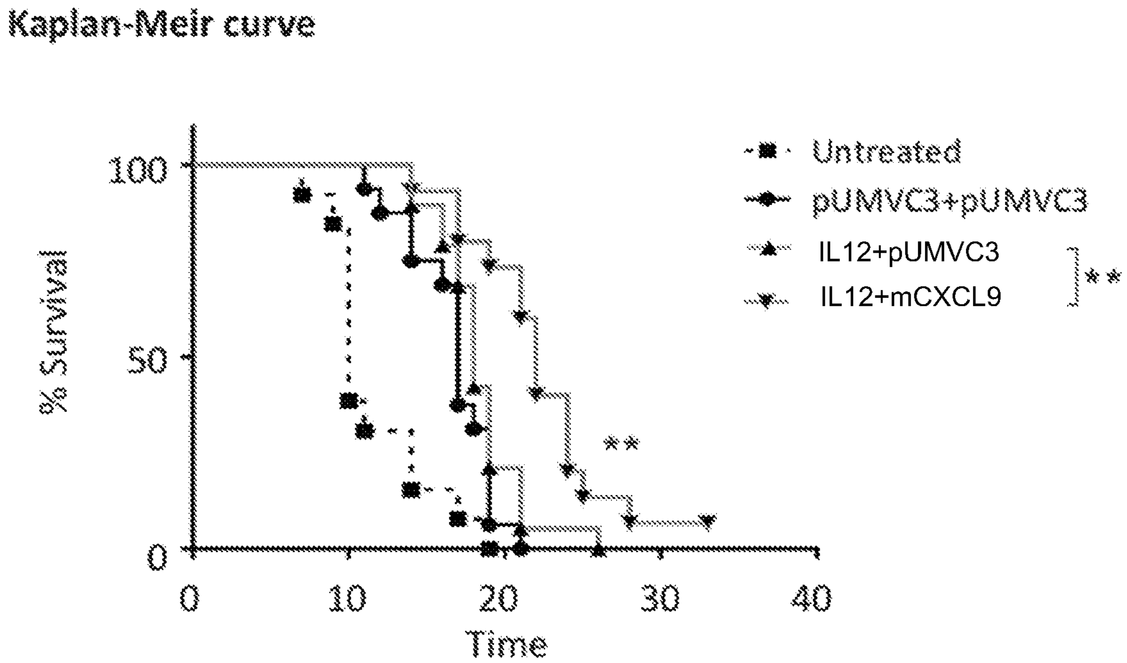
FIG. 6. Graphs illustrating Kaplan-Meir curves in untreated mice and mice treated with control vector, IT-EP IL12-2A alone, or IT-EP IL12-2A in combination with IT-EP CXCL9 (** P<0.005; log-rank (Mantel-Cox) test).

The data, shown in FIG. 6, show that mice treated with IT-EP mIL12-2A plus mCXCL9 therapy showed increased survival compared to untreated mice, mice treated with control vehicle, or mice treated with IT-EP mIL12-2A alone. Tumor bearing mice treated with IT-EP mIL12-2A plus mCXCL9~mCherry therapy also showed decreased primary (treated) and contralateral (untreated) tumor progression (FIG. 7A-B).

Figure 8:
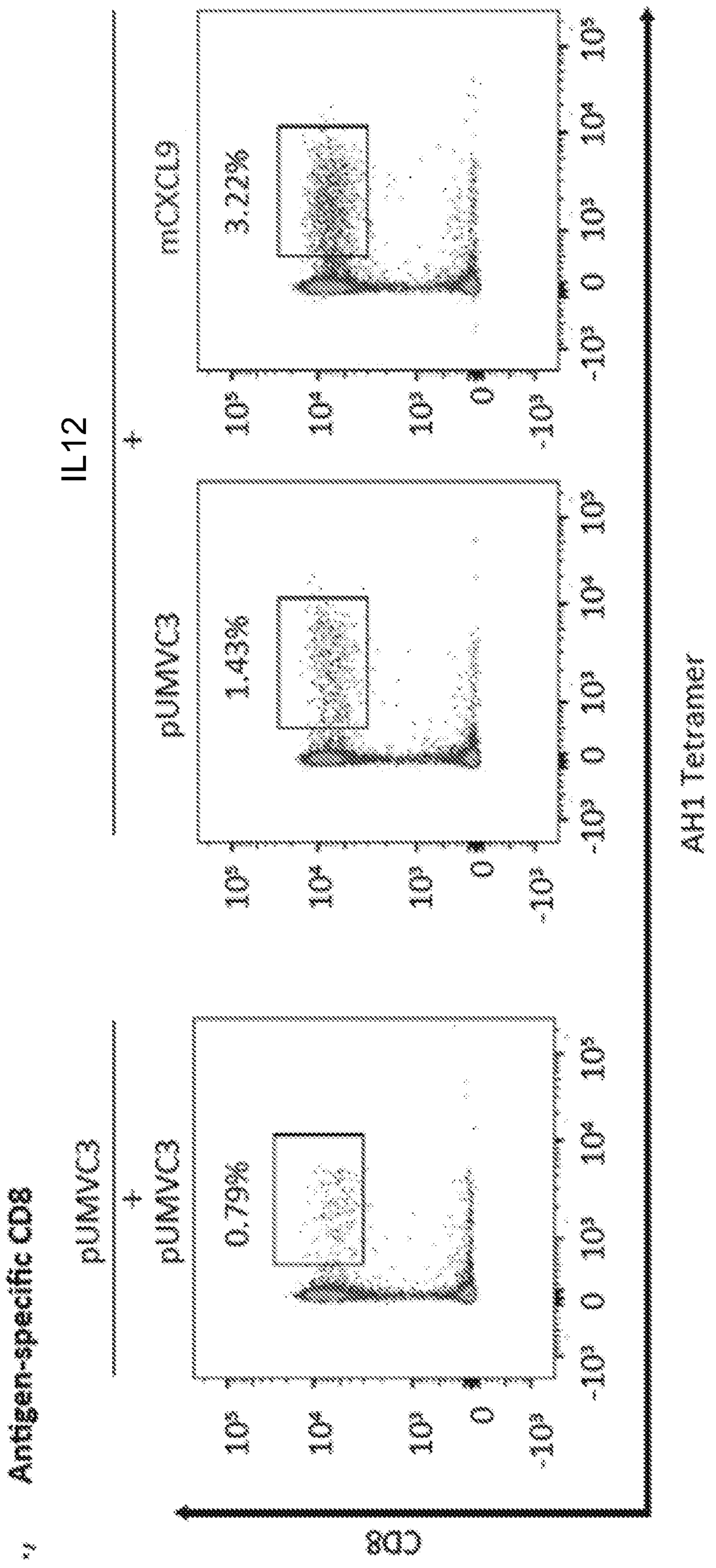
FIG. 8. Flow cytometric analysis of splenocytes from mice treated with IT-EP pUMCV3 or IL12-2A on day 0 and IT-EP pUMVC3 or mCXCL9 on days 4 and 7
Figure 9:
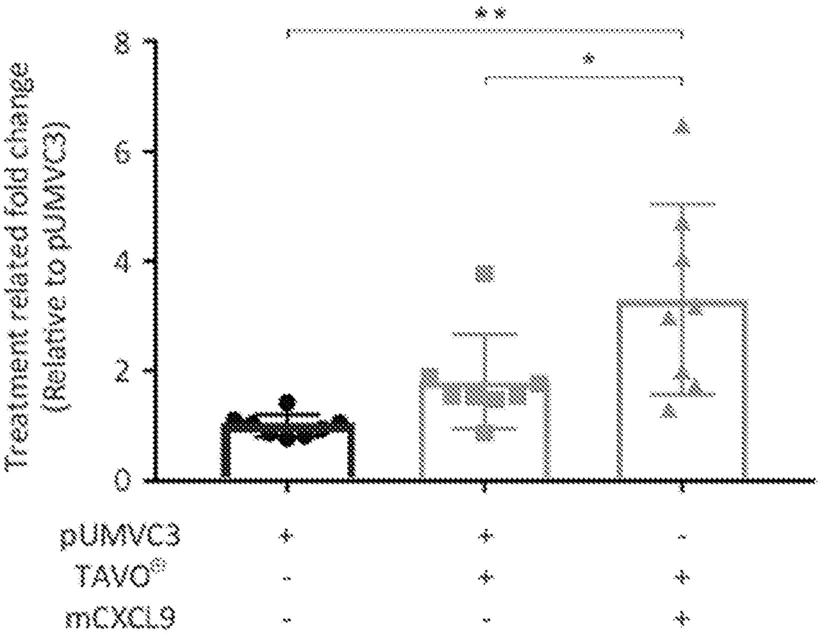
FIG. 9. Graph illustrating fold increase in the number of AH1+CD8+ T cells in mice tumors treated with control vector (pUMC3), IT-EP IL12 (IL-12 p35-P2A-IL-12 p40), or IT-EP IL12 plus IT-EP CXCL9. N=2 independent experiments with 3-5 animals/group; * P<0.05, ** P<, 0.005; One way ANOVA.

Example 6. IT-EP IL12-2A+IT-EP CXCL9 drives systemic expansion of antigen specific CD8 and short-lived effector cells (SLECs). On day −8, mice were implanted with tumor as described above. On day 0, tumors were treated with IT-EP mIL12-2A. On days 4 and 7, mice were treated with control plasmid or mCXCL9 (n=3/group) using IT-EP as described above. On day 9, spleens were harvested and $CD3^+CD8^+$ cells analyzed by FACS. FIG. 8 shows that $CD3^+$ T cell populations were significantly increased in mice treated with IL12-2A+CXCL9. Fold increase in the number of AH1+CD8+ T cells is shown in FIG. 9.

Example 7. Intratumoral CXCL9 synergizes with IL-12 to modulate the tumor microenvironment, expand antigen-specific T cells, and control contralateral tumor growth. A mouse model was used to evaluate intratumoral expression post electroporation.

CT26 tumors were implanted in mice on day −7. For NanoString analysis and flow based assays single, tumor model was used. Mice were treated on day 1 with IT-EP with a suboptimal dose of IL12-2A followed by treatment on days 4 and 7 with IT-EP using 100 μg of either mCXCL9 or pUMVC3. Tumor and immune response were then monitored. Tumor and splenocytes were harvested 2 days after last EP (i.e., Day 9) for NanoString and flow based analysis. Alternatively, tumor volumes were measured three times a week for regression/survival studies. Gene expression changes in electroporated CT26 lesions were assessed by NanoString nCounter4® technology. Intratumoral expression of mCXCL9 was confirmed using ELISA for mCXCL9 48 hrs post-electroporation in tumor lysates from mice bearing CT26 tumors (n=3; * $P<0.05$; T test with Welch correction).

Figure 28A:
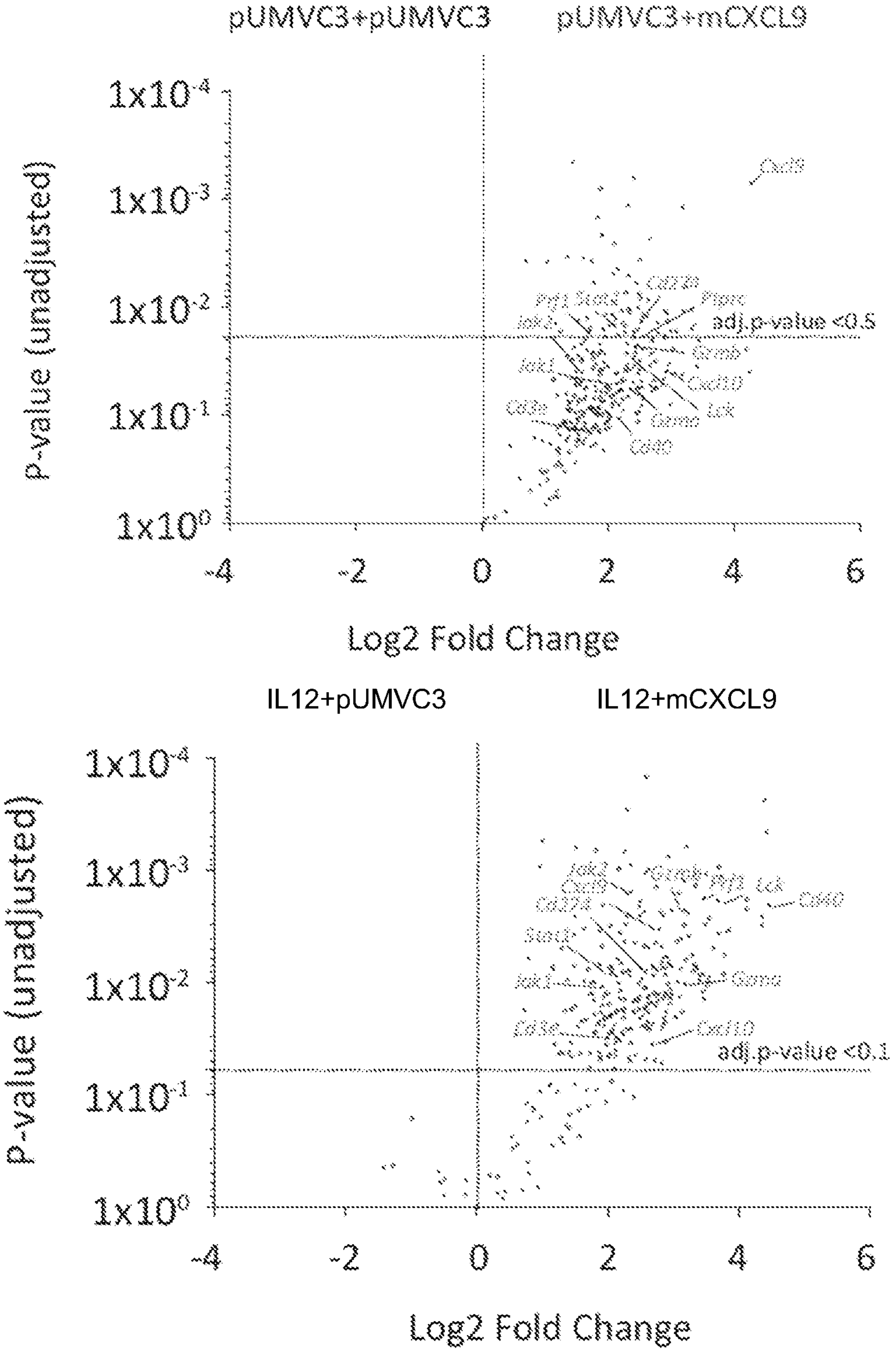
FIG. 28A. Volcano plots displaying p-values and log 2 fold change for the indicated genes. Differential gene expression was examined in mice treated with mCXCL9 alone (top panel) and mice treated with mCXCL9 in combination with IL12 (bottom panel). Horizontal lines indicate False Discovery Rate (FDR) thresholds.
Figure 28B:
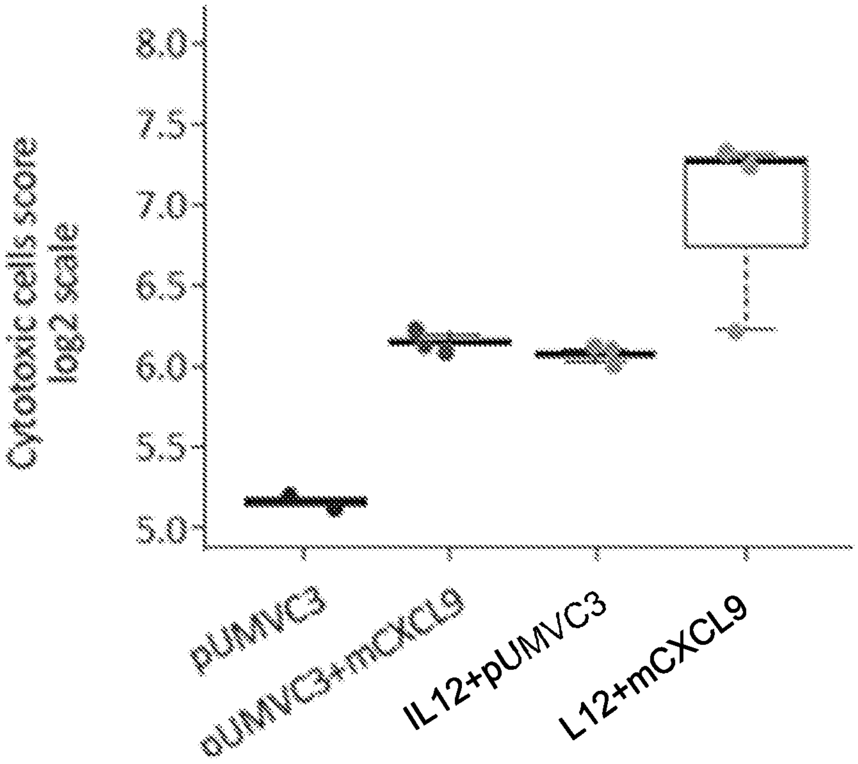
FIG. 28B. Graph illustrating 'Cytotoxic immune cells' cell type scores. Each cell type's score (Log 2 scale) has been centered to have mean 0.

Volcano plots displaying p-values and log 2 fold change for each gene were generated in mice treated with CXCL9 alone or CXCL9 in combination with IL12-2A (FIG. 28A). Analysis of cell type scores showed in increase in Cytotoxic immune cells in response to treatment with either CXCL9 or IL12-2A. A synergistic increase in Cytotoxic immune cell scores was further seen when CXCL9 was administered in combination with IL12-2A. 'Cytotoxic immune cells' cell type scores are shown in FIG. 28B.

Flow cytometric analysis of was used to analyze splenocytes in treated mice. Antigen specific AH1+CD84 T cells were measured via tetramer analysis (Immudex). Cells are gated on Singlets<Live<CD3-CD4− splenocytes (FIG. 8). The fold increase in the number of AH1+CD8+ T cells compared to empty vector control (N=2 independent experiments with 3-5 animals/group: * $P<0.05$,  $P<0.005$; One way ANOVA). In mice treated with control plasmid only, 0.79% of AH1 tetramer were CD8+. In mice treated with IT-EP IL12-2A, 1.43% of AH1 tetramer were CD8+. In mice treated with IT-EP IL12-2A and CXCL9, 3.22% of AH1 tetramer were CD8+. Fold increase in the number of AH1+ CD8+ T cells is shown in FIG. 9**.

The results show that IT-EP CXCL9 can substantially enhance anti-tumor immune response in animal previously treated with a suboptimal dose of IT-EP IL12-2A.

CD3 Half-BiTE

Figure 12A:
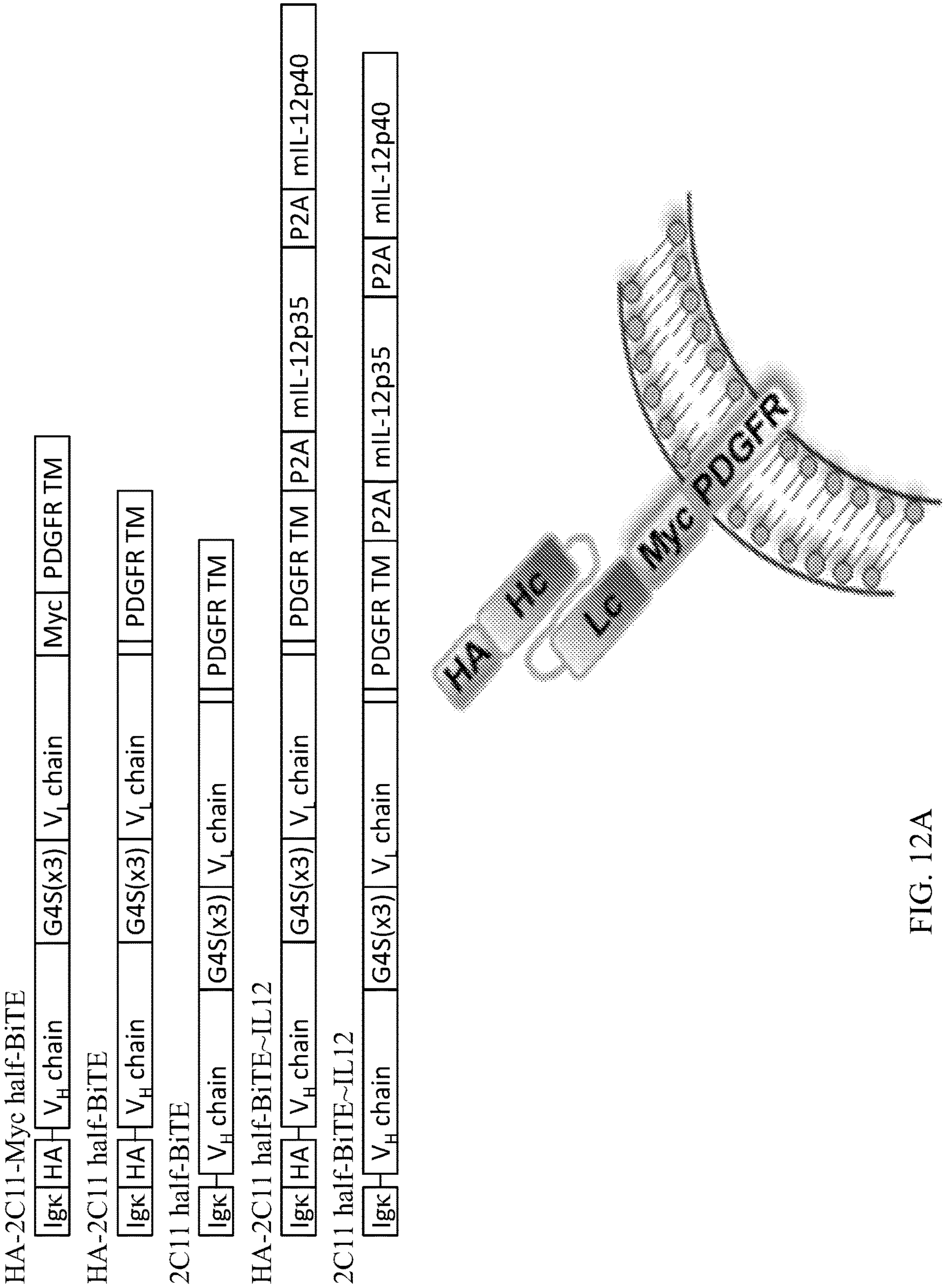
FIG. 12A. Illustrations of the mouse CD3 half-BiTE expression cassettes for HA-2C11-Myc scFv, HA-2C11 scFv, 2C11 scFv, and 2C11 scFv~hIL12.
Figure 12B:
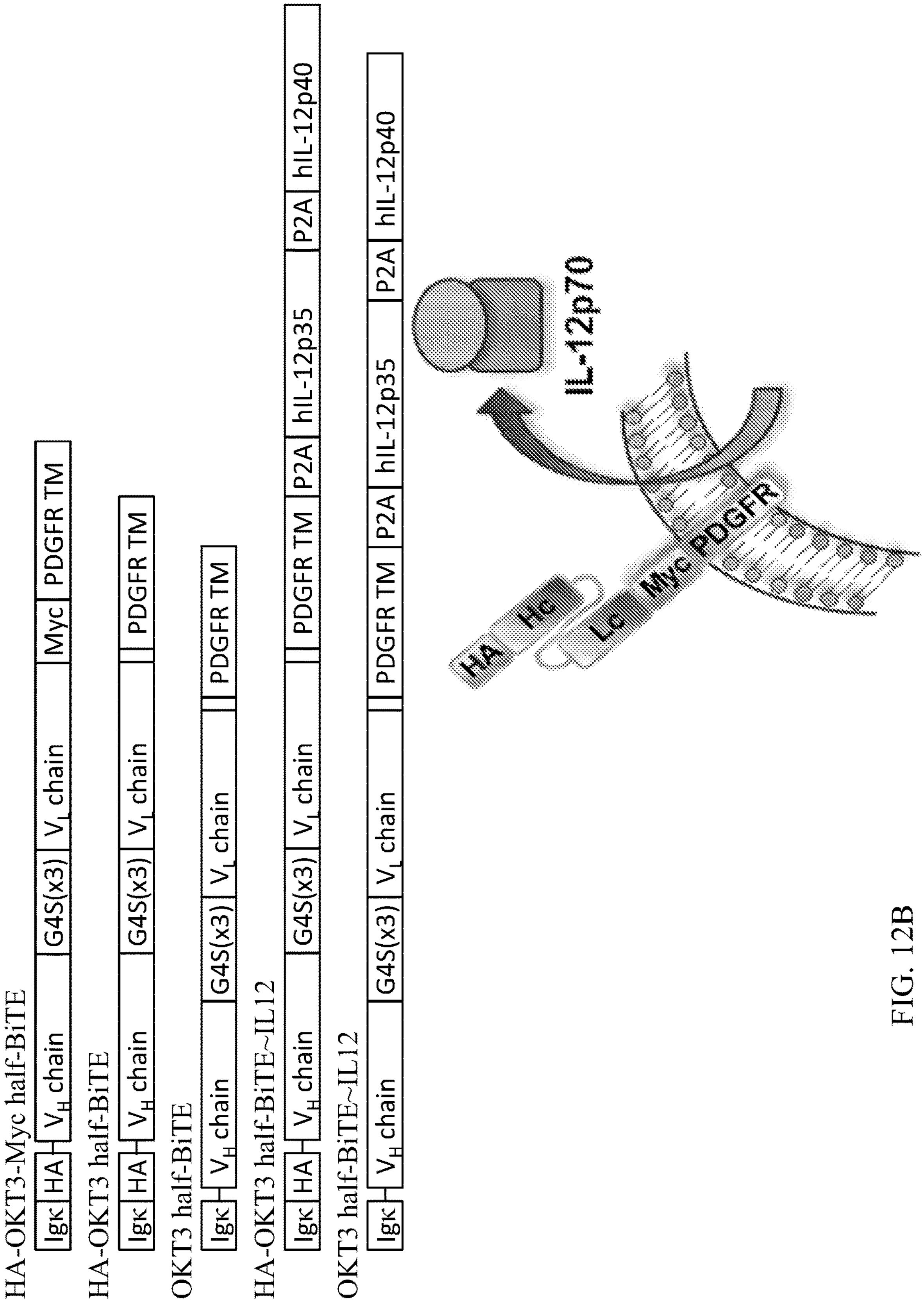
FIG. 12B. Illustrations of human CD3 half-BiTE expression cassettes for HA-OKT3-Myc scFv, HA-OKT3 scFv, OKT3 scFv, HA-OKT3 scFv~hIL12, and OKT3 scFv~hIL12.

Example 8. The Half-BiTE expression cassettes were made in a manner similar to that described above for the generation of CXCL9 plasmids (FIGS. 12A and 12B).

Figure 13:
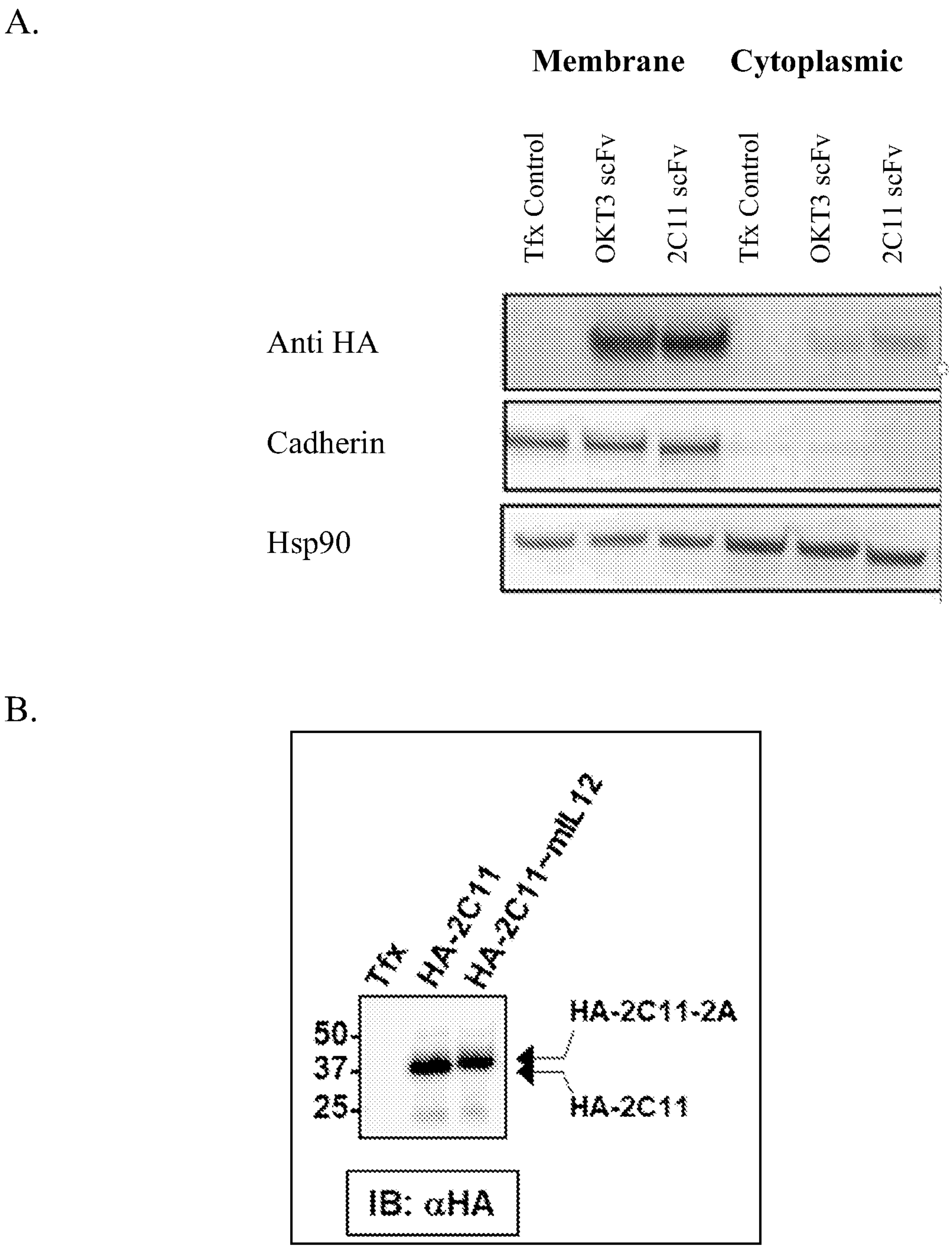
FIG. 13. Western blots showing: (A) expression of anti-CD3 scFv in HEK293 cells transfected with HA-OKT3 scFv and HA-2C11 scFv CD3 half-BiTE expression vectors, and (B) expression of CD3 half-BiTE in 816-F10 cells transfected with HA-2C11 scFv and HA-2C11 scFv~mIL12 expression vectors.

Example 9. Protein expression. The OKT3 scFv and 2C11 scFv, expression vectors were transfected into HEK293 cells in vitro. HA-2C11 scFv and HA-2C11 scFv~mIL12 were transfected into B16-F10 tumor cells. 24 h after transfection, supernatants were collected, and proteins were separated by gel electrophoresis. CD3 scFv, Cadherin (membrane protein) and Hsp90 were detected by Western blot analysis. The results, shown in FIG. 13 show that the expression vectors expressed the CD3 scFv protein. The CD3 scFv protein was predominantly located in the membrane fraction. expression vectors HA-OKT3 scFv, OKT3 scFv-hIL12 expression vectors were transfected into HEK293 cells in vitro. 72 h after transfection, cells were analyzed by FACS to detect CD3 scFv (FIG. 14A-C). HA-2C11 scFv and HA-2C11 scFv-mIL12 expression vectors were transfected into B16-F10 cells. Cells were analyzed by FACS to detect surface expression of CD3 scFv (FIG. 14D). Expression of IL12 from IL12-2A and HA-2C11 scFv~mIL12 expression vectors is shown in FIG. 14E.

Figure 15:
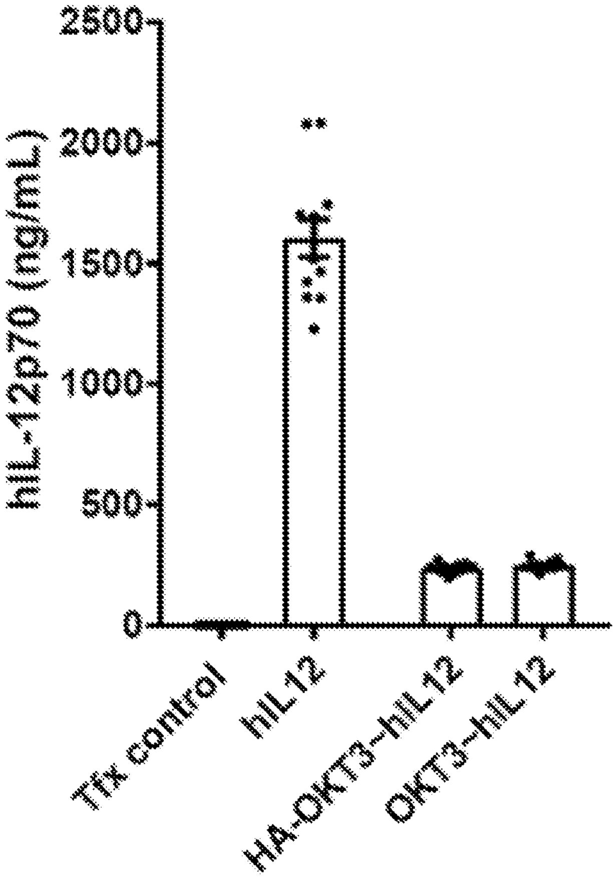
FIG. 15. Graph illustrating IL12p70 expression in HEK293 cells following transfection with hIL12-2A, HA-OKT3 scFv--hIL12, and OKT3 scFv~hIL12 expression vectors.

HA-OKT3 scFv-hIL12 and OKT3 scFv-hIL12 expression vectors were transfected into HEK293 cells in vitro. 72 h after transfection cells supernatant was collected and assayed for IL12p70 by ELISA. The results confirm that cells transfected with the HA-OKT3 scFv~hIL12 and OKT3 scFv~hIL12 expression vectors express and secrete hIL12p70 (FIG. 15).

Figure 16C:
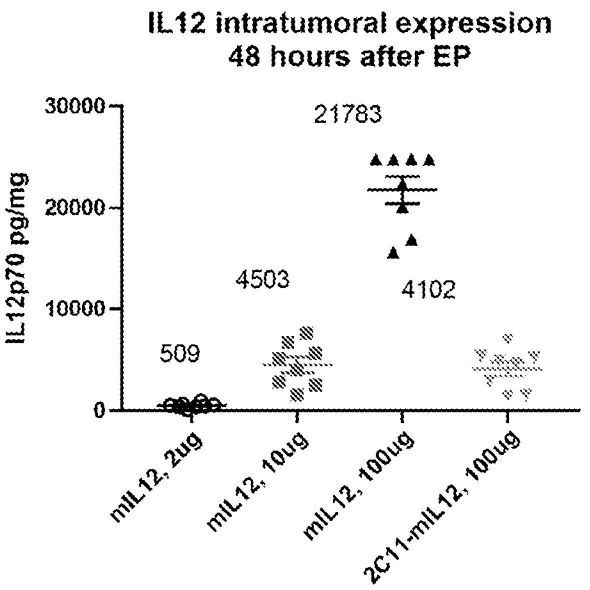
FIG. 16C. Graph illustrating IL12p70 expression in B16-F10 cells following intratumoral electroporation of mIL12-2A and HA-2C11 scFv~mIL12 expression vectors.

In vivo expression: Mice were inoculated with B16F10 melanoma cells or 4T1 breast cancer cells on day −7. On day 0, tumors were treated with IT-EP HA-2C11 scFv~hIL12 (FIG. 16). FIG. 16A-B show the CD3 half-BiTE is expressed on the surface of melanoma and breast cancer tumors following IT-EP. FIG. 16C shows that following IT-EP of HA-OKT3 scFv~hIL12, the expression vector also expresses IL-12.

Figure 17:
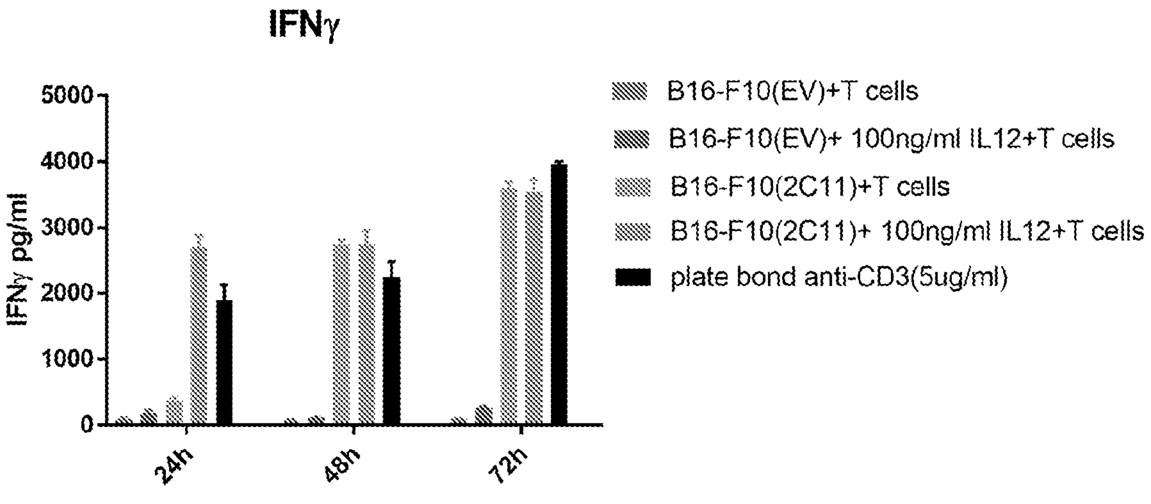
FIG. 17. Graph illustrating induction of INFγ expression following co-culture of naïve mouse splenocytes with B16F10 cells transfected in vitro with control vector (EV control), 2C11 scFv expression vector with or without recombinant mouse IL12, or with plate bound anti-CD3 (positive control).
Figure 18:
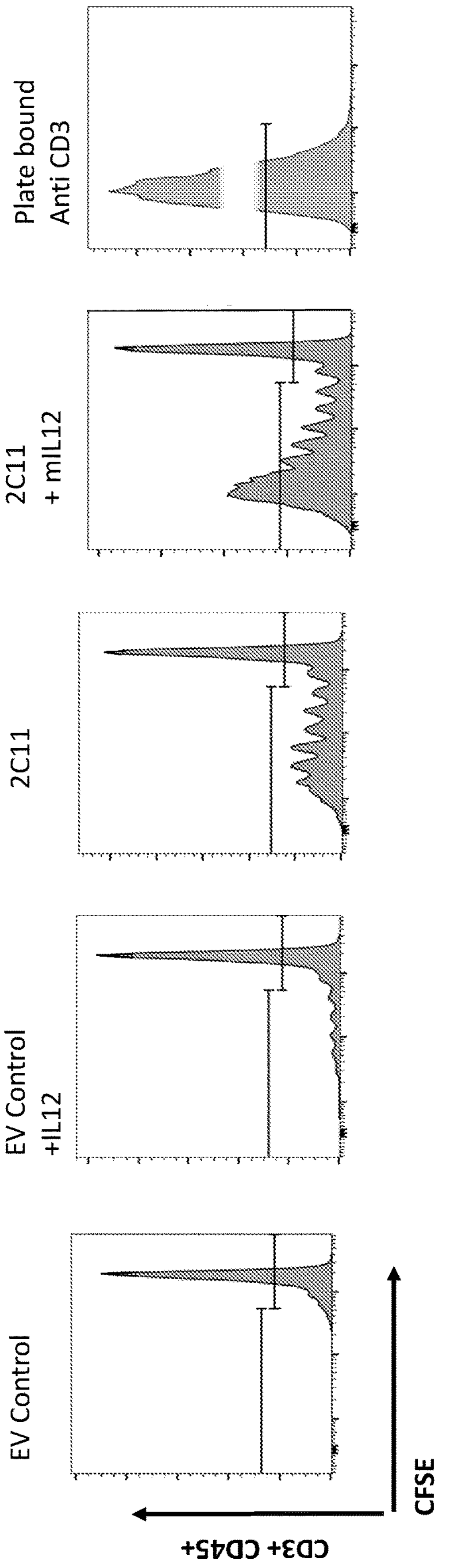
FIG. 18. Graphs illustrating FACS analyses of proliferation of CFSE labeled CD3+CD45+ T cells following co-culture of naïve mouse splenocytes with B16F10 cells transfected in vitro with control vector (Tfx control), 2C11 scFv expression vector with or without recombinant mouse IL12, or with plate bound anti-CD3 (positive control).

Example 10. In vitro Functional assay. B16F10 cells were transfected in vitro with control vector and 2C11 scFv expression vector with or without recombinant mouse IL12 Transfected B16F10 cells were then co-cultured with naïve mouse splenocytes for 23, 48, or 72 hours. Following co-culture, supernatants were assayed for IFNγ and cell proliferation was evaluated by FACS. Plate bound anti-CD3 was used as a positive control. The results, shown in FIG. 17, show that IFNγ expression was substantially increased when splenocytes were co-cultured with B16F10 expressing 2C11 scFv. FACS analyses were performed to analyze proliferation of CFSE labeled CD3-CD45+ T cells following co-culture of naïve mouse splenocytes with B16F10 cells transfected in vitro with control vector (Tfx control), 2C11 scFv expression vector with or without recombinant mouse IL12, or with plate bound anti-CD3 (positive control) (FIG. 18).

Figure 19:
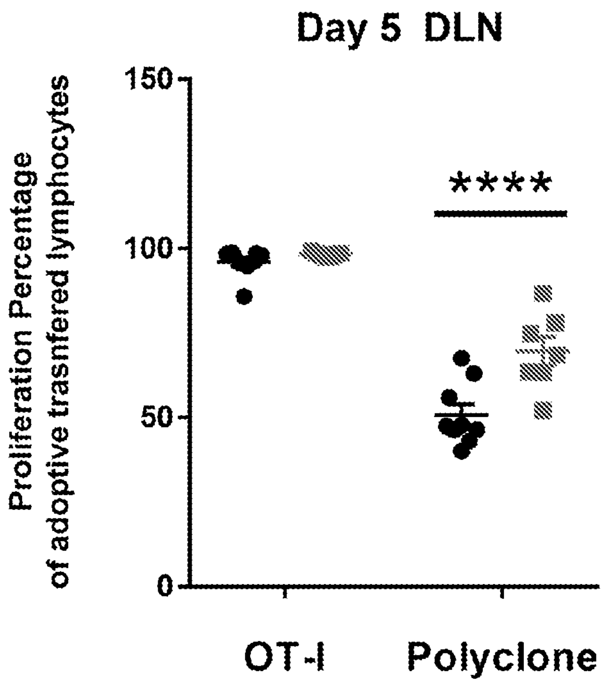
FIG. 19. Graph illustrating in vivo OT-1 and polyclonal T cell proliferation in DLN in B16-OVA tumor model mice treated with 2C11 scFv IT-EP or negative control.
Figure 20:
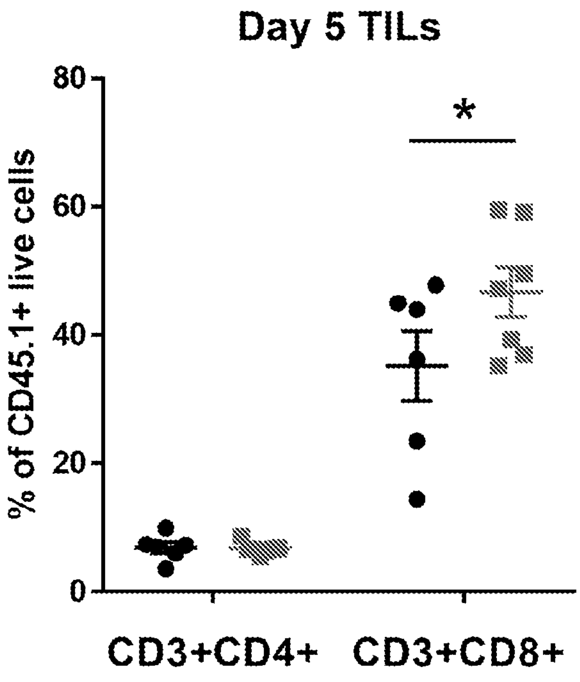
FIG. 20. Graphs illustrating an increased CD8+ T cells in CD45.1+ live cells in TILs in B16-OVA tumor model mice treated with 2C11 scFv IT-EP or negative control.
Figure 21:
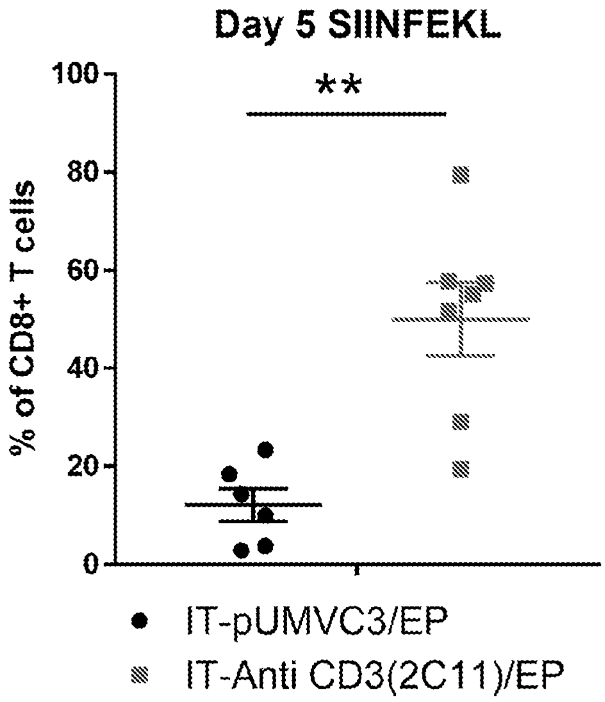
FIG. 21. Graph illustrating an increased antigen specific (SIINFEKL+) CD8+ T cells in TILs in B16-OVA tumor model mice treated with 2C11 scFv IT-EP or negative control.

Example 11. In Nivo functional assay. On day −9, B16-OVA cells were implanted in mice (n=8/group). On day 0, tumors were treated by IT-EP with 2C11 scFv expression vector or empty vector (negative control). On day 0, mice were also implanted, by adoptive transfer, with a 1:1 mix of OT-1 (GFP) $CD8^+$ cells T cells and naïve mouse lymphocytes. On day 5, adoptive transferred T cell proliferation in spleen and draining lymph node (DLN) were examined by FACS. Endogenous T cell populations and SIINFEKL (SEQ ID NO:90) expression in tumor infiltrating lymphocytes (TILs) were also examined by FACS. An increase in polyclonal T cell proliferation in DLN was observed in mice treated with IT-EP 2C11 scFv (FIG. 19). Increases in OT-I and polyclonal T cell populations were also observed in splenocytes in mice treated with IT-EP 2C11 scFv. An increase CD8+ T cells in CD45.1+ live cells in TILs was observed in B16-OVA tumor model mice treated with 2C11 scFv IT-EP (FIG. 20). An increase antigen specific (SIINFEKL+)(SEQ ID NO:90) CD8+ T cells in TILs was observed in B16-OVA tumor model mice treated with 2C11 scFv IT-EP FIG. 21. The results demonstrate that IT-EP with 2C11 results in proliferation of polyclonal T cells and enhanced tumor specific T cell response in the tumor.

Example 12. In vivo cytotoxic T cells killing assay. Lymphocytes were harvested from naïve mice and labeled with CFSE. Label lymphocytes were then either pulsed with OVA peptide to activate T cells (CFSE, treated) or left untreated ($CFSE^{lo}$, unpulsed). $CFSE^{hi}$ and $CFSE^{lo}$ lymphocytes were combined in an about 1:1 ratio for administration into the tumor bearing mice.

On Day −7, mice were implanted with B16-OVA tumor cells (B16 melanoma cells expressing ovalbumin) into the flank of c57/bl/6 mice. On Day 1, mice were treated with IT-EP anti-2C11 scFv or empty vector (pUMVC3). On day 2, mice administered pulsed target cells (cells pulsed with 2 μg/ml SIINFEKL (SEQ ID NO: 90) peptide labeled with 1 μM CFSE (5(6)-carboxyfluorescein N-hydroxysuccinimidyl ester)) and unpulsed cells by adoptive transfer. 18 hours after adoptive transfer, spleen and draining lymph nodes were collected and analyzed.

Figure 22:
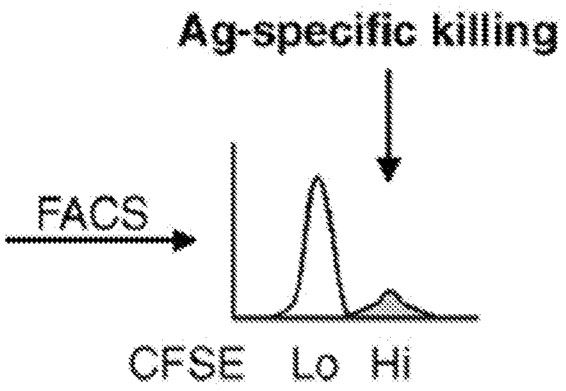
FIG. 22. FACS analysis of scan CFSE cells displaying (Hi) or not displaying (Lo) $OVA_{257-264}$ peptide showing increase lysis of $OVA_{257-264}$ peptide-displaying CFSE cells in B16-OVA tumor containing mice treated with 2C11 scFv IT-EP compare with negative transfected control.

Western blot analysis indicated the tumors expressed the CD3 half-BiTE. On day 3, 18 h after adoptive transfer, DLN were isolated. DLNs were then analyzed by FACS for the presence of $CFSE^{lo}$ and $CFSE^{hi}$ cells. The results, shown in FIG. 22, show a substantial decrease in the number of $CFSE^{hi}$ cells, indicated antigen-specific killing of cells displaying the OVA peptide. The decrease was quantitated using the following formula:

$$\% \text{ lysis} = 1 - \frac{[\text{pulsed/unpulsed of treated}]}{[\text{pulsed/unpulsed of naïve}]}$$

$$\% \text{ lysis} = 1 - \frac{\begin{bmatrix}\text{pulsed } (CFSE^{hi})EP \text{ anti-}CD3 \div \\ \text{unpulsed } (CFSE^{lo})EP \text{ anti-}CD3\end{bmatrix}}{\begin{bmatrix}\text{pulsed } (CFSE^{hi})\ EP\ contol \div \\ \text{unpulsed } (CFSE^{lo})\ EP \text{ control}\end{bmatrix}}$$

Figure 23:
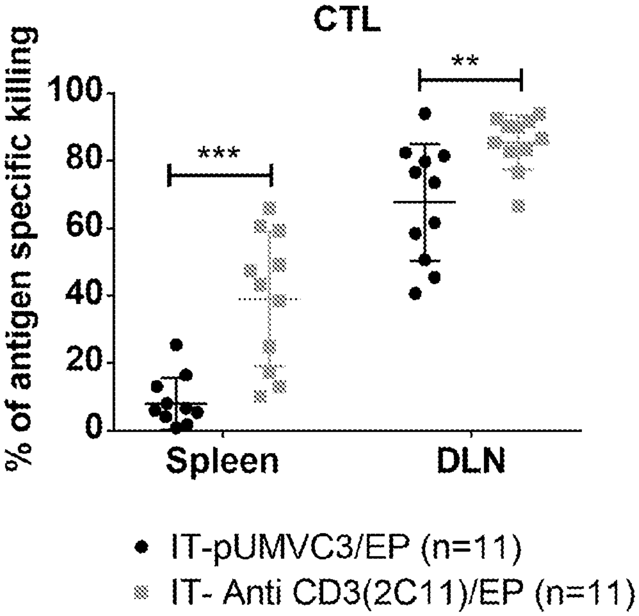
FIG. 23. Graph illustrating increase in lysis of adoptive transferred $OVA_{257-264}$-displaying CFSE cells in B16-OVA tumor containing mice treated with IT-EP CD3 half-BiTE. The increased T cell killing ability observed in both spleen and driven lymph node.
Figure 24:
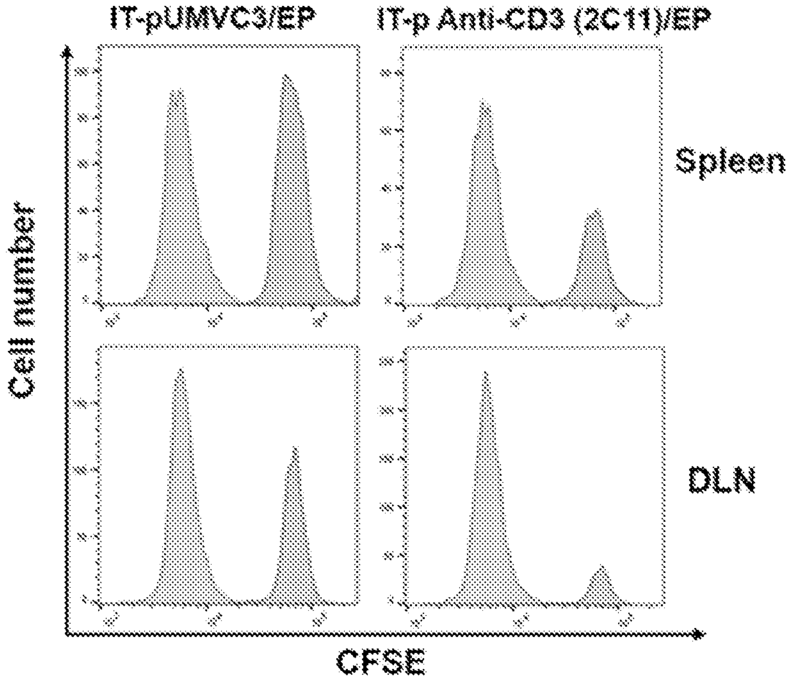
FIG. 24. FACS analysis of CFSE cells showing increase tumor-specific killing of OVA expressing cells in mice treated with IT-EP CD3 half-BiTE.

Results are shown in FIG. 23, showing an increase in lysis of $CFSE^{hi}$ cells in both splenocytes (SP) and DLN. FACS analysis of CFSE cells is shown in FIG. 24. In control mice, percent lysis of $CFSE^{hi}$ cells was 54.63±12.79%. In mice receiving IT-EP CD3 half-BiTE therapy, percent lysis of $CFSE^{hi}$ cells was 82.44±11.35%. OVA expressing cells were specifically killed in mice treated with IT-EP CD3 half-BiTE, indicating the enhancement of an antigen-specific cytotoxic T cell response. Activated T lymphocytes were preferentially retained in tumors expressing a CD3 half-BiTE. Thus, electroporation of nucleic acid encoding a CD3 half-BITE provides an effective tumor therapy.

IT-EP of CD3 half-BiTE resulted in increased targeting of tumor cells by T cells. Flow cytometric analysis of cells from spleen and draining lymph node demonstrating significant antigen specific killing in the IT-EP anti-CD3(2C11) group (FIGS. 23 and 26).

Example 13. Tumor Regression

Figure 25:
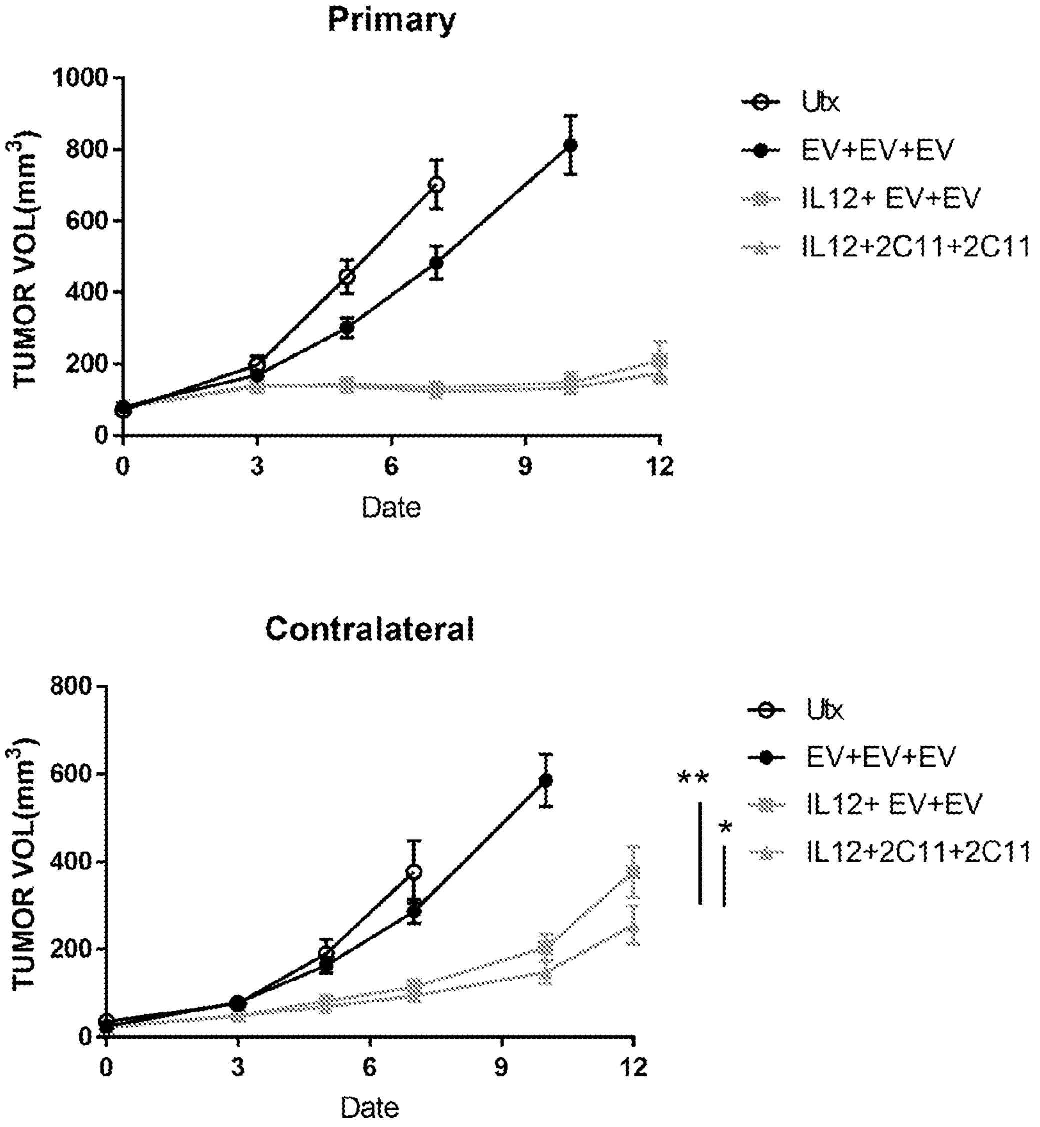
FIG. 25. Graph illustrating tumor progression of treated tumors in melanoma model mice treated with control, IL-12, or IL-12 plus CD3 half-BiTE IT-EP therapy.

A. Melanoma: On Day −7, mice were implanted with B16 melanoma cells. On Day 0, mice were treated with IT-EP with control empty vector, expression vector encoding IL12-2A. On days 4 and 7, mice were treated with IT-EP control vector or IT-EP 2C11 (CD3 half-BiTE) expression vector. Tumor progression was monitored every three days. The results show improved contralateral (untreated) tumor regression in mice treated with IL12-2A plus CD3 half-BiTE compared to treatment with IL12-2A alone (FIGS. 25A and 25B).

Figure 26C:
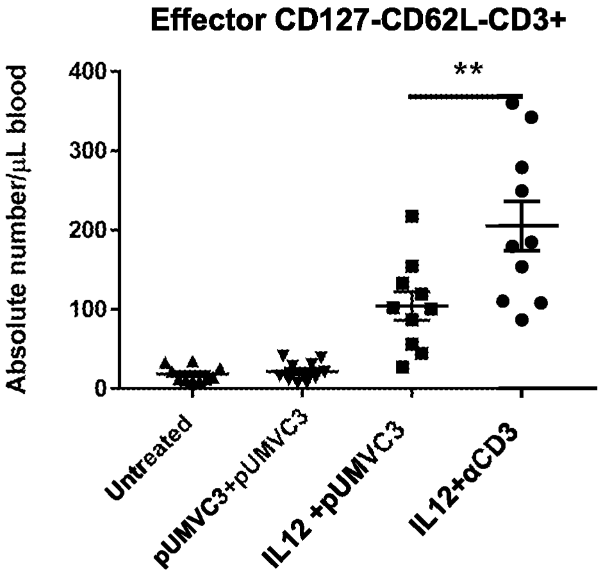
FIG. 26. (A) Graph illustrating tumor progression in breast cancer model mice treated with control, LL-12, or IL-12 plus 2C11 IT-EP therapy. (B) Graph illustrating lung metastasis nodules in 4T1 breast cancer model mice treated with control, IL12-2A or IL12-2A plus 2C11 IT-EP therapy. (C) Graph illustrating the absolute number of effector T cells (CD127-CD62L-CD3+) per μL peripheral blood in 4T1 breast cancer model mice treated with control. IL12-2A or IL12-2A plus 2C11 IT-EP therapy.

B. Breast Cancer: On Day −7, mice were implanted with 411 breast cancer cells. On Day 0, mice were treated with IT-EP with control vector, or IT-EP IL12-2A. On days 4 and 7, mice were treated with IT-EP with control vector or IT-EP 2C11 (CD3 half-BiTE) expression vector. Tumor progression was monitored every three days. The results show that combining IT-EP IL12-2A with CD3 half-BiTE therapy improves breast cancer tumor regression (FIG. 26A). IL12-2A plus CD3 half-BiTE therapy was also effective in treating lung metastases nodules in 4T1 breast cancer model mice (FIG. 26B). The absolute number of effector T cells (CD127-CD62L-CD3+) per μL peripheral blood in 4T1 breast cancer model mice is shown in FIG. 26C.

CXCL9/CD3 Half-BITE Combination Therapy

Figure 29A:
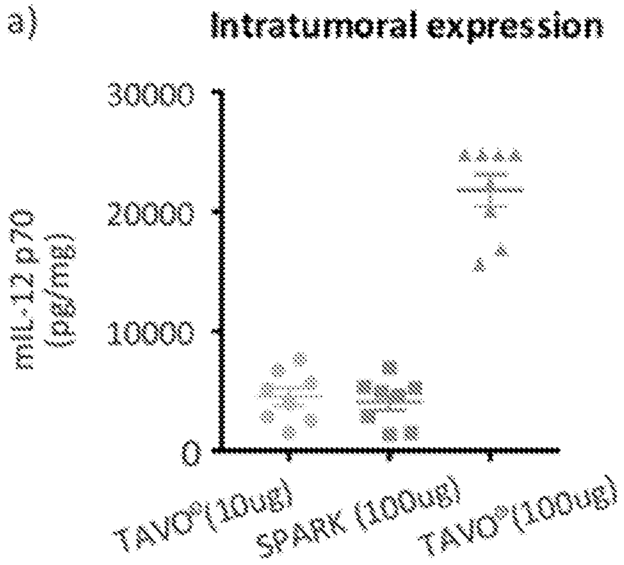
FIG. 29A. Graph illustrating IL12 p70 expression in 48 hr post electroporation in tumor lysates from mice bearing B16.F10 tumors after treatment with 10 μg or 100 μg of IL12-2A (TAVO) on days 1, 5, and 8, or 100 μg of IL12-~CXCL9 or CD3 half-BiTE~IL12 (SPARK) on each of days 1, 5, and 8 (n=8 animals; DuoSet ELISA DY419).

Example 14. CXCL9 plus CD3 half-BiTE combination therapy. B16.F10 tumor bearing mice were treated with IT-EP (days 1, 5, and 8) with 10 μg IL-12 expression plasmid, 100 μg IL-12 expression plasmid, or 100 μg IL-12-CXCL9/CD3 half-BiTE~IL12. For IL-12~CXCL9/CD3 half-BiTE-IL12, either IL-12~CXCL9 or CD3 half-BiTE~IL12 is administered on each of days 1, 5, and 8 provided the subject receives at least one IT-EP treatment with IL-12~CXCL9 and one IT-EP treatment with CD3 half-BiTE~IL12. Intratumoral expression of IL-12 was confirmed (ELISA) 48 hr post IT-EP in tumor lysates (n=8 animals). IL12 70 expression is shown in FIG. 29A. Growth of primary (electroporated lesion) and contralateral (non-electroporated lesion) B16.F10 lesions was measured 12 days after IT-EP therapy (FIG. 29B-C). With respect to IL12 p70 expression, animal treated with IT-EP with 10 μg IL12-2A expressed the same amount of IL12 as animals treated with 100 μg IL-12~CXCL9/CD3 half-BiTE~IL12 (FIG. 29A). Contralateral tumors were significantly smaller in IL-12~CXCL9/CD3 half-BiTE~IL12 treated animals compare to 10 μg IL12-2A treated mice (8-10 animals/group; statistical significance determined using two way ANOVA * $p<0.05$), illustrating enhancement of tumor regression using IT-EP IL-12~CXCL9/CD3 half-BiTE~IL12 therapy.

CLTA-4 scFv

Example 15. Intratumoral expression of anti-CTLA4 scFv. Mouse IgG1 ELISA (ab133045) was performed on RENCA tumor lysates to quantify intratumoral expression of anti-CTLA4 scFv. Expression of anti-CTLA4 scFv was detected only in the tumor and not in the serum highlighting local expression of the antibody upon intratumoral electroporation.

Figure 30:
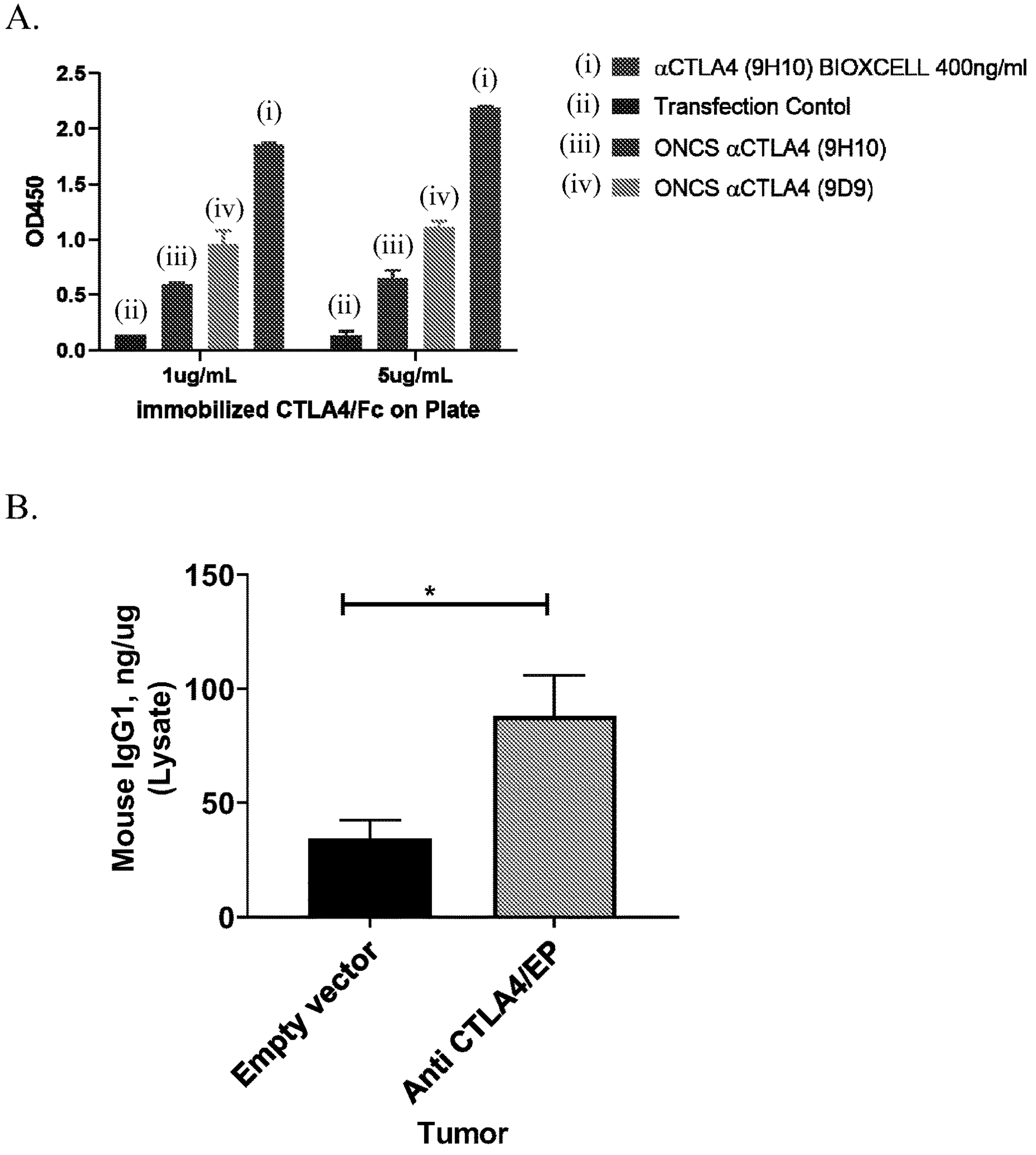
FIG. 30. Graph illustrating; (A) anti-CTLA4 scFv transfection supernatant binding to recombinant mCTLA-4/Fc, and (B) detection of anti-CLTA-4 scFv on RENCA tumor lysates.

Plasmid encoded anti-CTLA4 scFv bound to recombinant CTLA4 protein. Transfection-derived secreted anti-CTLA4 (scFv) were evaluated for their binding capacity to CTLA-4. Recombinant mouse CTLA-4/human IgG1 chimera (R&D Systems) were immobilized in 96-well plates (1 or 5 μg/mL, or 50 μg/well or 250 μg/well) for 18 hr at room temperature. Wells were washed three times with 0.1% Tween in PBS and blocked with 1% BSA in PBS. Conditioned medium from HEK293 cells transfected with 9H10-scFv (168 ng/mL) or 9D9-scFv (130 ng/mL) was added to the wells, and incubated for 2 h at room temperature. Wells were washed three times, and anti-mouse IgG-horseradish peroxidase (Jackson ImmunoResearch, 0.2 μg/mL) were added and incubated for 1.5 hours at room temperature. Wells were again washed three times, developed with HRP Substrate Reagent (R&D Systems) and stopped with Stop Solution, 2N sulfuric acid (R&D Systems). Optical density of each well was measured at 450 nm. Graphical representation of average OD values for each condition group are displayed demonstrating binding of plasmid derived anti CTLA4 scFv to recombinant CTLA4 protein (FIG. 30A).

Mouse IgG1 ELISA (ab133045) was performed on RENCA tumor lysates to quantify intratumoral expression of anti-CTLA4 scFv. Expression of anti-CTLA4 scFv was detected in the tumor (FIG. 30B). Statistically significant levels of anti-CTLA4 scFv was not observed in serum, indicating local expression of the antibody upon intratumoral electroporation.

It will be understood that the present invention has been described above by way of example only. The examples are not intended to limit the scope of the invention. Various modifications and embodiments can be made without departing from the scope and spirit of the invention, which is defined by the following claims only.

The invention claimed is:

1. An expression cassette comprising the formula represented by:

P-B-T-B'-T-A wherein P is a promoter, A encodes a CXCL9, T is a translation modification element, B encodes IL-12 p35, and B' encodes IL-12 p40;

wherein T comprises a 2A peptide selected from the group consisting of: a P2A peptide, a T2A peptide, a E2A peptide, and a F2A peptide; and wherein A encodes a polypeptide comprising the amino acid sequence of SEQ ID NO: 58; B encodes a polypeptide comprising the amino acid sequence of SEQ ID NO: 53; and B' encodes a polypeptide comprising the amino acid sequence of SEQ ID NO: 56.

2. The expression cassette of claim 1, wherein A comprises the nucleotide sequence of SEQ ID NO: 57; B comprises the nucleotide sequence of SEQ ID NO: 51, or 52; and B' comprises the nucleotide sequence of SEQ ID NO: 54, or 55.

3. The expression cassette of claim 1, wherein the expression cassette encodes a polypeptide comprising the amino acid sequence of SEQ ID NO: 82.

4. The expression cassette of claim 1, wherein the expression cassette comprises the nucleotide sequence of SEQ ID NO: 81.

5. The expression cassette of claim 1, wherein the expression cassette is in a plasmid.

6. A method of treating a subject having a tumor comprising administering intratumoral electroporation (IT-EP) IL12-CXCL9 therapy to the subject wherein the IT-EP IL12-CXCL9 therapy comprises injecting the tumor with an effective dose of the expression cassette of claim 1 and administering electroporation therapy to the tumor.

7. The method of claim 6, wherein the electroporation therapy comprises administration of at least one voltage pulse over a duration of about 100 microseconds to about 1 millisecond.

8. The method of claim 7, wherein the electroporation therapy comprises administering 1-10 voltage pulses having a field strength of about 200 V/cm to about 1500 V/cm.

9. The method of claim 6, wherein the expression cassette is injected into the tumor and the electroporation therapy is administered on day 1, day 5±2 days, and day 8±2 days of at least one cycle.

10. The method of claim 6, wherein the method further comprises administering IT-EP CD3 half-BiTE therapy to the subject wherein the IT-EP CD3 half-BiTE therapy comprises injecting the tumor with an effective dose of an expression cassette comprising a first nucleotide sequence encoding a CD3 half-BiTE, and administering electroporation therapy to the tumor, wherein the CD3 half-BiTE comprises an anti-CD3 scFv and a transmembrane domain wherein the transmembrane domain is linked to the C-terminal end of the anti-CD3 scFv, and wherein the first nucleotide sequence encodes a polypeptide comprising the amino acid sequence of SEQ ID NO: 60, 62, 74, or 76; and wherein (a) the IT-EP CD3 half-BiTE therapy is administered on day 1 and day 5±2 days, and the IT-EP IL12-CXCL9 therapy is administered on day 8±2 days;

(b) the IT-EP CD3 half-BiTE therapy is administered on day 1 and day 8±2 days, and the IT-EP IL12-CXCL9 therapy is administered on day 5±2 days;

(c) the IT-EP CD3 half-BiTE therapy is administered on day 5±2 days and day 8±2 days, and the IT-EP IL12-CXCL9 therapy is administered on day 1;

(d) the IT-EP IL12-CXCL9 therapy is administered on day 1 and day 5±2 days, and the IT-EP CD3 halfBiTE therapy is administered on day 8±2 days;

(e) the IT-EP IL12-CXCL9 therapy is administered on day 1 and day 8±2 days, and the IT-EP CD3 halfBiTE therapy is administered on day 5±2 days; or (f) the IT-EP IL12-CXCL9 therapy is administered on days 5±2 days and 8±2 days, and the IT-EP CD3 halfBiTE therapy is administered on day 1.

11. The method of claim 6, further comprising administering to the subject at least one additional therapeutic.

12. The method of claim 6, wherein the method results in one or more of: increased tumor infiltrating lymphocytes, increased activation and/or proliferation of tumor-specific T cells, regression of the treated tumor, and regression of one or more untreated tumors.

13. The method of claim 6, further comprising injecting the tumor with an effective dose of at least one plasmid encoding an anti-CTLA-4 antibody.

14. The method of claim 13, wherein the method further comprises one or more of: IT-EP IL12 therapy, IT-EP CXCL9 therapy, IT-EP CD3 half-BiTE therapy, and IT-EP CD3 half-BiTE-IL12 therapy.

* * * * *

SEQUENCE LISTING

```
<160> NUMBER OF SEQ ID NOS: 92

<210> SEQ ID NO 1
<211> LENGTH: 63
<212> TYPE: DNA
<213> ORGANISM: Artificial Sequence
<220> FEATURE:
<223> OTHER INFORMATION: IgKappa signal sequence

<400> SEQUENCE: 1

atggagacag acacactcct gctatgggta ctgctgctct gggttccagg ttccactggt     60

gac                                                                   63


<210> SEQ ID NO 2
<211> LENGTH: 21
<212> TYPE: PRT
<213> ORGANISM: Artificial Sequence
<220> FEATURE:
<223> OTHER INFORMATION: IgKappa signal sequence

<400> SEQUENCE: 2

Met Glu Thr Asp Thr Leu Leu Leu Trp Val Leu Leu Leu Trp Val Pro
1               5                   10                  15

Gly Ser Thr Gly Asp
            20


<210> SEQ ID NO 3
<211> LENGTH: 27
<212> TYPE: DNA
<213> ORGANISM: Artificial Sequence
<220> FEATURE:
<223> OTHER INFORMATION: HA tag sequence

<400> SEQUENCE: 3

tatccatatg atgttccaga ttatgct                                         27


<210> SEQ ID NO 4
<211> LENGTH: 9
<212> TYPE: PRT
<213> ORGANISM: Artificial Sequence
<220> FEATURE:
<223> OTHER INFORMATION: HA tag sequence

<400> SEQUENCE: 4

Tyr Pro Tyr Asp Val Pro Asp Tyr Ala
1               5


<210> SEQ ID NO 5
<211> LENGTH: 30
<212> TYPE: DNA
<213> ORGANISM: Artificial Sequence
<220> FEATURE:
<223> OTHER INFORMATION: Myc tag sequence

<400> SEQUENCE: 5

gaacaaaaac tcatctcaga agaggatctg                                      30


<210> SEQ ID NO 6
<211> LENGTH: 10
<212> TYPE: PRT
<213> ORGANISM: Artificial Sequence
<220> FEATURE:
<223> OTHER INFORMATION: Myc tag sequence
```

<400> SEQUENCE: 6

Glu Gln Lys Leu Ile Ser Glu Glu Asp Leu
1               5                   10

<210> SEQ ID NO 7
<211> LENGTH: 357
<212> TYPE: DNA
<213> ORGANISM: Artificial Sequence
<220> FEATURE:
<223> OTHER INFORMATION: 2C11 Variable heavy chain sequence

<400> SEQUENCE: 7
gaggtgcagc tggtggagtc tgggggaggc ttggtgcagc ctggaaagtc cctgaaactc     60
tcctgtgagg cctctggatt caccttcagc ggctatggca tgcactgggt ccgccaggct    120
ccagggaggg ggctggagtc ggtcgcatac attactagta gtagtattaa tatcaaatat    180
gctgacgctg tgaaaggccg gttcaccgtc tccagagaca atgccaagaa cttactgttt    240
ctacaaatga acattctcaa gtctgaggac acagccatgt actactgtgc aagattcgac    300
tgggacaaaa attactgggg ccaaggaacc atggtcaccg tctcctcagg tggcggt       357

<210> SEQ ID NO 8
<211> LENGTH: 119
<212> TYPE: PRT
<213> ORGANISM: Artificial Sequence
<220> FEATURE:
<223> OTHER INFORMATION: 2C11 Variable heavy chain sequence

<400> SEQUENCE: 8

Glu Val Gln Leu Val Glu Ser Gly Gly Gly Leu Val Gln Pro Gly Lys
1               5                   10                  15

Ser Leu Lys Leu Ser Cys Glu Ala Ser Gly Phe Thr Phe Ser Gly Tyr
            20                  25                  30

Gly Met His Trp Val Arg Gln Ala Pro Gly Arg Gly Leu Glu Ser Val
        35                  40                  45

Ala Tyr Ile Thr Ser Ser Ser Ile Asn Ile Lys Tyr Ala Asp Ala Val
    50                  55                  60

Lys Gly Arg Phe Thr Val Ser Arg Asp Asn Ala Lys Asn Leu Leu Phe
65                  70                  75                  80

Leu Gln Met Asn Ile Leu Lys Ser Glu Asp Thr Ala Met Tyr Tyr Cys
                85                  90                  95

Ala Arg Phe Asp Trp Asp Lys Asn Tyr Trp Gly Gln Gly Thr Met Val
            100                 105                 110

Thr Val Ser Ser Gly Gly Gly
        115

<210> SEQ ID NO 9
<211> LENGTH: 312
<212> TYPE: DNA
<213> ORGANISM: Artificial Sequence
<220> FEATURE:
<223> OTHER INFORMATION: 2C11 Variable light chain sequence

<400> SEQUENCE: 9
atgacccagt ctccatcatc actgcctgcc tccctgggag acagagtcac tatcaattgt     60
caggccagtc aggacattag caattattta aactggtacc agcagaaacc agggaaagct    120
cctaagctcc tgatctatta tacaaataaa ttggcagatg gagtcccatc aaggttcagt    180
ggcagtggtt ctgggagaga ttcttctttc actatcagca gcctggaatc cgaagatatt    240
ggatcttatt actgtcaaca gtattataac tatccgtgga cgttcggacc tggcaccaag 300
ctggaaatca aa 312

<210> SEQ ID NO 10
<211> LENGTH: 312
<212> TYPE: DNA
<213> ORGANISM: Artificial Sequence
<220> FEATURE:
<223> OTHER INFORMATION: 2C11 Variable light chain sequence

<400> SEQUENCE: 10
atgacccagt ctccatcatc actgcctgcc tccctgggag acagagtcac tatcaattgt 60
caggccagtc aggacattag caattattta aactggtatc agcagaaacc agggaaagct 120
cctaagctcc tgatctatta tacaaataaa ttggcagatg gagtcccatc aaggttcagt 180
ggcagtggtt ctgggagaga ttcttctttc actatcagca gcctggaatc cgaagatatt 240
ggatcttatt actgtcaaca gtattataac tatccgtgga cgttcggacc tggcaccaag 300
ctggaaatca aa 312

<210> SEQ ID NO 11
<211> LENGTH: 104
<212> TYPE: PRT
<213> ORGANISM: Artificial Sequence
<220> FEATURE:
<223> OTHER INFORMATION: 2C11 Variable light chain sequence

<400> SEQUENCE: 11

Met Thr Gln Ser Pro Ser Ser Leu Pro Ala Ser Leu Gly Asp Arg Val
1 5 10 15

Thr Ile Asn Cys Gln Ala Ser Gln Asp Ile Ser Asn Tyr Leu Asn Trp
20 25 30

Tyr Gln Gln Lys Pro Gly Lys Ala Pro Lys Leu Leu Ile Tyr Tyr Thr
35 40 45

Asn Lys Leu Ala Asp Gly Val Pro Ser Arg Phe Ser Gly Ser Gly Ser
50 55 60

Gly Arg Asp Ser Ser Phe Thr Ile Ser Ser Leu Glu Ser Glu Asp Ile
65 70 75 80

Gly Ser Tyr Tyr Cys Gln Gln Tyr Tyr Asn Tyr Pro Trp Thr Phe Gly
85 90 95

Pro Gly Thr Lys Leu Glu Ile Lys
100

<210> SEQ ID NO 12
<211> LENGTH: 45
<212> TYPE: DNA
<213> ORGANISM: Artificial Sequence
<220> FEATURE:
<223> OTHER INFORMATION: Linker sequence

<400> SEQUENCE: 12
agtggctctg gagggggctc tggcggtgga tctgggggtg gaagt 45

<210> SEQ ID NO 13
<211> LENGTH: 15
<212> TYPE: PRT
<213> ORGANISM: Artificial Sequence
<220> FEATURE:
<223> OTHER INFORMATION: Linker sequence

<400> SEQUENCE: 13

Ser Gly Ser Gly Gly Gly Ser Gly Gly Gly Ser Gly Gly Gly Ser
1 5 10 15

<210> SEQ ID NO 14
<211> LENGTH: 45
<212> TYPE: DNA
<213> ORGANISM: Artificial Sequence
<220> FEATURE:
<223> OTHER INFORMATION: Linker sequence

<400> SEQUENCE: 14
ggtggcggtg gctccggcgg tggtgggtcg ggtggcggcg gatct 45

<210> SEQ ID NO 15
<211> LENGTH: 15
<212> TYPE: PRT
<213> ORGANISM: Artificial Sequence
<220> FEATURE:
<223> OTHER INFORMATION: Linker sequence

<400> SEQUENCE: 15

Gly Gly Gly Gly Ser Gly Gly Gly Gly Ser Gly Gly Gly Gly Ser
1 5 10 15

<210> SEQ ID NO 16
<211> LENGTH: 36
<212> TYPE: DNA
<213> ORGANISM: Artificial Sequence
<220> FEATURE:
<223> OTHER INFORMATION: Linker sequence

<400> SEQUENCE: 16
ggctccggcg gtggtgggtc gggtggcggc ggatct 36

<210> SEQ ID NO 17
<211> LENGTH: 11
<212> TYPE: PRT
<213> ORGANISM: Artificial Sequence
<220> FEATURE:
<223> OTHER INFORMATION: Linker sequence

<400> SEQUENCE: 17

Gly Ser Gly Gly Gly Gly Ser Gly Gly Gly Gly
1 5 10

<210> SEQ ID NO 18
<211> LENGTH: 27
<212> TYPE: DNA
<213> ORGANISM: Artificial Sequence
<220> FEATURE:
<223> OTHER INFORMATION: Linker sequence

<400> SEQUENCE: 18
ggcagtggga gtgggagtgg gagtggg 27

<210> SEQ ID NO 19
<211> LENGTH: 9
<212> TYPE: PRT
<213> ORGANISM: Artificial Sequence
<220> FEATURE:
<223> OTHER INFORMATION: Linker sequence

<400> SEQUENCE: 19

Gly Ser Gly Ser Gly Ser Gly Ser Gly
1 5

<210> SEQ ID NO 20
<211> LENGTH: 15
<212> TYPE: DNA
<213> ORGANISM: Artificial Sequence
<220> FEATURE:
<223> OTHER INFORMATION: Linker sequence

<400> SEQUENCE: 20
ggcagtggga gtggg 15

<210> SEQ ID NO 21
<211> LENGTH: 5
<212> TYPE: PRT
<213> ORGANISM: Artificial Sequence
<220> FEATURE:
<223> OTHER INFORMATION: Linker sequence

<400> SEQUENCE: 21

Gly Ser Gly Ser Gly
1 5

<210> SEQ ID NO 22
<211> LENGTH: 15
<212> TYPE: DNA
<213> ORGANISM: Artificial Sequence
<220> FEATURE:
<223> OTHER INFORMATION: Linker sequence

<400> SEQUENCE: 22
tctagtggat ccggt 15

<210> SEQ ID NO 23
<211> LENGTH: 5
<212> TYPE: PRT
<213> ORGANISM: Artificial Sequence
<220> FEATURE:
<223> OTHER INFORMATION: Linker sequence

<400> SEQUENCE: 23

Ser Ser Gly Ser Gly
1 5

<210> SEQ ID NO 24
<211> LENGTH: 144
<212> TYPE: DNA
<213> ORGANISM: Homo sapiens

<400> SEQUENCE: 24
gtgggccagg acacgcagga ggtcatcgtg gtgccacact ccttgccctt taaggtggtg 60
gtgatctcag ccatcctggc cctggtggtg ctcaccatca tctcccttat catcctcatc 120
atgctttggc agaagaagcc acgt 144

<210> SEQ ID NO 25
<211> LENGTH: 48
<212> TYPE: PRT
<213> ORGANISM: Homo sapiens

<400> SEQUENCE: 25

Val Gly Gln Asp Thr Gln Glu Val Ile Val Val Pro His Ser Leu Pro
1 5 10 15

Phe Lys Val Val Val Ile Ser Ala Ile Leu Ala Leu Val Val Leu Thr
20 25 30

Ile Ile Ser Leu Ile Ile Leu Ile Met Leu Trp Gln Lys Lys Pro Arg 35 40 45

<210> SEQ ID NO 26
<211> LENGTH: 147
<212> TYPE: DNA
<213> ORGANISM: Homo sapiens

<400> SEQUENCE: 26
gctgtgggcc aggacacgca ggaggtcatc gtggtgccac actccttgcc ctttaaggtg 60
gtggtgatct cagccatcct ggccctggtg gtgctcacca tcatctccct tatcatcctc 120
atcatgcttt ggcagaagaa gccacgt 147

<210> SEQ ID NO 27
<211> LENGTH: 49
<212> TYPE: PRT
<213> ORGANISM: Homo sapiens

<400> SEQUENCE: 27

Ala Val Gly Gln Asp Thr Gln Glu Val Ile Val Val Pro His Ser Leu
1 5 10 15

Pro Phe Lys Val Val Val Ile Ser Ala Ile Leu Ala Leu Val Val Leu
20 25 30

Thr Ile Ile Ser Leu Ile Ile Leu Ile Met Leu Trp Gln Lys Lys Pro
35 40 45

Arg

<210> SEQ ID NO 28
<211> LENGTH: 66
<212> TYPE: DNA
<213> ORGANISM: Artificial Sequence
<220> FEATURE:
<223> OTHER INFORMATION: P2A sequence

<400> SEQUENCE: 28
ggatctgggg ccaccaactt ttcattgctc aagcaggcgg gcgatgtgga ggaaaaccct 60
ggcccc 66

<210> SEQ ID NO 29
<211> LENGTH: 22
<212> TYPE: PRT
<213> ORGANISM: Artificial Sequence
<220> FEATURE:
<223> OTHER INFORMATION: P2A sequence

<400> SEQUENCE: 29

Gly Ser Gly Ala Thr Asn Phe Ser Leu Leu Lys Gln Ala Gly Asp Val
1 5 10 15

Glu Glu Asn Pro Gly Pro
20

<210> SEQ ID NO 30
<211> LENGTH: 705
<212> TYPE: DNA
<213> ORGANISM: Mus musculus

<400> SEQUENCE: 30
gtcagcgttc caacagcctc accctcggca tccagcagct cctctcagtg ccggtccagc 60
atgtgtcaat cacgctacct cctctttttg gccacccttg ccctcctaaa ccacctcagt 120
ttggccaggg tcattccagt ctctggacct gccaggtgtc ttagccagtc ccgaaacctg 180
ctgaagacca cagatgacat ggtgaagacg gccagagaaa aactgaaaca ttattcctgc 240
actgctgaag acatcgatca tgaagacatc acacgggacc aaaccagcac attgaagacc 300
tgtttaccac tggaactaca caagaacgag agttgcctgg ctactagaga gacttcttcc 360
acaacaagag ggagctgcct gcccccacag aagacgtctt tgatgatgac cctgtgcctt 420
ggtagcatct atgaggactt gaagatgtac cagacagagt tccaggccat caacgcagca 480
cttcagaatc acaaccatca gcagatcatt cttgacaagg gcatgctggt ggccatcgat 540
gagctgatgc agtctctgaa tcataatggc gagactctgc gccagaaacc tcctgtggga 600
gaagcagacc cttacagagt gaaaatgaag ctctgcatcc tgcttcacgc cttcagcacc 660
cgcgtcgtga ccatcaacag ggtgatgggc tatctgagct ccgcc 705

<210> SEQ ID NO 31
<211> LENGTH: 238
<212> TYPE: PRT
<213> ORGANISM: Mus musculus

<400> SEQUENCE: 31

Val Ser Val Pro Thr Ala Ser Pro Ser Ala Ser Ser Ser Ser Ser Gln
1 5 10 15

Cys Arg Ser Ser Met Cys Gln Ser Arg Tyr Leu Leu Phe Leu Ala Thr
20 25 30

Leu Ala Leu Leu Asn His Leu Ser Leu Ala Arg Val Ile Pro Val Ser
35 40 45

Gly Pro Ala Arg Cys Leu Ser Gln Ser Arg Asn Leu Leu Lys Thr Thr
50 55 60

Asp Asp Met Val Lys Thr Ala Arg Glu Lys Leu Lys His Tyr Ser Cys
65 70 75 80

Thr Ala Glu Asp Ile Asp His Glu Asp Ile Thr Arg Asp Gln Thr Ser
85 90 95

Thr Leu Lys Thr Cys Leu Pro Leu Glu Leu His Lys Asn Glu Ser Cys
100 105 110

Leu Ala Thr Arg Glu Thr Ser Ser Thr Thr Arg Gly Ser Cys Leu Pro
115 120 125

Pro Gln Lys Thr Ser Leu Met Met Thr Leu Cys Leu Gly Ser Ile Tyr
130 135 140

Glu Asp Leu Lys Met Tyr Gln Thr Glu Phe Gln Ala Ile Asn Ala Ala
145 150 155 160

Leu Gln Asn His Asn His Gln Gln Ile Ile Leu Asp Lys Gly Met Leu
165 170 175

Val Ala Ile Asp Glu Leu Met Gln Ser Leu Asn His Asn Gly Glu Thr
180 185 190

Leu Arg Gln Lys Pro Pro Val Gly Glu Ala Asp Pro Tyr Arg Val Lys
195 200 205

Met Lys Leu Cys Ile Leu Leu His Ala Phe Ser Thr Arg Val Val Thr
210 215 220

Ile Asn Arg Val Met Gly Tyr Leu Ser Ser Ala Ala Ala Ala
225 230 235

<210> SEQ ID NO 32
<211> LENGTH: 1002
<212> TYPE: DNA
<213> ORGANISM: Mus musculus

<400> SEQUENCE: 32

-continued

```
tgtcctcaga agctaaccat ctcctggttt gccatcgttt tgctggtgtc tccactcatg      60

gccatgtggg agctggagaa agacgtttat gttgtagagg tggactggac tcccgatgcc     120

cctggagaaa cagtgaacct cacctgtgac acgcctgaag aagatgacat cacctggacc     180

tcagaccaga gacatggagt cataggctct ggaaagaccc tgaccatcac tgtcaaagag     240

tttcttgatg ctggccagta cacctgccac aaaggaggcg agactctgag ccactcacat     300

ctgctgctcc acaagaagga aaatggaatt tggtccactg aaattttaaa gaatttcaag     360

aacaagactt tcctgaagtg tgaagcacca aattactccg gacggttcac gtgctcatgg     420

ctggtgcaaa gaaacatgga cttgaagttc aacatcaaga gcagtagcag ttcccctgac     480

tctcgggcag tgacatgtgg aatggcgtct ctgtctgcag agaaggtcac actggaccaa     540

agggactatg agaagtattc agtgtcctgc caggaggatg tcacctgccc aactgccgag     600

gagaccctgc ccattgaact ggcgttggaa gcacggcagc agaataaata tgagaactac     660

agcaccagct tcttcatcag ggacatcatc aaaccagacc cgcccaagaa cttgcagatg     720

aagcctttga agaactcaca ggtggaggtc agctgggagt accctgactc ctggagcact     780

ccccattcct acttctccct caagttcttt gttcgaatcc agcgcaagaa agaaaagatg     840

aaggagacag aggaggggtg taaccagaaa ggtgcgttcc tcgtagagaa gacatctacc     900

gaagtccaat gcaaaggcgg gaatgtctgc gtgcaagctc aggatcgcta ttacaattcc     960

tcatgcagca agtgggcatg tgttccctgc agggtccgat cc                       1002
```

<210> SEQ ID NO 33
<211> LENGTH: 333
<212> TYPE: PRT
<213> ORGANISM: Mus musculus

<400> SEQUENCE: 33

```
Cys Pro Gln Lys Leu Thr Ile Ser Trp Phe Ala Ile Val Leu Leu Val
1               5                   10                  15

Ser Pro Leu Met Ala Met Trp Glu Leu Glu Lys Asp Val Tyr Val Val
            20                  25                  30

Glu Val Asp Trp Thr Pro Asp Ala Pro Gly Glu Thr Val Asn Leu Thr
        35                  40                  45

Cys Asp Thr Pro Glu Glu Asp Asp Ile Thr Trp Thr Ser Asp Gln Arg
    50                  55                  60

His Gly Val Ile Gly Ser Gly Lys Thr Leu Thr Ile Thr Val Lys Glu
65                  70                  75                  80

Phe Leu Asp Ala Gly Gln Tyr Thr Cys His Lys Gly Gly Glu Thr Leu
                85                  90                  95

Ser His Ser His Leu Leu Leu His Lys Lys Glu Asn Gly Ile Trp Ser
            100                 105                 110

Thr Glu Ile Leu Lys Asn Phe Lys Asn Lys Thr Phe Leu Lys Cys Glu
        115                 120                 125

Ala Pro Asn Tyr Ser Gly Arg Phe Thr Cys Ser Trp Leu Val Gln Arg
    130                 135                 140

Asn Met Asp Leu Lys Phe Asn Ile Lys Ser Ser Ser Ser Ser Pro Asp
145                 150                 155                 160

Ser Arg Ala Val Thr Cys Gly Met Ala Ser Leu Ser Ala Glu Lys Val
                165                 170                 175

Thr Leu Asp Gln Arg Asp Tyr Glu Lys Tyr Ser Val Ser Cys Gln Glu
            180                 185                 190

Asp Val Thr Cys Pro Thr Ala Glu Glu Thr Leu Pro Ile Glu Leu Ala
```

```
        195                 200                 205

Leu Glu Ala Arg Gln Gln Asn Lys Tyr Glu Asn Tyr Ser Thr Ser Phe
    210                 215                 220

Phe Ile Arg Asp Ile Ile Lys Pro Asp Pro Pro Lys Asn Leu Gln Met
225                 230                 235                 240

Lys Pro Leu Lys Asn Ser Gln Val Glu Val Ser Trp Glu Tyr Pro Asp
                245                 250                 255

Ser Trp Ser Thr Pro His Ser Tyr Phe Ser Leu Lys Phe Phe Val Arg
            260                 265                 270

Ile Gln Arg Lys Lys Glu Lys Met Lys Glu Thr Glu Glu Gly Cys Asn
        275                 280                 285

Gln Lys Gly Ala Phe Leu Val Glu Lys Thr Ser Thr Glu Val Gln Cys
    290                 295                 300

Lys Gly Gly Asn Val Cys Val Gln Ala Gln Asp Arg Tyr Tyr Asn Ser
305                 310                 315                 320

Ser Cys Ser Lys Trp Ala Cys Val Pro Cys Arg Val Arg
                325                 330
```

<210> SEQ ID NO 34
<211> LENGTH: 375
<212> TYPE: DNA
<213> ORGANISM: Mus musculus

<400> SEQUENCE: 34

```
aagtccgctg ttcttttcct cttgggcatc atcttcctgg agcagtgtgg agttcgagga     60

accctagtga taaggaatgc acgatgctcc tgcatcagca ccagccgagg cacgatccac    120

tacaaatccc tcaaagacct caaacagttt gccccaagcc ccaattgcaa caaaactgaa    180

atcattgcta cactgaagaa cggagatcaa acctgcctag atccggactc ggcaaatgtg    240

aagaagctga tgaaagaatg ggaaaagaag atcagccaaa agaaaaagca aaagaggggg    300

aaaaaacatc aaaagaacat gaaaaacaga aaacccaaaa caccccaaag tcgtcgtcgt    360

tcaaggaaga ctaca                                                     375
```

<210> SEQ ID NO 35
<211> LENGTH: 125
<212> TYPE: PRT
<213> ORGANISM: Mus musculus

<400> SEQUENCE: 35

```
Lys Ser Ala Val Leu Phe Leu Leu Gly Ile Ile Phe Leu Glu Gln Cys
1               5                   10                  15

Gly Val Arg Gly Thr Leu Val Ile Arg Asn Ala Arg Cys Ser Cys Ile
            20                  25                  30

Ser Thr Ser Arg Gly Thr Ile His Tyr Lys Ser Leu Lys Asp Leu Lys
        35                  40                  45

Gln Phe Ala Pro Ser Pro Asn Cys Asn Lys Thr Glu Ile Ile Ala Thr
    50                  55                  60

Leu Lys Asn Gly Asp Gln Thr Cys Leu Asp Pro Asp Ser Ala Asn Val
65                  70                  75                  80

Lys Lys Leu Met Lys Glu Trp Glu Lys Lys Ile Ser Gln Lys Lys Lys
                85                  90                  95

Gln Lys Arg Gly Lys Lys His Gln Lys Asn Met Lys Asn Arg Lys Pro
            100                 105                 110

Lys Thr Pro Gln Ser Arg Arg Arg Ser Arg Lys Thr Thr
        115                 120                 125
```

<210> SEQ ID NO 36
<211> LENGTH: 360
<212> TYPE: DNA
<213> ORGANISM: Artificial Sequence
<220> FEATURE:
<223> OTHER INFORMATION: anti-CTLA4 9D9 variable light chain sequence

<400> SEQUENCE: 36
gacattgtga tgacacagac cacactcagt ctccccgttt cccttggtga tcaagcctcc 60
atatcctgta ggtctagtca atctatcgtc cactccaacg gcaataccta tctggaatgg 120
tatcttcaaa agcccggaca atcaccaaag cttcttatct ataaggtgag caatagattt 180
agcggggtcc ctgaccgatt ctctggaagt ggctctggca cagactttac cttgaaaatc 240
tccagagttg aggctgagga ccttggtgta tactactgct tccaaggctc tcatgttccc 300
tacactttcg gaggcggaac aaaactggag ataaaacgag ccgacgcagc ccccactgtg 360

<210> SEQ ID NO 37
<211> LENGTH: 120
<212> TYPE: PRT
<213> ORGANISM: Artificial Sequence
<220> FEATURE:
<223> OTHER INFORMATION: anti-CTLA4 9D9 variable light chain sequence

<400> SEQUENCE: 37

Asp Ile Val Met Thr Gln Thr Thr Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Tyr Thr Phe Gly Gly Gly Thr Lys Leu Glu Ile Lys
            100                 105                 110

Arg Ala Asp Ala Ala Pro Thr Val
        115                 120

<210> SEQ ID NO 38
<211> LENGTH: 390
<212> TYPE: DNA
<213> ORGANISM: Artificial Sequence
<220> FEATURE:
<223> OTHER INFORMATION: anti-CTLA4 9D9 variable heavy chain sequence

<400> SEQUENCE: 38
gaggcaaagc ttcaggaatc tggtccagtg ttggtgaaac caggtgcatc cgtgaaaatg 60
tcctgcaaag caagcggtta cacttttact gactattata tgaactgggt aaagcaatcc 120
cacggcaaat ccctggaatg gattggtgtc atcaaccctt acaacggtga tacaagttac 180
aaccaaaagt tcaaaggtaa ggctacattg accgtagata agagtagcag tactgcatac 240
atggaactta actctcttac atccgaggac tccgctgttt actattgtgc acgctactac 300
gggagctggt tcgcttactg ggtcaaggc accctgataa cagtgtccac agccaaaacc 360
acacctccct ccgtctatcc tctcgctcca 390

<210> SEQ ID NO 39
<211> LENGTH: 130
<212> TYPE: PRT
<213> ORGANISM: Artificial Sequence
<220> FEATURE:
<223> OTHER INFORMATION: anti-CTLA4 9D9 variable heavy chain sequence

<400> SEQUENCE: 39

Glu Ala Lys Leu Gln Glu Ser Gly Pro Val Leu Val Lys Pro Gly Ala
1               5                   10                  15

Ser Val Lys Met Ser Cys Lys Ala Ser Gly Tyr Thr Phe Thr Asp Tyr
            20                  25                  30

Tyr Met Asn Trp Val Lys Gln Ser His Gly Lys Ser Leu Glu Trp Ile
        35                  40                  45

Gly Val Ile Asn Pro Tyr Asn Gly Asp Thr Ser Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Asn Ser Leu Thr Ser Glu Asp Ser Ala Val Tyr Tyr Cys
                85                  90                  95

Ala Arg Tyr Tyr Gly Ser Trp Phe Ala Tyr Trp Gly Gln Gly Thr Leu
            100                 105                 110

Ile Thr Val Ser Thr Ala Lys Thr Thr Pro Pro Ser Val Tyr Pro Leu
        115                 120                 125

Ala Pro
    130

<210> SEQ ID NO 40
<211> LENGTH: 333
<212> TYPE: DNA
<213> ORGANISM: Artificial Sequence
<220> FEATURE:
<223> OTHER INFORMATION: anti-CTLA4 9H10 variable light chain sequence

<400> SEQUENCE: 40
gacattgtga tgacacagag tccttcatcc cttgcagtca gtgtcggcga aaaagtaaca 60
atttcatgca agtctagtca atctctgttg tacggctcct ctcattacct cgcatggtat 120
caacaaaaag tgggtcaatc tcccaaattg ttgatatact gggcttcaac tagacacact 180
ggaatccctg acaggttcat tggtagcgga tcagggactg actttacact gtccctcagc 240
agcgtacaag cagaagacat ggccgactat ttctgccaac aatactttag tacaccatgg 300
acctttgggg ctgggaccag agttgagata aaa 333

<210> SEQ ID NO 41
<211> LENGTH: 111
<212> TYPE: PRT
<213> ORGANISM: Artificial Sequence
<220> FEATURE:
<223> OTHER INFORMATION: anti-CTLA4 9H10 variable light chain sequence

<400> SEQUENCE: 41

Asp Ile Val Met Thr Gln Ser Pro Ser Ser Leu Ala Val Ser Val Gly
1               5                   10                  15

Glu Lys Val Thr Ile Ser Cys Lys Ser Ser Gln Ser Leu Leu Tyr Gly
            20                  25                  30

Ser Ser His Tyr Leu Ala Trp Tyr Gln Gln Lys Val Gly Gln Ser Pro
        35                  40                  45

```
Lys Leu Leu Ile Tyr Trp Ala Ser Thr Arg His Thr Gly Ile Pro Asp
    50                  55                  60

Arg Phe Ile Gly Ser Gly Ser Gly Thr Asp Phe Thr Leu Ser Leu Ser
65                  70                  75                  80

Ser Val Gln Ala Glu Asp Met Ala Asp Tyr Phe Cys Gln Gln Tyr Phe
                85                  90                  95

Ser Thr Pro Trp Thr Phe Gly Ala Gly Thr Arg Val Glu Ile Lys
            100                 105                 110


<210> SEQ ID NO 42
<211> LENGTH: 384
<212> TYPE: DNA
<213> ORGANISM: Artificial Sequence
<220> FEATURE:
<223> OTHER INFORMATION: anti-CTLA4 9H10 variable heavy acid sequence

<400> SEQUENCE: 42

caagtgcagc tgcttcaatc cgaatcagaa ctcgtgaagc caggcgcttc agtgaaattg      60

tcttgtaaga cttcaggata cactttcact gattactata tacactgggt taagcagaag     120

cctggtcagg gtcttgaatg gattggcctc atcaatccca ataacgatgg cacaaactac     180

aaccagaaat ttcaaggaaa agccacactt accgcagaca aatccagttc taccgcatac     240

atggaactta atagtctcac ttttgatgac tcagtaatat atttctgtgc cagggccagt     300

agccgactta gaatggctag gactacctct gactactatg ccatggacta ttggggacag     360

ggcattcaag tgaccgtgag ctct                                            384


<210> SEQ ID NO 43
<211> LENGTH: 128
<212> TYPE: PRT
<213> ORGANISM: Artificial Sequence
<220> FEATURE:
<223> OTHER INFORMATION: anti-CTLA4 9H10 variable heavy sequence

<400> SEQUENCE: 43

Gln Val Gln Leu Leu Gln Ser Glu Ser Glu Leu Val Lys Pro Gly Ala
1               5                   10                  15

Ser Val Lys Leu Ser Cys Lys Thr Ser Gly Tyr Thr Phe Thr Asp Tyr
            20                  25                  30

Tyr Ile His Trp Val Lys Gln Lys Pro Gly Gln Gly Leu Glu Trp Ile
        35                  40                  45

Gly Leu Ile Asn Pro Asn Asn Asp Gly Thr Asn Tyr Asn Gln Lys Phe
    50                  55                  60

Gln Gly Lys Ala Thr Leu Thr Ala Asp Lys Ser Ser Ser Thr Ala Tyr
65                  70                  75                  80

Met Glu Leu Asn Ser Leu Thr Phe Asp Asp Ser Val Ile Tyr Phe Cys
                85                  90                  95

Ala Arg Ala Ser Ser Arg Leu Arg Met Ala Arg Thr Thr Ser Asp Tyr
            100                 105                 110

Tyr Ala Met Asp Tyr Trp Gly Gln Gly Ile Gln Val Thr Val Ser Ser
        115                 120                 125


<210> SEQ ID NO 44
<211> LENGTH: 669
<212> TYPE: DNA
<213> ORGANISM: Mus musculus

<400> SEQUENCE: 44
```

```
ggttgtaagc cttgcatatg tacagtccca gaagtatcat ctgtcttcat cttcccccca      60

aagcccaagg atgtgctcac cattactctg actcctaagg tcacgtgtgt tgtggtagac     120

atcagcaagg atgatcccga ggtccagttc agctggtttg tagatgatgt ggaggtgcac     180

acagctcaga cgcaaccccg ggaggagcag ttcaacagca ctttccgctc agtcagtgaa     240

cttcccatca tgcaccagga ctggctcaat ggcaaggagt tcaaatgcag ggtcaacagt     300

gcagctttcc ctgcccccat cgagaaaacc atctccaaaa ccaaaggcag accgaaggct     360

ccacaggtgt acaccattcc acctcccaag gagcagatgg ccaaggataa agtcagtctg     420

acctgcatga taacagactt cttccctgaa gacattactg tggagtggca gtggaatggg     480

cagccagcgg agaactacaa gaacactcag cccatcatgg acacagatgg ctcttacttc     540

gtctacagca agctcaatgt gcagaagagc aactgggagg caggaaatac tttcacctgc     600

tctgtgttac atgagggcct gcacaaccac catactgaga agagcctctc ccactctcct     660

ggtaaatga                                                             669
```

```
<210> SEQ ID NO 45
<211> LENGTH: 222
<212> TYPE: PRT
<213> ORGANISM: Mus musculus

<400> SEQUENCE: 45

Gly Cys Lys Pro Cys Ile Cys Thr Val Pro Glu Val Ser Ser Val Phe
1               5                   10                  15

Ile Phe Pro Pro Lys Pro Lys Asp Val Leu Thr Ile Thr Leu Thr Pro
            20                  25                  30

Lys Val Thr Cys Val Val Val Asp Ile Ser Lys Asp Asp Pro Glu Val
        35                  40                  45

Gln Phe Ser Trp Phe Val Asp Asp Val Glu Val His Thr Ala Gln Thr
    50                  55                  60

Gln Pro Arg Glu Glu Gln Phe Asn Ser Thr Phe Arg Ser Val Ser Glu
65                  70                  75                  80

Leu Pro Ile Met His Gln Asp Trp Leu Asn Gly Lys Glu Phe Lys Cys
                85                  90                  95

Arg Val Asn Ser Ala Ala Phe Pro Ala Pro Ile Glu Lys Thr Ile Ser
            100                 105                 110

Lys Thr Lys Gly Arg Pro Lys Ala Pro Gln Val Tyr Thr Ile Pro Pro
        115                 120                 125

Pro Lys Glu Gln Met Ala Lys Asp Lys Val Ser Leu Thr Cys Met Ile
    130                 135                 140

Thr Asp Phe Phe Pro Glu Asp Ile Thr Val Glu Trp Gln Trp Asn Gly
145                 150                 155                 160

Gln Pro Ala Glu Asn Tyr Lys Asn Thr Gln Pro Ile Met Asp Thr Asp
                165                 170                 175

Gly Ser Tyr Phe Val Tyr Ser Lys Leu Asn Val Gln Lys Ser Asn Trp
            180                 185                 190

Glu Ala Gly Asn Thr Phe Thr Cys Ser Val Leu His Glu Gly Leu His
        195                 200                 205

Asn His His Thr Glu Lys Ser Leu Ser His Ser Pro Gly Lys
    210                 215                 220

<210> SEQ ID NO 46
<211> LENGTH: 357
<212> TYPE: DNA
<213> ORGANISM: Artificial Sequence
```

<220> FEATURE:
<223> OTHER INFORMATION: OKT3 Variable heavy chain nucleic acid sequence

<400> SEQUENCE: 46
caggtgcagc tgcagcaatc tggggctgaa ctggcaagac ctggggcctc agtgaagatg 60
tcctgcaagg cttctggcta cacctttact aggtacacga tgcactgggt aaaacagagg 120
cctggacagg gtctggaatg gattggatac attaatccta gccgtggtta tactaattac 180
aatcagaagt tcaaggacaa ggccacattg actacagaca aatcctccag cacagcctac 240
atgcaactga gcagcctgac atctgaggac tctgcagtct attactgtgc aagatattat 300
gatgatcatt actgccttga ctactggggc caaggcacca cactcaccgt ctcctca 357

<210> SEQ ID NO 47
<211> LENGTH: 119
<212> TYPE: PRT
<213> ORGANISM: Artificial Sequence
<220> FEATURE:
<223> OTHER INFORMATION: OKT3 Variable heavy chain sequence

<400> SEQUENCE: 47

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser
        115

<210> SEQ ID NO 48
<211> LENGTH: 321
<212> TYPE: DNA
<213> ORGANISM: Artificial Sequence
<220> FEATURE:
<223> OTHER INFORMATION: OKT3 Variable light chain sequence

<400> SEQUENCE: 48
cagattgtgc tcacccagtc tccagcaatc atgtctgcat ctccagggga gaaggttacc 60
atgacctgca gtgccagctc aagtgtaagt tacatgaact ggtaccagca gaagtcaggc 120
acctccccca aaagatggat ttatgacaca tccaaactgg cttctggagt ccctgctcac 180
ttcaggggca gtgggtctgg gacctcttac tctctcacaa tcagcggcat ggaggctgaa 240
gatgctgcca cttattactg ccagcagtgg agtagtaacc cattcacgtt cggctcgggg 300
accaagctgg agatcaatcg t 321

<210> SEQ ID NO 49
<211> LENGTH: 321
<212> TYPE: DNA
<213> ORGANISM: Artificial Sequence
<220> FEATURE:

<223> OTHER INFORMATION: OKT3 Variable light chain sequence

<400> SEQUENCE: 49

```
cagattgtgc tcacccagtc tccagcaatc atgtctgcat ctccagggga gaaggttacc      60
atgacctgca gtgccagctc aagtgtaagt tacatgaact ggtatcagca gaagtcaggc     120
acctcccca aaagatggat ttatgacaca tccaaactgg cttctggagt ccctgctcac      180
ttcaggggca gtgggtctgg gacctcttac tctctcacaa tcagcggcat ggaggctgaa     240
gatgctgcca cttattactg ccagcagtgg agtagtaacc cattcacgtt cggctcgggg     300
accaagctgg agatcaatcg t                                               321
```

<210> SEQ ID NO 50
<211> LENGTH: 107
<212> TYPE: PRT
<213> ORGANISM: Homo sapiens

<400> SEQUENCE: 50

```
Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

Asn Trp Tyr Gln Gln Lys Ser Gly Thr Ser Pro Lys Arg Trp Ile Tyr
        35                  40                  45

Asp Thr Ser Lys Leu Ala Ser Gly Val Pro Ala His Phe Arg Gly Ser
    50                  55                  60

Gly Ser Gly Thr Ser Tyr Ser Leu Thr Ile Ser Gly Met Glu Ala Glu
65                  70                  75                  80

Asp Ala Ala Thr Tyr Tyr Cys Gln Gln Trp Ser Ser Asn Pro Phe Thr
                85                  90                  95

Phe Gly Ser Gly Thr Lys Leu Glu Ile Asn Arg
            100                 105
```

<210> SEQ ID NO 51
<211> LENGTH: 756
<212> TYPE: DNA
<213> ORGANISM: Homo sapiens

<400> SEQUENCE: 51

```
tggcccccctg ggtcagcctc ccagccaccg ccctcacctg ccgcggccac aggtctgcat     60
ccagcggctc gccctgtgtc cctgcagtgc cggctcagca tgtgtccagc gcgcagcctc    120
ctccttgtgg ctaccctggt cctcctggac cacctcagtt tggccagaaa cctccccgtg    180
gccactccag acccaggaat gttcccatgc cttcaccact cccaaaacct gctgagggcc    240
gtcagcaaca tgctccagaa ggccagacaa actctagaat tttacccttg cacttctgaa    300
gagattgatc atgaagatat cacaaaagat aaaaccagca cagtggaggc ctgtttacca    360
ttggaattaa ccaagaatga gagttgccta aattccagag agacctcttt cataactaat    420
gggagttgcc tggcctccag aaagacctct tttatgatgg ccctgtgcct tagtagtatt    480
tatgaagact tgaagatgta ccaggtggag ttcaagacca tgaatgcaaa gcttctgatg    540
gatcctaaga ggcagatctt tctagatcaa aacatgctgg cagttattga tgagctgatg    600
caggccctga atttcaacag tgagactgtg ccacaaaaat cctcccttga agaaccggat    660
ttttataaaa ctaaaatcaa gctctgcata cttcttcatg ctttcagaat tcgggcagtg    720
actattgata gagtgatgag ctatctgaat gcttcc                              756
```

<210> SEQ ID NO 52
<211> LENGTH: 756
<212> TYPE: DNA
<213> ORGANISM: Homo sapiens

<400> SEQUENCE: 52
tggccccctg ggtcagcctc ccagccaccg ccctcacctg ccgcggccac aggtctgcat 60
ccagcggctc gccctgtgtc cctgcagtgc cggctcagca tgtgtccagc gcgcagcctc 120
ctccttgtgg ctaccctggt cctcctggac cacctcagtt tggccagaaa cctccccgtg 180
gccactccag acccaggaat gttcccatgc cttcaccact cccaaaacct gctgagggcc 240
gtcagcaaca tgctccagaa ggccagacaa actctcgaat tttacccttg cacttctgaa 300
gagattgatc atgaagatat cacaaaagat aaaaccagca cagtggaggc ctgtttacca 360
ttggaattaa ccaagaatga gagttgccta aattccagag agacctcttt cataactaat 420
gggagttgcc tggcctccag aaagacctct tttatgatgg ccctgtgcct tagtagtatt 480
tatgaagact tgaagatgta ccaggtggag ttcaagacca tgaatgcaaa gcttctgatg 540
gaccctaaga ggcaaatctt cctagatcaa aacatgctgg cagttattga tgagctgatg 600
caggccctga atttcaacag tgagactgtg ccacaaaaat cctcccttga agaaccggat 660
ttctacaaga ctaaaatcaa gctctgcata cttcttcatg ctttcagaat ccgggcagtg 720
actattgata gagtgatgag ctatctgaat gcttcc 756

<210> SEQ ID NO 53
<211> LENGTH: 252
<212> TYPE: PRT
<213> ORGANISM: Homo sapiens

<400> SEQUENCE: 53

Trp Pro Pro Gly Ser Ala Ser Gln Pro Pro Pro Ser Pro Ala Ala Ala
1               5                   10                  15

Thr Gly Leu His Pro Ala Ala Arg Pro Val Ser Leu Gln Cys Arg Leu
            20                  25                  30

Ser Met Cys Pro Ala Arg Ser Leu Leu Leu Val Ala Thr Leu Val Leu
        35                  40                  45

Leu Asp His Leu Ser Leu Ala Arg Asn Leu Pro Val Ala Thr Pro Asp
    50                  55                  60

Pro Gly Met Phe Pro Cys Leu His His Ser Gln Asn Leu Leu Arg Ala
65                  70                  75                  80

Val Ser Asn Met Leu Gln Lys Ala Arg Gln Thr Leu Glu Phe Tyr Pro
                85                  90                  95

Cys Thr Ser Glu Glu Ile Asp His Glu Asp Ile Thr Lys Asp Lys Thr
            100                 105                 110

Ser Thr Val Glu Ala Cys Leu Pro Leu Glu Leu Thr Lys Asn Glu Ser
        115                 120                 125

Cys Leu Asn Ser Arg Glu Thr Ser Phe Ile Thr Asn Gly Ser Cys Leu
    130                 135                 140

Ala Ser Arg Lys Thr Ser Phe Met Met Ala Leu Cys Leu Ser Ser Ile
145                 150                 155                 160

Tyr Glu Asp Leu Lys Met Tyr Gln Val Glu Phe Lys Thr Met Asn Ala
                165                 170                 175

Lys Leu Leu Met Asp Pro Lys Arg Gln Ile Phe Leu Asp Gln Asn Met
            180                 185                 190

Leu Ala Val Ile Asp Glu Leu Met Gln Ala Leu Asn Phe Asn Ser Glu

```
        195                 200                 205

Thr Val Pro Gln Lys Ser Ser Leu Glu Glu Pro Asp Phe Tyr Lys Thr
    210                 215                 220

Lys Ile Lys Leu Cys Ile Leu Leu His Ala Phe Arg Ile Arg Ala Val
225                 230                 235                 240

Thr Ile Asp Arg Val Met Ser Tyr Leu Asn Ala Ser
                245                 250


<210> SEQ ID NO 54
<211> LENGTH: 984
<212> TYPE: DNA
<213> ORGANISM: Homo sapiens

<400> SEQUENCE: 54

tgtcaccagc agttggtcat ctcttggttt tccctggttt ttctggcatc tcccctcgtg      60

gccatatggg aactgaagaa agatgtttat gtcgtagaat tggattggta tccggatgcc     120

cctggagaaa tggtggtcct cacctgtgac acccctgaag aagatggtat cacctggacc     180

ttggaccaga gcagtgaggt cttaggctct ggcaaaaccc tgaccatcca agtcaaagag     240

tttggagatg ctggccagta cacctgtcac aaaggaggcg aggttctaag ccattcgctc     300

ctgctgcttc acaaaaagga agatggaatt tggtccactg atattttaaa ggaccagaaa     360

gaacccaaaa ataagacctt tctaagatgc gaggccaaga attattctgg acgtttcacc     420

tgctggtggc tgacgacaat cagtactgat ttgacattca gtgtcaaaag cagcagaggc     480

tcttctgacc cccaaggggt gacgtgcgga gctgctacac tctctgcaga gagagtcaga     540

ggggacaaca aggagtatga gtactcagtg gagtgccagg aggacagtgc ctgcccagct     600

gctgaggaga gtctgcccat tgaggtcatg gtggatgccg ttcacaagct caagtatgaa     660

aactacacca gcagcttctt catcagggac atcatcaaac ctgacccacc caagaacttg     720

cagctgaagc cattaaagaa ttctcggcag gtggaggtca gctgggagta ccctgacacc     780

tggagtactc cacattccta cttctccctg acattctgcg ttcaggtcca gggcaagagc     840

aagagagaaa agaaagatag agtcttcacg gacaagacct cagccacggt catctgccgc     900

aaaaatgcca gcattagcgt gcgggcccag gaccgctact atagctcatc ttggagcgaa     960

tgggcatctg tgccctgcag ttag                                            984


<210> SEQ ID NO 55
<211> LENGTH: 984
<212> TYPE: DNA
<213> ORGANISM: Homo sapiens

<400> SEQUENCE: 55

tgtcaccagc agttggtcat ctcttggttt tccctggttt ttctggcatc tcccctcgtg      60

gccatatggg aactgaagaa agatgtttat gtcgtagaat tggattggta tccggatgcc     120

cctggagaaa tggtggtcct cacctgtgac acccctgaag aagatggtat cacctggacc     180

ttggaccaga gcagtgaggt cttaggctct ggcaaaaccc tgaccatcca agtcaaagag     240

tttggagatg ctggccagta cacctgtcac aaaggaggcg aggttctaag ccattcgctc     300

ctgctgcttc acaaaaagga agatggaatt tggtccactg atattttaaa ggaccagaaa     360

gaacccaaaa ataagacctt tctaagatgc gaggccaaga attattctgg acgtttcacc     420

tgctggtggc tgacgacaat cagtactgat ttgacattca gtgtcaaaag cagcagaggc     480

tcttctgacc cccaaggggt gacgtgcgga gctgctacac tctctgcaga gagagtcaga     540
```

```
ggggacaaca aggagtatga gtactcagtg gagtgccagg aggacagtgc ctgcccagct    600

gctgaggaga gtctgcccat tgaggtcatg gtggatgccg ttcacaagct caagtatgaa    660

aactacacca gcagcttctt catcagggac atcatcaaac ctgacccacc caagaacttg    720

cagctgaagc cattaaagaa ctctcggcag gtggaggtca gctgggagta ccctgacacc    780

tggagtactc cacattccta cttctccctg acattctgcg ttcaggtcca gggcaagagc    840

aagagagaaa agaaagatag agtcttcacg gacaagacct cagccacggt catctgccgc    900

aaaaatgcca gcattagcgt gcgggcccag gaccgctact atagctcatc ttggagcgaa    960

tgggcatctg tgccctgcag ttcg                                           984


<210> SEQ ID NO 56
<211> LENGTH: 327
<212> TYPE: PRT
<213> ORGANISM: Homo sapiens

<400> SEQUENCE: 56

Cys His Gln Gln Leu Val Ile Ser Trp Phe Ser Leu Val Phe Leu Ala
1               5                   10                  15

Ser Pro Leu Val Ala Ile Trp Glu Leu Lys Lys Asp Val Tyr Val Val
            20                  25                  30

Glu Leu Asp Trp Tyr Pro Asp Ala Pro Gly Glu Met Val Val Leu Thr
        35                  40                  45

Cys Asp Thr Pro Glu Glu Asp Gly Ile Thr Trp Thr Leu Asp Gln Ser
    50                  55                  60

Ser Glu Val Leu Gly Ser Gly Lys Thr Leu Thr Ile Gln Val Lys Glu
65                  70                  75                  80

Phe Gly Asp Ala Gly Gln Tyr Thr Cys His Lys Gly Gly Glu Val Leu
                85                  90                  95

Ser His Ser Leu Leu Leu Leu His Lys Lys Glu Asp Gly Ile Trp Ser
            100                 105                 110

Thr Asp Ile Leu Lys Asp Gln Lys Glu Pro Lys Asn Lys Thr Phe Leu
        115                 120                 125

Arg Cys Glu Ala Lys Asn Tyr Ser Gly Arg Phe Thr Cys Trp Trp Leu
    130                 135                 140

Thr Thr Ile Ser Thr Asp Leu Thr Phe Ser Val Lys Ser Ser Arg Gly
145                 150                 155                 160

Ser Ser Asp Pro Gln Gly Val Thr Cys Gly Ala Ala Thr Leu Ser Ala
                165                 170                 175

Glu Arg Val Arg Gly Asp Asn Lys Glu Tyr Glu Tyr Ser Val Glu Cys
            180                 185                 190

Gln Glu Asp Ser Ala Cys Pro Ala Ala Glu Glu Ser Leu Pro Ile Glu
        195                 200                 205

Val Met Val Asp Ala Val His Lys Leu Lys Tyr Glu Asn Tyr Thr Ser
    210                 215                 220

Ser Phe Phe Ile Arg Asp Ile Ile Lys Pro Asp Pro Pro Lys Asn Leu
225                 230                 235                 240

Gln Leu Lys Pro Leu Lys Asn Ser Arg Gln Val Glu Val Ser Trp Glu
                245                 250                 255

Tyr Pro Asp Thr Trp Ser Thr Pro His Ser Tyr Phe Ser Leu Thr Phe
            260                 265                 270

Cys Val Gln Val Gln Gly Lys Ser Lys Arg Glu Lys Lys Asp Arg Val
        275                 280                 285

Phe Thr Asp Lys Thr Ser Ala Thr Val Ile Cys Arg Lys Asn Ala Ser
```

```
    290                 295                 300

Ile Ser Val Arg Ala Gln Asp Arg Tyr Tyr Ser Ser Ser Trp Ser Glu
305                 310                 315                 320

Trp Ala Ser Val Pro Cys Ser
                325


<210> SEQ ID NO 57
<211> LENGTH: 375
<212> TYPE: DNA
<213> ORGANISM: Homo sapiens

<400> SEQUENCE: 57

aagaaaagtg gtgttctttt cctcttgggc atcatcttgc tggttctgat tggagtgcaa      60

ggaaccccag tagtgagaaa gggtcgctgt tcctgcatca gcaccaacca agggactatc     120

cacctacaat ccttgaaaga ccttaaacaa tttgccccaa gcccttcctg cgagaaaatt     180

gaaatcattg ctacactgaa gaatggagtt caaacatgtc taaacccaga ttcagcagat     240

gtgaaggaac tgattaaaaa gtgggagaaa caggtcagcc aaaagaaaaa gcaaaagaat     300

gggaaaaaac atcaaaaaaa gaaagttctg aaagttcgaa aatctcaacg ttctcgtcaa     360

aagaagacta cataa                                                       375


<210> SEQ ID NO 58
<211> LENGTH: 124
<212> TYPE: PRT
<213> ORGANISM: Homo sapiens

<400> SEQUENCE: 58

Lys Lys Ser Gly Val Leu Phe Leu Leu Gly Ile Ile Leu Leu Val Leu
1               5                   10                  15

Ile Gly Val Gln Gly Thr Pro Val Val Arg Lys Gly Arg Cys Ser Cys
            20                  25                  30

Ile Ser Thr Asn Gln Gly Thr Ile His Leu Gln Ser Leu Lys Asp Leu
        35                  40                  45

Lys Gln Phe Ala Pro Ser Pro Ser Cys Glu Lys Ile Glu Ile Ile Ala
    50                  55                  60

Thr Leu Lys Asn Gly Val Gln Thr Cys Leu Asn Pro Asp Ser Ala Asp
65                  70                  75                  80

Val Lys Glu Leu Ile Lys Lys Trp Glu Lys Gln Val Ser Gln Lys Lys
                85                  90                  95

Lys Gln Lys Asn Gly Lys Lys His Gln Lys Lys Lys Val Leu Lys Val
            100                 105                 110

Arg Lys Ser Gln Arg Ser Arg Gln Lys Lys Thr Thr
        115                 120


<210> SEQ ID NO 59
<211> LENGTH: 1011
<212> TYPE: DNA
<213> ORGANISM: Artificial Sequence
<220> FEATURE:
<223> OTHER INFORMATION: Igkappa-HA-2C11VHC-Linker-C211VLC-Myc-PDGFR
      nucleic acid sequence

<400> SEQUENCE: 59

atggagacag acacactcct gctatgggta ctgctgctct gggttccagg ttccactggt      60

gactatccat atgatgttcc agattatgct ggggcccagc cggccagatc tgaggtgcag     120

ctggtggagt ctgggggagg cttggtgcag cctggaaagt ccctgaaact ctcctgtgag     180
```

```
gcctctggat tcaccttcag cggctatggc atgcactggg tccgccaggc tccagggagg    240

gggctggagt cggtcgcata cattactagt agtagtatta atatcaaata tgctgacgct    300

gtgaaaggcc ggttcaccgt ctccagagac aatgccaaga acttactgtt tctacaaatg    360

aacattctca agtctgagga cacagccatg tactactgtg caagattcga ctgggacaaa    420

aattactggg gccaaggaac catggtcacc gtctcctcag gtggcggtgg ctccggcggt    480

ggtgggtcgg gtggcggcgg atctgacatc cagatgaccc agtctccatc atcactgcct    540

gcctccctgg gagacagagt cactatcaat tgtcaggcca gtcaggacat tagcaattat    600

ttaaactggt accagcagaa accagggaaa gctcctaagc tcctgatcta ttatacaaat    660

aaattggcag atggagtccc atcaaggttc agtggcagtg gttctgggag agattcttct    720

ttcactatca gcagcctgga atccgaagat attggatctt attactgtca acagtattat    780

aactatccgt ggacgttcgg acctggcacc aagctggaaa tcaaagtcga cgaacaaaaa    840

ctcatctcag aagaggatct gtacactgtg ggccaggaca cgcaggaggt catcgtggtg    900

ccacactcct tgccctttaa ggtggtggtg atctcagcca tcctggccct ggtggtgctc    960

accatcatct cccttatcat cctcatcatg ctttggcaga agaagccacg t            1011
```

```
<210> SEQ ID NO 60
<211> LENGTH: 337
<212> TYPE: PRT
<213> ORGANISM: Artificial Sequence
<220> FEATURE:
<223> OTHER INFORMATION: Igkappa-HA-2C11VHC-Linker-C211VLC-Myc-PDGFR
      amino acid sequence

<400> SEQUENCE: 60

Met Glu Thr Asp Thr Leu Leu Leu Trp Val Leu Leu Leu Trp Val Pro
1               5                   10                  15

Gly Ser Thr Gly Asp Tyr Pro Tyr Asp Val Pro Asp Tyr Ala Gly Ala
            20                  25                  30

Gln Pro Ala Arg Ser Glu Val Gln Leu Val Glu Ser Gly Gly Gly Leu
        35                  40                  45

Val Gln Pro Gly Lys Ser Leu Lys Leu Ser Cys Glu Ala Ser Gly Phe
    50                  55                  60

Thr Phe Ser Gly Tyr Gly Met His Trp Val Arg Gln Ala Pro Gly Arg
65                  70                  75                  80

Gly Leu Glu Ser Val Ala Tyr Ile Thr Ser Ser Ser Ile Asn Ile Lys
                85                  90                  95

Tyr Ala Asp Ala Val Lys Gly Arg Phe Thr Val Ser Arg Asp Asn Ala
            100                 105                 110

Lys Asn Leu Leu Phe Leu Gln Met Asn Ile Leu Lys Ser Glu Asp Thr
        115                 120                 125

Ala Met Tyr Tyr Cys Ala Arg Phe Asp Trp Asp Lys Asn Tyr Trp Gly
    130                 135                 140

Gln Gly Thr Met Val Thr Val Ser Ser Gly Gly Gly Gly Ser Gly Gly
145                 150                 155                 160

Gly Gly Ser Gly Gly Gly Gly Ser Asp Ile Gln Met Thr Gln Ser Pro
                165                 170                 175

Ser Ser Leu Pro Ala Ser Leu Gly Asp Arg Val Thr Ile Asn Cys Gln
            180                 185                 190

Ala Ser Gln Asp Ile Ser Asn Tyr Leu Asn Trp Tyr Gln Gln Lys Pro
        195                 200                 205

Gly Lys Ala Pro Lys Leu Leu Ile Tyr Tyr Thr Asn Lys Leu Ala Asp
```

-continued 210 215 220

Gly Val Pro Ser Arg Phe Ser Gly Ser Gly Ser Gly Arg Asp Ser Ser
225 230 235 240

Phe Thr Ile Ser Ser Leu Glu Ser Glu Asp Ile Gly Ser Tyr Tyr Cys
245 250 255

Gln Gln Tyr Tyr Asn Tyr Pro Trp Thr Phe Gly Pro Gly Thr Lys Leu
260 265 270

Glu Ile Lys Val Asp Glu Gln Lys Leu Ile Ser Glu Glu Asp Leu Tyr
275 280 285

Thr Val Gly Gln Asp Thr Gln Glu Val Ile Val Val Pro His Ser Leu
290 295 300

Pro Phe Lys Val Val Val Ile Ser Ala Ile Leu Ala Leu Val Val Leu
305 310 315 320

Thr Ile Ile Ser Leu Ile Ile Leu Ile Met Leu Trp Gln Lys Lys Pro
325 330 335

Arg

<210> SEQ ID NO 61
<211> LENGTH: 1002
<212> TYPE: DNA
<213> ORGANISM: Artificial Sequence
<220> FEATURE:
<223> OTHER INFORMATION: Igkappa-HA-2C11VHC-Linker-2C11VLC-Linker-PDGFR sequence

<400> SEQUENCE: 61
atggagacag acacactcct gctatgggta ctgctgctct gggttccagg ttccactggt 60
gactatccat atgatgttcc agattatgct ggggcccagc cggccagatc tgaggtgcag 120
ctggtggagt ctgggggagg cttggtgcag cctggaaagt ccctgaaact ctcctgtgag 180
gcctctggat tcaccttcag cggctatggc atgcactggg tccgccaggc tccagggagg 240
gggctggagt cggtcgcata cattactagt agtagtatta atatcaaata tgctgacgct 300
gtgaaaggcc ggttcaccgt ctccagagac aatgccaaga acttactgtt tctacaaatg 360
aacattctca agtctgagga cacagccatg tactactgtg caagattcga ctgggacaaa 420
aattactggg gccaaggaac catggtcacc gtctcctcag gtggcggtgg ctccggcggt 480
ggtgggtcgg gtggcggcgg atctgacatc cagatgaccc agtctccatc atcactgcct 540
gcctccctgg gagacagagt cactatcaat tgtcaggcca gtcaggacat tagcaattat 600
ttaaactggt atcagcagaa accagggaaa gctcctaagc tcctgatcta ttatacaaat 660
aaattggcag atggagtccc atcaaggttc agtggcagtg gttctgggag agattcttct 720
ttcactatca gcagcctgga atccgaagat attggatctt attactgtca acagtattat 780
aactatccgt ggacgttcgg acctggcacc aagctggaaa tcaaaggcag tgggagtggg 840
agtgggagtg ggaatgctgt gggccaggac acgcaggagg tcatcgtggt gccacactcc 900
ttgcccttta aggtggtggt gatctcagcc atcctggccc tggtggtgct caccatcatc 960
tcccttatca tcctcatcat gctttggcag aagaagccac gt 1002

<210> SEQ ID NO 62
<211> LENGTH: 334
<212> TYPE: PRT
<213> ORGANISM: Artificial Sequence
<220> FEATURE:
<223> OTHER INFORMATION: Igkappa-HA-2C11VHC-Linker-2C11VLC-Linker-PDGFR sequence

<400> SEQUENCE: 62

```
Met Glu Thr Asp Thr Leu Leu Leu Trp Val Leu Leu Leu Trp Val Pro
1               5                   10                  15

Gly Ser Thr Gly Asp Tyr Pro Tyr Asp Val Pro Asp Tyr Ala Gly Ala
            20                  25                  30

Gln Pro Ala Arg Ser Glu Val Gln Leu Val Glu Ser Gly Gly Gly Leu
        35                  40                  45

Val Gln Pro Gly Lys Ser Leu Lys Leu Ser Cys Glu Ala Ser Gly Phe
    50                  55                  60

Thr Phe Ser Gly Tyr Gly Met His Trp Val Arg Gln Ala Pro Gly Arg
65                  70                  75                  80

Gly Leu Glu Ser Val Ala Tyr Ile Thr Ser Ser Ser Ile Asn Ile Lys
                85                  90                  95

Tyr Ala Asp Ala Val Lys Gly Arg Phe Thr Val Ser Arg Asp Asn Ala
            100                 105                 110

Lys Asn Leu Leu Phe Leu Gln Met Asn Ile Leu Lys Ser Glu Asp Thr
        115                 120                 125

Ala Met Tyr Tyr Cys Ala Arg Phe Asp Trp Asp Lys Asn Tyr Trp Gly
    130                 135                 140

Gln Gly Thr Met Val Thr Val Ser Ser Gly Gly Gly Gly Ser Gly Gly
145                 150                 155                 160

Gly Gly Ser Gly Gly Gly Gly Ser Asp Ile Gln Met Thr Gln Ser Pro
                165                 170                 175

Ser Ser Leu Pro Ala Ser Leu Gly Asp Arg Val Thr Ile Asn Cys Gln
            180                 185                 190

Ala Ser Gln Asp Ile Ser Asn Tyr Leu Asn Trp Tyr Gln Gln Lys Pro
        195                 200                 205

Gly Lys Ala Pro Lys Leu Leu Ile Tyr Tyr Thr Asn Lys Leu Ala Asp
    210                 215                 220

Gly Val Pro Ser Arg Phe Ser Gly Ser Gly Ser Gly Arg Asp Ser Ser
225                 230                 235                 240

Phe Thr Ile Ser Ser Leu Glu Ser Glu Asp Ile Gly Ser Tyr Tyr Cys
                245                 250                 255

Gln Gln Tyr Tyr Asn Tyr Pro Trp Thr Phe Gly Pro Gly Thr Lys Leu
            260                 265                 270

Glu Ile Lys Gly Ser Gly Ser Gly Ser Gly Ser Gly Asn Ala Val Gly
        275                 280                 285

Gln Asp Thr Gln Glu Val Ile Val Val Pro His Ser Leu Pro Phe Lys
    290                 295                 300

Val Val Val Ile Ser Ala Ile Leu Ala Leu Val Val Leu Thr Ile Ile
305                 310                 315                 320

Ser Leu Ile Ile Leu Ile Met Leu Trp Gln Lys Lys Pro Arg
                325                 330
```

<210> SEQ ID NO 63
<211> LENGTH: 2853
<212> TYPE: DNA
<213> ORGANISM: Artificial Sequence
<220> FEATURE:
<223> OTHER INFORMATION: Igkappa-HA-2C11VHC-Linker-2C11VLC-Linker-PDGFR-P2A-mIL-12p35-P2A-mIL-12p40 sequence

<400> SEQUENCE: 63

```
atggagacag acacactcct gctatgggta ctgctgctct gggttccagg ttccactggt      60

gactatccat atgatgttcc agattatgct ggggcccagc cggccagatc tgaggtgcag     120
```

```
ctggtggagt ctgggggagg cttggtgcag cctggaaagt ccctgaaact ctcctgtgag    180
gcctctggat tcaccttcag cggctatggc atgcactggg tccgccaggc tccagggagg    240
gggctggagt cggtcgcata cattactagt agtagtatta atatcaaata tgctgacgct    300
gtgaaaggcc ggttcaccgt ctccagagac aatgccaaga acttactgtt tctacaaatg    360
aacattctca agtctgagga cacagccatg tactactgtg caagattcga ctgggacaaa    420
aattactggg gccaaggaac catggtcacc gtctcctcag gtggcggtgg ctccggcggt    480
ggtgggtcgg gtggcggcgg atctgacatc cagatgaccc agtctccatc atcactgcct    540
gcctccctgg gagacagagt cactatcaat tgtcaggcca gtcaggacat tagcaattat    600
ttaaactggt atcagcagaa accagggaaa gctcctaagc tcctgatcta ttatacaaat    660
aaattggcag atggagtccc atcaaggttc agtggcagtg gttctgggag agattcttct    720
ttcactatca gcagcctgga atccgaagat attggatctt attactgtca acagtattat    780
aactatccgt ggacgttcgg acctggcacc aagctggaaa tcaaaggcag tgggagtggg    840
aatgctgtgg gccaggacac gcaggaggtc atcgtggtgc cacactcctt gccctttaag    900
gtggtggtga tctcagccat cctggccctg gtggtgctca ccatcatctc ccttatcatc    960
ctcatcatgc tttggcagaa gaagccacgt ggatctgggg ccaccaactt ttcattgctc   1020
aagcaggcgg gcgatgtgga ggaaaaccct ggccccggta ccgtcagcgt tccaacagcc   1080
tcaccctcgg catccagcag ctcctctcag tgccggtcca gcatgtgtca atcacgctac   1140
ctcctctttt tggccaccct tgccctccta aaccacctca gtttggccag ggtcattcca   1200
gtctctggac ctgccaggtg tcttagccag tcccgaaacc tgctgaagac cacagatgac   1260
atggtgaaga cggccagaga aaaactgaaa cattattcct gcactgctga agacatcgat   1320
catgaagaca tcacacggga ccaaaccagc acattgaaga cctgtttacc actggaacta   1380
cacaagaacg agagttgcct ggctactaga gagacttctt ccacaacaag agggagctgc   1440
ctgcccccac agaagacgtc tttgatgatg accctgtgcc ttggtagcat ctatgaggac   1500
ttgaagatgt accagacaga gttccaggcc atcaacgcag cacttcagaa tcacaaccat   1560
cagcagatca ttcttgacaa gggcatgctg gtggccatcg atgagctgat gcagtctctg   1620
aatcataatg gcgagactct gcgccagaaa cctcctgtgg gagaagcaga cccttacaga   1680
gtgaaaatga agctctgcat cctgcttcac gccttcagca cccgcgtcgt gaccatcaac   1740
agggtgatgg gctatctgag ctccgccgcg gccgcaggat ctggggccac caacttttca   1800
ttgctcaagc aggcgggcga tgtggaggaa aaccctggcc ccggatcctg tcctcagaag   1860
ctaaccatct cctggtttgc catcgttttg ctggtgtctc cactcatggc catgtgggag   1920
ctggagaaag acgtttatgt tgtagaggtg gactggactc ccgatgcccc tggagaaaca   1980
gtgaacctca cctgtgacac gcctgaagaa gatgacatca cctggacctc agaccagaga   2040
catggagtca taggctctgg aaagaccctg accatcactg tcaaagagtt tcttgatgct   2100
ggccagtaca cctgccacaa aggaggcgag actctgagcc actcacatct gctgctccac   2160
aagaaggaaa atggaatttg gtccactgaa attttaaaga atttcaagaa caagactttc   2220
ctgaagtgtg aagcaccaaa ttactccgga cggttcacgt gctcatggct ggtgcaaaga   2280
aacatggact tgaagttcaa catcaagagc agtagcagtt cccctgactc tcgggcagtg   2340
acatgtggaa tggcgtctct gtctgcagag aaggtcacac tggaccaaag ggactatgag   2400
aagtattcag tgtcctgcca ggaggatgtc acctgcccaa ctgccgagga gaccctgccc   2460
```

attgaactgg cgttggaagc acggcagcag aataaatatg agaactacag caccagcttc 2520
ttcatcaggg acatcatcaa accagacccg cccaagaact tgcagatgaa gcctttgaag 2580
aactcacagg tggaggtcag ctgggagtac cctgactcct ggagcactcc ccattcctac 2640
ttctccctca agttctttgt tcgaatccag cgcaagaaag aaaagatgaa ggagacagag 2700
gaggggtgta accagaaagg tgcgttcctc gtagagaaga catctaccga agtccaatgc 2760
aaaggcggga atgtctgcgt gcaagctcag gatcgctatt acaattcctc atgcagcaag 2820
tgggcatgtg ttccctgcag ggtccgatcc tag 2853

<210> SEQ ID NO 64
<211> LENGTH: 950
<212> TYPE: PRT
<213> ORGANISM: Artificial Sequence
<220> FEATURE:
<223> OTHER INFORMATION: Igkappa-HA-2C11VHC-Linker-2C11VLC-Linker-PDGFR-
P2A-mIL-12p35-P2A-mIL-12p40 sequence

<400> SEQUENCE: 64

Met Glu Thr Asp Thr Leu Leu Leu Trp Val Leu Leu Leu Trp Val Pro
1 5 10 15

Gly Ser Thr Gly Asp Tyr Pro Tyr Asp Val Pro Asp Tyr Ala Gly Ala
20 25 30

Gln Pro Ala Arg Ser Glu Val Gln Leu Val Glu Ser Gly Gly Gly Leu
35 40 45

Val Gln Pro Gly Lys Ser Leu Lys Leu Ser Cys Glu Ala Ser Gly Phe
50 55 60

Thr Phe Ser Gly Tyr Gly Met His Trp Val Arg Gln Ala Pro Gly Arg
65 70 75 80

Gly Leu Glu Ser Val Ala Tyr Ile Thr Ser Ser Ser Ile Asn Ile Lys
85 90 95

Tyr Ala Asp Ala Val Lys Gly Arg Phe Thr Val Ser Arg Asp Asn Ala
100 105 110

Lys Asn Leu Leu Phe Leu Gln Met Asn Ile Leu Lys Ser Glu Asp Thr
115 120 125

Ala Met Tyr Tyr Cys Ala Arg Phe Asp Trp Asp Lys Asn Tyr Trp Gly
130 135 140

Gln Gly Thr Met Val Thr Val Ser Ser Gly Gly Gly Gly Ser Gly Gly
145 150 155 160

Gly Gly Ser Gly Gly Gly Gly Ser Asp Ile Gln Met Thr Gln Ser Pro
165 170 175

Ser Ser Leu Pro Ala Ser Leu Gly Asp Arg Val Thr Ile Asn Cys Gln
180 185 190

Ala Ser Gln Asp Ile Ser Asn Tyr Leu Asn Trp Tyr Gln Gln Lys Pro
195 200 205

Gly Lys Ala Pro Lys Leu Leu Ile Tyr Tyr Thr Asn Lys Leu Ala Asp
210 215 220

Gly Val Pro Ser Arg Phe Ser Gly Ser Gly Ser Gly Arg Asp Ser Ser
225 230 235 240

Phe Thr Ile Ser Ser Leu Glu Ser Glu Asp Ile Gly Ser Tyr Tyr Cys
245 250 255

Gln Gln Tyr Tyr Asn Tyr Pro Trp Thr Phe Gly Pro Gly Thr Lys Leu
260 265 270

Glu Ile Lys Gly Ser Gly Ser Gly Asn Ala Val Gly Gln Asp Thr Gln
275 280 285

```
Glu Val Ile Val Val Pro His Ser Leu Pro Phe Lys Val Val Val Ile
    290                 295                 300

Ser Ala Ile Leu Ala Leu Val Val Leu Thr Ile Ile Ser Leu Ile Ile
305                 310                 315                 320

Leu Ile Met Leu Trp Gln Lys Lys Pro Arg Gly Ser Gly Ala Thr Asn
                325                 330                 335

Phe Ser Leu Leu Lys Gln Ala Gly Asp Val Glu Glu Asn Pro Gly Pro
            340                 345                 350

Gly Thr Val Ser Val Pro Thr Ala Ser Pro Ser Ala Ser Ser Ser Ser
        355                 360                 365

Ser Gln Cys Arg Ser Ser Met Cys Gln Ser Arg Tyr Leu Leu Phe Leu
    370                 375                 380

Ala Thr Leu Ala Leu Leu Asn His Leu Ser Leu Ala Arg Val Ile Pro
385                 390                 395                 400

Val Ser Gly Pro Ala Arg Cys Leu Ser Gln Ser Arg Asn Leu Leu Lys
                405                 410                 415

Thr Thr Asp Asp Met Val Lys Thr Ala Arg Glu Lys Leu Lys His Tyr
            420                 425                 430

Ser Cys Thr Ala Glu Asp Ile Asp His Glu Asp Ile Thr Arg Asp Gln
        435                 440                 445

Thr Ser Thr Leu Lys Thr Cys Leu Pro Leu Glu Leu His Lys Asn Glu
    450                 455                 460

Ser Cys Leu Ala Thr Arg Glu Thr Ser Ser Thr Thr Arg Gly Ser Cys
465                 470                 475                 480

Leu Pro Pro Gln Lys Thr Ser Leu Met Met Thr Leu Cys Leu Gly Ser
                485                 490                 495

Ile Tyr Glu Asp Leu Lys Met Tyr Gln Thr Glu Phe Gln Ala Ile Asn
            500                 505                 510

Ala Ala Leu Gln Asn His Asn His Gln Gln Ile Ile Leu Asp Lys Gly
        515                 520                 525

Met Leu Val Ala Ile Asp Glu Leu Met Gln Ser Leu Asn His Asn Gly
    530                 535                 540

Glu Thr Leu Arg Gln Lys Pro Pro Val Gly Glu Ala Asp Pro Tyr Arg
545                 550                 555                 560

Val Lys Met Lys Leu Cys Ile Leu Leu His Ala Phe Ser Thr Arg Val
                565                 570                 575

Val Thr Ile Asn Arg Val Met Gly Tyr Leu Ser Ser Ala Ala Ala Ala
            580                 585                 590

Gly Ser Gly Ala Thr Asn Phe Ser Leu Leu Lys Gln Ala Gly Asp Val
        595                 600                 605

Glu Glu Asn Pro Gly Pro Gly Ser Cys Pro Gln Lys Leu Thr Ile Ser
    610                 615                 620

Trp Phe Ala Ile Val Leu Leu Val Ser Pro Leu Met Ala Met Trp Glu
625                 630                 635                 640

Leu Glu Lys Asp Val Tyr Val Val Glu Val Asp Trp Thr Pro Asp Ala
                645                 650                 655

Pro Gly Glu Thr Val Asn Leu Thr Cys Asp Thr Pro Glu Glu Asp Asp
            660                 665                 670

Ile Thr Trp Thr Ser Asp Gln Arg His Gly Val Ile Gly Ser Gly Lys
        675                 680                 685

Thr Leu Thr Ile Thr Val Lys Glu Phe Leu Asp Ala Gly Gln Tyr Thr
    690                 695                 700

Cys His Lys Gly Gly Glu Thr Leu Ser His Ser His Leu Leu Leu His
```

```
705                 710                 715                 720

Lys Lys Glu Asn Gly Ile Trp Ser Thr Glu Ile Leu Lys Asn Phe Lys
                725                 730                 735

Asn Lys Thr Phe Leu Lys Cys Glu Ala Pro Asn Tyr Ser Gly Arg Phe
            740                 745                 750

Thr Cys Ser Trp Leu Val Gln Arg Asn Met Asp Leu Lys Phe Asn Ile
        755                 760                 765

Lys Ser Ser Ser Ser Ser Pro Asp Ser Arg Ala Val Thr Cys Gly Met
    770                 775                 780

Ala Ser Leu Ser Ala Glu Lys Val Thr Leu Asp Gln Arg Asp Tyr Glu
785                 790                 795                 800

Lys Tyr Ser Val Ser Cys Gln Glu Asp Val Thr Cys Pro Thr Ala Glu
                805                 810                 815

Glu Thr Leu Pro Ile Glu Leu Ala Leu Glu Ala Arg Gln Gln Asn Lys
            820                 825                 830

Tyr Glu Asn Tyr Ser Thr Ser Phe Phe Ile Arg Asp Ile Ile Lys Pro
        835                 840                 845

Asp Pro Pro Lys Asn Leu Gln Met Lys Pro Leu Lys Asn Ser Gln Val
    850                 855                 860

Glu Val Ser Trp Glu Tyr Pro Asp Ser Trp Ser Thr Pro His Ser Tyr
865                 870                 875                 880

Phe Ser Leu Lys Phe Phe Val Arg Ile Gln Arg Lys Lys Glu Lys Met
                885                 890                 895

Lys Glu Thr Glu Glu Gly Cys Asn Gln Lys Gly Ala Phe Leu Val Glu
            900                 905                 910

Lys Thr Ser Thr Glu Val Gln Cys Lys Gly Gly Asn Val Cys Val Gln
        915                 920                 925

Ala Gln Asp Arg Tyr Tyr Asn Ser Ser Cys Ser Lys Trp Ala Cys Val
    930                 935                 940

Pro Cys Arg Val Arg Ser
945                 950


<210> SEQ ID NO 65
<211> LENGTH: 2826
<212> TYPE: DNA
<213> ORGANISM: Artificial Sequence
<220> FEATURE:
<223> OTHER INFORMATION: Igkappa-2C11VHC-Linker-2C11VLC-Linker-PDGFR-
      P2A-mIL-12p35-P2A-mIL-12p40 sequence

<400> SEQUENCE: 65

atggagacag acacactcct gctatgggta ctgctgctct gggttccagg ttccactggt      60

gacggggccc agccggccag atctgaggtg cagctggtgg agtctggggg aggcttggtg     120

cagcctggaa agtccctgaa actctcctgt gaggcctctg gattcacctt cagcggctat     180

ggcatgcact gggtccgcca ggctccaggg agggggctgg agtcggtcgc atacattact     240

agtagtagta ttaatatcaa atatgctgac gctgtgaaag gccggttcac cgtctccaga     300

gacaatgcca agaacttact gtttctacaa atgaacattc tcaagtctga ggacacagcc     360

atgtactact gtgcaagatt cgactgggac aaaaattact ggggccaagg aaccatggtc     420

accgtctcct caggtggcgg tggctccggc ggtggtgggt cgggtggcgg cggatctgac     480

atccagatga cccagtctcc atcatcactg cctgcctccc tgggagacag agtcactatc     540

aattgtcagg ccagtcagga cattagcaat tatttaaact ggtatcagca gaaaccaggg     600

aaagctccta agctcctgat ctattataca aataaattgg cagatggagt cccatcaagg     660
```

```
ttcagtggca gtggttctgg gagagattct tctttcacta tcagcagcct ggaatccgaa    720
gatattggat cttattactg tcaacagtat tataactatc cgtggacgtt cggacctggc    780
accaagctgg aaatcaaagg cagtgggagt gggaatgctg tgggccagga cacgcaggag    840
gtcatcgtgg tgccacactc cttgcccttt aaggtggtgg tgatctcagc catcctggcc    900
ctggtggtgc tcaccatcat ctcccttatc atcctcatca tgctttggca gaagaagcca    960
cgtggatctg gggccaccaa cttttcattg ctcaagcagg cgggcgatgt ggaggaaaac   1020
cctggccccg gtaccgtcag cgttccaaca gcctcaccct cggcatccag cagctcctct   1080
cagtgccggt ccagcatgtg tcaatcacgc tacctcctct tttggccacc ccttgccctc   1140
ctaaaccacc tcagtttggc cagggtcatt ccagtctctg gacctgccag gtgtcttagc   1200
cagtcccgaa acctgctgaa gaccacagat gacatggtga agacggccag agaaaaactg   1260
aaacattatt cctgcactgc tgaagacatc gatcatgaag acatcacacg ggaccaaacc   1320
agcacattga agacctgttt accactggaa ctacacaaga acgagagttg cctggctact   1380
agagagactt cttccacaac aagagggagc tgcctgcccc cacagaagac gtctttgatg   1440
atgaccctgt gccttggtag catctatgag gacttgaaga tgtaccagac agagttccag   1500
gccatcaacg cagcacttca gaatcacaac catcagcaga tcattcttga caagggcatg   1560
ctggtggcca tcgatgagct gatgcagtct ctgaatcata atggcgagac tctgcgccag   1620
aaacctcctg tgggagaagc agacccttac agagtgaaaa tgaagctctg catcctgctt   1680
cacgccttca gcacccgcgt cgtgaccatc aacagggtga tgggctatct gagctccgcc   1740
gcggccgcag gatctggggc caccaacttt tcattgctca agcaggcggg cgatgtggag   1800
gaaaaccctg gccccggatc ctgtcctcag aagctaacca tctcctggtt tgccatcgtt   1860
ttgctggtgt ctccactcat ggccatgtgg gagctggaga aagacgttta tgttgtagag   1920
gtggactgga ctcccgatgc ccctggagaa acagtgaacc tcacctgtga cacgcctgaa   1980
gaagatgaca tcacctggac ctcagaccag agacatggag tcataggctc tggaaagacc   2040
ctgaccatca ctgtcaaaga gtttcttgat gctggccagt acacctgcca caaaggaggc   2100
gagactctga gccactcaca tctgctgctc cacaagaagg aaaatggaat ttggtccact   2160
gaaattttaa agaatttcaa gaacaagact ttcctgaagt gtgaagcacc aaattactcc   2220
ggacggttca cgtgctcatg gctggtgcaa agaaacatgg acttgaagtt caacatcaag   2280
agcagtagca gttcccctga ctctcgggca gtgacatgtg gaatggcgtc tctgtctgca   2340
gagaaggtca cactggacca aagggactat gagaagtatt cagtgtcctg ccaggaggat   2400
gtcacctgcc caactgccga ggagaccctg cccattgaac tggcgttgga agcacggcag   2460
cagaataaat atgagaacta cagcaccagc ttcttcatca gggacatcat caaaccagac   2520
ccgcccaaga acttgcagat gaagcctttg aagaactcac aggtggaggt cagctgggag   2580
taccctgact cctggagcac tccccattcc tacttctccc tcaagttctt tgttcgaatc   2640
cagcgcaaga aagaaaagat gaaggagaca gaggaggggt gtaaccagaa aggtgcgttc   2700
ctcgtagaga agacatctac cgaagtccaa tgcaaaggcg ggaatgtctg cgtgcaagct   2760
caggatcgct attacaattc ctcatgcagc aagtgggcat gtgttccctg cagggtccga   2820
tcctag                                                              2826
```

<210> SEQ ID NO 66
<211> LENGTH: 941
<212> TYPE: PRT

<213> ORGANISM: Artificial Sequence
<220> FEATURE:
<223> OTHER INFORMATION: Igkappa-2C11VHC-Linker-2C11VLC-Linker-PDGFR-
P2A-mIL-12p35-P2A-mIL-12p40 sequence

<400> SEQUENCE: 66

```
Met Glu Thr Asp Thr Leu Leu Leu Trp Val Leu Leu Leu Trp Val Pro
1               5                   10                  15

Gly Ser Thr Gly Asp Gly Ala Gln Pro Ala Arg Ser Glu Val Gln Leu
            20                  25                  30

Val Glu Ser Gly Gly Gly Leu Val Gln Pro Gly Lys Ser Leu Lys Leu
        35                  40                  45

Ser Cys Glu Ala Ser Gly Phe Thr Phe Ser Gly Tyr Gly Met His Trp
    50                  55                  60

Val Arg Gln Ala Pro Gly Arg Gly Leu Glu Ser Val Ala Tyr Ile Thr
65                  70                  75                  80

Ser Ser Ser Ile Asn Ile Lys Tyr Ala Asp Ala Val Lys Gly Arg Phe
                85                  90                  95

Thr Val Ser Arg Asp Asn Ala Lys Asn Leu Leu Phe Leu Gln Met Asn
            100                 105                 110

Ile Leu Lys Ser Glu Asp Thr Ala Met Tyr Tyr Cys Ala Arg Phe Asp
        115                 120                 125

Trp Asp Lys Asn Tyr Trp Gly Gln Gly Thr Met Val Thr Val Ser Ser
    130                 135                 140

Gly Gly Gly Gly Ser Gly Gly Gly Gly Ser Gly Gly Gly Gly Ser Asp
145                 150                 155                 160

Ile Gln Met Thr Gln Ser Pro Ser Ser Leu Pro Ala Ser Leu Gly Asp
                165                 170                 175

Arg Val Thr Ile Asn Cys Gln Ala Ser Gln Asp Ile Ser Asn Tyr Leu
            180                 185                 190

Asn Trp Tyr Gln Gln Lys Pro Gly Lys Ala Pro Lys Leu Leu Ile Tyr
        195                 200                 205

Tyr Thr Asn Lys Leu Ala Asp Gly Val Pro Ser Arg Phe Ser Gly Ser
    210                 215                 220

Gly Ser Gly Arg Asp Ser Ser Phe Thr Ile Ser Ser Leu Glu Ser Glu
225                 230                 235                 240

Asp Ile Gly Ser Tyr Tyr Cys Gln Gln Tyr Tyr Asn Tyr Pro Trp Thr
                245                 250                 255

Phe Gly Pro Gly Thr Lys Leu Glu Ile Lys Gly Ser Gly Ser Gly Asn
            260                 265                 270

Ala Val Gly Gln Asp Thr Gln Glu Val Ile Val Val Pro His Ser Leu
        275                 280                 285

Pro Phe Lys Val Val Val Ile Ser Ala Ile Leu Ala Leu Val Val Leu
    290                 295                 300

Thr Ile Ile Ser Leu Ile Ile Leu Ile Met Leu Trp Gln Lys Lys Pro
305                 310                 315                 320

Arg Gly Ser Gly Ala Thr Asn Phe Ser Leu Leu Lys Gln Ala Gly Asp
                325                 330                 335

Val Glu Glu Asn Pro Gly Pro Gly Thr Val Ser Val Pro Thr Ala Ser
            340                 345                 350

Pro Ser Ala Ser Ser Ser Ser Ser Gln Cys Arg Ser Ser Met Cys Gln
        355                 360                 365

Ser Arg Tyr Leu Leu Phe Leu Ala Thr Leu Ala Leu Leu Asn His Leu
    370                 375                 380
```

```
Ser Leu Ala Arg Val Ile Pro Val Ser Gly Pro Ala Arg Cys Leu Ser
385                 390                 395                 400

Gln Ser Arg Asn Leu Leu Lys Thr Thr Asp Asp Met Val Lys Thr Ala
                405                 410                 415

Arg Glu Lys Leu Lys His Tyr Ser Cys Thr Ala Glu Asp Ile Asp His
            420                 425                 430

Glu Asp Ile Thr Arg Asp Gln Thr Ser Thr Leu Lys Thr Cys Leu Pro
        435                 440                 445

Leu Glu Leu His Lys Asn Glu Ser Cys Leu Ala Thr Arg Glu Thr Ser
    450                 455                 460

Ser Thr Thr Arg Gly Ser Cys Leu Pro Pro Gln Lys Thr Ser Leu Met
465                 470                 475                 480

Met Thr Leu Cys Leu Gly Ser Ile Tyr Glu Asp Leu Lys Met Tyr Gln
                485                 490                 495

Thr Glu Phe Gln Ala Ile Asn Ala Ala Leu Gln Asn His Asn His Gln
            500                 505                 510

Gln Ile Ile Leu Asp Lys Gly Met Leu Val Ala Ile Asp Glu Leu Met
        515                 520                 525

Gln Ser Leu Asn His Asn Gly Glu Thr Leu Arg Gln Lys Pro Pro Val
    530                 535                 540

Gly Glu Ala Asp Pro Tyr Arg Val Lys Met Lys Leu Cys Ile Leu Leu
545                 550                 555                 560

His Ala Phe Ser Thr Arg Val Val Thr Ile Asn Arg Val Met Gly Tyr
                565                 570                 575

Leu Ser Ser Ala Ala Ala Ala Gly Ser Gly Ala Thr Asn Phe Ser Leu
            580                 585                 590

Leu Lys Gln Ala Gly Asp Val Glu Glu Asn Pro Gly Pro Gly Ser Cys
        595                 600                 605

Pro Gln Lys Leu Thr Ile Ser Trp Phe Ala Ile Val Leu Leu Val Ser
    610                 615                 620

Pro Leu Met Ala Met Trp Glu Leu Glu Lys Asp Val Tyr Val Val Glu
625                 630                 635                 640

Val Asp Trp Thr Pro Asp Ala Pro Gly Glu Thr Val Asn Leu Thr Cys
                645                 650                 655

Asp Thr Pro Glu Glu Asp Asp Ile Thr Trp Thr Ser Asp Gln Arg His
            660                 665                 670

Gly Val Ile Gly Ser Gly Lys Thr Leu Thr Ile Thr Val Lys Glu Phe
        675                 680                 685

Leu Asp Ala Gly Gln Tyr Thr Cys His Lys Gly Gly Glu Thr Leu Ser
    690                 695                 700

His Ser His Leu Leu Leu His Lys Lys Glu Asn Gly Ile Trp Ser Thr
705                 710                 715                 720

Glu Ile Leu Lys Asn Phe Lys Asn Lys Thr Phe Leu Lys Cys Glu Ala
                725                 730                 735

Pro Asn Tyr Ser Gly Arg Phe Thr Cys Ser Trp Leu Val Gln Arg Asn
            740                 745                 750

Met Asp Leu Lys Phe Asn Ile Lys Ser Ser Ser Ser Ser Pro Asp Ser
        755                 760                 765

Arg Ala Val Thr Cys Gly Met Ala Ser Leu Ser Ala Glu Lys Val Thr
    770                 775                 780

Leu Asp Gln Arg Asp Tyr Glu Lys Tyr Ser Val Ser Cys Gln Glu Asp
785                 790                 795                 800

Val Thr Cys Pro Thr Ala Glu Glu Thr Leu Pro Ile Glu Leu Ala Leu
```

```
                805                 810                 815

Glu Ala Arg Gln Gln Asn Lys Tyr Glu Asn Tyr Ser Thr Ser Phe Phe
            820                 825                 830

Ile Arg Asp Ile Ile Lys Pro Asp Pro Pro Lys Asn Leu Gln Met Lys
        835                 840                 845

Pro Leu Lys Asn Ser Gln Val Glu Val Ser Trp Glu Tyr Pro Asp Ser
    850                 855                 860

Trp Ser Thr Pro His Ser Tyr Phe Ser Leu Lys Phe Phe Val Arg Ile
865                 870                 875                 880

Gln Arg Lys Lys Glu Lys Met Lys Glu Thr Glu Glu Gly Cys Asn Gln
                885                 890                 895

Lys Gly Ala Phe Leu Val Glu Lys Thr Ser Thr Glu Val Gln Cys Lys
            900                 905                 910

Gly Gly Asn Val Cys Val Gln Ala Gln Asp Arg Tyr Tyr Asn Ser Ser
        915                 920                 925

Cys Ser Lys Trp Ala Cys Val Pro Cys Arg Val Arg Ser
    930                 935                 940


<210> SEQ ID NO 67
<211> LENGTH: 2244
<212> TYPE: DNA
<213> ORGANISM: Artificial Sequence
<220> FEATURE:
<223> OTHER INFORMATION: mIL-12 p35-P2A-mIL-12 p40-P2A-mCXCL9 sequence

<400> SEQUENCE: 67

atggtcagcg ttccaacagc ctcaccctcg gcatccagca gctcctctca gtgccggtcc     60

agcatgtgtc aatcacgcta cctcctcttt ttggccaccc ttgccctcct aaaccacctc    120

agtttggcca gggtcattcc agtctctgga cctgccaggt gtcttagcca gtcccgaaac    180

ctgctgaaga ccacagatga catggtgaag acggccagag aaaaactgaa acattattcc    240

tgcactgctg aagacatcga tcatgaagac atcacacggg accaaaccag cacattgaag    300

acctgtttac cactggaact acacaagaac gagagttgcc tggctactag agagacttct    360

tccacaacaa gagggagctg cctgccccca cagaagacgt ctttgatgat gaccctgtgc    420

cttggtagca tctatgagga cttgaagatg taccagacag agttccaggc catcaacgca    480

gcacttcaga atcacaacca tcagcagatc attctggaca agggcatgct ggtggccatc    540

gatgagctga tgcagtctct gaatcataat ggcgagactc tgcgccagaa acctcctgtg    600

ggagaagcag acccttacag agtgaaaatg aagctctgca tcctgcttca cgccttcagc    660

acccgcgtcg tgaccatcaa cagggtgatg ggctatctga gctccgccgc ggccgcagga    720

tctggggcca ccaacttttc attgctcaag caggcgggcg atgtggagga aaaccctggc    780

cccggatcct gtcctcagaa gctaaccatc tcctggtttg ccatcgtttt gctggtgtct    840

ccactcatgg ccatgtggga gctggagaaa gacgtttatg ttgtagaggt ggactggact    900

cccgatgccc ctggagaaac agtgaacctc acctgtgaca cgcctgaaga agatgacatc    960

acctggacct cagaccagag acatggagtc ataggctctg gaaagaccct gaccatcact   1020

gtcaaagagt ttcttgatgc tggccagtac acctgccaca aaggaggcga gactctgagc   1080

cactcacatc tgctgctcca caagaaggaa aatggaattt ggtccactga aattttaaag   1140

aatttcaaga acaagacttt cctgaagtgt gaagcaccaa attactccgg acggttcacg   1200

tgctcatggc tggtgcaaag aaacatggac ttgaagttca acatcaagag cagtagcagt   1260

tcccctgact ctcgggcagt gacatgtgga atggcgtctc tgtctgcaga gaaggtcaca   1320
```

```
ctggaccaaa gggactatga gaagtattca gtgtcctgcc aggaggatgt cacctgccca   1380

actgccgagg agaccctgcc cattgaactg gcgttggaag cacggcagca gaataaatat   1440

gagaactaca gcaccagctt cttcatcagg gacatcatca aaccagaccc gcccaagaac   1500

ttgcagatga agcctttgaa gaactcacag gtggaggtca gctgggagta ccctgactcc   1560

tggagcactc cccattccta cttctccctc aagttctttg ttcgaatcca gcgcaagaaa   1620

gaaaagatga aggagacaga ggaggggtgt aaccagaaag gtgcgttcct cgtagagaag   1680

acatctaccg aagtccaatg caaaggcggg aatgtctgcg tgcaagctca ggatcgctat   1740

tacaattcct catgcagcaa gtgggcatgt gttccctgca gggtccgatc ctcgtctaga   1800

ggatctgggg ccaccaactt ttcattgctc aagcaggcgg gcgatgtgga ggaaaaccct   1860

ggccccaagt ccgctgttct ttcctcttg ggcatcatct tcctggagca gtgtggagtt    1920

cgaggaaccc tagtgataag gaatgcacga tgctcctgca tcagcaccag ccgaggcacg   1980

atccactaca aatccctcaa agacctcaaa cagtttgccc caagccccaa ttgcaacaaa   2040

actgaaatca ttgctacact gaagaacgga gatcaaacct gcctagatcc ggactcggca   2100

aatgtgaaga agctgatgaa agaatgggaa aagaagatca gccaaaagaa aaagcaaaag   2160

agggggaaaa aacatcaaaa gaacatgaaa aacagaaaac ccaaaacacc ccaaagtcgt   2220

cgtcgttcaa ggaagactac ataa                                         2244
```

```
<210> SEQ ID NO 68
<211> LENGTH: 747
<212> TYPE: PRT
<213> ORGANISM: Artificial Sequence
<220> FEATURE:
<223> OTHER INFORMATION: mIL-12 p35-P2A-mIL-12 p40-P2A-mCXCL9 sequence

<400> SEQUENCE: 68

Met Val Ser Val Pro Thr Ala Ser Pro Ser Ala Ser Ser Ser Ser Ser
1               5                   10                  15

Gln Cys Arg Ser Ser Met Cys Gln Ser Arg Tyr Leu Leu Phe Leu Ala
            20                  25                  30

Thr Leu Ala Leu Leu Asn His Leu Ser Leu Ala Arg Val Ile Pro Val
        35                  40                  45

Ser Gly Pro Ala Arg Cys Leu Ser Gln Ser Arg Asn Leu Leu Lys Thr
    50                  55                  60

Thr Asp Asp Met Val Lys Thr Ala Arg Glu Lys Leu Lys His Tyr Ser
65                  70                  75                  80

Cys Thr Ala Glu Asp Ile Asp His Glu Asp Ile Thr Arg Asp Gln Thr
                85                  90                  95

Ser Thr Leu Lys Thr Cys Leu Pro Leu Glu Leu His Lys Asn Glu Ser
            100                 105                 110

Cys Leu Ala Thr Arg Glu Thr Ser Ser Thr Thr Arg Gly Ser Cys Leu
        115                 120                 125

Pro Pro Gln Lys Thr Ser Leu Met Met Thr Leu Cys Leu Gly Ser Ile
    130                 135                 140

Tyr Glu Asp Leu Lys Met Tyr Gln Thr Glu Phe Gln Ala Ile Asn Ala
145                 150                 155                 160

Ala Leu Gln Asn His Asn His Gln Gln Ile Ile Leu Asp Lys Gly Met
                165                 170                 175

Leu Val Ala Ile Asp Glu Leu Met Gln Ser Leu Asn His Asn Gly Glu
            180                 185                 190
```

```
Thr Leu Arg Gln Lys Pro Pro Val Gly Glu Ala Asp Pro Tyr Arg Val
        195                 200                 205

Lys Met Lys Leu Cys Ile Leu Leu His Ala Phe Ser Thr Arg Val Val
    210                 215                 220

Thr Ile Asn Arg Val Met Gly Tyr Leu Ser Ser Ala Ala Ala Ala Gly
225                 230                 235                 240

Ser Gly Ala Thr Asn Phe Ser Leu Leu Lys Gln Ala Gly Asp Val Glu
                245                 250                 255

Glu Asn Pro Gly Pro Gly Ser Cys Pro Gln Lys Leu Thr Ile Ser Trp
            260                 265                 270

Phe Ala Ile Val Leu Leu Val Ser Pro Leu Met Ala Met Trp Glu Leu
        275                 280                 285

Glu Lys Asp Val Tyr Val Val Glu Val Asp Trp Thr Pro Asp Ala Pro
    290                 295                 300

Gly Glu Thr Val Asn Leu Thr Cys Asp Thr Pro Glu Glu Asp Asp Ile
305                 310                 315                 320

Thr Trp Thr Ser Asp Gln Arg His Gly Val Ile Gly Ser Gly Lys Thr
                325                 330                 335

Leu Thr Ile Thr Val Lys Glu Phe Leu Asp Ala Gly Gln Tyr Thr Cys
            340                 345                 350

His Lys Gly Gly Glu Thr Leu Ser His Ser His Leu Leu Leu His Lys
        355                 360                 365

Lys Glu Asn Gly Ile Trp Ser Thr Glu Ile Leu Lys Asn Phe Lys Asn
    370                 375                 380

Lys Thr Phe Leu Lys Cys Glu Ala Pro Asn Tyr Ser Gly Arg Phe Thr
385                 390                 395                 400

Cys Ser Trp Leu Val Gln Arg Asn Met Asp Leu Lys Phe Asn Ile Lys
                405                 410                 415

Ser Ser Ser Ser Ser Pro Asp Ser Arg Ala Val Thr Cys Gly Met Ala
            420                 425                 430

Ser Leu Ser Ala Glu Lys Val Thr Leu Asp Gln Arg Asp Tyr Glu Lys
        435                 440                 445

Tyr Ser Val Ser Cys Gln Glu Asp Val Thr Cys Pro Thr Ala Glu Glu
    450                 455                 460

Thr Leu Pro Ile Glu Leu Ala Leu Glu Ala Arg Gln Gln Asn Lys Tyr
465                 470                 475                 480

Glu Asn Tyr Ser Thr Ser Phe Phe Ile Arg Asp Ile Ile Lys Pro Asp
                485                 490                 495

Pro Pro Lys Asn Leu Gln Met Lys Pro Leu Lys Asn Ser Gln Val Glu
            500                 505                 510

Val Ser Trp Glu Tyr Pro Asp Ser Trp Ser Thr Pro His Ser Tyr Phe
        515                 520                 525

Ser Leu Lys Phe Phe Val Arg Ile Gln Arg Lys Lys Glu Lys Met Lys
    530                 535                 540

Glu Thr Glu Glu Gly Cys Asn Gln Lys Gly Ala Phe Leu Val Glu Lys
545                 550                 555                 560

Thr Ser Thr Glu Val Gln Cys Lys Gly Gly Asn Val Cys Val Gln Ala
                565                 570                 575

Gln Asp Arg Tyr Tyr Asn Ser Ser Cys Ser Lys Trp Ala Cys Val Pro
            580                 585                 590

Cys Arg Val Arg Ser Ser Ser Arg Gly Ser Gly Ala Thr Asn Phe Ser
        595                 600                 605

Leu Leu Lys Gln Ala Gly Asp Val Glu Glu Asn Pro Gly Pro Lys Ser
```

```
    610                 615                 620

Ala Val Leu Phe Leu Leu Gly Ile Ile Phe Leu Glu Gln Cys Gly Val
625                 630                 635                 640

Arg Gly Thr Leu Val Ile Arg Asn Ala Arg Cys Ser Cys Ile Ser Thr
                645                 650                 655

Ser Arg Gly Thr Ile His Tyr Lys Ser Leu Lys Asp Leu Lys Gln Phe
            660                 665                 670

Ala Pro Ser Pro Asn Cys Asn Lys Thr Glu Ile Ile Ala Thr Leu Lys
        675                 680                 685

Asn Gly Asp Gln Thr Cys Leu Asp Pro Asp Ser Ala Asn Val Lys Lys
    690                 695                 700

Leu Met Lys Glu Trp Glu Lys Lys Ile Ser Gln Lys Lys Lys Gln Lys
705                 710                 715                 720

Arg Gly Lys Lys His Gln Lys Asn Met Lys Asn Arg Lys Pro Lys Thr
                725                 730                 735

Pro Gln Ser Arg Arg Arg Ser Arg Lys Thr Thr
            740                 745
```

<210> SEQ ID NO 69
<211> LENGTH: 1596
<212> TYPE: DNA
<213> ORGANISM: Artificial Sequence
<220> FEATURE:
<223> OTHER INFORMATION: Igkappa-HA-9D9 VLC-Linker-9D9 VHC-Linker-mIgG1 Fc domain (anti-CTLA4 scFv) sequence

<400> SEQUENCE: 69

```
atggagacag acacactcct gctatgggta ctgctgctct gggttccagg ttccactggt     60

gactatccat atgatgttcc agattatgct ggggcccagc cggccagatc tgacattgtg    120

atgacacaga ccacactcag tctccccgtt tcccttggtg atcaagcctc catatcctgt    180

aggtctagtc aatctatcgt ccactccaac ggcaatacct atctggaatg gtatcttcaa    240

aagcccggac aatcaccaaa gcttcttatc tataaggtga gcaatagatt tagcggggtc    300

cctgaccgat tctctggaag tggctctggc acagacttta ccttgaaaat ctccagagtt    360

gaggctgagg accttggtgt atactactgc ttccaaggct ctcatgttcc ctacactttc    420

ggaggcggaa caaaactgga gataaaacga gccgacgcag cccccactgt gagtggctct    480

ggagggggct ctggcggtgg atctgggggt ggaagtgagg caaagcttca ggaatctggt    540

ccagtgttgg tgaaaccagg tgcatccgtg aaaatgtcct gcaaagcaag cggttacact    600

tttactgact attatatgaa ctgggtaaag caatcccacg gcaaatccct ggaatggatt    660

ggtgtcatca acccttacaa cggtgataca agttacaacc aaaagttcaa aggtaaggct    720

acattgaccg tagataagag tagcagtact gcatacatgg aacttaactc tcttacatcc    780

gaggactccg ctgtttacta ttgtgcacgc tactacggga gctggttcgc ttactggggt    840

caaggcaccc tgataacagt gtccacagcc aaaaccacac ctccctccgt ctatcctctc    900

gctccagtcg actctagtgg atccggtggt tgtaagcctt gcatatgtac agtcccagaa    960

gtatcatctg tcttcatctt ccccccaaag cccaaggatg tgctcaccat tactctgact   1020

cctaaggtca cgtgtgttgt ggtagacatc agcaaggatg atcccgaggt ccagttcagc   1080

tggtttgtag atgatgtgga ggtgcacaca gctcagacgc aaccccggga ggagcagttc   1140

aacagcactt tccgctcagt cagtgaactt cccatcatgc accaggactg gctcaatggc   1200

aaggagttca aatgcagggt caacagtgca gctttccctg cccccatcga gaaaaccatc   1260
```

tccaaaacca aaggcagacc gaaggctcca caggtgtaca ccattccacc tcccaaggag 1320
cagatggcca aggataaagt cagtctgacc tgcatgataa cagacttctt ccctgaagac 1380
attactgtgg agtggcagtg gaatgggcag ccagcggaga actacaagaa cactcagccc 1440
atcatggaca cagatggctc ttacttcgtc tacagcaagc tcaatgtgca gaagagcaac 1500
tgggaggcag gaaatacttt cacctgctct gtgttacatg agggcctgca caaccaccat 1560
actgagaaga gcctctccca ctctcctggt aaatga 1596

<210> SEQ ID NO 70
<211> LENGTH: 531
<212> TYPE: PRT
<213> ORGANISM: Artificial Sequence
<220> FEATURE:
<223> OTHER INFORMATION: Igkappa-HA-9D9 VLC-Linker-9D9 VHC-Linker-mIgG1 Fc domain (anti-CTLA4 scFv) sequence

<400> SEQUENCE: 70

Met Glu Thr Asp Thr Leu Leu Leu Trp Val Leu Leu Leu Trp Val Pro
1 5 10 15

Gly Ser Thr Gly Asp Tyr Pro Tyr Asp Val Pro Asp Tyr Ala Gly Ala
20 25 30

Gln Pro Ala Arg Ser Asp Ile Val Met Thr Gln Thr Thr Leu Ser Leu
35 40 45

Pro Val Ser Leu Gly Asp Gln Ala Ser Ile Ser Cys Arg Ser Ser Gln
50 55 60

Ser Ile Val His Ser Asn Gly Asn Thr Tyr Leu Glu Trp Tyr Leu Gln
65 70 75 80

Lys Pro Gly Gln Ser Pro Lys Leu Leu Ile Tyr Lys Val Ser Asn Arg
85 90 95

Phe Ser Gly Val Pro Asp Arg Phe Ser Gly Ser Gly Ser Gly Thr Asp
100 105 110

Phe Thr Leu Lys Ile Ser Arg Val Glu Ala Glu Asp Leu Gly Val Tyr
115 120 125

Tyr Cys Phe Gln Gly Ser His Val Pro Tyr Thr Phe Gly Gly Gly Thr
130 135 140

Lys Leu Glu Ile Lys Arg Ala Asp Ala Ala Pro Thr Val Ser Gly Ser
145 150 155 160

Gly Gly Gly Ser Gly Gly Gly Ser Gly Gly Gly Ser Glu Ala Lys Leu
165 170 175

Gln Glu Ser Gly Pro Val Leu Val Lys Pro Gly Ala Ser Val Lys Met
180 185 190

Ser Cys Lys Ala Ser Gly Tyr Thr Phe Thr Asp Tyr Tyr Met Asn Trp
195 200 205

Val Lys Gln Ser His Gly Lys Ser Leu Glu Trp Ile Gly Val Ile Asn
210 215 220

Pro Tyr Asn Gly Asp Thr Ser Tyr Asn Gln Lys Phe Lys Gly Lys Ala
225 230 235 240

Thr Leu Thr Val Asp Lys Ser Ser Ser Thr Ala Tyr Met Glu Leu Asn
245 250 255

Ser Leu Thr Ser Glu Asp Ser Ala Val Tyr Tyr Cys Ala Arg Tyr Tyr
260 265 270

Gly Ser Trp Phe Ala Tyr Trp Gly Gln Gly Thr Leu Ile Thr Val Ser
275 280 285

Thr Ala Lys Thr Thr Pro Pro Ser Val Tyr Pro Leu Ala Pro Val Asp
290 295 300

```
Ser Ser Gly Ser Gly Gly Cys Lys Pro Cys Ile Cys Thr Val Pro Glu
305                 310                 315                 320

Val Ser Ser Val Phe Ile Phe Pro Pro Lys Pro Lys Asp Val Leu Thr
                325                 330                 335

Ile Thr Leu Thr Pro Lys Val Thr Cys Val Val Val Asp Ile Ser Lys
            340                 345                 350

Asp Asp Pro Glu Val Gln Phe Ser Trp Phe Val Asp Asp Val Glu Val
        355                 360                 365

His Thr Ala Gln Thr Gln Pro Arg Glu Glu Gln Phe Asn Ser Thr Phe
    370                 375                 380

Arg Ser Val Ser Glu Leu Pro Ile Met His Gln Asp Trp Leu Asn Gly
385                 390                 395                 400

Lys Glu Phe Lys Cys Arg Val Asn Ser Ala Ala Phe Pro Ala Pro Ile
                405                 410                 415

Glu Lys Thr Ile Ser Lys Thr Lys Gly Arg Pro Lys Ala Pro Gln Val
            420                 425                 430

Tyr Thr Ile Pro Pro Pro Lys Glu Gln Met Ala Lys Asp Lys Val Ser
        435                 440                 445

Leu Thr Cys Met Ile Thr Asp Phe Phe Pro Glu Asp Ile Thr Val Glu
    450                 455                 460

Trp Gln Trp Asn Gly Gln Pro Ala Glu Asn Tyr Lys Asn Thr Gln Pro
465                 470                 475                 480

Ile Met Asp Thr Asp Gly Ser Tyr Phe Val Tyr Ser Lys Leu Asn Val
                485                 490                 495

Gln Lys Ser Asn Trp Glu Ala Gly Asn Thr Phe Thr Cys Ser Val Leu
            500                 505                 510

His Glu Gly Leu His Asn His His Thr Glu Lys Ser Leu Ser His Ser
        515                 520                 525

Pro Gly Lys
    530
```

<210> SEQ ID NO 71
<211> LENGTH: 1563
<212> TYPE: DNA
<213> ORGANISM: Artificial Sequence
<220> FEATURE:
<223> OTHER INFORMATION: Igkappa-HA-9H10 VLC-Linker-9H10 VHC-Linker-mIgG1 Fc domain (anti-CTLA4 scFv) sequence

<400> SEQUENCE: 71

```
atggagacag acacactcct gctatgggta ctgctgctct gggttccagg ttccactggt     60

gactatccat atgatgttcc agattatgct ggggcccagc cggccagatc tgacattgtg    120

atgacacaga gtccttcatc ccttgcagtc agtgtcggcg aaaaagtaac aatttcatgc    180

aagtctagtc aatctctgtt gtacggctcc tctcattacc tcgcatggta tcaacaaaaa    240

gtgggtcaat ctcccaaatt gttgatatac tgggcttcaa ctagacacac tggaatccct    300

gacaggttca ttggtagcgg atcagggact gactttacac tgtccctcag cagcgtacaa    360

gcagaagaca tggccgacta tttctgccaa caatacttta gtacaccatg gacctttggg    420

gctgggacca gagttgagat aaaaagtggc tctggagggg gctctggcgg tggatctggg    480

ggtggaagtc aagtgcagct gcttcaatcc gaatcagaac tcgtgaagcc aggcgcttca    540

gtgaaattgt cttgtaagac ttcaggatac actttcactg attactatat acactgggtt    600

aagcagaagc ctggtcaggg tcttgaatgg attggcctca tcaatcccaa taacgatggc    660
```

acaaactaca accagaaatt tcaaggaaaa gccacactta ccgcagacaa atccagttct 720
accgcataca tggaacttaa tagtctcact tttgatgact cagtaatata tttctgtgcc 780
agggccagta gccgacttag aatggctagg actacctctg actactatgc catggactat 840
tggggacagg gcattcaagt gaccgtgagc tctgtcgact ctagtggatc cggtggttgt 900
aagccttgca tatgtacagt cccagaagta tcatctgtct tcatcttccc cccaaagccc 960
aaggatgtgc tcaccattac tctgactcct aaggtcacgt gtgttgtggt agacatcagc 1020
aaggatgatc ccgaggtcca gttcagctgg tttgtagatg atgtggaggt gcacacagct 1080
cagacgcaac ccgggaggga gcagttcaac agcactttcc gctcagtcag tgaacttccc 1140
atcatgcacc aggactggct caatggcaag gagttcaaat gcagggtcaa cagtgcagct 1200
ttccctgccc ccatcgagaa aaccatctcc aaaaccaaag gcagaccgaa ggctccacag 1260
gtgtacacca ttccacctcc caaggagcag atggccaagg ataaagtcag tctgacctgc 1320
atgataacag acttcttccc tgaagacatt actgtggagt ggcagtggaa tgggcagcca 1380
gcggagaact acaagaacac tcagcccatc atggacacag atggctctta cttcgtctac 1440
agcaagctca atgtgcagaa gagcaactgg gaggcaggaa atactttcac ctgctctgtg 1500
ttacatgagg gcctgcacaa ccaccatact gagaagagcc tctcccactc tcctggtaaa 1560
tga 1563

<210> SEQ ID NO 72
<211> LENGTH: 520
<212> TYPE: PRT
<213> ORGANISM: Artificial Sequence
<220> FEATURE:
<223> OTHER INFORMATION: Igkappa-HA-9H10 VLC-Linker-9H10 VHC-Linker-
mIgG1 Fc domain (anti-CTLA4 scFv) sequence

<400> SEQUENCE: 72

Met Glu Thr Asp Thr Leu Leu Leu Trp Val Leu Leu Leu Trp Val Pro
1 5 10 15

Gly Ser Thr Gly Asp Tyr Pro Tyr Asp Val Pro Asp Tyr Ala Gly Ala
20 25 30

Gln Pro Ala Arg Ser Asp Ile Val Met Thr Gln Ser Pro Ser Ser Leu
35 40 45

Ala Val Ser Val Gly Glu Lys Val Thr Ile Ser Cys Lys Ser Ser Gln
50 55 60

Ser Leu Leu Tyr Gly Ser Ser His Tyr Leu Ala Trp Tyr Gln Gln Lys
65 70 75 80

Val Gly Gln Ser Pro Lys Leu Leu Ile Tyr Trp Ala Ser Thr Arg His
85 90 95

Thr Gly Ile Pro Asp Arg Phe Ile Gly Ser Gly Ser Gly Thr Asp Phe
100 105 110

Thr Leu Ser Leu Ser Ser Val Gln Ala Glu Asp Met Ala Asp Tyr Phe
115 120 125

Cys Gln Gln Tyr Phe Ser Thr Pro Trp Thr Phe Gly Ala Gly Thr Arg
130 135 140

Val Glu Ile Lys Ser Gly Ser Gly Gly Gly Ser Gly Gly Gly Ser Gly
145 150 155 160

Gly Gly Ser Gln Val Gln Leu Leu Gln Ser Glu Ser Glu Leu Val Lys
165 170 175

Pro Gly Ala Ser Val Lys Leu Ser Cys Lys Thr Ser Gly Tyr Thr Phe
180 185 190

```
Thr Asp Tyr Tyr Ile His Trp Val Lys Gln Lys Pro Gly Gln Gly Leu
        195                 200                 205

Glu Trp Ile Gly Leu Ile Asn Pro Asn Asn Asp Gly Thr Asn Tyr Asn
    210                 215                 220

Gln Lys Phe Gln Gly Lys Ala Thr Leu Thr Ala Asp Lys Ser Ser Ser
225                 230                 235                 240

Thr Ala Tyr Met Glu Leu Asn Ser Leu Thr Phe Asp Asp Ser Val Ile
                245                 250                 255

Tyr Phe Cys Ala Arg Ala Ser Ser Arg Leu Arg Met Ala Arg Thr Thr
            260                 265                 270

Ser Asp Tyr Tyr Ala Met Asp Tyr Trp Gly Gln Gly Ile Gln Val Thr
        275                 280                 285

Val Ser Ser Val Asp Ser Ser Gly Ser Gly Gly Cys Lys Pro Cys Ile
    290                 295                 300

Cys Thr Val Pro Glu Val Ser Ser Val Phe Ile Phe Pro Pro Lys Pro
305                 310                 315                 320

Lys Asp Val Leu Thr Ile Thr Leu Thr Pro Lys Val Thr Cys Val Val
                325                 330                 335

Val Asp Ile Ser Lys Asp Asp Pro Glu Val Gln Phe Ser Trp Phe Val
            340                 345                 350

Asp Asp Val Glu Val His Thr Ala Gln Thr Gln Pro Arg Glu Glu Gln
        355                 360                 365

Phe Asn Ser Thr Phe Arg Ser Val Ser Glu Leu Pro Ile Met His Gln
    370                 375                 380

Asp Trp Leu Asn Gly Lys Glu Phe Lys Cys Arg Val Asn Ser Ala Ala
385                 390                 395                 400

Phe Pro Ala Pro Ile Glu Lys Thr Ile Ser Lys Thr Lys Gly Arg Pro
                405                 410                 415

Lys Ala Pro Gln Val Tyr Thr Ile Pro Pro Pro Lys Glu Gln Met Ala
            420                 425                 430

Lys Asp Lys Val Ser Leu Thr Cys Met Ile Thr Asp Phe Phe Pro Glu
        435                 440                 445

Asp Ile Thr Val Glu Trp Gln Trp Asn Gly Gln Pro Ala Glu Asn Tyr
    450                 455                 460

Lys Asn Thr Gln Pro Ile Met Asp Thr Asp Gly Ser Tyr Phe Val Tyr
465                 470                 475                 480

Ser Lys Leu Asn Val Gln Lys Ser Asn Trp Glu Ala Gly Asn Thr Phe
                485                 490                 495

Thr Cys Ser Val Leu His Glu Gly Leu His Asn His His Thr Glu Lys
            500                 505                 510

Ser Leu Ser His Ser Pro Gly Lys
        515                 520
```

```
<210> SEQ ID NO 73
<211> LENGTH: 1020
<212> TYPE: DNA
<213> ORGANISM: Artificial Sequence
<220> FEATURE:
<223> OTHER INFORMATION: Igkappa-HA-OKT3 VHC-Linker-OKT3 VLC-Myc-PDGFR
      sequence

<400> SEQUENCE: 73

atggagacag acacactcct gctatgggta ctgctgctct gggttccagg ttccactggt      60

gactatccat atgatgttcc agattatgct ggggcccagc cggccagatc tcaggtgcag     120

ctgcagcaat ctggggctga actggcaaga cctggggcct cagtgaagat gtcctgcaag     180
```

```
gcttctggct acacctttac taggtacacg atgcactggg taaaacagag gcctggacag    240

ggtctggaat ggattggata cattaatcct agccgtggtt atactaatta caatcagaag    300

ttcaaggaca aggccacatt gactacagac aaatcctcca gcacagccta catgcaactg    360

agcagcctga catctgagga ctctgcagtc tattactgtg caagatatta tgatgatcat    420

tactgccttg actactgggg ccaaggcacc acactcaccg tctcctcagg tggcggtggc    480

tccggcggtg gtgggtcggg tggcggcgga tctcagattg tgctcaccca gtctccagca    540

atcatgtctg catctccagg ggagaaggtt accatgacct gcagtgccag ctcaagtgta    600

agttacatga actggtacca gcagaagtca ggcacctccc ccaaaagatg gatttatgac    660

acatccaaac tggcttctgg agtccctgct cacttcaggg gcagtgggtc tgggacctct    720

tactctctca caatcagcgg catggaggct gaagatgctg ccacttatta ctgccagcag    780

tggagtagta acccattcac gttcggctcg gggaccaagc tggagatcaa tcgtgtcgac    840

gaacaaaaac tcatctcaga agaggatctg aatgctgtgg gccaggacac gcaggaggtc    900

atcgtggtgc cacactcctt gccctttaag gtggtggtga tctcagccat cctggccctg    960

gtggtgctca ccatcatctc ccttatcatc ctcatcatgc tttggcagaa gaagccacgt   1020
```

```
<210> SEQ ID NO 74
<211> LENGTH: 340
<212> TYPE: PRT
<213> ORGANISM: Artificial Sequence
<220> FEATURE:
<223> OTHER INFORMATION: Igkappa-HA-OKT3 VHC-Linker-OKT3 VLC-Myc-PDGFR
      sequence

<400> SEQUENCE: 74

Met Glu Thr Asp Thr Leu Leu Leu Trp Val Leu Leu Leu Trp Val Pro
1               5                   10                  15

Gly Ser Thr Gly Asp Tyr Pro Tyr Asp Val Pro Asp Tyr Ala Gly Ala
            20                  25                  30

Gln Pro Ala Arg Ser Gln Val Gln Leu Gln Gln Ser Gly Ala Glu Leu
        35                  40                  45

Ala Arg Pro Gly Ala Ser Val Lys Met Ser Cys Lys Ala Ser Gly Tyr
    50                  55                  60

Thr Phe Thr Arg Tyr Thr Met His Trp Val Lys Gln Arg Pro Gly Gln
65                  70                  75                  80

Gly Leu Glu Trp Ile Gly Tyr Ile Asn Pro Ser Arg Gly Tyr Thr Asn
                85                  90                  95

Tyr Asn Gln Lys Phe Lys Asp Lys Ala Thr Leu Thr Thr Asp Lys Ser
            100                 105                 110

Ser Ser Thr Ala Tyr Met Gln Leu Ser Ser Leu Thr Ser Glu Asp Ser
        115                 120                 125

Ala Val Tyr Tyr Cys Ala Arg Tyr Tyr Asp Asp His Tyr Cys Leu Asp
    130                 135                 140

Tyr Trp Gly Gln Gly Thr Thr Leu Thr Val Ser Ser Gly Gly Gly Gly
145                 150                 155                 160

Ser Gly Gly Gly Gly Ser Gly Gly Gly Gly Ser Gln Ile Val Leu Thr
                165                 170                 175

Gln Ser Pro Ala Ile Met Ser Ala Ser Pro Gly Glu Lys Val Thr Met
            180                 185                 190

Thr Cys Ser Ala Ser Ser Ser Val Ser Tyr Met Asn Trp Tyr Gln Gln
        195                 200                 205
```

```
Lys Ser Gly Thr Ser Pro Lys Arg Trp Ile Tyr Asp Thr Ser Lys Leu
    210                 215                 220

Ala Ser Gly Val Pro Ala His Phe Arg Gly Ser Gly Ser Gly Thr Ser
225                 230                 235                 240

Tyr Ser Leu Thr Ile Ser Gly Met Glu Ala Glu Asp Ala Ala Thr Tyr
                245                 250                 255

Tyr Cys Gln Gln Trp Ser Ser Asn Pro Phe Thr Phe Gly Ser Gly Thr
            260                 265                 270

Lys Leu Glu Ile Asn Arg Val Asp Glu Gln Lys Leu Ile Ser Glu Glu
        275                 280                 285

Asp Leu Asn Ala Val Gly Gln Asp Thr Gln Glu Val Ile Val Val Pro
    290                 295                 300

His Ser Leu Pro Phe Lys Val Val Val Ile Ser Ala Ile Leu Ala Leu
305                 310                 315                 320

Val Val Leu Thr Ile Ile Ser Leu Ile Ile Leu Ile Met Leu Trp Gln
                325                 330                 335

Lys Lys Pro Arg
            340
```

<210> SEQ ID NO 75
<211> LENGTH: 1011
<212> TYPE: DNA
<213> ORGANISM: Artificial Sequence
<220> FEATURE:
<223> OTHER INFORMATION: Igkappa-HA-OKT3 VHC-Linker-OKT3 VLC-Linker-
PDGFR sequence

<400> SEQUENCE: 75

```
atggagacag acacactcct gctatgggta ctgctgctct gggttccagg ttccactggt     60

gactatccat atgatgttcc agattatgct ggggcccagc cggccagatc tcaggtgcag    120

ctgcagcaat ctggggctga actggcaaga cctggggcct cagtgaagat gtcctgcaag    180

gcttctggct acacctttac taggtacacg atgcactggg taaaacagag gcctggacag    240

ggtctggaat ggattggata cattaatcct agccgtggtt atactaatta caatcagaag    300

ttcaaggaca aggccacatt gactacagac aaatcctcca gcacagccta catgcaactg    360

agcagcctga catctgagga ctctgcagtc tattactgtg caagatatta tgatgatcat    420

tactgccttg actactgggg ccaaggcacc acactcaccg tctcctcagg tggcggtggc    480

tccggcggtg gtgggtcggg tggcggcgga tctcagattg tgctcaccca gtctccagca    540

atcatgtctg catctccagg ggagaaggtt accatgacct gcagtgccag ctcaagtgta    600

agttacatga actggtatca gcagaagtca ggcacctccc ccaaaagatg gatttatgac    660

acatccaaac tggcttctgg agtccctgct cacttcaggg gcagtgggtc tgggacctct    720

tactctctca caatcagcgg catggaggct gaagatgctg ccacttatta ctgccagcag    780

tggagtagta acccattcac gttcggctcg gggaccaagc tggagatcaa tcgtggcagt    840

gggagtggga gtgggagtgg gaatgctgtg ggccaggaca cgcaggaggt catcgtggtg    900

ccacactcct tgccctttaa ggtggtggtg atctcagcca tcctggccct ggtggtgctc    960

accatcatct cccttatcat cctcatcatg ctttggcaga agaagccacg t            1011
```

<210> SEQ ID NO 76
<211> LENGTH: 337
<212> TYPE: PRT
<213> ORGANISM: Artificial Sequence
<220> FEATURE:
<223> OTHER INFORMATION: Igkappa-HA-OKT3 VHC-Linker-OKT3 VLC-Linker- PDGFR sequence

<400> SEQUENCE: 76

```
Met Glu Thr Asp Thr Leu Leu Leu Trp Val Leu Leu Leu Trp Val Pro
1               5                   10                  15

Gly Ser Thr Gly Asp Tyr Pro Tyr Asp Val Pro Asp Tyr Ala Gly Ala
            20                  25                  30

Gln Pro Ala Arg Ser Gln Val Gln Leu Gln Gln Ser Gly Ala Glu Leu
        35                  40                  45

Ala Arg Pro Gly Ala Ser Val Lys Met Ser Cys Lys Ala Ser Gly Tyr
    50                  55                  60

Thr Phe Thr Arg Tyr Thr Met His Trp Val Lys Gln Arg Pro Gly Gln
65                  70                  75                  80

Gly Leu Glu Trp Ile Gly Tyr Ile Asn Pro Ser Arg Gly Tyr Thr Asn
                85                  90                  95

Tyr Asn Gln Lys Phe Lys Asp Lys Ala Thr Leu Thr Thr Asp Lys Ser
            100                 105                 110

Ser Ser Thr Ala Tyr Met Gln Leu Ser Ser Leu Thr Ser Glu Asp Ser
        115                 120                 125

Ala Val Tyr Tyr Cys Ala Arg Tyr Tyr Asp Asp His Tyr Cys Leu Asp
    130                 135                 140

Tyr Trp Gly Gln Gly Thr Thr Leu Thr Val Ser Ser Gly Gly Gly Gly
145                 150                 155                 160

Ser Gly Gly Gly Gly Ser Gly Gly Gly Gly Ser Gln Ile Val Leu Thr
                165                 170                 175

Gln Ser Pro Ala Ile Met Ser Ala Ser Pro Gly Glu Lys Val Thr Met
            180                 185                 190

Thr Cys Ser Ala Ser Ser Ser Val Ser Tyr Met Asn Trp Tyr Gln Gln
        195                 200                 205

Lys Ser Gly Thr Ser Pro Lys Arg Trp Ile Tyr Asp Thr Ser Lys Leu
    210                 215                 220

Ala Ser Gly Val Pro Ala His Phe Arg Gly Ser Gly Ser Gly Thr Ser
225                 230                 235                 240

Tyr Ser Leu Thr Ile Ser Gly Met Glu Ala Glu Asp Ala Ala Thr Tyr
                245                 250                 255

Tyr Cys Gln Gln Trp Ser Ser Asn Pro Phe Thr Phe Gly Ser Gly Thr
            260                 265                 270

Lys Leu Glu Ile Asn Arg Gly Ser Gly Ser Gly Ser Gly Ser Gly Asn
        275                 280                 285

Ala Val Gly Gln Asp Thr Gln Glu Val Ile Val Val Pro His Ser Leu
    290                 295                 300

Pro Phe Lys Val Val Val Ile Ser Ala Ile Leu Ala Leu Val Val Leu
305                 310                 315                 320

Thr Ile Ile Ser Leu Ile Ile Leu Ile Met Leu Trp Gln Lys Lys Pro
                325                 330                 335

Arg
```

<210> SEQ ID NO 77
<211> LENGTH: 2877
<212> TYPE: DNA
<213> ORGANISM: Artificial Sequence
<220> FEATURE:
<223> OTHER INFORMATION: Igkappa-HA-OKT3 VHC-Linker-OKT3 VLC-Linker-
PDGFR-P2A-hIL-12 p35-P2A-hIL-12 p40 sequence

<400> SEQUENCE: 77
atggagacag acacactcct gctatgggta ctgctgctct gggttccagg ttccactggt 60
gactatccat atgatgttcc agattatgct ggggcccagc cggccagatc tcaggtgcag 120
ctgcagcaat ctggggctga actggcaaga cctggggcct cagtgaagat gtcctgcaag 180
gcttctggct acacctttac taggtacacg atgcactggg taaaacagag gcctggacag 240
ggtctggaat ggattggata cattaatcct agccgtggtt atactaatta caatcagaag 300
ttcaaggaca aggccacatt gactacagac aaatcctcca gcacagccta catgcaactg 360
agcagcctga catctgagga ctctgcagtc tattactgtg caagatatta tgatgatcat 420
tactgccttg actactgggg ccaaggcacc acactcaccg tctcctcagg tggcggtggc 480
tccggcggtg gtgggtcggg tggcggcgga tctcagattg tgctcaccca gtctccagca 540
atcatgtctg catctccagg ggagaaggtt accatgacct gcagtgccag ctcaagtgta 600
agttacatga actggtatca gcagaagtca ggcacctccc ccaaaagatg gatttatgac 660
acatccaaac tggcttctgg agtccctgct cacttcaggg gcagtgggtc tgggacctct 720
tactctctca caatcagcgg catggaggct gaagatgctg ccacttatta ctgccagcag 780
tggagtagta acccattcac gttcggctcg gggaccaagc tggagatcaa tcgtggcagt 840
gggagtggga atgctgtggg ccaggacacg caggaggtca tcgtggtgcc acactccttg 900
ccctttaagg tggtggtgat ctcagccatc ctggccctgg tggtgctcac catcatctcc 960
cttatcatcc tcatcatgct ttggcagaag aagccacgtg gatctggggc caccaacttt 1020
tcattgctca agcaggcggg cgatgtggag gaaaaccctg gccccggtac ctggccccct 1080
gggtcagcct cccagccacc gccctcacct gccgcggcca caggtctgca tccagcggct 1140
cgccctgtgt ccctgcagtg ccggctcagc atgtgtccag cgcgcagcct cctccttgtg 1200
gctaccctgg tcctcctgga ccacctcagt ttggccagaa acctccccgt ggccactcca 1260
gacccaggaa tgttcccatg ccttcaccac tcccaaaacc tgctgagggc cgtcagcaac 1320
atgctccaga aggccagaca aactctagaa ttttaccctt gcacttctga agagattgat 1380
catgaagata tcacaaaaga taaaaccagc acagtggagg cctgtttacc attggaatta 1440
accaagaatg agagttgcct aaattccaga gagacctctt tcataactaa tgggagttgc 1500
ctggcctcca gaaagacctc ttttatgatg gccctgtgcc ttagtagtat ttatgaagac 1560
ttgaagatgt accaggtgga gttcaagacc atgaatgcaa agcttctgat ggatcctaag 1620
aggcagatct ttctagatca aaacatgctg gcagttattg atgagctgat gcaggccctg 1680
aatttcaaca gtgagactgt gccacaaaaa tcctcccttg aagaaccgga tttttataaa 1740
actaaaatca agctctgcat acttcttcat gctttcagaa ttcgggcagt gactattgat 1800
agagtgatga gctatctgaa tgcttccgga tctggggcca ccaacttttc attgctcaag 1860
caggcgggcg atgtggagga aaaccctggc ccctgtcacc agcagttggt catctcttgg 1920
ttttccctgg tttttctggc atctcccctc gtggccatat gggaactgaa gaaagatgtt 1980
tatgtcgtag aattggattg gtatccggat gcccctggag aaatggtggt cctcacctgt 2040
gacacccctg aagaagatgg tatcacctgg accttggacc agagcagtga ggtcttaggc 2100
tctggcaaaa ccctgaccat ccaagtcaaa gagtttggag atgctggcca gtacacctgt 2160
cacaaaggag gcgaggttct aagccattcg ctcctgctgc ttcacaaaaa ggaagatgga 2220
atttggtcca ctgatatttt aaaggaccag aaagaaccca aaaataagac ctttctaaga 2280
tgcgaggcca agaattattc tggacgtttc acctgctggt ggctgacgac aatcagtact 2340

```
gatttgacat tcagtgtcaa aagcagcaga ggctcttctg acccccaagg ggtgacgtgc   2400

ggagctgcta cactctctgc agagagagtc agaggggaca acaaggagta tgagtactca   2460

gtggagtgcc aggaggacag tgcctgccca gctgctgagg agagtctgcc cattgaggtc   2520

atggtggatg ccgttcacaa gctcaagtat gaaaactaca ccagcagctt cttcatcagg   2580

gacatcatca aacctgaccc acccaagaac ttgcagctga agccattaaa gaattctcgg   2640

caggtggagg tcagctggga gtaccctgac acctggagta ctccacattc ctacttctcc   2700

ctgacattct gcgttcaggt ccagggcaag agcaagagag aaaagaaaga tagagtcttc   2760

acggacaaga cctcagccac ggtcatctgc cgcaaaaatg ccagcattag cgtgcgggcc   2820

caggaccgct actatagctc atcttggagc gaatgggcat ctgtgccctg cagttag      2877


<210> SEQ ID NO 78
<211> LENGTH: 958
<212> TYPE: PRT
<213> ORGANISM: Artificial Sequence
<220> FEATURE:
<223> OTHER INFORMATION: Igkappa-HA-OKT3 VHC-Linker-OKT3 VLC-Linker-
      PDGFR-P2A-hIL-12 p35-P2A-hIL-12 p40 sequence

<400> SEQUENCE: 78

Met Glu Thr Asp Thr Leu Leu Leu Trp Val Leu Leu Leu Trp Val Pro
1               5                   10                  15

Gly Ser Thr Gly Asp Tyr Pro Tyr Asp Val Pro Asp Tyr Ala Gly Ala
            20                  25                  30

Gln Pro Ala Arg Ser Gln Val Gln Leu Gln Gln Ser Gly Ala Glu Leu
        35                  40                  45

Ala Arg Pro Gly Ala Ser Val Lys Met Ser Cys Lys Ala Ser Gly Tyr
    50                  55                  60

Thr Phe Thr Arg Tyr Thr Met His Trp Val Lys Gln Arg Pro Gly Gln
65                  70                  75                  80

Gly Leu Glu Trp Ile Gly Tyr Ile Asn Pro Ser Arg Gly Tyr Thr Asn
                85                  90                  95

Tyr Asn Gln Lys Phe Lys Asp Lys Ala Thr Leu Thr Thr Asp Lys Ser
            100                 105                 110

Ser Ser Thr Ala Tyr Met Gln Leu Ser Ser Leu Thr Ser Glu Asp Ser
        115                 120                 125

Ala Val Tyr Tyr Cys Ala Arg Tyr Tyr Asp Asp His Tyr Cys Leu Asp
    130                 135                 140

Tyr Trp Gly Gln Gly Thr Thr Leu Thr Val Ser Ser Gly Gly Gly Gly
145                 150                 155                 160

Ser Gly Gly Gly Gly Ser Gly Gly Gly Gly Ser Gln Ile Val Leu Thr
                165                 170                 175

Gln Ser Pro Ala Ile Met Ser Ala Ser Pro Gly Glu Lys Val Thr Met
            180                 185                 190

Thr Cys Ser Ala Ser Ser Ser Val Ser Tyr Met Asn Trp Tyr Gln Gln
        195                 200                 205

Lys Ser Gly Thr Ser Pro Lys Arg Trp Ile Tyr Asp Thr Ser Lys Leu
    210                 215                 220

Ala Ser Gly Val Pro Ala His Phe Arg Gly Ser Gly Ser Gly Thr Ser
225                 230                 235                 240

Tyr Ser Leu Thr Ile Ser Gly Met Glu Ala Glu Asp Ala Ala Thr Tyr
                245                 250                 255

Tyr Cys Gln Gln Trp Ser Ser Asn Pro Phe Thr Phe Gly Ser Gly Thr
            260                 265                 270
```

-continued

```
Lys Leu Glu Ile Asn Arg Gly Ser Gly Ser Gly Asn Ala Val Gly Gln
        275                 280                 285

Asp Thr Gln Glu Val Ile Val Val Pro His Ser Leu Pro Phe Lys Val
    290                 295                 300

Val Val Ile Ser Ala Ile Leu Ala Leu Val Val Leu Thr Ile Ile Ser
305                 310                 315                 320

Leu Ile Ile Leu Ile Met Leu Trp Gln Lys Lys Pro Arg Gly Ser Gly
                325                 330                 335

Ala Thr Asn Phe Ser Leu Leu Lys Gln Ala Gly Asp Val Glu Glu Asn
            340                 345                 350

Pro Gly Pro Gly Thr Trp Pro Pro Gly Ser Ala Ser Gln Pro Pro Pro
        355                 360                 365

Ser Pro Ala Ala Ala Thr Gly Leu His Pro Ala Ala Arg Pro Val Ser
    370                 375                 380

Leu Gln Cys Arg Leu Ser Met Cys Pro Ala Arg Ser Leu Leu Leu Val
385                 390                 395                 400

Ala Thr Leu Val Leu Leu Asp His Leu Ser Leu Ala Arg Asn Leu Pro
                405                 410                 415

Val Ala Thr Pro Asp Pro Gly Met Phe Pro Cys Leu His His Ser Gln
            420                 425                 430

Asn Leu Leu Arg Ala Val Ser Asn Met Leu Gln Lys Ala Arg Gln Thr
        435                 440                 445

Leu Glu Phe Tyr Pro Cys Thr Ser Glu Glu Ile Asp His Glu Asp Ile
    450                 455                 460

Thr Lys Asp Lys Thr Ser Thr Val Glu Ala Cys Leu Pro Leu Glu Leu
465                 470                 475                 480

Thr Lys Asn Glu Ser Cys Leu Asn Ser Arg Glu Thr Ser Phe Ile Thr
                485                 490                 495

Asn Gly Ser Cys Leu Ala Ser Arg Lys Thr Ser Phe Met Met Ala Leu
            500                 505                 510

Cys Leu Ser Ser Ile Tyr Glu Asp Leu Lys Met Tyr Gln Val Glu Phe
        515                 520                 525

Lys Thr Met Asn Ala Lys Leu Leu Met Asp Pro Lys Arg Gln Ile Phe
    530                 535                 540

Leu Asp Gln Asn Met Leu Ala Val Ile Asp Glu Leu Met Gln Ala Leu
545                 550                 555                 560

Asn Phe Asn Ser Glu Thr Val Pro Gln Lys Ser Ser Leu Glu Glu Pro
                565                 570                 575

Asp Phe Tyr Lys Thr Lys Ile Lys Leu Cys Ile Leu Leu His Ala Phe
            580                 585                 590

Arg Ile Arg Ala Val Thr Ile Asp Arg Val Met Ser Tyr Leu Asn Ala
        595                 600                 605

Ser Gly Ser Gly Ala Thr Asn Phe Ser Leu Leu Lys Gln Ala Gly Asp
    610                 615                 620

Val Glu Glu Asn Pro Gly Pro Cys His Gln Gln Leu Val Ile Ser Trp
625                 630                 635                 640

Phe Ser Leu Val Phe Leu Ala Ser Pro Leu Val Ala Ile Trp Glu Leu
                645                 650                 655

Lys Lys Asp Val Tyr Val Val Glu Leu Asp Trp Tyr Pro Asp Ala Pro
            660                 665                 670

Gly Glu Met Val Val Leu Thr Cys Asp Thr Pro Glu Glu Asp Gly Ile
        675                 680                 685
```

```
Thr Trp Thr Leu Asp Gln Ser Ser Glu Val Leu Gly Ser Gly Lys Thr
    690                 695                 700

Leu Thr Ile Gln Val Lys Glu Phe Gly Asp Ala Gly Gln Tyr Thr Cys
705                 710                 715                 720

His Lys Gly Gly Glu Val Leu Ser His Ser Leu Leu Leu Leu His Lys
                725                 730                 735

Lys Glu Asp Gly Ile Trp Ser Thr Asp Ile Leu Lys Asp Gln Lys Glu
            740                 745                 750

Pro Lys Asn Lys Thr Phe Leu Arg Cys Glu Ala Lys Asn Tyr Ser Gly
        755                 760                 765

Arg Phe Thr Cys Trp Trp Leu Thr Thr Ile Ser Thr Asp Leu Thr Phe
    770                 775                 780

Ser Val Lys Ser Ser Arg Gly Ser Ser Asp Pro Gln Gly Val Thr Cys
785                 790                 795                 800

Gly Ala Ala Thr Leu Ser Ala Glu Arg Val Arg Gly Asp Asn Lys Glu
                805                 810                 815

Tyr Glu Tyr Ser Val Glu Cys Gln Glu Asp Ser Ala Cys Pro Ala Ala
            820                 825                 830

Glu Glu Ser Leu Pro Ile Glu Val Met Val Asp Ala Val His Lys Leu
        835                 840                 845

Lys Tyr Glu Asn Tyr Thr Ser Ser Phe Phe Ile Arg Asp Ile Ile Lys
    850                 855                 860

Pro Asp Pro Pro Lys Asn Leu Gln Leu Lys Pro Leu Lys Asn Ser Arg
865                 870                 875                 880

Gln Val Glu Val Ser Trp Glu Tyr Pro Asp Thr Trp Ser Thr Pro His
                885                 890                 895

Ser Tyr Phe Ser Leu Thr Phe Cys Val Gln Val Gln Gly Lys Ser Lys
            900                 905                 910

Arg Glu Lys Lys Asp Arg Val Phe Thr Asp Lys Thr Ser Ala Thr Val
        915                 920                 925

Ile Cys Arg Lys Asn Ala Ser Ile Ser Val Arg Ala Gln Asp Arg Tyr
    930                 935                 940

Tyr Ser Ser Ser Trp Ser Glu Trp Ala Ser Val Pro Cys Ser
945                 950                 955
```

<210> SEQ ID NO 79
<211> LENGTH: 2850
<212> TYPE: DNA
<213> ORGANISM: Artificial Sequence
<220> FEATURE:
<223> OTHER INFORMATION: Igkappa-OKT3 VHC-Linker-OKT3 VLC-Linker-PDGFR-P2A-hIL-12 p35-P2A-hIL-12 p40 sequence

<400> SEQUENCE: 79

```
atggagacag acacactcct gctatgggta ctgctgctct gggttccagg ttccactggt      60

gacggggccc agccggccag atctcaggtg cagctgcagc aatctggggc tgaactggca     120

agacctgggg cctcagtgaa gatgtcctgc aaggcttctg gctacacctt tactaggtac     180

acgatgcact gggtaaaaca gaggcctgga cagggtctgg aatggattgg atacattaat     240

cctagccgtg gttatactaa ttacaatcag aagttcaagg acaaggccac attgactaca     300

gacaaatcct ccagcacagc ctacatgcaa ctgagcagcc tgacatctga ggactctgca     360

gtctattact gtgcaagata ttatgatgat cattactgcc ttgactactg gggccaaggc     420

accacactca ccgtctcctc aggtggcggt ggctccggcg gtggtgggtc gggtggcggc     480

ggatctcaga ttgtgctcac ccagtctcca gcaatcatgt ctgcatctcc aggggagaag     540
```

```
gttaccatga cctgcagtgc cagctcaagt gtaagttaca tgaactggta tcagcagaag    600
tcaggcacct cccccaaaag atggatttat gacacatcca aactggcttc tggagtccct    660
gctcacttca ggggcagtgg gtctgggacc tcttactctc tcacaatcag cggcatggag    720
gctgaagatg ctgccactta ttactgccag cagtggagta gtaacccatt cacgttcggc    780
tcggggacca agctggagat caatcgtggc agtgggagtg ggaatgctgt gggccaggac    840
acgcaggagg tcatcgtggt gccacactcc ttgcccttta aggtggtggt gatctcagcc    900
atcctggccc tggtggtgct caccatcatc tcccttatca tcctcatcat gctttggcag    960
aagaagccac gtggatctgg ggccaccaac ttttcattgc tcaagcaggc gggcgatgtg   1020
gaggaaaacc ctggccccgg tacctggccc cctgggtcag cctcccagcc accgccctca   1080
cctgccgcgg ccacaggtct gcatccagcg gctcgccctg tgtccctgca gtgccggctc   1140
agcatgtgtc cagcgcgcag cctcctcctt gtggctaccc tggtcctcct ggaccacctc   1200
agtttggcca gaaacctccc cgtggccact ccagacccag gaatgttccc atgccttcac   1260
cactcccaaa acctgctgag ggccgtcagc aacatgctcc agaaggccag acaaactcta   1320
gaattttacc cttgcacttc tgaagagatt gatcatgaag atatcacaaa agataaaacc   1380
agcacagtgg aggcctgttt accattggaa ttaaccaaga atgagagttg cctaaattcc   1440
agagagacct ctttcataac taatgggagt tgcctggcct ccagaaagac ctcttttatg   1500
atggccctgt gccttagtag tatttatgaa gacttgaaga tgtaccaggt ggagttcaag   1560
accatgaatg caaagcttct gatggatcct aagaggcaga tctttctaga tcaaaacatg   1620
ctggcagtta ttgatgagct gatgcaggcc ctgaatttca acagtgagac tgtgccacaa   1680
aaatcctccc ttgaagaacc ggatttttat aaaactaaaa tcaagctctg catacttctt   1740
catgctttca gaattcgggc agtgactatt gatagagtga tgagctatct gaatgcttcc   1800
ggatctgggg ccaccaactt ttcattgctc aagcaggcgg gcgatgtgga ggaaaaccct   1860
ggcccctgtc accagcagtt ggtcatctct tggttttccc tggtttttct ggcatctccc   1920
ctcgtggcca tatgggaact gaagaaagat gtttatgtcg tagaattgga ttggtatccg   1980
gatgcccctg gagaaatggt ggtcctcacc tgtgacaccc ctgaagaaga tggtatcacc   2040
tggaccttgg accagagcag tgaggtctta ggctctggca aaaccctgac catccaagtc   2100
aaagagtttg gagatgctgg ccagtacacc tgtcacaaag gaggcgaggt tctaagccat   2160
tcgctcctgc tgcttcacaa aaaggaagat ggaatttggt ccactgatat tttaaaggac   2220
cagaaagaac ccaaaaataa gacctttcta agatgcgagg ccaagaatta ttctggacgt   2280
ttcacctgct ggtggctgac gacaatcagt actgatttga cattcagtgt caaaagcagc   2340
agaggctctt ctgaccccca aggggtgacg tgcggagctg ctacactctc tgcagagaga   2400
gtcagagggg acaacaagga gtatgagtac tcagtggagt gccaggagga cagtgcctgc   2460
ccagctgctg aggagagtct gcccattgag gtcatggtgg atgccgttca caagctcaag   2520
tatgaaaact acaccagcag cttcttcatc agggacatca tcaaacctga cccacccaag   2580
aacttgcagc tgaagccatt aaagaattct cggcaggtgg aggtcagctg ggagtaccct   2640
gacacctgga gtactccaca ttcctacttc tccctgacat tctgcgttca ggtccagggc   2700
aagagcaaga gagaaaagaa agatagagtc ttcacggaca agacctcagc cacggtcatc   2760
tgccgcaaaa atgccagcat tagcgtgcgg gcccaggacc gctactatag ctcatcttgg   2820
agcgaatggg catctgtgcc ctgcagttag                                    2850
```

<210> SEQ ID NO 80
<211> LENGTH: 949
<212> TYPE: PRT
<213> ORGANISM: Artificial Sequence
<220> FEATURE:
<223> OTHER INFORMATION: Igkappa-OKT3 VHC-Linker-OKT3 VLC-Linker-PDGFR-
P2A-hIL-12 p35-P2A-hIL-12 p40 sequence

<400> SEQUENCE: 80

Met Glu Thr Asp Thr Leu Leu Leu Trp Val Leu Leu Leu Trp Val Pro
1 5 10 15

Gly Ser Thr Gly Asp Gly Ala Gln Pro Ala Arg Ser Gln Val Gln Leu
20 25 30

Gln Gln Ser Gly Ala Glu Leu Ala Arg Pro Gly Ala Ser Val Lys Met
35 40 45

Ser Cys Lys Ala Ser Gly Tyr Thr Phe Thr Arg Tyr Thr Met His Trp
50 55 60

Val Lys Gln Arg Pro Gly Gln Gly Leu Glu Trp Ile Gly Tyr Ile Asn
65 70 75 80

Pro Ser Arg Gly Tyr Thr Asn Tyr Asn Gln Lys Phe Lys Asp Lys Ala
85 90 95

Thr Leu Thr Thr Asp Lys Ser Ser Ser Thr Ala Tyr Met Gln Leu Ser
100 105 110

Ser Leu Thr Ser Glu Asp Ser Ala Val Tyr Tyr Cys Ala Arg Tyr Tyr
115 120 125

Asp Asp His Tyr Cys Leu Asp Tyr Trp Gly Gln Gly Thr Thr Leu Thr
130 135 140

Val Ser Ser Gly Gly Gly Gly Ser Gly Gly Gly Gly Ser Gly Gly Gly
145 150 155 160

Gly Ser Gln Ile Val Leu Thr Gln Ser Pro Ala Ile Met Ser Ala Ser
165 170 175

Pro Gly Glu Lys Val Thr Met Thr Cys Ser Ala Ser Ser Ser Val Ser
180 185 190

Tyr Met Asn Trp Tyr Gln Gln Lys Ser Gly Thr Ser Pro Lys Arg Trp
195 200 205

Ile Tyr Asp Thr Ser Lys Leu Ala Ser Gly Val Pro Ala His Phe Arg
210 215 220

Gly Ser Gly Ser Gly Thr Ser Tyr Ser Leu Thr Ile Ser Gly Met Glu
225 230 235 240

Ala Glu Asp Ala Ala Thr Tyr Tyr Cys Gln Gln Trp Ser Ser Asn Pro
245 250 255

Phe Thr Phe Gly Ser Gly Thr Lys Leu Glu Ile Asn Arg Gly Ser Gly
260 265 270

Ser Gly Asn Ala Val Gly Gln Asp Thr Gln Glu Val Ile Val Val Pro
275 280 285

His Ser Leu Pro Phe Lys Val Val Val Ile Ser Ala Ile Leu Ala Leu
290 295 300

Val Val Leu Thr Ile Ile Ser Leu Ile Ile Leu Ile Met Leu Trp Gln
305 310 315 320

Lys Lys Pro Arg Gly Ser Gly Ala Thr Asn Phe Ser Leu Leu Lys Gln
325 330 335

Ala Gly Asp Val Glu Glu Asn Pro Gly Pro Gly Thr Trp Pro Pro Gly
340 345 350

Ser Ala Ser Gln Pro Pro Pro Ser Pro Ala Ala Ala Thr Gly Leu His
355 360 365

```
Pro Ala Ala Arg Pro Val Ser Leu Gln Cys Arg Leu Ser Met Cys Pro
    370                 375                 380

Ala Arg Ser Leu Leu Leu Val Ala Thr Leu Val Leu Leu Asp His Leu
385                 390                 395                 400

Ser Leu Ala Arg Asn Leu Pro Val Ala Thr Pro Asp Pro Gly Met Phe
                405                 410                 415

Pro Cys Leu His His Ser Gln Asn Leu Leu Arg Ala Val Ser Asn Met
            420                 425                 430

Leu Gln Lys Ala Arg Gln Thr Leu Glu Phe Tyr Pro Cys Thr Ser Glu
        435                 440                 445

Glu Ile Asp His Glu Asp Ile Thr Lys Asp Lys Thr Ser Thr Val Glu
    450                 455                 460

Ala Cys Leu Pro Leu Glu Leu Thr Lys Asn Glu Ser Cys Leu Asn Ser
465                 470                 475                 480

Arg Glu Thr Ser Phe Ile Thr Asn Gly Ser Cys Leu Ala Ser Arg Lys
                485                 490                 495

Thr Ser Phe Met Met Ala Leu Cys Leu Ser Ser Ile Tyr Glu Asp Leu
            500                 505                 510

Lys Met Tyr Gln Val Glu Phe Lys Thr Met Asn Ala Lys Leu Leu Met
        515                 520                 525

Asp Pro Lys Arg Gln Ile Phe Leu Asp Gln Asn Met Leu Ala Val Ile
    530                 535                 540

Asp Glu Leu Met Gln Ala Leu Asn Phe Asn Ser Glu Thr Val Pro Gln
545                 550                 555                 560

Lys Ser Ser Leu Glu Glu Pro Asp Phe Tyr Lys Thr Lys Ile Lys Leu
                565                 570                 575

Cys Ile Leu Leu His Ala Phe Arg Ile Arg Ala Val Thr Ile Asp Arg
            580                 585                 590

Val Met Ser Tyr Leu Asn Ala Ser Gly Ser Gly Ala Thr Asn Phe Ser
        595                 600                 605

Leu Leu Lys Gln Ala Gly Asp Val Glu Glu Asn Pro Gly Pro Cys His
    610                 615                 620

Gln Gln Leu Val Ile Ser Trp Phe Ser Leu Val Phe Leu Ala Ser Pro
625                 630                 635                 640

Leu Val Ala Ile Trp Glu Leu Lys Lys Asp Val Tyr Val Val Glu Leu
                645                 650                 655

Asp Trp Tyr Pro Asp Ala Pro Gly Glu Met Val Val Leu Thr Cys Asp
            660                 665                 670

Thr Pro Glu Glu Asp Gly Ile Thr Trp Thr Leu Asp Gln Ser Ser Glu
        675                 680                 685

Val Leu Gly Ser Gly Lys Thr Leu Thr Ile Gln Val Lys Glu Phe Gly
    690                 695                 700

Asp Ala Gly Gln Tyr Thr Cys His Lys Gly Gly Glu Val Leu Ser His
705                 710                 715                 720

Ser Leu Leu Leu Leu His Lys Lys Glu Asp Gly Ile Trp Ser Thr Asp
                725                 730                 735

Ile Leu Lys Asp Gln Lys Glu Pro Lys Asn Lys Thr Phe Leu Arg Cys
            740                 745                 750

Glu Ala Lys Asn Tyr Ser Gly Arg Phe Thr Cys Trp Trp Leu Thr Thr
        755                 760                 765

Ile Ser Thr Asp Leu Thr Phe Ser Val Lys Ser Ser Arg Gly Ser Ser
    770                 775                 780
```

```
Asp Pro Gln Gly Val Thr Cys Gly Ala Ala Thr Leu Ser Ala Glu Arg
785                 790                 795                 800

Val Arg Gly Asp Asn Lys Glu Tyr Glu Tyr Ser Val Glu Cys Gln Glu
                805                 810                 815

Asp Ser Ala Cys Pro Ala Ala Glu Glu Ser Leu Pro Ile Glu Val Met
            820                 825                 830

Val Asp Ala Val His Lys Leu Lys Tyr Glu Asn Tyr Thr Ser Ser Phe
        835                 840                 845

Phe Ile Arg Asp Ile Ile Lys Pro Asp Pro Pro Lys Asn Leu Gln Leu
    850                 855                 860

Lys Pro Leu Lys Asn Ser Arg Gln Val Glu Val Ser Trp Glu Tyr Pro
865                 870                 875                 880

Asp Thr Trp Ser Thr Pro His Ser Tyr Phe Ser Leu Thr Phe Cys Val
                885                 890                 895

Gln Val Gln Gly Lys Ser Lys Arg Glu Lys Lys Asp Arg Val Phe Thr
            900                 905                 910

Asp Lys Thr Ser Ala Thr Val Ile Cys Arg Lys Asn Ala Ser Ile Ser
        915                 920                 925

Val Arg Ala Gln Asp Arg Tyr Tyr Ser Ser Ser Trp Ser Glu Trp Ala
    930                 935                 940

Ser Val Pro Cys Ser
945


<210> SEQ ID NO 81
<211> LENGTH: 2271
<212> TYPE: DNA
<213> ORGANISM: Artificial Sequence
<220> FEATURE:
<223> OTHER INFORMATION: hIL-12 p35-P2A-hIL-12p40-P2A-hCXCL9 sequence

<400> SEQUENCE: 81

atgtggcccc ctgggtcagc ctcccagcca ccgccctcac ctgccgcggc cacaggtctg     60

catccagcgg ctcgccctgt gtccctgcag tgccggctca gcatgtgtcc agcgcgcagc    120

ctcctccttg tggctaccct ggtcctcctg gaccacctca gtttggccag aaacctcccc    180

gtggccactc cagacccagg aatgttccca tgccttcacc actcccaaaa cctgctgagg    240

gccgtcagca acatgctcca gaaggccaga caaactctcg aattttaccc ttgcacttct    300

gaagagattg atcatgaaga tatcacaaaa gataaaacca gcacagtgga ggcctgttta    360

ccattggaat taaccaagaa tgagagttgc ctaaattcca gagagacctc tttcataact    420

aatgggagtt gcctggcctc cagaaagacc tcttttatga tggccctgtg ccttagtagt    480

atttatgaag acttgaagat gtaccaggtg gagttcaaga ccatgaatgc aaagcttctg    540

atggacccta agaggcaaat cttcctagat caaaacatgc tggcagttat tgatgagctg    600

atgcaggccc tgaatttcaa cagtgagact gtgccacaaa aatcctccct tgaagaaccg    660

gatttctaca agactaaaat caagctctgc atacttcttc atgctttcag aatccgggca    720

gtgactattg atagagtgat gagctatctg aatgcttccg cggccgcagg atctggggcc    780

accaactttt cattgctcaa gcaggcgggc gatgtggagg aaaaccctgg ccccggatcc    840

tgtcaccagc agttggtcat ctcttggttt tccctggttt ttctggcatc tcccctcgtg    900

gccatatggg aactgaagaa agatgtttat gtcgtagaat tggattggta tccggatgcc    960

cctggagaaa tggtggtcct cacctgtgac acccctgaag aagatggtat cacctggacc   1020

ttggaccaga gcagtgaggt cttaggctct ggcaaaaccc tgaccatcca agtcaaagag   1080
```

```
tttggagatg ctggccagta cacctgtcac aaaggaggcg aggttctaag ccattcgctc   1140

ctgctgcttc acaaaaagga agatggaatt tggtccactg atattttaaa ggaccagaaa   1200

gaacccaaaa ataagacctt tctaagatgc gaggccaaga attattctgg acgtttcacc   1260

tgctggtggc tgacgacaat cagtactgat ttgacattca gtgtcaaaag cagcagaggc   1320

tcttctgacc cccaaggggt gacgtgcgga gctgctacac tctctgcaga gagagtcaga   1380

ggggacaaca aggagtatga gtactcagtg gagtgccagg aggacagtgc ctgcccagct   1440

gctgaggaga gtctgcccat tgaggtcatg gtggatgccg ttcacaagct caagtatgaa   1500

aactacacca gcagcttctt catcagggac atcatcaaac ctgacccacc caagaacttg   1560

cagctgaagc cattaaagaa ctctcggcag gtggaggtca gctgggagta ccctgacacc   1620

tggagtactc cacattccta cttctccctg acattctgcg ttcaggtcca gggcaagagc   1680

aagagagaaa agaaagatag agtcttcacg gacaagacct cagccacggt catctgccgc   1740

aaaaatgcca gcattagcgt gcgggcccag gaccgctact atagctcatc ttggagcgaa   1800

tgggcatctg tgccctgcag ttcgtctaga ggatctgggg ccaccaactt ttcattgctc   1860

aagcaggcgg gcgatgtgga ggaaaaccct ggccccaaga aaagtggtgt tcttttcctc   1920

ttgggcatca tcttgctggt tctgattgga gtgcaaggaa ccccagtagt gagaaagggt   1980

cgctgttcct gcatcagcac caaccaaggg actatccacc tacaatcctt gaaagacctt   2040

aaacaatttg ccccaagccc ttcctgcgag aaaattgaaa tcattgctac actgaagaat   2100

ggagttcaaa catgtctaaa cccagattca gcagatgtga aggaactgat taaaaagtgg   2160

gagaaacagg tcagccaaaa gaaaaagcaa aagaatggga aaaaacatca aaaaaagaaa   2220

gttctgaaag ttcgaaaatc tcaacgttct cgtcaaaaga agactacata a             2271
```

<210> SEQ ID NO 82
<211> LENGTH: 756
<212> TYPE: PRT
<213> ORGANISM: Artificial Sequence
<220> FEATURE:
<223> OTHER INFORMATION: hIL-12 p35-P2A-hIL-12p40-P2A-hCXCL9 sequence

<400> SEQUENCE: 82

```
Met Trp Pro Pro Gly Ser Ala Ser Gln Pro Pro Pro Ser Pro Ala Ala
1               5                   10                  15

Ala Thr Gly Leu His Pro Ala Ala Arg Pro Val Ser Leu Gln Cys Arg
            20                  25                  30

Leu Ser Met Cys Pro Ala Arg Ser Leu Leu Leu Val Ala Thr Leu Val
        35                  40                  45

Leu Leu Asp His Leu Ser Leu Ala Arg Asn Leu Pro Val Ala Thr Pro
    50                  55                  60

Asp Pro Gly Met Phe Pro Cys Leu His His Ser Gln Asn Leu Leu Arg
65                  70                  75                  80

Ala Val Ser Asn Met Leu Gln Lys Ala Arg Gln Thr Leu Glu Phe Tyr
                85                  90                  95

Pro Cys Thr Ser Glu Glu Ile Asp His Glu Asp Ile Thr Lys Asp Lys
            100                 105                 110

Thr Ser Thr Val Glu Ala Cys Leu Pro Leu Glu Leu Thr Lys Asn Glu
        115                 120                 125

Ser Cys Leu Asn Ser Arg Glu Thr Ser Phe Ile Thr Asn Gly Ser Cys
    130                 135                 140

Leu Ala Ser Arg Lys Thr Ser Phe Met Met Ala Leu Cys Leu Ser Ser
145                 150                 155                 160
```

```
Ile Tyr Glu Asp Leu Lys Met Tyr Gln Val Glu Phe Lys Thr Met Asn
                165                 170                 175

Ala Lys Leu Leu Met Asp Pro Lys Arg Gln Ile Phe Leu Asp Gln Asn
            180                 185                 190

Met Leu Ala Val Ile Asp Glu Leu Met Gln Ala Leu Asn Phe Asn Ser
        195                 200                 205

Glu Thr Val Pro Gln Lys Ser Ser Leu Glu Glu Pro Asp Phe Tyr Lys
    210                 215                 220

Thr Lys Ile Lys Leu Cys Ile Leu Leu His Ala Phe Arg Ile Arg Ala
225                 230                 235                 240

Val Thr Ile Asp Arg Val Met Ser Tyr Leu Asn Ala Ser Ala Ala Ala
                245                 250                 255

Gly Ser Gly Ala Thr Asn Phe Ser Leu Leu Lys Gln Ala Gly Asp Val
            260                 265                 270

Glu Glu Asn Pro Gly Pro Gly Ser Cys His Gln Gln Leu Val Ile Ser
        275                 280                 285

Trp Phe Ser Leu Val Phe Leu Ala Ser Pro Leu Val Ala Ile Trp Glu
    290                 295                 300

Leu Lys Lys Asp Val Tyr Val Val Glu Leu Asp Trp Tyr Pro Asp Ala
305                 310                 315                 320

Pro Gly Glu Met Val Val Leu Thr Cys Asp Thr Pro Glu Glu Asp Gly
                325                 330                 335

Ile Thr Trp Thr Leu Asp Gln Ser Ser Glu Val Leu Gly Ser Gly Lys
            340                 345                 350

Thr Leu Thr Ile Gln Val Lys Glu Phe Gly Asp Ala Gly Gln Tyr Thr
        355                 360                 365

Cys His Lys Gly Gly Glu Val Leu Ser His Ser Leu Leu Leu Leu His
    370                 375                 380

Lys Lys Glu Asp Gly Ile Trp Ser Thr Asp Ile Leu Lys Asp Gln Lys
385                 390                 395                 400

Glu Pro Lys Asn Lys Thr Phe Leu Arg Cys Glu Ala Lys Asn Tyr Ser
                405                 410                 415

Gly Arg Phe Thr Cys Trp Trp Leu Thr Thr Ile Ser Thr Asp Leu Thr
            420                 425                 430

Phe Ser Val Lys Ser Ser Arg Gly Ser Ser Asp Pro Gln Gly Val Thr
        435                 440                 445

Cys Gly Ala Ala Thr Leu Ser Ala Glu Arg Val Arg Gly Asp Asn Lys
    450                 455                 460

Glu Tyr Glu Tyr Ser Val Glu Cys Gln Glu Asp Ser Ala Cys Pro Ala
465                 470                 475                 480

Ala Glu Glu Ser Leu Pro Ile Glu Val Met Val Asp Ala Val His Lys
                485                 490                 495

Leu Lys Tyr Glu Asn Tyr Thr Ser Ser Phe Phe Ile Arg Asp Ile Ile
            500                 505                 510

Lys Pro Asp Pro Pro Lys Asn Leu Gln Leu Lys Pro Leu Lys Asn Ser
        515                 520                 525

Arg Gln Val Glu Val Ser Trp Glu Tyr Pro Asp Thr Trp Ser Thr Pro
    530                 535                 540

His Ser Tyr Phe Ser Leu Thr Phe Cys Val Gln Val Gln Gly Lys Ser
545                 550                 555                 560

Lys Arg Glu Lys Lys Asp Arg Val Phe Thr Asp Lys Thr Ser Ala Thr
                565                 570                 575
```

-continued

```
Val Ile Cys Arg Lys Asn Ala Ser Ile Ser Val Arg Ala Gln Asp Arg
            580                 585                 590

Tyr Tyr Ser Ser Ser Trp Ser Glu Trp Ala Ser Val Pro Cys Ser Ser
        595                 600                 605

Ser Arg Gly Ser Gly Ala Thr Asn Phe Ser Leu Leu Lys Gln Ala Gly
    610                 615                 620

Asp Val Glu Glu Asn Pro Gly Pro Lys Lys Ser Gly Val Leu Phe Leu
625                 630                 635                 640

Leu Gly Ile Ile Leu Leu Val Leu Ile Gly Val Gln Gly Thr Pro Val
                645                 650                 655

Val Arg Lys Gly Arg Cys Ser Cys Ile Ser Thr Asn Gln Gly Thr Ile
            660                 665                 670

His Leu Gln Ser Leu Lys Asp Leu Lys Gln Phe Ala Pro Ser Pro Ser
        675                 680                 685

Cys Glu Lys Ile Glu Ile Ile Ala Thr Leu Lys Asn Gly Val Gln Thr
    690                 695                 700

Cys Leu Asn Pro Asp Ser Ala Asp Val Lys Glu Leu Ile Lys Lys Trp
705                 710                 715                 720

Glu Lys Gln Val Ser Gln Lys Lys Lys Gln Lys Asn Gly Lys Lys His
                725                 730                 735

Gln Lys Lys Lys Val Leu Lys Val Arg Lys Ser Gln Arg Ser Arg Gln
            740                 745                 750

Lys Lys Thr Thr
        755
```

<210> SEQ ID NO 83
<211> LENGTH: 21
<212> TYPE: PRT
<213> ORGANISM: Mus musculus

<400> SEQUENCE: 83

```
Val Val Ile Ser Ala Ile Leu Ala Leu Val Val Leu Thr Val Ile Ser
1               5                   10                  15

Leu Ile Ile Leu Ile
            20
```

<210> SEQ ID NO 84
<211> LENGTH: 21
<212> TYPE: PRT
<213> ORGANISM: Homo sapiens

<400> SEQUENCE: 84

```
Val Val Ile Ser Ala Ile Leu Ala Leu Val Val Leu Thr Ile Ile Ser
1               5                   10                  15

Leu Ile Ile Leu Ile
            20
```

<210> SEQ ID NO 85
<211> LENGTH: 21
<212> TYPE: PRT
<213> ORGANISM: Homo sapiens

<400> SEQUENCE: 85

```
Ala Ala Val Leu Val Leu Leu Val Ile Val Ile Ile Ser Leu Ile Val
1               5                   10                  15

Leu Val Val Ile Trp
            20
```

<210> SEQ ID NO 86
<211> LENGTH: 21
<212> TYPE: PRT
<213> ORGANISM: Mus musculus

<400> SEQUENCE: 86

Ala Ala Val Leu Val Leu Leu Val Ile Val Ile Val Ser Leu Ile Val
1 5 10 15

Leu Val Val Ile Trp
20

<210> SEQ ID NO 87
<211> LENGTH: 62
<212> TYPE: DNA
<213> ORGANISM: Homo sapiens

<400> SEQUENCE: 87
tggtgatctc agccatcctg gccctggtgg tgctcaccat catctccctt atcatcctca 60
tc 62

<210> SEQ ID NO 88
<211> LENGTH: 63
<212> TYPE: DNA
<213> ORGANISM: Homo sapiens

<400> SEQUENCE: 88
gtggtgatct cagccatcct ggccctggtg gtgctcacca tcatctccct tatcatcctc 60
atc 63

<210> SEQ ID NO 89
<211> LENGTH: 65
<212> TYPE: DNA
<213> ORGANISM: Homo sapiens

<400> SEQUENCE: 89
gctgcagtcc tggtgctgtt ggtgattgtg atcatctcac ttattgtcct ggttgtcatt 60
tggaa 65

<210> SEQ ID NO 90
<211> LENGTH: 8
<212> TYPE: PRT
<213> ORGANISM: Artificial Sequence
<220> FEATURE:
<223> OTHER INFORMATION: Synthetic

<400> SEQUENCE: 90

Ser Ile Ile Asn Phe Glu Lys Leu
1 5

<210> SEQ ID NO 91
<211> LENGTH: 25
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (9)..(25)
<223> OTHER INFORMATION: may be absent

<400> SEQUENCE: 91

Gly Gly Gly Gly Ser Gly Gly Gly Gly Ser Gly Gly Gly Gly Ser Gly
1 5 10 15

-continued

```
Gly Gly Gly Ser Gly Gly Gly Gly Ser
            20                  25


<210> SEQ ID NO 92
<211> LENGTH: 16
<212> TYPE: PRT
<213> ORGANISM: Artificial Sequence
<220> FEATURE:
<223> OTHER INFORMATION: synthetic

<400> SEQUENCE: 92

Gly Gly Gly Gly Gly Ser Gly Gly Gly Gly Ser Gly Gly Gly Gly Ser
1               5                   10                  15
```